US012180480B2

(12) United States Patent
Dindot

(10) Patent No.: US 12,180,480 B2
(45) **Date of Patent: *Dec. 31, 2024**

(54) ANGELMAN SYNDROME ANTISENSE TREATMENT

(71) Applicant: The Texas A&M University System, College Station, TX (US)

(72) Inventor: Scott Victor Dindot, College Station, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/345,452

(22) Filed: Jun. 30, 2023

(65) Prior Publication Data

US 2023/0332152 A1 Oct. 19, 2023

Related U.S. Application Data

(63) Continuation of application No. 18/055,212, filed on Nov. 14, 2022, now Pat. No. 11,739,328, which is a continuation of application No. 17/523,456, filed on Nov. 10, 2021, now Pat. No. 11,685,920, which is a continuation of application No. 16/767,916, filed as application No. PCT/US2018/063416 on Nov. 30, 2018, now Pat. No. 11,198,869.

(60) Provisional application No. 62/676,034, filed on May 24, 2018, provisional application No. 62/593,431, filed on Dec. 1, 2017.

(51) Int. Cl.
*C12N 15/113* (2010.01)
*C07H 21/04* (2006.01)
*C12Q 1/68* (2018.01)

(52) U.S. Cl.
CPC ........... *C12N 15/113* (2013.01); *C07H 21/04* (2013.01); *C12N 2310/113* (2013.01); *C12N 2310/341* (2013.01); *C12N 2310/346* (2013.01); *C12N 2320/30* (2013.01)

(58) Field of Classification Search
None
See application file for complete search history.

(56) References Cited

U.S. PATENT DOCUMENTS

2018/0305689 A1* 10/2018 Sætrom ............... C12N 15/113

* cited by examiner

*Primary Examiner* — Sean McGarry
(74) *Attorney, Agent, or Firm* — Thomas | Horstemeyer, LLP

(57) ABSTRACT

Disclosed herein are antisense oligonucleotides that are capable of inducing expression of ubiquitin-protein ligase E3A (UBE3A) from the paternal allele in animal or human neurons. The oligonucleotides target the suppressor of the UBE3A paternal allele by hybridization to SNHG14 long non-coding RNA at the 5'-end of UBE3A-AS, which is downstream of SNORD115-45 snoRNA. Also disclosed are pharmaceutical compositions and methods for treatment of Angelman syndrome.

13 Claims, 30 Drawing Sheets

Specification includes a Sequence Listing.

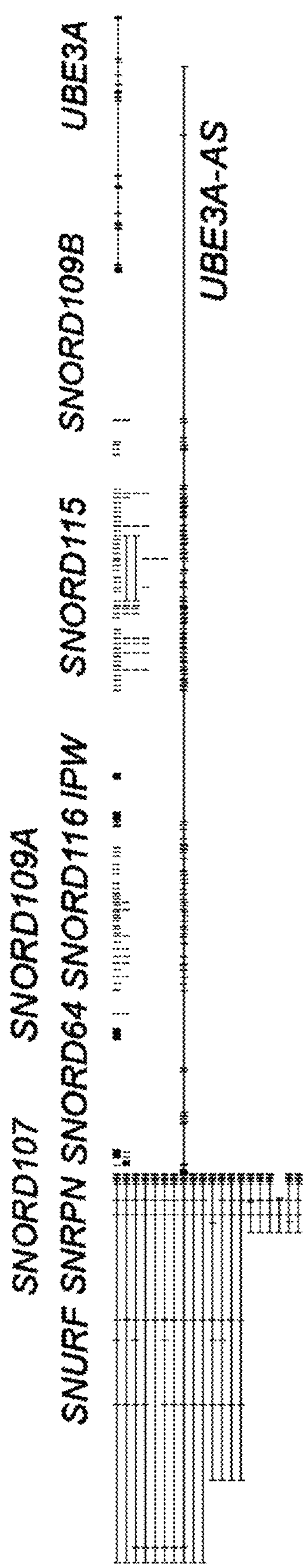
FIG. 1A
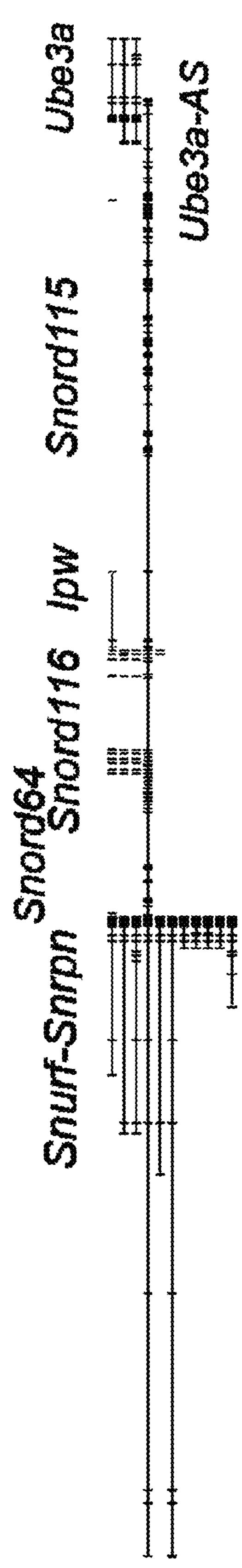
FIG. 1B
UBE3A
FIG. 1C

ASO-C

Topotecan

ASO-B

ASO-1.1

Ube3a$^{YFP}$

Human *UBE3A-AS*

ASO 1 4 5 3 2 6 7

GABAergic iPSC-Neurons

Tx End

0 DIV 29 35

Glutamatergic iPSC-Neurons

Tx End

0 DIV 14 20

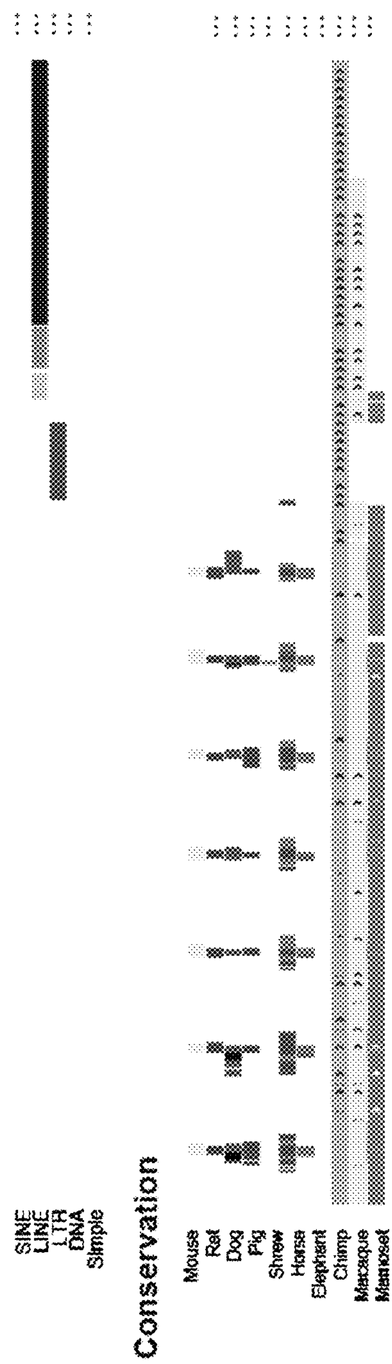
FIG. 7D
FIG. 7E
FIG. 7F
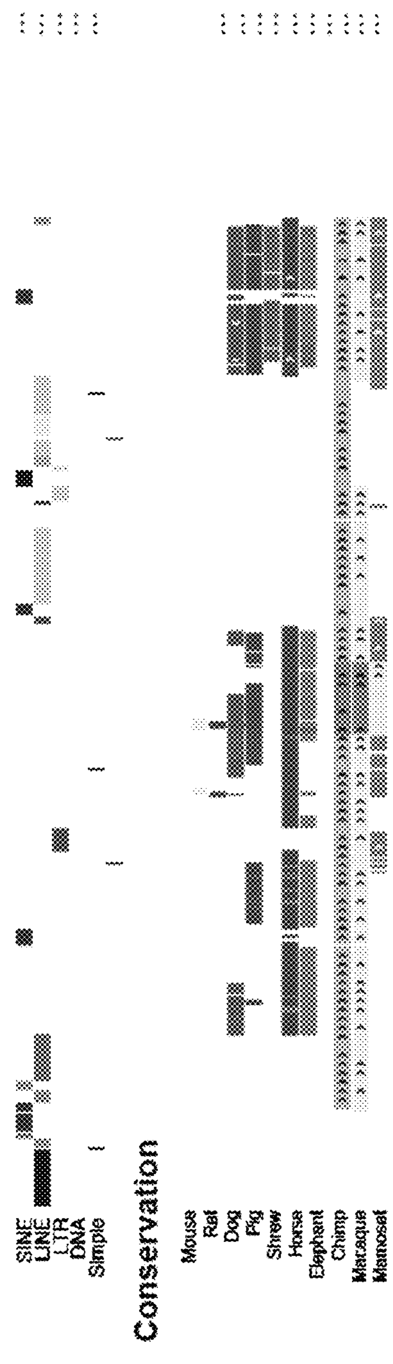
FIG. 7D cont...
FIG. 7E cont...
FIG. 7F cont...

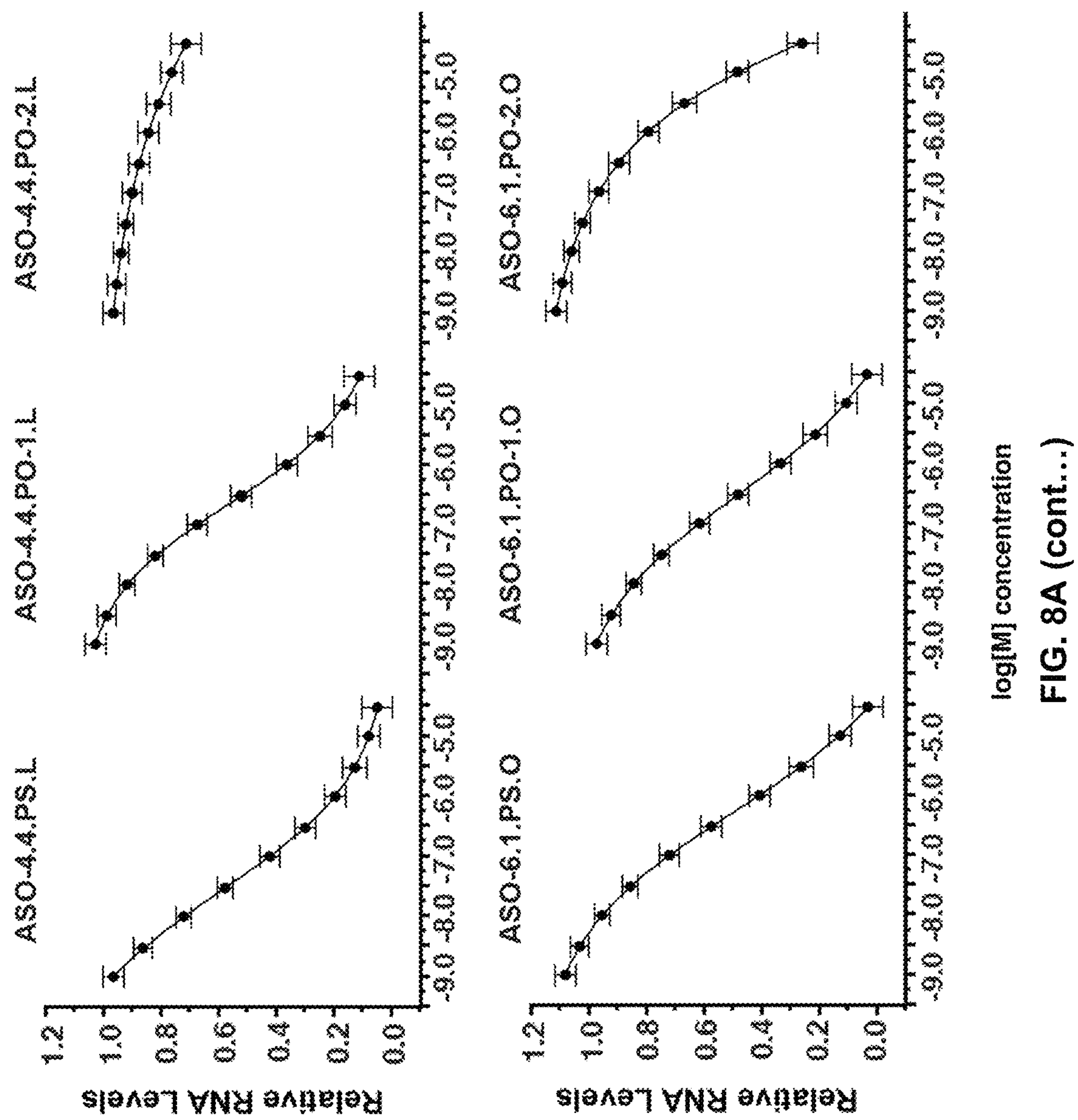
FIG. 8A (cont...)

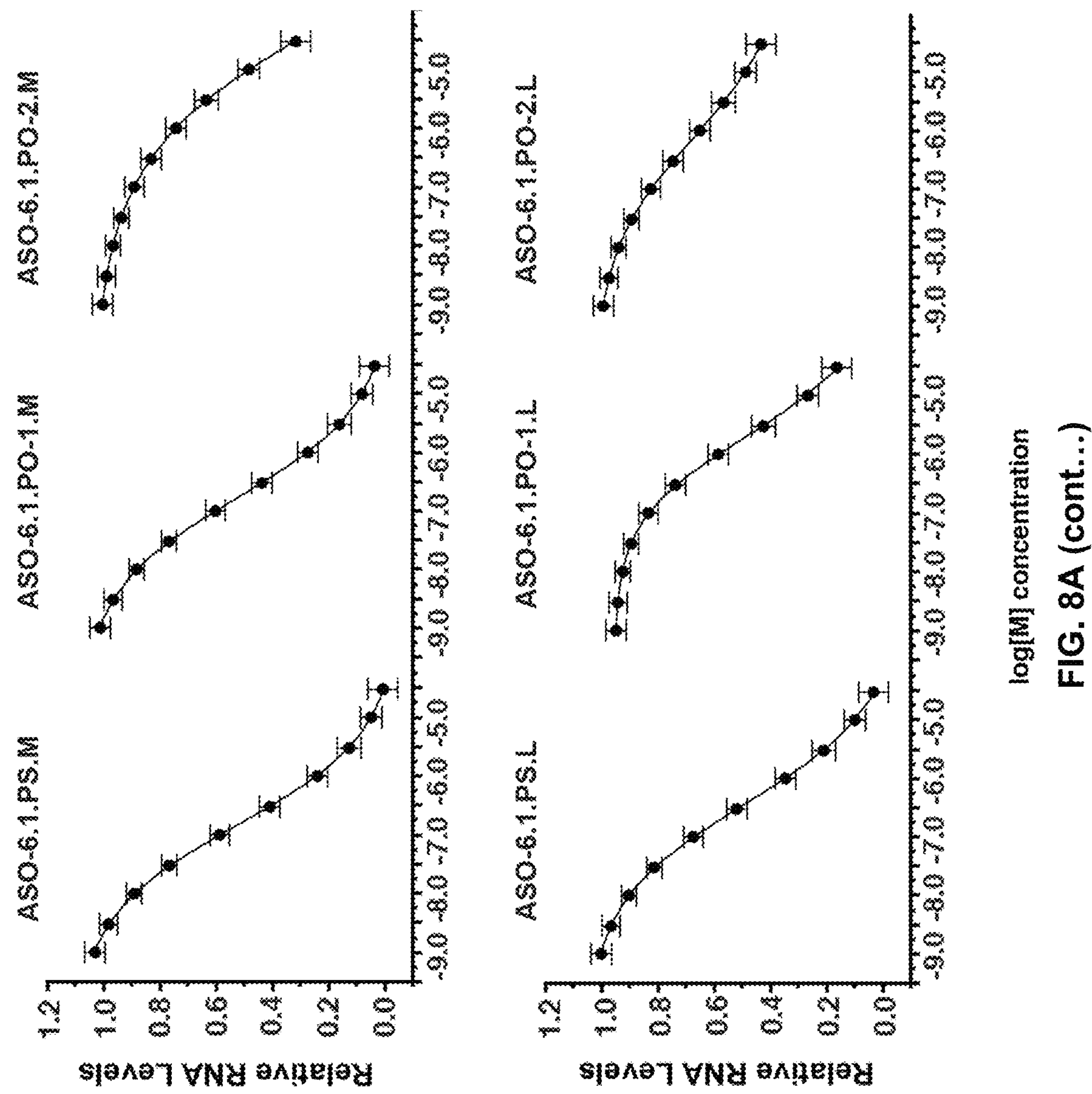
FIG. 8A (cont...)

ANGELMAN SYNDROME ANTISENSE TREATMENT

CROSS-REFERENCE TO RELATED APPLICATIONS

This application is a continuation of copending application Ser. No. 18/055,212, filed Nov. 14, 2022, which is a continuation of copending application Ser. No. 17/523,456, filed Nov. 10, 2021, which is a continuation of copending application Ser. No. 16/767,916, filed May 28, 2020, is a National Stage of International Application No. PCT/US2018/063416, filed Nov. 30, 2018, which claims benefit of U.S. Provisional Application No. 62/593,431, filed Dec. 1, 2017, and Application Ser. No. 62/676,034, filed May 24, 2018, which are hereby incorporated herein by reference in their entirety.

SEQUENCE LISTING

This application contains a sequence listing filed in ST.26 format entitled "922001-1023 Sequence Listing" created on May 16, 2023 and having 956,036 bytes. The content of the sequence listing is incorporated herein in its entirety.

BACKGROUND

Angelman syndrome (AS) is a neurodevelopmental disorder that is associated with severe cognitive and motor deficits, epilepsy, sleep-disorder, and an atypical 'happy' disposition. Individuals with AS are often diagnosed at 2-3 years of age and have a normal life-span. They require assisted living and medical care throughout their lives. There are currently few treatment options for individuals with AS, most of which involve anti-epileptic medications to treat seizures.

Angelman syndrome is caused by mutations that affect the expression or function of the maternally inherited ubiquitin-protein ligase E3A (UBE3A) gene. Unlike most genes, UBE3A is subject to genomic imprinting, which is a rare, naturally occurring phenomenon that turns-off one allele of a gene while leaving the other allele on. In neurons of the central nervous system (CNS), the paternal UBE3A allele is off, whereas in all other cell types of the body, both alleles of UBE3A are on. Because of this, AS is always caused by mutations that affect the maternally inherited UBE3A allele.

The paternal UBE3A allele is turned-off by the UBE3A antisense transcript (UBE3A-AS), which is a component of a long RNA transcript that expresses several protein coding and noncoding transcripts. UBE3A-AS is expressed from the paternal allele and only in neurons of the CNS and is both sufficient and necessary to turn-off expression of the paternal UBE3A allele. It's unclear why UBE3A is imprinted in neurons, but it creates a unique opportunity to treat individuals with AS, because there is a functional, albeit inactive, copy of UBE3A on the paternal chromosome. Studies to date indicate that turning on the paternal UBE3A allele is a viable therapy to treat AS.

SUMMARY

Disclosed herein is a region in the 5'-end of UBE3A-AS transcript that is important for its stability. Based on these findings, antisense oligonucleotides (ASOs) were designed to target this region in order to terminate transcription of UBE3A-AS and reactivate expression of the paternal UBE3A allele. These ASOs targeting the 5'-end of UBE3A-AS are capable of stopping transcription of UBE3A-AS and turning on the paternal UBE3A allele. SNHG14 is a polycistronic transcript that encodes several different RNAs, including UBE3A-AS.

Accordingly, disclosed herein are ASOs containing a contiguous nucleotide sequence of 10 to 30 nucleotides (i.e., 10, 11, 12, 13, 14, 15, 16, 17, 18, 19, 20, 21, 22, 23, 24, 25, 26, 27, 28, 29, or 30) in length with at least 98% (i.e. 98%, 99%, or 100%) complementarity to target exons between the 3'-end of the SNORD115 and the 5'-end of SNORD109B, which is thought to represent the 5'-end of the UBE3A antisense transcript (UBE3A-AS). In particular the target exons can be in the 5'-end of UBE3A-AS, corresponding to position 25,511,577 to 25,516,681 on human chromosome 15 human genome assembly hg19. In some embodiments, the target nucleic acid is one of five exons located in the 5'-end of UBE3A-AS, which can correspond to positions 25,511,577 to 25,511,761 (exon 1), 25,512,059 to 25,512,191 (exon 2), 25,513,476 to 25,513,600 (exon 3), 25,514,752 to 25,514,880 (exon 4), and 25,516,565 to 25,516,681 (exon 5). Therefore, the target nucleic acid can be a contiguous nucleic acid sequence of 10 to 30 nucleotides within SEQ ID NO:1, 2, 3, 4, or 5.

In some embodiments, the target sequence is an exonic boundary involving UBE3A-AS exons 1-5, UBE3A-AS exon 5 and SNORD109B exon 1, and/or SNORD109B exons 1-2.

Methods and strategies for designing ASOs are known in the art. In some embodiments, the ASO is designed to target sequences that are conserved among human subjects. In some embodiments, the ASO is designed to target sequences that are conserved among primate subjects.

The oligonucleotide can be an antisense oligonucleotide (i.e., as will be understood by those of ordinary skill in the art—antisense to its target nucleic acid), e.g., with a gapmer design. The disclosed oligonucleotide is capable of inducing paternal UBE3A expression in a neuron by degradation, reduction, or removal of the UBE3A-AS transcript. It does this by targeting the 5'-end of UBE3A-AS at a site upstream of SNORD109B snoRNA. Examples of ASO designed to target exons 1-5 are provided in Tables 1, 2, 3, 4, or 5. For example, in some embodiments, the ASO comprises the nucleic acid sequence SEQ ID NO: 6, 7, 8, 9, 10, or 11.

The disclosed ASOs can also have one or more modifications to improve stability, solubility, activity, cellular distribution, and/or cellular uptake. For example, the disclosed ASO can contain one or more sugar-modified nucleosides and/or modified internucleoside linkages. For example, in some embodiments, the oligonucleotide comprises one or more internucleoside linkages modified from the natural phosphodiester to a linkage that is for example more resistant to nuclease attack. In some embodiments, the ASO contains one or more modified nucleobases that differ from naturally occurring nucleobases, but are functional during nucleic acid hybridization.

In some embodiments, the ASO is a DNA oligonucleotide. In some embodiments, the ASO is an RNA oligonucleotide. In still other embodiments, the ASO contains both deoxynucleotides and ribonucleotides. For example, the ASO can be a gapmer, headmer, or tailmer oligonucleotide. In some embodiments, the central block of a gapmer is flanked by blocks of modified ribonucleotides that protect the internal block from nuclease degradation. For example, the ASO can contain a stretch of 7, 8, 9, 10, or more natural DNA monomers to activate RNase H cleavage of the target RNA, along with 3, 4, or 5 modified ribonucleotide monomers at the 3'- and 5'-ends for protection against exonucleases. In some cases, the modified ribonucleotides are 2'-O-Methyl (OMe) RNA nucleotides, 2'-O-methoxyethyl (MOE)-modified nucleotides, or 2'-Locked Nucleic Acids (LNAs). Examples of gapmer ASOs are provided Tables 7, 11, and 17. Therefore, in some embodiments, the disclosed ASO has a nucleic acid sequence selected from SEQ ID NOs:362 to 392.

Also disclosed are pharmaceutical compositions comprising one or more of the ASOs disclosed herein and pharmaceutically acceptable diluents, carriers, salts and/or adjuvants.

Also disclosed are methods for in vivo or in vitro induction of UBE3A expression in a target cell where expression of paternal UBE3A is suppressed, by administering one or more of the disclosed ASOs or composition disclosed herein in an effective amount to said cell.

Also disclosed are methods for treating or preventing a disease, disorder or dysfunction associated with in vivo activity of UBE3A comprising administering a therapeutically or prophylactically effective amount of one or more of the disclosed ASOs to a subject suffering from or susceptible to the disease, disorder or dysfunction, such as Angelman syndrome.

The details of one or more embodiments of the invention are set forth in the accompanying drawings and the description below. Other features, objects, and advantages of the invention will be apparent from the description and drawings, and from the claims. For example, those skilled in the art, reading the specification will appreciate that the present disclosure demonstrates usefulness of certain sequences as described herein to impact expression of UBE3A, and furthermore teaches usefulness of oligonucleotide formats that are, or target (e.g., are complementary to), such sequences. Those skilled in the art will appreciate that the present disclosure is not limited to any particular mechanism of action—provided oligonucleotides may be useful regardless of whether they act via an antisense mechanism, for example, involving RNase H activity, and other therapeutic formats (e.g., siRNA, shRNA, nuclease gRNA, etc.) of oligonucleotides that are or target such sequences are also provided. Analogously, those skilled in the art will appreciate that the present disclosure, by defining useful sequences as described herein, also describes a variety of formats for such sequences (e.g., as part of a nucleic acid vector such as a vector from which they may be expressed (e.g., in vivo, in vitro, or both, etc.). Thus, those skilled in the art, reading the present disclosure, will appreciate that reference to “ASOs” herein is exemplary, and appropriate nucleic acids (e.g., oligonucleotides) may be utilized regardless of mechanism of action; those skilled in the art are aware of extensive literature regarding appropriate format and structure of nucleic acids (e.g., oligonucleotides) that operate via any of a variety of mechanisms (e.g., siRNA, shRNA, nuclease gRNA, etc.). In some embodiments, provided nucleic acids incorporate format and/or structural features known in the art to be useful in one or more mechanistic contexts (e.g., involving RNase H, RISC, a nucleic-acid-directed nuclease such as a Cas, etc.).

DESCRIPTION OF DRAWINGS

FIGS. 1A to 1D illustrate the Prader-Willi/Angelman syndrome (PWS/AS) imprinted region in human and mouse. FIG. 1A shows RefSeq annotation of human PWS/AS imprinted region. FIG. 1B shows RefSeq annotation of PWS/AS imprinted orthologous region in mouse. FIG. 1C shows UBE3A-AS and 3'-end of UBE3A. FIG. 1D shows chain alignment showing orthologous regions between human, macaque (Cynomolgus macaque), pig, elephant, mouse, and rat. The target region is conserved among non-human primates but not rodents. FIG. 1D also shows genomic evolutionary rate profiling (GERP) plot of region. Positive values represent evolutionary constraint at specific DNA bases.

FIGS. 2A to 2E show an analysis of ASOs targeting mouse Ube3a-AS. FIG. 2A is a schematic of mouse Ube3a-AS transcript and approximate location of mouse-specific ASOs. Boxes and lines represent exons and introns, respectively. Arrow represents direction of transcription. FIG. 2B is a schematic of Ube3aYFP reporter allele used to measure paternal Ube3a protein levels. The Ube3aYFP mouse model was generated by targeting the yellow fluorescent protein (YFP) to the 3'-end of the endogenous Ube3a locus. Expression of Ube3a-AS inhibits transcription of the paternal Ube3aYFP allele, and loss of Ube3a-AS reactivates paternal Ube3aYFP expression, which can be detected by immunofluorescence imaging using an anti-YFP antibody. FIG. 2C is a schematic of experimental timeline to examine ASOs in mouse primary hippocampal neurons. Mouse primary hippocampal neurons were generated from newborn mice with a paternally inherited Ube3aYFP allele (0 DIV) and treated after 7 days in vitro (7 DIV). Three days post-treatment (10 DIV), Ube3aYFP protein levels were measured in individual cells. FIG. 2D contains immunofluorescent images showing paternal Ube3aYFP protein in primary neurons treated with vehicle (veh), a negative control ASO (ASO-C), Topotecan (Topo), ASO-B, and ASO 1.1. FIG. 2E shows mean paternal Ube3aYFP intensity levels in individual neuronal cells treated with vehicle (veh, 1% DMSO; n=3), control ASO (ASO-C, 15 μM; n=3), Topotecan (Topo, 0.3 μM; n=3), ASO-B (1, 5, 15 μM; n=3), ASO-1.1 (1, 5, 15 μM), ASO-1.2 (1, 5, 15 μM), and ASO 3.1 (1, 5, 15 μM). Abbreviations: YFP, yellow fluorescent protein; Tx, treatment; DIV, days in vitro; n.s., not significant. Error bars represent standard error of mean.

FIGS. 3A to 3D show analysis of ASOs targeting human UBE3A-AS. FIG. 3A is a schematic showing of human UBE3A-AS and approximate location of human-specific ASOs (ASOs 1-6). ASO-7 is located in an intron of UBE3A-AS. Boxes and lines represent exons and introns, respectively. FIG. 3B is a schematic of experimental timeline to examine ASOs in human GABAergic induced pluripotent stem cell (iPSC) derived neurons from a karyotypically normal individual. Human iPSC-derived neurons were treated after 14 DIV and then processed for RNA isolation at 20 DIV. FIGS. 3C and 3D show relative steady state RNA levels (normalized to ASO-C) of UBE3A-AS (FIG. 3C) and UBE3A (FIG. 3D) in iPSC-derived neurons treated with control ASO (ASO-C, 10 μM), and ASOs 1-7 (10 μM), and Topotecan (Topo, 1 μM). Abbreviations: Tx, treatment; DIV, days in vitro. Error bars represent standard error of mean.

FIGS. 4A to 4F show relative expression (normalized to 1 nM) of UBE3A-AS (FIG. 4A), SNORD116 (FIG. 4B), IPW (FIG. 4C), SNORD115 (FIG. 4D), SNORD109A/B (FIG. 4E), and UBE3A (FIG. 4F) steady state RNA levels in iPSC-derived neurons treated with a 10-point ½ log dose curve of ASO-4 and Topotecan (1 nM, 3 nM, 10 nM, 30 nM, 100 nM, 300 nM, 1 μM, 3 μM, 10 μM, and 30 μM). FIG. 4G is a schematic of experimental timeline to examine ASO-4 in GABAergic iPSC-derived neurons treated at 59 DIV. FIG. 4H to 4I shows relative expression (normalized to ASO-C) of UBE3A-AS (FIG. 4H) and UBE3A (FIG. 4I) steady state RNA levels in iPSC-derived neurons treated with ASO-C(10 μM) and ASO-4 (1, 5, and 10 μM). Abbreviations: Tx, treatment. Error bars represent standard error of mean.

FIG. 5A is a schematic of experimental timeline to examine optimized ASOs in GABAergic iPSC-derived neurons. FIG. 5B shows relative expression of (normalized to water control) of UBE3A-AS steady state RNA levels in iPSC-derived neurons treated with a 5-point ½ log dose curve (30 nM, 100 nM, 300 nM, 1 μM, 3 μM; n=6) of ASO-3.1, ASO-3.2, ASO-4.1, ASO-4.2, ASO-4.3, ASO-4.4, ASO-6.1, ASO-4.1, and ASO-4.S. ASO-4.1 and ASO-4.S represent ASO-4 manufactured by two companies (ASO-4.1, Integrated DNA Technologies; ASO-4.S, Sigma-Aldrich). FIG. 5C is a schematic of experimental timeline to examine ASO-4 and ASO-6.1 in GABAergic iPSC-derived neurons. FIG. 5D shows relative expression of (normalized to 1 nM) of UBE3A-AS and UBE3A steady state RNA levels in iPSC-derived neurons treated with a 10-point ½ log dose curve (1 nM, 3 nM, 10 nM, 30 nM, 100 nM, 300 nM, 1 μM, 3 μM, 10 μM, and 30 μM; n=3) of ASO-4 (ASO-4.1 and ASO-4.S) and ASO-6.1. FIG. 5E is a schematic of experimental timeline to examine ASO-4 and ASO-6.1 in glutamatergic iPSC-derived neurons. FIG. 5F shows relative expression of (normalized to water control) of UBE3A-AS and UBE3A steady state RNA levels in iPSC-derived neurons treated with a 10-point ½ log dose curve (1 nM, 3 nM, 10 nM, 30 nM, 100 nM, 300 nM, 1 μM, 3 μM, 10 μM, and 30 uM; n=3) of ASO-4 (ASO-4.1 and ASO-4.S) and ASO-6.1. Error bars represent standard error of mean.

FIG. 6A shows RefSeq annotation of the orthologous PWS/AS imprinted region on mouse chromosome 7C. FIG. 6B illustrates a transcript assembly generated from RNA-sequencing (RNA-seq) data from mouse brain. FIG. 6C shows ASO target region showing Snord115 snoRNAs retained in exons of the Snord115 host-gene transcript/5'-end of Ube3a-AS. Aligned RNA-seq reads are depicted below assembled transcripts. Exons and introns are depicted by boxes and lines, respectively. FIG. 6D is a sequence alignment of snoRNAs in retained exons Snord115 ENSMUST00000101836 (SEQ ID NO:490), Snord115 ENSMUST00000101936 (SEQ ID NO:491), Snord115 ENSMUST00000104493 (SEQ ID NO:492), Snord115 ENSMUST00000082443 (SEQ ID NO:493), andSnord115 ENSMUST00000104427 (SEQ ID NO:494), showing retained snoRNAs have a degenerate C Box, which is required for functional snoRNA formation.

FIGS. 7A to 7G show identification of ASO target region in human PWS/AS imprinted region. FIG. 7A shows RefSeq annotation of Prader-Willi/Angelman syndrome (PWS/AS) imprinted region. FIG. 7B shows RNA-seq assembly of the human PWS polycistronic transcript. FIG. 7C shows SNORD115-45 is retained in an exon at the 3'-end of the SNORD115 host-gene transcript/5'-end of UBE3A-AS. Aligned RNA-seq reads generated from adult human brain showing L1 LINE is transcribed. FIG. 7D shows RefSeq annotation of 3'-end of SNORD115 cluster (SNORD115-39-48 and SNORD109B). FIG. 7E shows location of L1 LINE element between SNORD115-44 and SNORD115-45. FIG. 7F shows chain alignment of placental mammals representing major clades showing conservation at SNORD115-45-48 region, albeit reduced in rodents. FIG. 7G shows sequence alignment of snoRNAs in target region to SNORD115-44 (functional snoRNA) (SEQ ID NO:495), SNORD115-48 (SEQ ID NO:496), SNORD115-45 (SEQ ID NO:497), SNORD115-46 (SEQ ID NO:498), and SNORD115-47 (SEQ ID NO:499), showing SNORD115-45 (retained), SNORD115-46 (partially retained), and SNORD116-47 have degenerate C Box, which is required for functional snoRNA formation.

FIG. 8A shows fitted dose response curves of normalized UBE3A-AS steady state RNA levels in GABAergic iPSC-derived neurons treated with a 10-point ½ log dose curve (1 nM, 3 nM, 10 nM, 30 nM, 100 nM, 300 nM, 1 μM, 3 μM, 10 μM, and 30 μM; n=2) of ASO-4 and ASO-6.1 with different backbone and RNA modification designs. Dose response curves fitted using a 4-parameter logistic regression model (Hill). Graphs represent fitted models and standard error. The Y axis represents relative UBE3A-AS RNA levels and X axis represents log molar (M) concentrations of ASO. FIGS. 8B and 8C are hierarchical clustering dendrogram and constellation plots of fitted dose response curves showing relationship between candidate ASOs and grouping into 3 clusters.

DETAILED DESCRIPTION

Figure 1D:
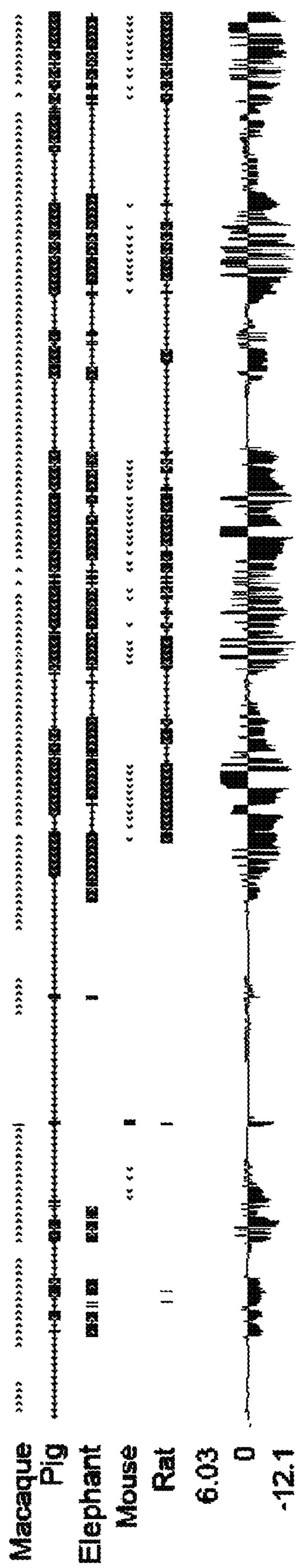

The UBE3A-AS/Ube3a-AS transcript, otherwise known as ubiquitin-protein ligase E3A antisense transcript and UBE3A-AS/Ube3a-AS, is the name for the transcript generated by transcription of the UBE3A-AS transcript, which is on the antisense DNA strand relative to the UBE3A gene. Note that gene names with all caps indicate human genes (e.g. UBE3A) and gene names with only the first letter capped indicate mouse genes (e.g. Ube3a). The UBE3A-AS transcript is transcribed as part of a large polycistronic transcription unit that encodes SNURF-SNRPN, a cluster of orphan C/D box small nucleolar RNAs (SNORDs), and several uncharacterized long noncoding RNAs. In both mouse and human, the UBE3A/Ube3a gene is imprinted in neurons of the central nervous system, where it is expressed only from the maternal allele. The UBE3A-AS/Ube3a-AS transcript is both necessary and sufficient to silence transcription of the paternal UBE3A/Ube3a allele, and inhibition of UBE3A-AS/Ube3a-AS reactivates transcription of the paternal UBE3A/Ube3a allele. Mutations affecting the function or expression of the maternally inherited UBE3A allele cause Angelman syndrome (AS). In AS, the paternal allele is functional but epigenetically silenced. If unsilenced in AS patients, the paternal UBE3A allele could be a source of functional UBE3A in neurons.

The polycistronic transcription unit (hereafter referred to as the PTU) encoding UBE3A-AS is about 450,000 basepairs long. Transcription of the PTU starts at upstream exons (U-exons) in the SNURF-SNRPN locus and stops towards the 5'-end of UBE3A. The PTU is organized (5'-3') as follows: SNURF-SNRPN, SNORD107, SNORD64, SNORD109A, SNORD116 (29 copies), IPW, SNORD115 (48 copies), SNORD109B, and UBE3A, which is orientated in the opposite direction of the upstream transcripts. The polycistronic transcript is alternatively spliced and subject to alternative 3'-processing. SNURF-SNRPN encodes two polypeptides. The SNORDs are in the introns of a host-gene transcript (SNHG14) and are generated by exonucleolytic debranching of the spliced introns. UBE3A-AS represents the 3'-end of the transcript that overlaps the UBE3A gene. Most C/D box snoRNAs play a role in ribosome biogenesis where they direct 2'-O-methylation of ribosomal RNAs (rRNA); however, the snoRNAs located in the PWS/AS region lack any sequence complementarity to known rRNAs; however, the SNORD115 snoRNA has been found to change the alternative splicing of the serotonin receptor 2C pre-mRNA.

Disclosed herein is evidence that the 5'-end of UBE3A-AS transcript is important for its stability. As disclosed herein, ASOs targeting the 5'-end of UBE3A-AS are capable of reducing UBE3A-AS levels, presumably by stopping transcription of UBE3A-AS, and turning-on the paternal UBE3A allele.

The term "oligonucleotide" as used herein is defined as it is generally understood by the skilled person as a molecule comprising two or more covalently linked nucleosides. Such covalently bound nucleosides may also be referred to as nucleic acid molecules or oligomers. Oligonucleotides are commonly made in the laboratory by solid-phase chemical synthesis followed by purification. When referring to a sequence of the oligonucleotide, reference is made to the sequence or order of nucleobase moieties, or modifications thereof, of the covalently linked nucleotides or nucleosides. The oligonucleotide disclosed herein is man-made, e.g., chemically synthesized. The oligonucleotide disclosed herein may also comprise one or more modified nucleosides or nucleotides.

The term "antisense oligonucleotide" as used herein is defined as oligonucleotides capable of modulating expression of a target gene by hybridizing to a target nucleic acid, in particular to a contiguous sequence on a target nucleic acid. In some embodiments, the antisense oligonucleotides disclosed herein are single stranded.

The term "contiguous nucleotide sequence" refers to the region of the oligonucleotide which is complementary to the target nucleic acid. The term is used interchangeably herein with the term "contiguous nucleobase sequence" and the term "oligonucleotide motif sequence". In some embodiments all the nucleotides of the oligonucleotide are present in the contiguous nucleotide sequence. In some embodiments the oligonucleotide comprises the contiguous nucleotide sequence and may, optionally comprise further nucleotide(s), for example a nucleotide linker region which may be used to attach a functional group to the contiguous nucleotide sequence. The nucleotide linker region may or may not be complementary to the target nucleic acid.

Nucleotides are the building blocks of oligonucleotides and polynucleotides, and can include both naturally occurring and non-naturally occurring nucleotides. In nature, nucleotides, such as DNA and RNA nucleotides comprise a ribose sugar moiety, a nucleobase moiety and one or more phosphate groups (which is absent in nucleosides). Nucleosides and nucleotides may also interchangeably be referred to as "units" or "monomers".

The term "modified nucleoside" or "nucleoside modification" as used herein refers to nucleosides modified as compared to the equivalent DNA or RNA nucleoside by the introduction of one or more modifications of the sugar moiety or the (nucleo)base moiety. In some embodiments, the modified nucleoside comprises a modified sugar moiety. The term modified nucleoside may also be used herein interchangeably with the term "nucleoside analogue" or modified "units" or modified "monomers".

The term "modified internucleoside linkage" is defined as generally understood by the skilled person as linkages other than phosphodiester (PO) linkages or natural phosphate linkages that covalently couples two nucleosides together. Nucleotides with modified internucleoside linkage are also termed "modified nucleotides". In some embodiments, the modified internucleoside linkage increases the nuclease resistance of the oligonucleotide compared to a phosphodiester linkage. For naturally occurring oligonucleotides, the internucleoside linkage includes phosphate groups creating a phosphodiester bond between adjacent nucleosides. Modified internucleoside linkages are particularly useful in stabilizing oligonucleotides for in vivo use, and may serve to protect against nuclease cleavage at regions of DNA or RNA nucleosides in the oligonucleotide disclosed herein, for example, within the gap region of a gapmer oligonucleotide, as well as in regions of modified nucleosides.

In some embodiments, the oligonucleotide comprises one or more internucleoside linkages modified from the natural phosphodiester to a linkage that is, for example, more resistant to nuclease attack. Nuclease resistance may be determined by incubating the oligonucleotide in blood serum or by using a nuclease resistance assay [e.g., snake venom phosphodiesterase (SVPD)], both are well known in the art. Internucleoside linkages which are capable of enhancing the nuclease resistance of an oligonucleotide are referred to as nuclease resistant internucleoside linkages.

In some embodiments at least 50% of the internucleoside linkages in the oligonucleotide, or contiguous nucleotide sequence thereof, are modified, such as at least 60%, such as at least 70%, such as at least 80% or such as at least 90% of the internucleoside linkages in the oligonucleotide, or contiguous nucleotide sequence thereof, are modified. In some embodiments all of the internucleoside linkages of the oligonucleotide, or contiguous nucleotide sequence thereof, are modified.

It will be recognized that, in some embodiments, the internucleoside linkages which link the oligonucleotide to a non-nucleotide functional group, such as a conjugate, may be phosphodiester. In some embodiments, the internucleoside linkages which link the oligonucleotide to a non-nucleotide functional group are modified.

In some embodiments all of the internucleoside linkages of the oligonucleotide, or contiguous nucleotide sequence thereof, are nuclease resistant internucleoside linkages.

Modified internucleoside linkages may, for example, be selected from the group comprising phosphorothioate, diphosphorothioate, and boranophosphate. In some embodiments, the modified internucleoside linkages are compatible with the RNase H recruitment of the oligonucleotide disclosed herein, for example, phosphorothioate, diphosphorothioate, or boranophosphate.

In some embodiments the internucleoside linkage comprises sulphur (S), such as a phosphorothioate internucleoside linkage.

A phosphorothioate internucleoside linkage is particularly useful due to nuclease resistance, beneficial pharmacokinetics and ease of manufacture. In preferred embodiments at least 50% of the internucleoside linkages in the oligonucleotide, or contiguous nucleotide sequence thereof, are phosphorothioate, such as at least 60%, such as at least 70%, such as at least 80%, or such as at least 90% of the internucleoside linkages in the oligonucleotide, or contiguous nucleotide sequence thereof, are phosphorothioate. In some embodiments all of the internucleoside linkages of the oligonucleotide, or contiguous nucleotide sequence thereof, are phosphorothioate.

In some embodiments, the oligonucleotide comprises one or more neutral internucleoside linkage, particularly a internucleoside linkage selected from phosphotriester, methylphosphonate, MMI, amide-3, formacetal or thioformacetal. Further internucleoside linkages are disclosed in WO2009/124238 (incorporated herein by reference). In an embodiment the internucleoside linkage is selected from linkers disclosed in WO2007/031091 (incorporated herein by reference).

Nuclease resistant linkages, such as phosphorothioate linkages, are particularly useful in oligonucleotide regions capable of recruiting nuclease when forming a duplex with the target nucleic acid, such as region G for gapmers, or the non-modified nucleoside region of headmers and tailmers. Phosphorothioate linkages may, however, also be useful in non-nuclease recruiting regions and/or affinity enhancing regions such as regions F and F' for gapmers, or the modified nucleoside region of headmers and tailmers.

Each of the design regions may however comprise internucleoside linkages other than phosphorothioate, such as phosphodiester linkages, in particularly in regions where modified nucleosides, such as LNA, protect the linkage against nuclease degradation. Inclusion of phosphodiester linkages, such as one or two linkages, particularly between or adjacent to modified nucleoside units (typically in the non-nuclease recruiting regions) can modify the bioavailability and/or bio-distribution of an oligonucleotide. WO2008/113832 is incorporated herein by reference for the teaching of oligonucleotides having phosphodiester linkages.

In some embodiments, all the internucleoside linkages in the oligonucleotide are phosphorothioate and/or boranophosphate linkages. In some embodiments, all the internucleoside linkages in the oligonucleotide are phosphorothioate linkages.

The term nucleobase includes the purine (e.g., adenine and guanine) and pyrimidine (e.g., uracil, thymine, and cytosine) moiety present in nucleosides and nucleotides which form hydrogen bonds in nucleic acid hybridization. The term nucleobase also encompasses modified nucleobases which may differ from naturally occurring nucleobases but are functional during nucleic acid hybridization. In this context "nucleobase" refers to both naturally occurring nucleobases, such as adenine, guanine, cytosine, thymidine, uracil, xanthine, and hypoxanthine, as well as non-naturally occurring variants.

In some embodiments the nucleobase moiety is modified by changing the purine or pyrimidine into a modified purine or pyrimidine, such as substituted purine or substituted pyrimidine, such as a nucleobased selected from isocytosine, pseudoisocytosine, 5-methyl-cytosine, 5-thiozolo-cytosine, 5-propynyl-cytosine, 5-propynyl-uracil, 5-bromouracil 5-thiazolo-uracil, 2-thio-uracil, 2'thio-thymine, inosine, diaminopurine, 6-aminopurine, 2-aminopurine, 2,6-diaminopurine, and 2-chloro-6-aminopurine.

The nucleobase moieties may be indicated by the letter code for each corresponding nucleobase, e.g., A, T, G, C, or U, wherein each letter may optionally include modified nucleobases of equivalent function. For example, in the exemplified oligonucleotides, the nucleobase moieties are selected from A, T, G, C, and 5-methyl cytosine (5mC). Combinations of these modifications may also be used. For example, 5mC LNA nucleosides may be used. Likewise, 2"-hydroxymethyl (2"-OMe) 5mC may be used.

The term "complementarity" describes the capacity for Watson-Crick base-pairing of nucleosides/nucleotides. Watson-Crick base pairs are guanine (G)-cytosine (C) and adenine (A)-thymine (T)/uracil (U). It will be understood that oligonucleotides may comprise nucleosides with modified nucleobases, for example, 5-methyl cytosine is often used in place of cytosine, and as such the term complementarity encompasses Watson Crick base-paring between non-modified and modified nucleobases.

The term "% complementary" as used herein, refers to the number of nucleotides in percent of a contiguous nucleotide sequence in a nucleic acid molecule (e.g., oligonucleotide) which, at a given position, are complementary to (i.e., form Watson Crick base pairs with) a contiguous nucleotide sequence, at a given position of a separate nucleic acid molecule (e.g., the target nucleic acid). The percentage is calculated by counting the number of aligned bases that form pairs between the two sequences, dividing by the total number of nucleotides in the oligonucleotide and multiplying by 100. In such a comparison a nucleobase/35 nucleotide which does not align (form a base pair) is termed a mismatch.

The term "hybridizing" or "hybridizes" as used herein is to be understood as two nucleic acid strands (e.g., an oligonucleotide and a target nucleic acid) forming hydrogen bonds between base pairs on opposite strands thereby forming a duplex. The affinity of the binding between two nucleic acid strands is the strength of the hybridization. It is often described in terms of the melting temperature (Tm) defined as the temperature at which half of the oligonucleotides are duplexed with the target nucleic acid. At physiological conditions, Tm is not strictly proportional to the affinity (Mergny and Lacroix, 2003, Oligonucleotides 13:515-537). The standard state Gibbs free energy $\Delta G°$ is a more accurate representation of binding affinity and is related to the dissociation constant (Kd) of the reaction by $\Delta G°=-RTIn(Kd)$, where R is the gas constant and T is the absolute temperature. Therefore, a very low $\Delta G°$ of the reaction between an oligonucleotide and the target nucleic acid reflects a strong hybridization between the oligonucleotide and target nucleic acid. $\Delta G°$ is the energy associated with a reaction where aqueous concentrations are 1M, the pH is 7, and the temperature is 37° C. The hybridization of oligonucleotides to a target nucleic acid is a spontaneous reaction and for spontaneous reactions $\Delta G°$ is less than zero. $\Delta G°$ can be measured experimentally, for example, by use of the isothermal titration calorimetry (ITC) method as described in Hansen et al., 1965, Chem. Comm. 36-38 and Holdgate et al., 2005, Drug Discov Today. The skilled person will know that commercial equipment is available for ΔG° measurements. ΔG° can also be estimated numerically by using the nearest neighbor model as described by SantaLucia, 1998, Proc Natl Acad Sci USA. 95: 1460-1465 using appropriately derived thermodynamic parameters described by Sugimoto et al., 1995, Biochemistry 34:11211-11216 and McTigue et al., 2004, Biochemistry 43:5388-5405. In order to have the possibility of modulating its intended nucleic acid target by hybridization, oligonucleotides disclosed herein hybridize to a target nucleic acid with estimated ΔG° values below −10 kcal for oligonucleotides that are 10-30 nucleotides in length. In some embodiments the degree or strength of hybridization is measured by the standard state Gibbs free energy ΔG°. The oligonucleotides may hybridize to a target nucleic acid with estimated ΔG° values below the range of −10 kcal, such as below −15 kcal, such as below −20 kcal and such as below −25 kcal for oligonucleotides that are 8-30 nucleotides in length. In some embodiments the oligonucleotides hybridize to a target nucleic acid with an estimated ΔG° value of −10 to −60 kcal, such as −12 to −40, such as from −15 to −30 kcal or −16 to −27 kcal such as −18 to −25 kcal.

In some embodiments, the disclosed oligonucleotide comprises a contiguous nucleotide sequence of at least 8 nucleotides which is complementary to or hybridizes to a target sequence present in the target nucleic acid molecule. The contiguous nucleotide sequence (and therefore the target sequence) comprises of at least 8 contiguous nucleotides, such as 9, 10, 11, 12, 13, 14, 15, 16, 17, 18, 19, 20, 21, 22, 23, 24, 25, 26, 27, 28, 29 or 30 contiguous nucleotides, such as from 12-25, such as from 14-18 contiguous nucleotides.

In some embodiments, the disclosed oligonucleotide is a functional nucleic acid, such as a siRNA, shRNA, or nuclease gRNA, that inhibits, mutates, or deletes the target nucleic acid sequence.

The term "modulation of expression" as used herein is to be understood as an overall term for an oligonucleotide's ability to alter the amount of UBE3A RNA/protein when compared to the amount of UBE3A before administration of the oligonucleotide. Alternatively modulation of expression may be determined by reference to a control experiment where the disclosed oligonucleotide is not administered. The modulation effected by the oligonucleotide is related to its ability to reduce, remove, prevent, lessen, lower or terminate the suppression of the paternal UBE3A-AS transcript, i.e., by targeting the 5'-end of UBE3A-AS, which is downstream of SNORD115-45 snoRNA. The modulation can also be viewed as the oligonucleotide's ability to restore, increase or enhance expression of paternal UBE3A, e.g., by removal or blockage of inhibitory mechanisms affected by UBE3A-AS.

The disclosed oligonucleotide may comprise one or more nucleosides which have a modified sugar moiety, i.e., a modification of the sugar moiety when compared to the ribose sugar moiety found in DNA and RNA. Numerous nucleosides with modification of the ribose sugar moiety have been made, primarily with the aim of improving certain properties of oligonucleotides, such as affinity and/or nuclease resistance. Such modifications include those where the ribose ring structure is modified, e.g., by replacement with a hexose ring (HNA), or a bicyclic ring, which typically have a biradicle bridge between the C2 and C4 carbons on the ribose ring (LNA), or an unlinked ribose ring which typically lacks a bond between the C2 and C3 carbons (e.g., UNA). Other sugar modified nucleosides include, for example, bicyclohexose nucleosides (WO2011/017521) or tricyclic nucleosides (WO2013/154798). Modified nucleosides also include nucleosides where the sugar moiety is replaced with a non-sugar moiety, for example, in the case of peptide nucleic acids (PNA) or morpholino nucleic acids.

Sugar modifications also include modifications made via altering the substituent groups on the ribose ring to groups other than hydrogen, or the 2'—OH group naturally found in DNA and RNA nucleosides. Substituents may, for example, be introduced at the 2', 3', 4' or 5' positions. Nucleosides with modified sugar moieties also include 2' modified nucleosides, such as 2' substituted nucleosides. Indeed, much focus has been spent on developing 2' substituted nucleosides, and numerous 2' substituted nucleosides have been found to have beneficial properties when incorporated into oligonucleotides, such as enhanced nucleoside resistance and enhanced affinity.

A 2' sugar modified nucleoside is a nucleoside which has a substituent other than H or —OH at the 2' position (2' substituted nucleoside) or comprises a 2' linked biradical, and includes 2' substituted nucleosides and LNA (2'-4' biradical bridged) nucleosides. For example, the 2' modified sugar may provide enhanced binding affinity and/or increased nuclease resistance to the oligonucleotide. Examples of 2' substituted modified nucleosides are 2'-O-alkyl-RNA, 2'-O-methyl-RNA (0-Me), 2'-alkoxy-RNA, 2'-O-methoxyethyl-RNA (MOE), 2'-amino-DNA, 2'-Fluoro-RNA, and 2'-fluoro-ANA (F-ANA). For further examples, please see Freier & Altmann; Nucl. Acid Res., 1997, 25, 4429-4443 and Uhlmann; Curr. Opinion in Drug Development, 2000, 3(2), 293-213; and Deleavey and Damha, Chemistry and Biology 2012, 19, 937.

Locked Nucleic Acid (LNA) nucleosides are modified nucleosides which comprise a linker group (referred to as a biradical or a bridge) between C2' and C4' of the ribose sugar ring of a nucleotide. These nucleosides are also termed bridged nucleic acid or bicyclic nucleic acid (BNA) in the literature.

Nuclease mediated degradation refers to an oligonucleotide capable of mediating degradation of a complementary nucleotide sequence when forming a duplex with such a sequence.

In some embodiments, the oligonucleotide may function via nuclease mediated degradation of the target nucleic acid, where the disclosed oligonucleotides are capable of recruiting a nuclease, particularly and endonuclease, preferably endoribonuclease (RNase), such as RNase H. Examples of oligonucleotide designs which operate via nuclease mediated mechanisms are oligonucleotides which typically comprise a region of at least 5 or 6 DNA nucleosides and are flanked on one side or both sides by affinity enhancing nucleosides, for example, gapmers, headmers, and tailmers.

The term "gapmer" as used herein refers to an antisense oligonucleotide which comprises a region of RNase H recruiting oligonucleotides (gap) which is flanked 5' and 3' by one or more affinity enhancing modified nucleosides (flanks). Various gapmer designs are described herein. Headmers and tailmers are oligonucleotides capable of recruiting RNase H where one of the flanks is missing, i.e., only one of the ends of the oligonucleotide comprises affinity enhancing modified nucleosides. For headmers the 3' flank is missing (i.e. the 5' flank comprise affinity enhancing modified nucleosides) and for tailmers the 5' flank is missing (i.e. the 3' flank comprises affinity enhancing modified nucleosides).

Conjugation of the disclosed oligonucleotide to one or more non-nucleotide moieties may improve the pharmacology of the oligonucleotide, e.g., by affecting the activity, cellular distribution, cellular uptake, or stability of the oligonucleotide. In some embodiments the conjugate moiety modify or enhance the pharmacokinetic properties of the oligonucleotide by improving cellular distribution, bioavailability, metabolism, excretion, permeability, and/or cellular uptake of the oligonucleotide. In particular the conjugate may target the oligonucleotide to a specific organ, tissue, or cell type and thereby enhance the effectiveness of the oligonucleotide in that organ, tissue, or cell type. At the same time the conjugate may serve to reduce activity of the oligonucleotide in non-target cell types, tissues or organs, e.g., off target activity or activity in non-target cell types, tissues or organs. WO 93/07883 and WO 2013/033230 provides suitable conjugate moieties, which are hereby incorporated by reference. WO 2012/143379 provides a method of delivering a drug across the blood-brain-barrier by conjugation to an antibody fragment with affinity to the transferrin receptor, which are hereby incorporated by reference.

In some embodiments, the non-nucleotide moiety (conjugate moiety) is selected from the group consisting of carbohydrates, cell surface receptor ligands, drug substances, hormones, lipophilic substances, polymers, proteins, peptides, toxins (e.g., bacterial toxins), vitamins, viral proteins (e.g., capsids) or combinations thereof. In some embodiments the non-nucleotide moiety an antibody or antibody fragment, such as an antibody or antibody fragment that facilitates delivery across the blood-brain-barrier, in particular an antibody or antibody fragment targeting the transferrin receptor.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The term "pharmaceutically acceptable" refers to those compounds, materials, compositions, and/or dosage forms, which are within the scope of sound medical judgment, suitable for use in contact with the tissues of human beings and animals without excessive toxicity, irritation, allergic response, or other problems or complications commensurate with a reasonable benefit/risk ratio.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "inhibit" refers to a decrease in an activity, response, condition, disease, or other biological parameter, which those skilled in the art will appreciate may be assessed at a particular point in time, such that in some embodiments, inhibition may be or comprise a delay in onset or reduction in frequency. In some embodiments, inhibition can include, but is not limited to, the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

Antisense oligonucleotides (ASOs) were designed to target exons at the 5'-end of the SNORD115 host-gene transcript (AF400500), which encompasses SNORD115-46, SNORD115-47, SNORD115-48, and SNORD109E3snoRNAs and is thought to represent the 5'-end of the UBE3A antisense transcript (UBE3A-AS). In particular the target nucleic acid can be the 5'-end of UBE3A-AS, corresponding to position 25,511,577 to 25,516,681 on human chromosome 15 human genome assembly hg19. In some embodiments, the target nucleic acid is one of five exons located in the 5'-end of UBE3A-AS, which can correspond to positions 25,511,577 to 25,511,761 (exon 1), 25,512,059 to 25,512,191 (exon 2), 25,513,476 to 25,513,600 (exon 3), 25,514,752 to 25,514,880 (exon 4), and 25,516,565 to 25,516,681 (exon 5).

Therefore, in some embodiments, the target nucleic acid is

```
                                    (Exon 1, SEQ ID NO: 1)
ATGATGATATGGAAGAAAAGCACTCTTTGGCCTGTTGTGACTGGGACAG

TTGACAGCACCCAGGTGTCCTTTAATGAAAATGCTCTTGACACCAATGC

ATCCTAGCATCACAGCTTCAGGAAGCCTTCTCAAGTGTGCATGGGGAGT

ACTATGTCTTTCATCAATAATGAAATCTTCTGATTTG.
```

In some embodiments, the target nucleic acid is

```
                                    (Exon 2, SEQ ID NO: 2)
TAAGACATGCTGCCAAGAGATGTGCCATTCTATTATAAAAGATCAGTAG

CTTCCTTTACCGACGTGTATATTCTATCTAGAACATTGAGCTATGGAAG

ACTCCCACCTAAGGGAATTAGTTTTACACCTTCAG.
```

In some embodiments, the target nucleic acid is

```
                                    (Exon 3, SEQ ID NO: 3)
ATAAAGACTGCTGAGAAGAGCACCCTCTGGTGTTGTCACAGAGGCAAGT

GCTACCGCACAGGCATGCTGCAGTGAATTTAACTGATCCTCTGTCCCTG

CAACCGTTGTTTAAGGATGCTATTCTG.
```

In some embodiments, the target nucleic acid is

```
                                    (Exon 4, SEQ ID NO: 4)
AAAAGACTGTGGAGGAAGAAAACCCTTTACCCTGTTGTTCAGGGAGAAA

CTGACACCACTCAACTGCCTGGCACTGAAAATGTGGCATCCAGTCCACT

TTACCATCAGTGTTTAAGGAAACCATCTCTG.
```

In some embodiments, the target nucleic acid is (Exon 5, SEQ ID NO: 5)
ATAAGGATGACTGAGGAAGAGTACTCTTTGGCTTGTTGACACCAGCACA

GCTGACACACCCAGATATCTGTTTGGTCTCCTGTGAACTTTCAACCAGG

ATTTAAGGATGCCACTCTG.

In some embodiments, the disclosed ASO has the nucleic acid sequence (ASO-1, SEQ ID NO: 6)
TAGAGGTGAAGGCCAGGCAC.

In some embodiments, the ASO has the nucleic acid sequence (ASO-2, SEQ ID NO: 7)
GTACTCTTCCTCAGTCATCC.

In some embodiments, the disclosed ASO has the nucleic acid sequence (ASO-3, SEQ ID NO: 8)
TGTCAGTTTCTCCCTGAACA.

In some embodiments, the disclosed ASO has the nucleic acid sequence (ASO-4, SEQ ID NO: 9)
TAGAATGGCACATCTCTTGG.

In some embodiments, the disclosed ASO has the nucleic acid sequence (ASO-6, SEQ ID NO: 10)
GTTTTCTTCCTCCACAGTCT.

In some embodiments, the disclosed ASO has the nucleic acid sequence (ASO-7, SEQ ID NO: 11)
CTGGTGTCAACAAGCCAAAG.

Additional ASOs that can target exon 1 of the 3'-end of the SNORD115 region are provided below in Table 1. Example ASOs that can target exon 2 of the 3'-end of the SNORD115 are provided below in Table 2. Example ASOs that can target exon 3 of the 3'-end of the SNORD115 are provided below in Table 3. Example ASOs that can target exon 4 of the 3'-end of the SNORD115 are provided below in Table 4. Example ASOs that can target exon 5 of the 3'-end of the SNORD115 are provided below in Table 5.

TABLE 1

| Exon 1 ASOs | |
|---|---|
| Target Sequence (5'→3') | ASO (5'→3') |
| GAAAAUGCUCUUGACACC (SEQ ID NO: 12) | GGTGTCAAGAGCATTTTC (SEQ ID NO: 15) |
| GAAAAUGCUCUUGACACCA (SEQ ID NO: 13) | TGGTGTCAAGAGCATTTTC (SEQ ID NO: 16) |
| GAAAAUGCUCUUGACACCAA (SEQ ID NO: 14) | TTGGTGTCAAGAGCATTTTC (SEQ ID NO: 17) |

TABLE 2

| Exon 2 ASOs | |
|---|---|
| Target Sequence (5'→3') | ASO (5'→3') |
| CAUGCUGCCAAGAGAUGU (SEQ ID NO: 18) | ACATCTCTTGGCAGCATG (SEQ ID NO: 67) |
| CAUGCUGCCAAGAGAUGUG (SEQ ID NO: 19) | CACATCTCTTGGCAGCATG (SEQ ID NO: 68) |
| CAUGCUGCCAAGAGAUGUGC (SEQ ID NO: 20) | GCACATCTCTTGGCAGCATG (SEQ ID NO: 69) |
| AUGCUGCCAAGAGAUGUG (SEQ ID NO: 21) | CACATCTCTTGGCAGCAT (SEQ ID NO: 70) |
| AUGCUGCCAAGAGAUGUGC (SEQ ID NO: 22) | GCACATCTCTTGGCAGCAT (SEQ ID NO: 71) |
| AUGCUGCCAAGAGAUGUGCC (SEQ ID NO: 23) | GGCACATCTCTTGGCAGCAT (SEQ ID NO: 72) |
| UGCUGCCAAGAGAUGUGCC (SEQ ID NO: 24) | GGCACATCTCTTGGCAGCA (SEQ ID NO: 73) |
| UGCUGCCAAGAGAUGUGCCA (SEQ ID NO: 25) | TGGCACATCTCTTGGCAGCA (SEQ ID NO: 74) |
| GCUGCCAAGAGAUGUGCCA (SEQ ID NO: 26) | TGGCACATCTCTTGGCAGC (SEQ ID NO: 75) |
| GCUGCCAAGAGAUGUGCCAU (SEQ ID NO: 27) | ATGGCACATCTCTTGGCAGC (SEQ ID NO: 76) |
| CUGCCAAGAGAUGUGCCA(SEQ ID NO: 28) | TGGCACATCTCTTGGCAG (SEQ ID NO: 77) |
| CUGCCAAGAGAUGUGCCAU (SEQ ID NO: 29) | ATGGCACATCTCTTGGCAG (SEQ ID NO: 78) |
| CUGCCAAGAGAUGUGCCAUU (SEQ ID NO: 30) | AATGGCACATCTCTTGGCAG (SEQ ID NO: 79) |

TABLE 2-continued

| Exon 2 ASOs | |
|---|---|
| Target Sequence (5'→3') | ASO (5'→3') |
| UGCCAAGAGAUGUGCCAU (SEQ ID NO: 31) | ATGGCACATCTCTTGGCA (SEQ ID NO: 80) |
| UGCCAAGAGAUGUGCCAUU (SEQ ID NO: 32) | AATGGCACATCTCTTGGCA (SEQ ID NO: 81) |
| UGCCAAGAGAUGUGCCAUUC (SEQ ID NO: 33) | GAATGGCACATCTCTTGGCA (SEQ ID NO: 82) |
| GCCAAGAGAUGUGCCAUU (SEQ ID NO: 34) | AATGGCACATCTCTTGGC (SEQ ID NO: 83) |
| GCCAAGAGAUGUGCCAUUC (SEQ ID NO: 35) | GAATGGCACATCTCTTGGC (SEQ ID NO: 84) |
| GCCAAGAGAUGUGCCAUUCU (SEQ ID NO: 36) | AGAATGGCACATCTCTTGGC (SEQ ID NO: 85) |
| CCAAGAGAUGUGCCAUUC (SEQ ID NO: 37) | GAATGGCACATCTCTTGG (SEQ ID NO: 86) |
| CCAAGAGAUGUGCCAUUCU (SEQ ID NO: 38) | AGAATGGCACATCTCTTGG (SEQ ID NO: 87) |
| CCAAGAGAUGUGCCAUUCUA (SEQ ID NO: 39) | TAGAATGGCACATCTCTTGG (SEQ ID NO: 88) |
| CAAGAGAUGUGCCAUUCU (SEQ ID NO: 40) | AGAATGGCACATCTCTTG (SEQ ID NO: 89) |
| CAAGAGAUGUGCCAUUCUA (SEQ ID NO: 41) | TAGAATGGCACATCTCTTG (SEQ ID NO: 90) |
| CAAGAGAUGUGCCAUUCUAU (SEQ ID NO: 42) | ATAGAATGGCACATCTCTTG (SEQ ID NO: 91) |
| UCCUUUACCGACGUGUAU (SEQ ID NO: 43) | ATACACGTCGGTAAAGGA (SEQ ID NO: 92) |
| UCCUUUACCGACGUGUAUA (SEQ ID NO: 44) | TATACACGTCGGTAAAGGA (SEQ ID NO: 93) |
| UCCUUUACCGACGUGUAUAU (SEQ ID NO: 45) | ATATACACGTCGGTAAAGGA (SEQ ID NO: 94) |
| CCUUUACCGACGUGUAUA (SEQ ID NO: 46) | TATACACGTCGGTAAAGG (SEQ ID NO: 95) |
| CCUUUACCGACGUGUAUAU (SEQ ID NO: 47) | ATATACACGTCGGTAAAGG (SEQ ID NO: 96) |
| CCUUUACCGACGUGUAUAUU (SEQ ID NO: 48) | AATATACACGTCGGTAAAGG (SEQ ID NO: 97) |
| ACCGACGUGUAUAUUCUAUC (SEQ ID NO: 49) | GATAGAATATACACGTCGGT (SEQ ID NO: 98) |
| CCGACGUGUAUAUUCUAUC (SEQ ID NO: 50) | GATAGAATATACACGTCGG (SEQ ID NO: 99) |
| CCGACGUGUAUAUUCUAUCU (SEQ ID NO: 51) | AGATAGAATATACACGTCGG (SEQ ID NO: 100) |
| UCUAGAACAUUGAGCUAUGG (SEQ ID NO: 52) | CCATAGCTCAATGTTCTAGA (SEQ ID NO: 101) |
| CAUUGAGCUAUGGAAGAC (SEQ ID NO: 53) | GTCTTCCATAGCTCAATG (SEQ ID NO: 102) |
| CUAUGGAAGACUCCCACCUA (SEQ ID NO: 54) | TAGGTGGGAGTCTTCCATAG (SEQ ID NO: 103) |
| UAUGGAAGACUCCCACCUA (SEQ ID NO: 55) | TAGGTGGGAGTCTTCCATA (SEQ ID NO: 104) |
| UAUGGAAGACUCCCACCUAA (SEQ ID NO: 56) | TTAGGTGGGAGTCTTCCATA (SEQ ID NO: 105) |
| AUGGAAGACUCCCACCUA (SEQ ID NO: 57) | TAGGTGGGAGTCTTCCAT (SEQ ID NO: 106) |
| AUGGAAGACUCCCACCUAA (SEQ ID NO: 58) | TTAGGTGGGAGTCTTCCAT (SEQ ID NO: 107) |
| UGGAAGACUCCCACCUAA (SEQ ID NO: 59) | TTAGGTGGGAGTCTTCCA (SEQ ID NO: 108) |
| GACUCCCACCUAAGGGAAUU (SEQ ID NO: 60) | AATTCCCTTAGGTGGGAGTC (SEQ ID NO: 109) |
| ACUCCCACCUAAGGGAAU (SEQ ID NO: 61) | ATTCCCTTAGGTGGGAGT (SEQ ID NO: 110) |
| ACUCCCACCUAAGGGAAUU (SEQ ID NO: 62) | AATTCCCTTAGGTGGGAGT (SEQ ID NO: 111) |
| ACUCCCACCUAAGGGAAUUA (SEQ ID NO: 63) | TAATTCCCTTAGGTGGGAGT (SEQ ID NO: 112) |
| CUCCCACCUAAGGGAAUU (SEQ ID NO: 64) | AATTCCCTTAGGTGGGAG (SEQ ID NO: 113) |
| CUCCCACCUAAGGGAAUUA (SEQ ID NO: 65) | TAATTCCCTTAGGTGGGAG (SEQ ID NO: 114) |
| UCCCACCUAAGGGAAUUA (SEQ ID NO: 66) | TAATTCCCTTAGGTGGGA (SEQ ID NO: 115) |

TABLE 3

| Exon 3 ASOs | |
|---|---|
| Target Sequence (5'→3') | ASO (5'→3') |
| GAUAAAGACUGCUGAGAAGA (SEQ ID NO: 116) | TCTTCTCAGCAGTCTTTATC (SEQ ID NO: 139) |
| AUAAAGACUGCUGAGAAGAG (SEQ ID NO: 117) | CTCTTCTCAGCAGTCTTTAT (SEQ ID NO: 140) |
| UAAAGACUGCUGAGAAGAGC (SEQ ID NO: 118) | GCTCTTCTCAGCAGTCTTTA (SEQ ID NO: 141) |
| AAAGACUGCUGAGAAGAGCA (SEQ ID NO: 119) | TGCTCTTCTCAGCAGTCTTT (SEQ ID NO: 142) |
| AAGACUGCUGAGAAGAGCAC (SEQ ID NO: 120) | GTGCTCTTCTCAGCAGTCTT (SEQ ID NO: 143) |
| AGACUGCUGAGAAGAGCACC (SEQ ID NO: 121) | GGTGCTCTTCTCAGCAGTCT (SEQ ID NO: 144) |
| GACUGCUGAGAAGAGCACCC (SEQ ID NO: 122) | GGGTGCTCTTCTCAGCAGTC (SEQ ID NO: 145) |
| CAAGUGCUACCGCACAGGCA (SEQ ID NO: 123) | TGCCTGTGCGGTAGCACTTG (SEQ ID NO: 146) |
| AAGUGCUACCGCACAGGCAU (SEQ ID NO: 124) | ATGCCTGTGCGGTAGCACTT (SEQ ID NO: 147) |
| AGUGCUACCGCACAGGCAUG (SEQ ID NO: 125) | CATGCCTGTGCGGTAGCACT (SEQ ID NO: 148) |
| UGCUACCGCACAGGCAUGCU (SEQ ID NO: 126) | AGCATGCCTGTGCGGTAGCA (SEQ ID NO: 149) |
| UACCGCACAGGCAUGCUGCA (SEQ ID NO: 127) | TGCAGCATGCCTGTGCGGTA (SEQ ID NO: 150) |
| GCACAGGCAUGCUGCAGUGA (SEQ ID NO: 128) | TCACTGCAGCATGCCTGTGC (SEQ ID NO: 151) |
| CACAGGCAUGCUGCAGUGAA (SEQ ID NO: 129) | TTCACTGCAGCATGCCTGTG (SEQ ID NO: 152) |
| ACAGGCAUGCUGCAGUGAAU (SEQ ID NO: 130) | ATTCACTGCAGCATGCCTGT (SEQ ID NO: 153) |
| CAGGCAUGCUGCAGUGAAUU (SEQ ID NO: 131) | AATTCACTGCAGCATGCCTG (SEQ ID NO: 154) |
| AGGCAUGCUGCAGUGAAUUU (SEQ ID NO: 132) | AAATTCACTGCAGCATGCCT (SEQ ID NO: 155) |
| GGCAUGCUGCAGUGAAUUUA (SEQ ID NO: 133) | TAAATTCACTGCAGCATGCC (SEQ ID NO: 156) |
| GCAUGCUGCAGUGAAUUUAA (SEQ ID NO: 134) | TTAAATTCACTGCAGCATGC (SEQ ID NO: 157) |
| CAUGCUGCAGUGAAUUUAAC (SEQ ID NO: 135) | GTTAAATTCACTGCAGCATG (SEQ ID NO: 158) |
| GCAGUGAAUUUAACUGAUCC (SEQ ID NO: 136) | GGATCAGTTAAATTCACTGC (SEQ ID NO: 159) |
| UCCCUGCAACCGUUGUUUAA (SEQ ID NO: 137) | TTAAACAACGGTTGCAGGGA (SEQ ID NO: 160) |
| CCCUGCAACCGUUGUUUAAG (SEQ ID NO: 138) | CTTAAACAACGGTTGCAGGG (SEQ ID NO: 161) |

TABLE 4

| Exon 4 ASOs | |
|---|---|
| Target Sequence (5'→3') | ASO (5'→3') |
| AAAAGACUGUGGAGGAAGA (SEQ ID NO: 162) | TCTTCCTCCACAGTCTTTT (SEQ ID NO: 237) |
| AAAAGACUGUGGAGGAAGAA (SEQ ID NO: 163) | TTCTTCCTCCACAGTCTTTT (SEQ ID NO: 238) |
| AAAGACUGUGGAGGAAGAA (SEQ ID NO: 164) | TTCTTCCTCCACAGTCTTT (SEQ ID NO: 239) |
| AAAGACUGUGGAGGAAGAAA (SEQ ID NO: 165) | TTTCTTCCTCCACAGTCTTT (SEQ ID NO: 240) |
| AAGACUGUGGAGGAAGAAAA(SEQ ID NO: 166) | TTTTCTTCCTCCACAGTCTT (SEQ ID NO: 241) |
| AGACUGUGGAGGAAGAAAAC (SEQ ID NO: 167) | GTTTTCTTCCTCCACAGTCT (SEQ ID NO: 242) |
| ACUGUGGAGGAAGAAAAC (SEQ ID NO: 168) | GTTTTCTTCCTCCACAGT (SEQ ID NO: 243) |
| ACUGUGGAGGAAGAAAACC (SEQ ID NO: 169) | GGTTTTCTTCCTCCACAGT (SEQ ID NO: 244) |
| ACUGUGGAGGAAGAAAACCC (SEQ ID NO: 170) | GGGTTTTCTTCCTCCACAGT (SEQ ID NO: 245) |
| CUGUGGAGGAAGAAAACC (SEQ ID NO: 171) | GGTTTTCTTCCTCCACAG (SEQ ID NO: 246) |
| CUGUGGAGGAAGAAAACCC (SEQ ID NO: 172) | GGGTTTTCTTCCTCCACAG (SEQ ID NO: 247) |

TABLE 4-continued

| Exon 4 ASOs | |
|---|---|
| Target Sequence (5'→3') | ASO (5'→3') |
| AAAACCCUUUACCCUGUUG (SEQ ID NO: 173) | CAACAGGGTAAAGGGTTTT (SEQ ID NO: 248) |
| AAAACCCUUUACCCUGUUGU (SEQ ID NO: 174) | ACAACAGGGTAAAGGGTTTT (SEQ ID NO: 249) |
| AAACCCUUUACCCUGUUGUU (SEQ ID NO: 175) | AACAACAGGGTAAAGGGTTT (SEQ ID NO: 250) |
| UUGUUCAGGGAGAAACUG (SEQ ID NO: 176) | CAGTTTCTCCCTGAACAA (SEQ ID NO: 251) |
| UUGUUCAGGGAGAAACUGAC (SEQ ID NO: 177) | GTCAGTTTCTCCCTGAACAA (SEQ ID NO: 252) |
| UGUUCAGGGAGAAACUGA (SEQ ID NO: 178) | TCAGTTTCTCCCTGAACA (SEQ ID NO: 253) |
| UGUUCAGGGAGAAACUGAC (SEQ ID NO: 179) | GTCAGTTTCTCCCTGAACA (SEQ ID NO: 254) |
| UGUUCAGGGAGAAACUGACA(SEQ ID NO: 180) | TGTCAGTTTCTCCCTGAACA (SEQ ID NO: 255) |
| GUUCAGGGAGAAACUGACA (SEQ ID NO: 181) | TGTCAGTTTCTCCCTGAAC (SEQ ID NO: 256) |
| UCAGGGAGAAACUGACACCA (SEQ ID NO: 182) | TGGTGTCAGTTTCTCCCTGA (SEQ ID NO: 257) |
| CAGGGAGAAACUGACACCA (SEQ ID NO: 183) | TGGTGTCAGTTTCTCCCTG (SEQ ID NO: 258) |
| AGGGAGAAACUGACACCA (SEQ ID NO: 184) | TGGTGTCAGTTTCTCCCT (SEQ ID NO: 259) |
| AGGGAGAAACUGACACCAC (SEQ ID NO: 185) | GTGGTGTCAGTTTCTCCCT (SEQ ID NO: 260) |
| AGGGAGAAACUGACACCACU (SEQ ID NO: 186) | AGTGGTGTCAGTTTCTCCCT (SEQ ID NO: 261) |
| GGGAGAAACUGACACCAC (SEQ ID NO: 187) | GTGGTGTCAGTTTCTCCC (SEQ ID NO: 262) |
| GGGAGAAACUGACACCACU (SEQ ID NO: 188) | AGTGGTGTCAGTTTCTCCC (SEQ ID NO: 263) |
| GGGAGAAACUGACACCACUC (SEQ ID NO: 189) | GAGTGGTGTCAGTTTCTCCC (SEQ ID NO: 264) |
| GGAGAAACUGACACCACU (SEQ ID NO: 190) | AGTGGTGTCAGTTTCTCC (SEQ ID NO: 265) |
| GGAGAAACUGACACCACUC (SEQ ID NO: 191) | GAGTGGTGTCAGTTTCTCC (SEQ ID NO: 266) |
| GGAGAAACUGACACCACUCA (SEQ ID NO: 192) | TGAGTGGTGTCAGTTTCTCC (SEQ ID NO: 267) |
| GAGAAACUGACACCACUC (SEQ ID NO: 193) | GAGTGGTGTCAGTTTCTC (SEQ ID NO: 268) |
| GAGAAACUGACACCACUCA (SEQ ID NO: 194) | TGAGTGGTGTCAGTTTCTC (SEQ ID NO: 269) |
| GAGAAACUGACACCACUCAA (SEQ ID NO: 195) | TTGAGTGGTGTCAGTTTCTC (SEQ ID NO: 270) |
| AGAAACUGACACCACUCA (SEQ ID NO: 196) | TGAGTGGTGTCAGTTTCT (SEQ ID NO: 271) |
| AGAAACUGACACCACUCAA (SEQ ID NO: 197) | TTGAGTGGTGTCAGTTTCT (SEQ ID NO: 272) |
| AGAAACUGACACCACUCAAC (SEQ ID NO: 198) | GTTGAGTGGTGTCAGTTTCT (SEQ ID NO: 273) |
| GAAACUGACACCACUCAA (SEQ ID NO: 199) | TTGAGTGGTGTCAGTTTC (SEQ ID NO: 274) |
| GAAACUGACACCACUCAAC (SEQ ID NO: 200) | GTTGAGTGGTGTCAGTTTC (SEQ ID NO: 275) |
| GAAACUGACACCACUCAACU (SEQ ID NO: 201) | AGTTGAGTGGTGTCAGTTTC (SEQ ID NO: 276) |
| AAACUGACACCACUCAAC (SEQ ID NO: 202) | GTTGAGTGGTGTCAGTTT (SEQ ID NO: 277) |
| AAACUGACACCACUCAACU (SEQ ID NO: 203) | AGTTGAGTGGTGTCAGTTT (SEQ ID NO: 278) |
| AAACUGACACCACUCAACUG (SEQ ID NO: 204) | CAGTTGAGTGGTGTCAGTTT (SEQ ID NO: 279) |
| AACUGACACCACUCAACU (SEQ ID NO: 205) | AGTTGAGTGGTGTCAGTT (SEQ ID NO: 280) |
| AACUGACACCACUCAACUG (SEQ ID NO: 206) | CAGTTGAGTGGTGTCAGTT (SEQ ID NO: 281) |
| AACUGACACCACUCAACUGC (SEQ ID NO: 207) | GCAGTTGAGTGGTGTCAGTT (SEQ ID NO: 282) |
| ACUGACACCACUCAACUG (SEQ ID NO: 208) | CAGTTGAGTGGTGTCAGT (SEQ ID NO: 283) |
| ACUGACACCACUCAACUGC (SEQ ID NO: 209) | GCAGTTGAGTGGTGTCAGT (SEQ ID NO: 284) |
| ACUGACACCACUCAACUGCC (SEQ ID NO: 210) | GGCAGTTGAGTGGTGTCAGT (SEQ ID NO: 285) |

TABLE 4-continued

| Exon 4 ASOs | |
|---|---|
| Target Sequence (5'→3') | ASO (5'→3') |
| CUGACACCACUCAACUGC (SEQ ID NO: 211) | GCAGTTGAGTGGTGTCAG (SEQ ID NO: 286) |
| CUGACACCACUCAACUGCC (SEQ ID NO: 212) | GGCAGTTGAGTGGTGTCAG (SEQ ID NO: 287) |
| CUGACACCACUCAACUGCCU (SEQ ID NO: 213) | AGGCAGTTGAGTGGTGTCAG (SEQ ID NO: 288) |
| UGACACCACUCAACUGCC (SEQ ID NO: 214) | GGCAGTTGAGTGGTGTCA (SEQ ID NO: 289) |
| UGACACCACUCAACUGCCU (SEQ ID NO: 215) | AGGCAGTTGAGTGGTGTCA (SEQ ID NO: 290) |
| UGACACCACUCAACUGCCUG (SEQ ID NO: 216) | CAGGCAGTTGAGTGGTGTCA (SEQ ID NO: 291) |
| GACACCACUCAACUGCCU (SEQ ID NO: 217) | AGGCAGTTGAGTGGTGTC (SEQ ID NO: 292) |
| GACACCACUCAACUGCCUG (SEQ ID NO: 218) | CAGGCAGTTGAGTGGTGTC (SEQ ID NO: 293) |
| GACACCACUCAACUGCCUGG (SEQ ID NO: 219) | CCAGGCAGTTGAGTGGTGTC (SEQ ID NO: 294) |
| ACACCACUCAACUGCCUG (SEQ ID NO: 220) | CAGGCAGTTGAGTGGTGT (SEQ ID NO: 295) |
| ACACCACUCAACUGCCUGG (SEQ ID NO: 221) | CCAGGCAGTTGAGTGGTGT (SEQ ID NO: 296) |
| ACACCACUCAACUGCCUGGC (SEQ ID NO: 222) | GCCAGGCAGTTGAGTGGTGT (SEQ ID NO: 297) |
| CACCACUCAACUGCCUGGCA (SEQ ID NO: 223) | TGCCAGGCAGTTGAGTGGTG (SEQ ID NO: 298) |
| GAAAAUGUGGCAUCCAGU (SEQ ID NO: 224) | ACTGGATGCCACATTTTC (SEQ ID NO: 299) |
| AAAAUGUGGCAUCCAGUC (SEQ ID NO: 225) | GACTGGATGCCACATTTT (SEQ ID NO: 300) |
| GCAUCCAGUCCACUUUACCA (SEQ ID NO: 226) | TGGTAAAGTGGACTGGATGC (SEQ ID NO: 301) |
| CAUCCAGUCCACUUUACC (SEQ ID NO: 227) | GGTAAAGTGGACTGGATG (SEQ ID NO: 302) |
| CAUCCAGUCCACUUUACCA (SEQ ID NO: 228) | TGGTAAAGTGGACTGGATG (SEQ ID NO: 303) |
| CAUCCAGUCCACUUUACCAU (SEQ ID NO: 229) | ATGGTAAAGTGGACTGGATG (SEQ ID NO: 304) |
| AUCCAGUCCACUUUACCA (SEQ ID NO: 230) | TGGTAAAGTGGACTGGAT (SEQ ID NO: 305) |
| AUCCAGUCCACUUUACCAU (SEQ ID NO: 231) | ATGGTAAAGTGGACTGGAT (SEQ ID NO: 306) |
| AUCCAGUCCACUUUACCAUC (SEQ ID NO: 232) | GATGGTAAAGTGGACTGGAT (SEQ ID NO: 307) |
| GUUUAAGGAAACCAUCUCUG (SEQ ID NO: 233) | CAGAGATGGTTTCCTTAAAC (SEQ ID NO: 308) |
| UUUAAGGAAACCAUCUCUGG (SEQ ID NO: 234) | CCAGAGATGGTTTCCTTAAA (SEQ ID NO: 309) |
| UUAAGGAAACCAUCUCUGG (SEQ ID NO: 235) | CCAGAGATGGTTTCCTTAA (SEQ ID NO: 310) |
| UAAGGAAACCAUCUCUGG (SEQ ID NO: 236) | CCAGAGATGGTTTCCTTA (SEQ ID NO: 311) |

TABLE 5

| Exon 5 ASOs | |
|---|---|
| Target Sequence (5'→3') | ASO (5'→3') |
| AUAAGGAUGACUGAGGAAG (SEQ ID NO: 312) | CTTCCTCAGTCATCCTTAT (SEQ ID NO: 335) |
| AUAAGGAUGACUGAGGAAGA (SEQ ID NO: 313) | TCTTCCTCAGTCATCCTTAT (SEQ ID NO: 336) |
| UAAGGAUGACUGAGGAAG (SEQ ID NO: 314) | CTTCCTCAGTCATCCTTA (SEQ ID NO: 337) |
| UAAGGAUGACUGAGGAAGA (SEQ ID NO: 315) | TCTTCCTCAGTCATCCTTA (SEQ ID NO: 338) |
| UAAGGAUGACUGAGGAAGAG (SEQ ID NO: 316) | CTCTTCCTCAGTCATCCTTA (SEQ ID NO: 339) |
| AAGGAUGACUGAGGAAGA (SEQ ID NO: 317) | TCTTCCTCAGTCATCCTT (SEQ ID NO: 340) |
| AAGGAUGACUGAGGAAGAG (SEQ ID NO: 318) | CTCTTCCTCAGTCATCCTT (SEQ ID NO: 341) |

TABLE 5-continued

| Exon 5 ASOs | |
|---|---|
| Target Sequence (5'→3') | ASO (5'→3') |
| AAGGAUGACUGAGGAAGAGU (SEQ ID NO: 319) | ACTCTTCCTCAGTCATCCTT (SEQ ID NO: 342) |
| AGGAUGACUGAGGAAGAG (SEQ ID NO: 320) | CTCTTCCTCAGTCATCCT (SEQ ID NO: 343) |
| AGGAUGACUGAGGAAGAGU (SEQ ID NO: 321) | ACTCTTCCTCAGTCATCCT (SEQ ID NO: 344) |
| AGGAUGACUGAGGAAGAGUA (SEQ ID NO: 322) | TACTCTTCCTCAGTCATCCT (SEQ ID NO: 345) |
| GGAUGACUGAGGAAGAGU (SEQ ID NO: 323) | ACTCTTCCTCAGTCATCC (SEQ ID NO: 346) |
| GGAUGACUGAGGAAGAGUA (SEQ ID NO: 324) | TACTCTTCCTCAGTCATCC (SEQ ID NO: 347) |
| GGAUGACUGAGGAAGAGUAC (SEQ ID NO: 325) | GTACTCTTCCTCAGTCATCC (SEQ ID NO: 348) |
| GAUGACUGAGGAAGAGUA (SEQ ID NO: 326) | TACTCTTCCTCAGTCATC (SEQ ID NO: 349) |
| GAUGACUGAGGAAGAGUAC (SEQ ID NO: 327) | GTACTCTTCCTCAGTCATC (SEQ ID NO: 350) |
| GAUGACUGAGGAAGAGUACU (SEQ ID NO: 328) | AGTACTCTTCCTCAGTCATC (SEQ ID NO: 351) |
| AUGACUGAGGAAGAGUAC (SEQ ID NO: 329) | GTACTCTTCCTCAGTCAT (SEQ ID NO: 352) |
| AUGACUGAGGAAGAGUACU (SEQ ID NO: 330) | AGTACTCTTCCTCAGTCAT (SEQ ID NO: 353) |
| AUGACUGAGGAAGAGUACUC (SEQ ID NO: 331) | GAGTACTCTTCCTCAGTCAT (SEQ ID NO: 354) |
| UGACUGAGGAAGAGUACU (SEQ ID NO: 332) | AGTACTCTTCCTCAGTCA (SEQ ID NO: 355) |
| UGACUGAGGAAGAGUACUC (SEQ ID NO: 333) | GAGTACTCTTCCTCAGTCA (SEQ ID NO: 356) |
| UGACUGAGGAAGAGUACUCU (SEQ ID NO: 334) | AGAGTACTCTTCCTCAGTCA (SEQ ID NO: 357) |

The disclosed oligonucleotide is capable of modulating expression of paternal UBE3A, in particular induction or up-regulation of paternally expressed UBE3A in neuronal cells. The modulation is achieved by hybridizing to the 5'-end of UBE3A-AS. In certain embodiments the oligonucleotide disclosed herein hybridizes to a sub-sequence of the target nucleic acid of SEQ ID NO:1 with a ΔG° below −10 kcal, such as with a ΔG° between −10 to −60 kcal, such as −12 to −40, such as from −15 to −30 kcal or −16 to −27 kcal such as −18 to −25 kcal.

In some embodiments the disclosed oligonucleotides are capable of increasing the expression of UBE3A by least 20% compared to the expression level of UBE3A in a neuronal cell treated with saline or a non-targeting oligonucleotide, more preferably by at least 30%, 35%, 40%, 45%, 50%, 55%, 60%, 80%, 100%, 120%, 150%, 160%, 170%, 180%, 190%, 200%, 210%, 220%, 230%, 240% or 250% compared to the expression level of UBE3A in a neuronal cell treated with saline or a non-targeting oligonucleotide. In some embodiments, the disclosed oligonucleotides are capable of decreasing the level of the SNHG14 transcript downstream of SNORD115-45 by at least 20% compared to the level of the SNHG14 transcript downstream of SNORD1115-45 in a neuronal cell treated with saline or a non-targeting oligonucleotide, more preferably by at least 30%, 40%, 50%, 60%, 70%, 80%, 90% or 95% compared to the level of the SNHG14 transcript downstream of SNORD115-45 in a neuronal cell treated with saline or a non-targeting oligonucleotide.

Target modulation by the disclosed oligonucleotide is triggered by hybridization between a contiguous nucleotide sequence of the oligonucleotide and the target nucleic acid. In some embodiments the disclosed oligonucleotide comprises mismatches between the oligonucleotide and the target nucleic acid. Despite mismatches hybridization to the target nucleic acid may still be sufficient to show a desired modulation of UBE3A expression. Reduced binding affinity resulting from mismatches may advantageously be compensated by increased number of nucleotides in the oligonucleotide and/or an increased number of modified nucleosides capable of increasing the binding affinity to the target, such as 2' modified nucleosides, including LNA, present within the oligonucleotide sequence.

The disclosed antisense oligonucleotide can have a contiguous nucleotide sequence of 10 to 30 nucleotides in length with at least 90% complementary, such as at least 91%, such as at least 92%, such as at least 93%, such as at least 94%, such as at least 95%, such as at least 96%, such as at least 97%, such as at least 98%, or 100% complementarity to one of five exons located in the 5'-end of UBE3A-AS disclosed herein.

Oligonucleotide design refers to the pattern of nucleoside sugar modifications in the oligonucleotide sequence. The disclosed antisense oligonucleotide comprises sugar-modified nucleosides and may also comprise DNA, RNA, or arabino nucleic acid (ANA) nucleosides. In some embodiments, the oligonucleotide comprises sugar-modified nucleosides and DNA nucleosides. In some embodiments, the oligonucleotide comprises sugar-modified nucleosides and RNA nucleosides. In some embodiments, the oligonucleotide comprises sugar-modified nucleosides and ANA nucleosides.

In some embodiments, the oligonucleotide comprises at least 1 modified nucleoside, such as at least 2, at least 3, at least 4, at least 5, at least 6, at least 7, at least 8, at least 9, at least 10, at least 11, at least 12, at least 13, at least 14, at least 15 or at least 16 modified nucleosides. In an embodiment the oligonucleotide comprises from 1 to 10 modified nucleosides, such as from 2 to 9 modified nucleosides, such as from 3 to 8 modified nucleosides, such as from 4 to 7 modified nucleosides, such as 6 or 7 modified nucleosides.

In some embodiments, the oligonucleotide comprises at least one modified internucleoside linkage. In some embodiments, the internucleoside linkages within the contiguous nucleotide sequence are phosphorothioate or boranophosphate internucleoside linkages.

In some embodiments, the disclosed antisense oligonucleotide comprises one or more sugar modified nucleosides, such as 2' sugar modified nucleosides. Preferably the disclosed antisense oligonucleotides comprise one or more LNA nucleosides or 2' sugar modified nucleoside wherein the 2' position is replaced by a substituent independently selected from the group consisting of, —F; —$CF_3$, —CN, —$N_3$, —NO, —$NO_2$, —O—($C_1$-$C_{10}$ alkyl), —S—($C_1$-$C_{10}$ alkyl), —NH—($C_1$-$C_{10}$ alkyl), or —N($C_1$-$C_{10}$ alkyl)$_2$; —O—($C_2$-$C_{10}$ alkenyl), —S—($C_2$-$C_{10}$ alkenyl), —NH—($C_2$-$C_{10}$ alkenyl), or —N($C_2$-$C_{10}$ alkenyl)$_2$; —O—($C_2$-$C_{10}$ alkynyl), —S—($C_2$-$C_{10}$ alkynyl), —NH—($C_2$-$C_{10}$ alkynyl), —N($C_2$-$C_{10}$ alkynyl)$_2$, alkylene)—O—($C_1$-$C_{10}$ alkyl), —O—($C_1$-$C_{10}$ alkylene)—NH—($C_1$-$C_{10}$ alkyl), —O—($C_1$-$C_{10}$ alkylene)—NH($C_1$-$C_{10}$ alkyl)$_2$, alkylene)—O—($C_1$-$C_{10}$ alkyl), and —N($C_1$-$C_{10}$ alkylene)—O—($C_1$-$C_{10}$ alkyl).

In some embodiments, the disclosed oligonucleotides comprises at least one LNA unit, such as 1, 2, 3, 4, 5, 6, 7, or 8 LNA units, such as from 2 to 6 LNA units, such as from 3 to 7 LNA units, 4 to 8 LNA units or 3, 4, 5, 6 or 7 LNA units. In some embodiments, all the modified nucleosides are LNA nucleosides. In some embodiments, LNA comprises a 2'-4' biradical bridge of -L-, wherein -L- is —O—$CH_2$—, wherein —$CH_2$— is optionally substituted. In some embodiments, LNA comprises a 2'-4' biradical bridge of -L-, wherein -L- is —O—$CH_2$—. In some embodiments, LNA comprises a 2'-4' biradical bridge of -L-, wherein -L- is —O—CH(Et)-. In a further embodiment, the oligonucleotide may comprise both beta-D-oxy-LNA, and one or more of the following LNA units: thio-LNA, amino-LNA, oxy-LNA, and/or ENA in either the beta-D or alpha-L configurations or combinations thereof. In a further embodiment, all LNA cytosine units are 5-methyl-cytosine. In some embodiments, the oligonucleotide or contiguous nucleotide sequence has at least 1 LNA unit at the 5' end and at least 2 LNA units at the 3' end of the nucleotide sequence.

In some embodiments, the disclosed oligonucleotide is capable of recruiting RNase H. In some embodiments, the oligonucleotide has a gapmer design or structure also referred herein merely as "Gapmer". In a gapmer structure the oligonucleotide comprises at least three distinct structural regions a 5'-flank, a gap and a 3'-flank, F-G-F' in '5→3' orientation. In this design, flanking regions F and F' (also termed wing regions) comprise a contiguous stretch of modified nucleosides, which are complementary to the UBE3A-AS target nucleic acid, while the gap region, G, comprises a contiguous stretch of nucleotides which are capable of recruiting a nuclease, preferably an endonuclease such as RNase, for example, RNase H, when the oligonucleotide is in duplex with the target nucleic acid. Nucleosides which are capable of recruiting a nuclease, in particular RNase H, can be selected from the group consisting of DNA, alpha-L-oxy-LNA, 2'-Flouro-ANA and UNA. Regions F and F', flanking the 5' and 3' ends of region G, preferably comprise non-nuclease recruiting nucleosides (nucleosides with a 3' endo structure), more preferably one or more affinity enhancing modified nucleosides. In some embodiments, the 3' flank comprises at least one LNA nucleoside, preferably at least 2 LNA nucleosides. In some embodiments, the 5' flank comprises at least one LNA nucleoside. In some embodiments both the 5' and 3' flanking regions comprise a LNA nucleoside. In some embodiments all the nucleosides in the flanking regions are LNA nucleosides. In other embodiments, the flanking regions may comprise both LNA nucleosides and other nucleosides (mixed flanks), such as DNA nucleosides and/or non-LNA modified nucleosides, such as 2' substituted nucleosides. In this case the gap is defined as a contiguous sequence of at least 5 RNase H recruiting nucleosides (nucleosides with a 2' endo structure, preferably DNA) flanked at the 5' and 3' end by an affinity enhancing modified nucleoside, preferably LNA, such as beta-D-oxy-LNA. Consequently, the nucleosides of the 5' flanking region and the 3' flanking region which are adjacent to the gap region are modified nucleosides, preferably non-nuclease recruiting nucleosides. In oligonucleotides with mixed flanks where the flanks comprise DNA the 5' and 3' nucleosides are modified nucleosides.

Methods for manufacturing the disclosed oligonucleotides are known. In some cases, the method uses phophoramidite chemistry (see for example Caruthers et al, 1987, Methods in Enzymology vol. 154, pages 287-313). In a further embodiment the method further comprises reacting the contiguous nucleotide sequence with a conjugating moiety (ligand).

In some embodiments, oligonucleotide synthesis methodologies are utilized that provide control of stereochemistry at one or more modified internucleoside linkages that include(s) a chiral atom. See, for example, WO2010/064146, WO2014/012081, WO2015/107425, WO2016/079183, WO2016/079181, WO2016/096938, WO2017/194498, and WO2018/177825, which are incorporated by reference for these methodologies.

Those skilled in the art will appreciate that useful nucleic acids provided by the present disclosure include those that store and/or express sequences of oligonucleotides described herein. In some embodiments, such nucleic acids may be or comprise vectors appropriate for delivery into and/or replication and/or expression in a cell (e.g., a microbial cell, for example for production and/or a mammalian cell, for example for treatment). Those skilled in the art are aware of a variety of technologies (e.g., recombinant nucleic acid technologies such as, for instance, that utilize one or more of amplification such as by polymerase chain reaction, cleavage such as by restriction digestion, linkage such as by ligation—whether in vitro or in vivo e.g., by gap repair, etc.).

Also disclosed are pharmaceutical compositions comprising any of the aforementioned oligonucleotides and/or oligonucleotide conjugates and a pharmaceutically acceptable diluent, carrier, salt and/or adjuvant. A pharmaceutically acceptable diluent includes phosphate-buffered saline (PBS) and pharmaceutically acceptable salts include, but are not limited to, sodium and potassium salts. In some embodiments, the diluent is artificial cerebrospinal fluid (aCSF).

The disclosed oligonucleotides may be mixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

Those skilled in the art are aware of a variety of formulation strategies useful for storage and/or administration of nucleic acid therapeutics such as oligonucleotide therapeutics. See, for example, Pushpendra et al "Nucleic Acids as Therapeutics" in From Nucleic Acid Sequences to Molecular Medicines, ed. Erdmann and Barciszewski, Springer-Verlag, 2012; Juliano "The Delivery of Therapeutic Oligonucleotides" Nuc. Acids. Res. 44:6518, 2016; etc.

In some embodiments, the oligonucleotide is formulated as a prodrug. In particular with respect to oligonucleotide conjugates, the conjugate moiety can be cleaved off the oligonucleotide once the prodrug is delivered to the site of action, e.g., the target cell.

Also disclosed are methods for treating or preventing a disease, comprising administering a therapeutically or prophylactically effective amount of an oligonucleotide, an oligonucleotide conjugate or a pharmaceutical composition disclosed herein to a subject suffering from or susceptible to the disease.

Also disclosed is use of the disclosed oligonucleotides for the manufacture of a medicament for the treatment of a disorder as referred to herein, or for a method of the treatment of as a disorder as referred to herein.

The disclosed pharmaceutical compositions may be administered by topical (such as, to the skin, inhalation, ophthalmic or otic) or enteral (such as, orally or through the gastrointestinal tract) or parenteral (such as, intravenous, subcutaneous, intra-muscular, intracerebral, intracerebroventricular or intrathecal) administration. In some embodiments, the disclosed pharmaceutical compositions are administered by a parenteral route including intravenous, intraarterial, subcutaneous, intraperitoneal or intramuscular injection or infusion, intrathecal or intracranial, e.g., intracerebral or intraventricular, administration. In some embodiments, the oligonucleotide is administered by intracerebral or intracerebroventricular injection. In another embodiment the active oligonucleotide or oligonucleotide conjugate is administered intrathecally. In some embodiments, the pharmaceutical composition is administered by intracisternae *magna* injection.

In some embodiments, AS therapy with pharmaceutical compositions described herein is administered to subject(s) suffering from or susceptible to AS. In some embodiments, a subject has been determined to have genetic characteristic associated with a defect in a maternal UBE3A gene. In some embodiments, an AS-associated genetic characteristic is or comprises a maternal deletion. In some embodiments, an AS-associated genetic characteristic is or comprises uniparental disomy. In some embodiments, an AS-associated genetic characteristic is or comprises a UBE3A mutation. In some embodiments, an AS-associated genetic characteristic is or comprises an imprinting defect.

In some embodiments, a subject has been determined to have one or more developmental history and/or laboratory finding characteristics that have been associated with AS such as, for example, one or more of:

(i) normal prenatal and birth history with normal head circumference and absence of major birth defects;
(ii) feeding difficulties as a neonate and/or as an infant;
(iii) developmental delay evident by 6-12 months of age, sometimes associated with truncal hypotonus;
(iv) unsteady limb movements and/or increased smiling;
(v) delayed but forward progression of development (no loss of skills);
(vi) normal metabolic, hematologic and chemical laboratory profiles;
(vii) structurally normal brain when assessed using MRI or CT (may have mild cortical atrophy or dysmyelination).

Alternatively or additionally, in some embodiments, a subject has been determined to display one or more clinical features that are consistently associated with AS such as, for example, one or more of:

(i) developmental delay, functionally severe
(ii) movement or balance disorder, usually ataxia of gait and/or tremulous movement of limbs. In some embodiments, such movement disorder can be mild. In some embodiments, such movement disorder may not appear as frank ataxia but can be or involve, for example, forward lurching, unsteadiness, clumsiness, or quick, jerky motion;
(iii) behavioral uniqueness: any combination of frequent laughter/smiling; apparent happy demeanor; easily excitable personality, often with uplifted hand-flapping or waving movements; hypermotoric behavior
(iv) speech impairment, such as for example absent or minimal use of words; alternatively or additionally, receptive and non-verbal communication skills higher than verbal ones.

Alternatively or additionally, in some embodiments, a subject has been determined to display one or more clinical features that are frequently (e.g., about 80% of the time) associated with AS such as, for example, one or more of:

(i) delayed, disproportionate growth in head circumference, usually resulting in microcephaly (≤2 S.D. of normal OFC) by age 2 years. In some embodiments, microcephaly is more pronounced in those with 15q11.2-q13 deletions;
(ii) seizures, onset usually <3 yrs. of age. In some embodiments, seizure severity may decrease with age but regardless, in some embodiments, the seizure disorder lasts throughout adulthood.
(iv) abnormal EEG, with a characteristic pattern, as is known in the art. In some embodiments, EEG abnormalities can occur in the first 2 years of life and can precede clinical features, and may not be correlated to clinical seizure events.

Alternatively or additionally, in some embodiments, a subject has been determined to display one or more clinical features that are sometimes (e.g., about 20-80% of the time) associated with AS such as, for example, one or more of:

(i) flat occiput
(ii) occipital groove
(iii) protruding tongue
(iv) tongue thrusting; suck/swallowing disorders
(v) feeding problems and/or truncal hypotonia during infancy
(vi) prognathia
(vii) wide mouth, wide-spaced teeth
(viii) frequent drooling
(ix) excessive chewing/mouthing behaviors
(x) strabismus
(xi) hypopigmented skin, light hair and eye color, in some embodiments determined as compared to family, and typically seen only in deletion cases
(xii) hyperactive lower extremity deep tendon reflexes
(xiii) uplifted, flexed arm position especially during ambulation
(xiv) wide-based gait with pronated or valgus-positioned ankles
(xv) increased sensitivity to heat
(xvi) abnormal sleep wake cycles and diminished need for sleep
(xvii) attraction to/fascination with water; fascination with crinkly items such as certain papers and plastics
(xviii) abnormal food related behaviors
(xix) obesity (in the older child)
(xx)scoliosis
(xxi) constipation In some embodiments, a therapeutic regimen for the treatment of AS with a nucleic acid therapeutic (e.g., an oligonucleotide therapeutic such as an ASO) as described herein is or comprises administration of one or more doses of a pharmaceutical composition that comprises and/or delivers an oligonucleotide as described herein.

In some embodiments, a subject to whom a provided therapeutic regimen is administered is receiving or has received one or more other AS therapeutics including, for example, one or more other nucleic acid therapeutics (e.g., one or more other oligonucleotides that target UBE3A-AS). See, for example, WO2014004572A3, U.S. Pat. No. 9,617,539B2, US20170362592A1, and EP2864479B1.

In some embodiments, a subject to whom a provided therapeutic regimen is administered has suffered or is suffering from one or more seizures and/or is receiving or has received anti-seizure therapy. For example. In some embodiments, a subject may have received or be receiving one or more of valproic acid, clonazepam, phenobarbital, topiramate, carbamazepine, lamotrigine, leveltiracetam, phenytoin, zonisamide, ethosuxaminde, gabapentin, felbatame, oxcarbazepine, tranxene, ACTS, nitrazapam, pregabalin, mysoline, vigabatrin, etc. In some particular embodiments, a subject may have received or be receiving one or more of valproic acid, clonazepam, phenobarbital, topiramate, carbamazepine, lamotrigine, and/or levetiracetam.

Alternatively or additionally, in some embodiments, a subject may have received or be receiving dietary therapy such as, for example, a ketogenic diet, low glycemic index therapy, etc.

Still further alternatively or additionally, in some embodiments, a subject may have received or be receiving treatment with a vagal nerve stimulator.

As will be apparent to those skilled in the art reading the present disclosure, provided methods of treatment involve administering one or both of an oligonucleotide as described herein and an additional therapy (e.g., an alternative oligonucleotide and/or anti-epileptic therapy and/or one or more other therapeutic interventions), so that the subject receives combination therapy (e.g., is simultaneously exposed thereto, for example via overlapping dosing etc.). Also disclosed is the use of an oligonucleotide disclosed herein for the manufacture of a medicament wherein the medicament is in a dosage form for intrathecal administration.

Also disclosed is the use of an oligonucleotide disclosed herein for the manufacture of a medicament wherein the medicament is in a dosage form for intracerebral or intraventricular administration.

Also disclosed is the use of an oligonucleotide disclosed herein for the manufacture of a medicament wherein the medicament is in a dosage form for intracerebroventricular administration.

In some embodiments the oligonucleotide disclosed herein is for use in a combination treatment with another therapeutic agent. The therapeutic agent can for example be anticonvulsant medication.

A number of embodiments of the invention have been described. Nevertheless, it will be understood that various modifications may be made without departing from the spirit and scope of the invention. Accordingly, other embodiments are within the scope of the following claims.

EXAMPLES

Example 1

Results

RNA-sequencing analysis of mouse and human CNS identified a region believed to be important for the stability and/or transcription of UBE3A-AS. Further analysis of the region showed low levels of sequence conservation between mouse and human (FIGS. 1A-1D).

Figure 2A:
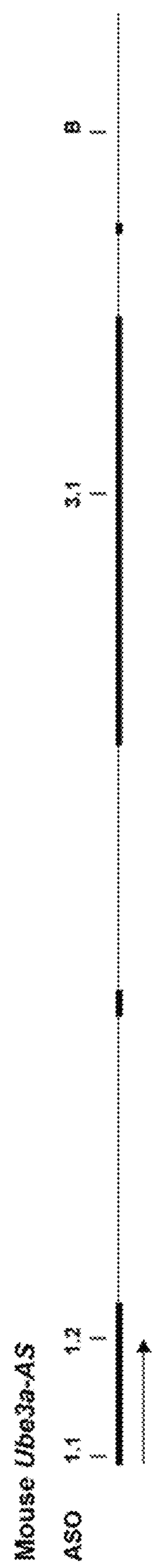
Figure 2B:
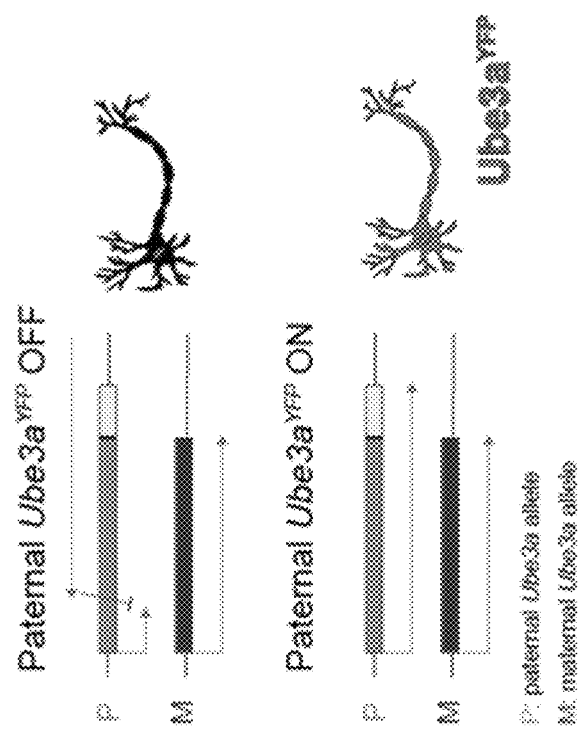
Figure 2C:
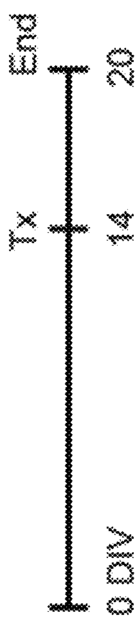
Figure 2D:
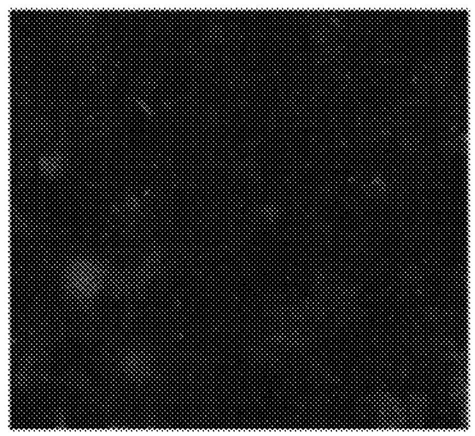
Figure 2D:
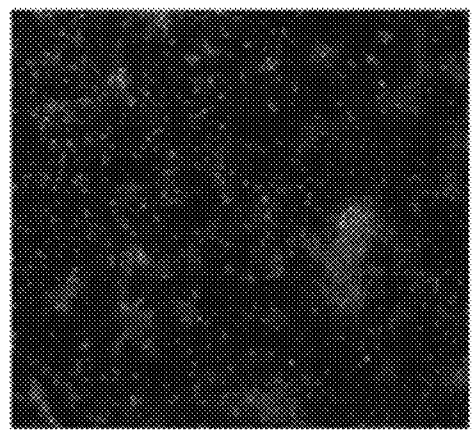
Figure 2D:
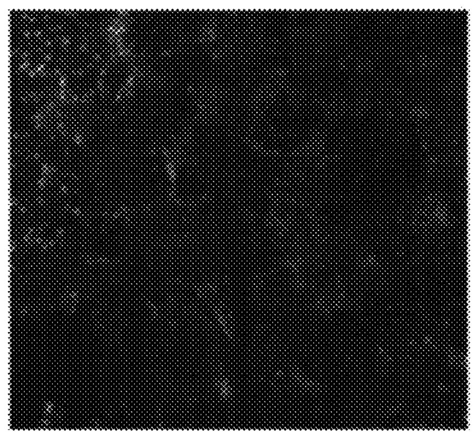
Figure 2D:
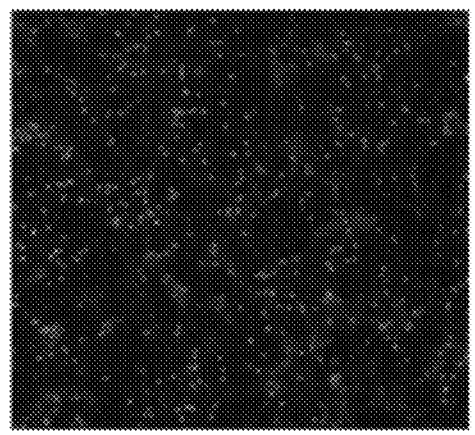
Figure 2E:
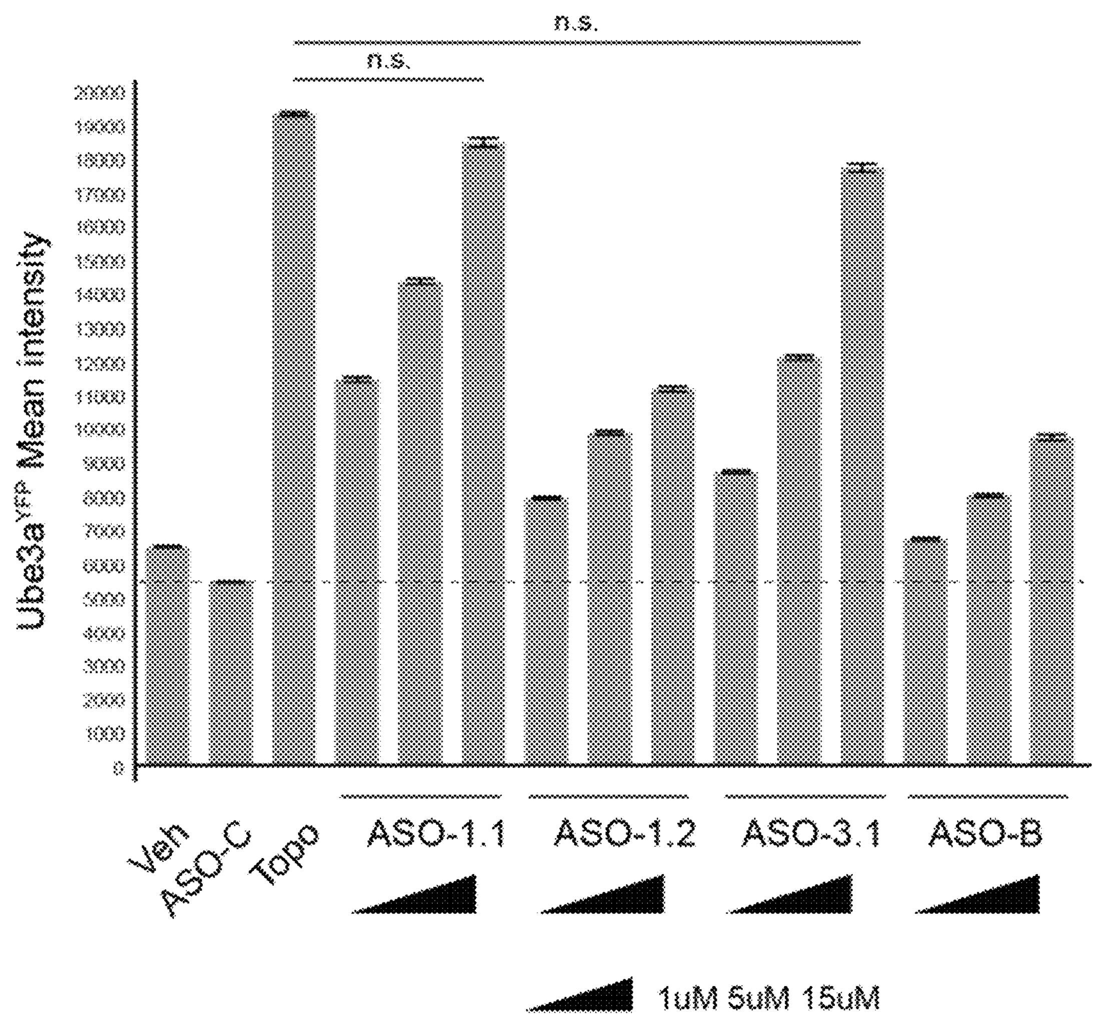

Based on these findings, mouse-specific ASOs were designed to target a specific region in the Ube3a-AS transcript (Table 6 and FIG. 2A). To test whether ASOs targeting this region reactivate expression of the paternal Ube3a allele, primary hippocampal neuronal cultures were generated from the Ube3aYFP reporter mouse model (Ube3a+/YFP; FIG. 2B) and treated at 7 days in vitro (DIV) with a control ASO [ASO-C(10 uM, n=3)], three ASOs targeting Ube3a-AS [ASO-1.1, ASO-1.2, ASO-3.1 (1 μM, 5 μM, and 15 μM, n=3)], and ASO-B (1 μM, 5 μM, and 15 μM, n=3)]. As a positive control, neurons were also treated with Topotecan [Topo (300 nM, n=3)] and a negative vehicle control [Veh (1%, n=3); FIG. 2C]. Three days post-treatment (10 DIV), immunofluorescent imaging was used to quantify paternal Ube3aYFP protein levels in individual cells. Compared to controls (ASO-C and Veh), each treatment substantially increased paternal Ube3aYFP protein levels, with similar levels achieved in ASO-1.1 (15 μM), ASO-3.1 (15 μM), and Topotecan treatments (FIGS. 2D and 2E).

Figures 3A, 3B:
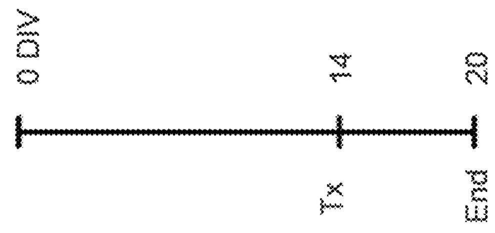
Figure 3C:
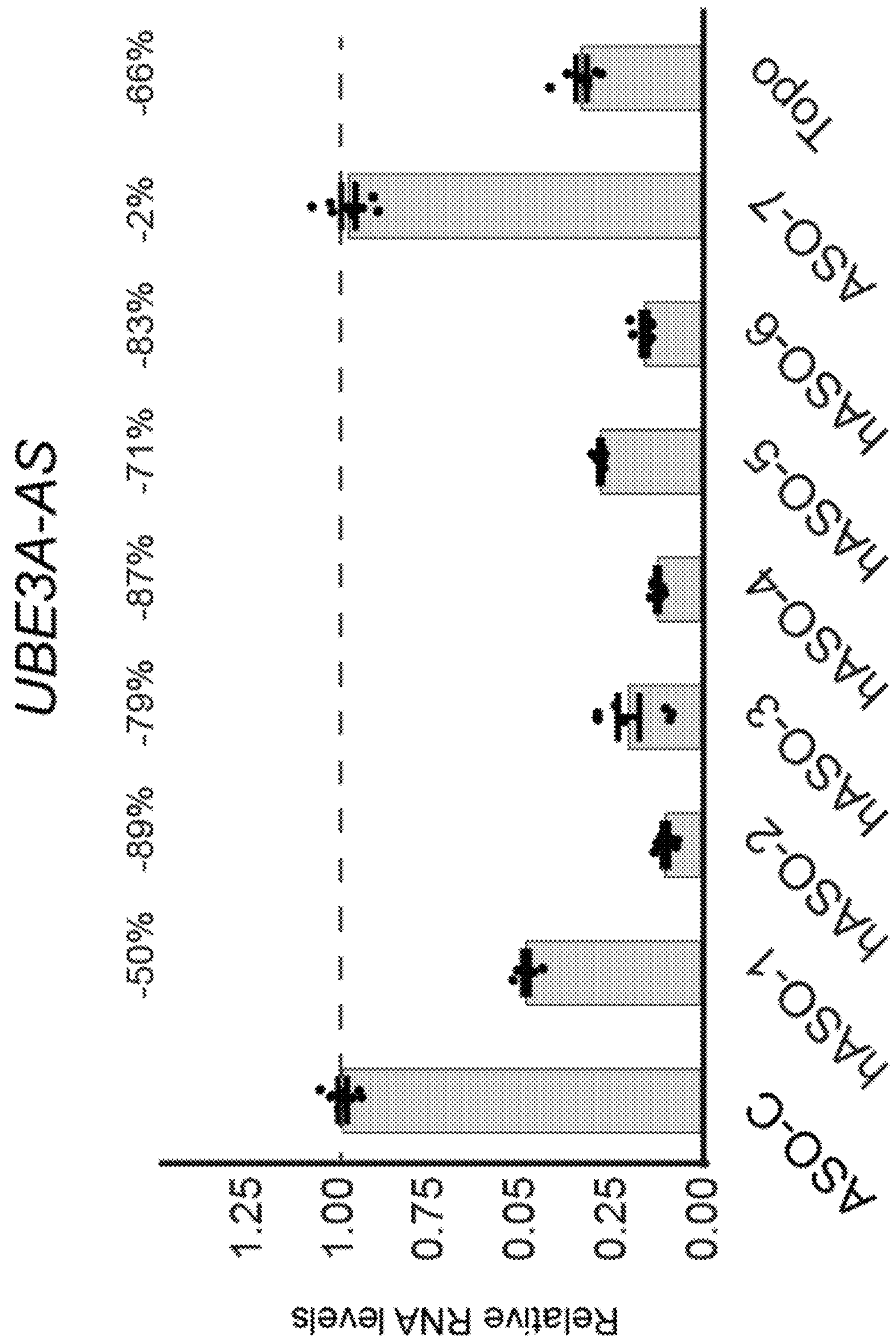
Figure 3D:
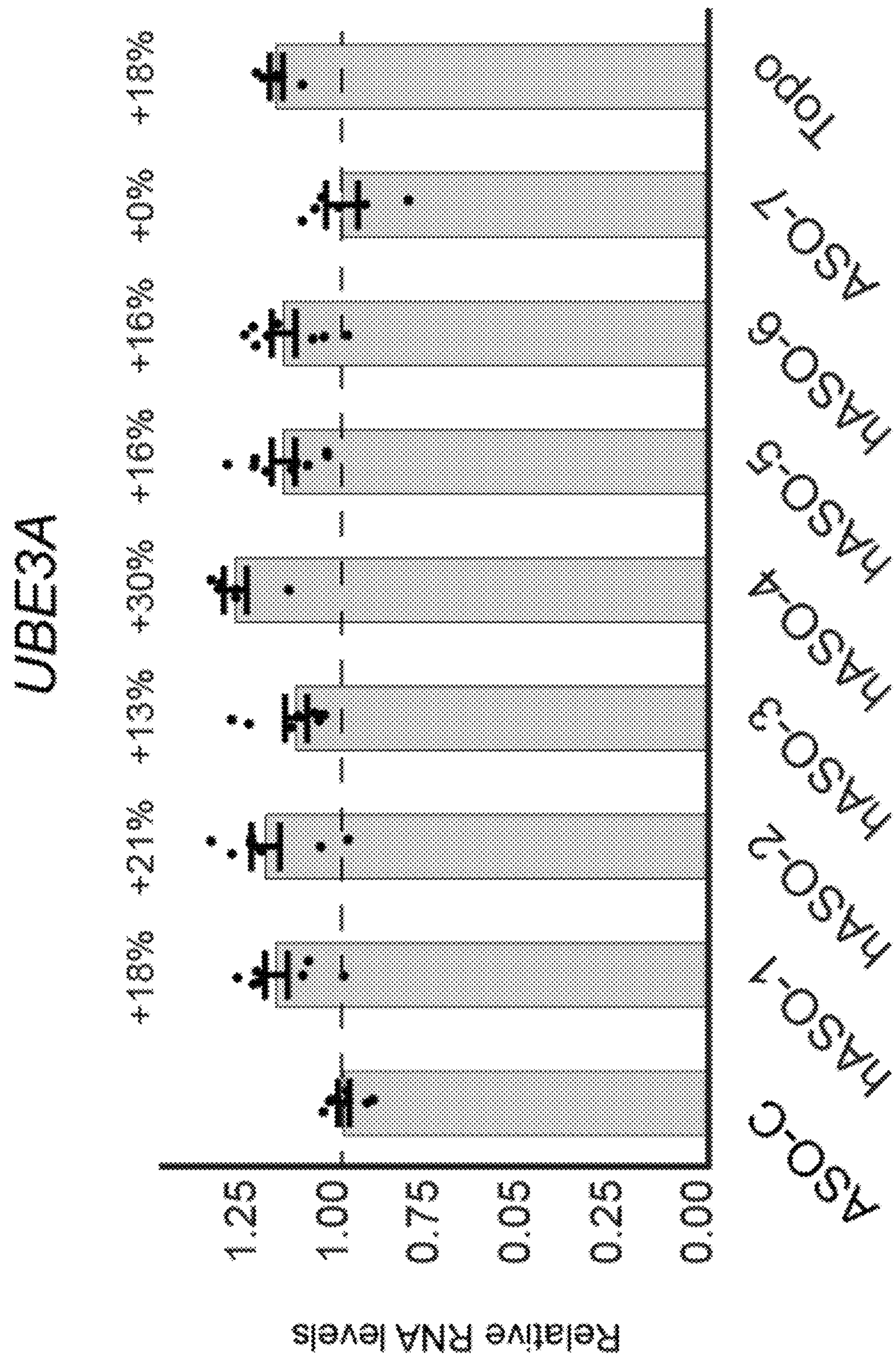

Human-specific ASOs were then designed to target this region, which included four ASOs targeting non-polymorphic regions in human and regions conserved (100%) with macaque (Rhesus and Cynomolgus) (Table 7 and FIG. 3A). Human induced pluripotent stem cell (iPSC) neural precursor cells were differentiated into GABAergic neurons for 14 DIV and then treated with a control ASO [ASO-C(10 μM, n=3)], Topotecan [Topo (1 μM, n=2)], and six ASOs targeting UBE3A-AS [ASO-1, ASO-2, ASO-3, ASO-4, ASO-5, and ASO-6 (10 μM, n=3)]. Additionally, an ASO targeting an intronic region downstream of SNORD109B was included (ASO-7). Six days post-treatment (20 DIV), RNA was isolated from the neurons and the steady state RNA levels of UBE3A-AS and UBE3A were estimated relative to the control treatment (FIG. 3B). With the exception of ASO-7, each ASO significantly decreased UBE3A-AS RNA levels, with ASO-2 and ASO-4 having the largest effect (Table 8 and FIG. 3C). UBE3A RNA levels also increased after treatment with each ASO (FIG. 3D).

Figures 4A, 4B, 4C:
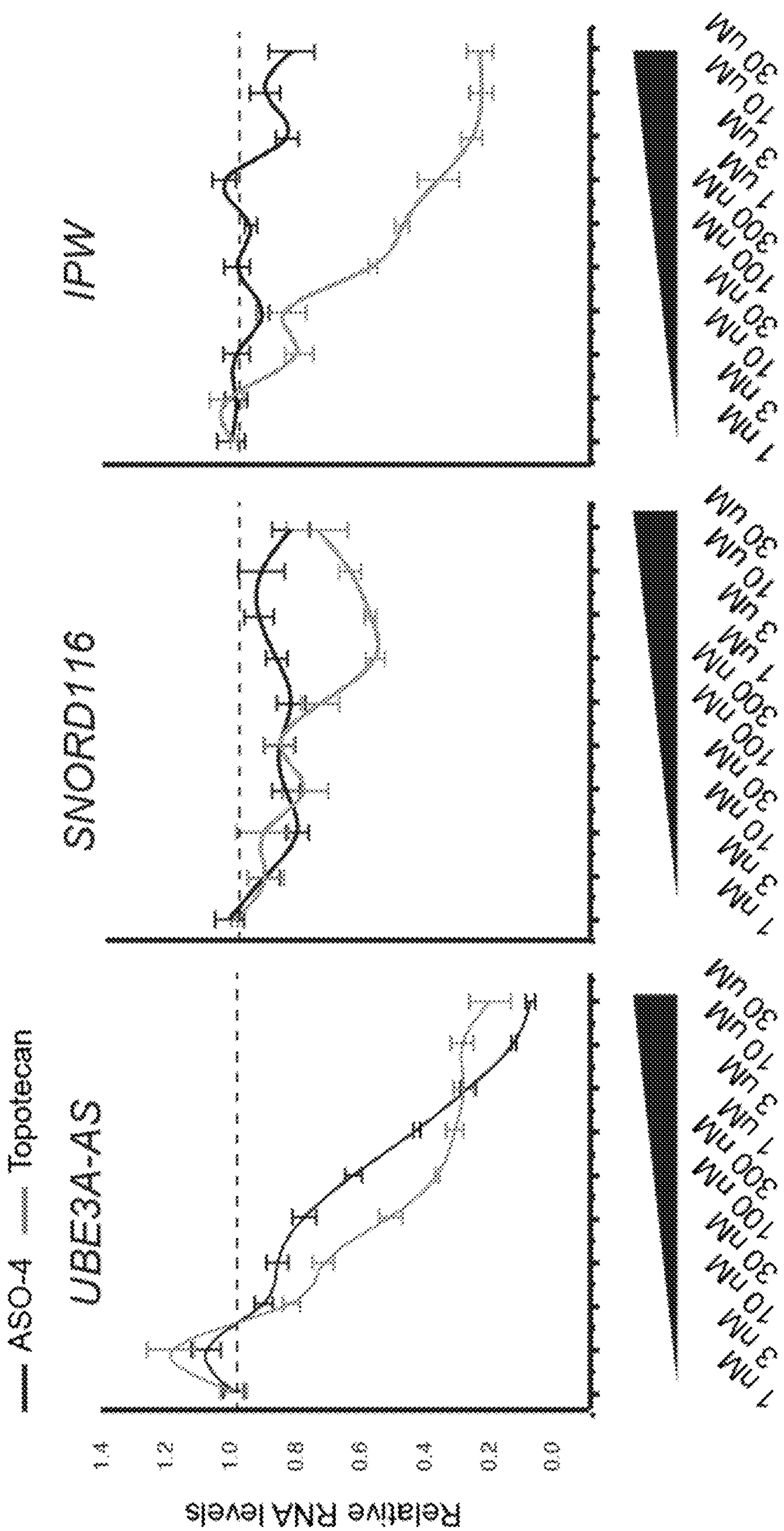
FIGS. 4A to 4I show analysis of human ASO-4 and Topotecan in GABAergic iPSC-derived neurons.

The potency of ASO-4 was further examined given its effect on UBE3A-AS RNA levels. GABAergic iPSC-derived neurons were treated at 14 DIV with a 10-point ½ log dose response curve of ASO-4 and Topotecan, as a positive control and for comparisons between treatment [1 nM, 3 nM, 10 nM, 30 nM, 100 nM, 300 nM, 1 μM, 3 μM, 10 μM, and 30 μM (ASO-4, n=6; Topotecan, n=2)]. At 20 DIV, the steady state RNA levels of UBE3A-AS were measured and dose response curves fitted to estimate the $IC_{50}$ and $E_{max}$ (i.e., maximum UBE3A-AS inhibition) (Table 9 and FIG. 4A). The dose response curves of ASO-4 and Topotecan were significantly different (Parallelism test: $F_{(3,145)}=11.2$, $p<0.0001$), thus the relative potencies were not estimated. An equivalence test indicated that the $IC_{50}$ and $E_{max}$ of ASO-4 and Topotecan were not equivalent [ASO-4/Topotecan $IC_{50}$ ratio: =1.2 (Lower confidence limit=1.1; Upper confidence limit=1.3); $E_{max}$ ratio=−4.1 (Lower confidence limit=−12.9; Upper confidence limit=4.8)].

Figures 4D, 4E, 4F:
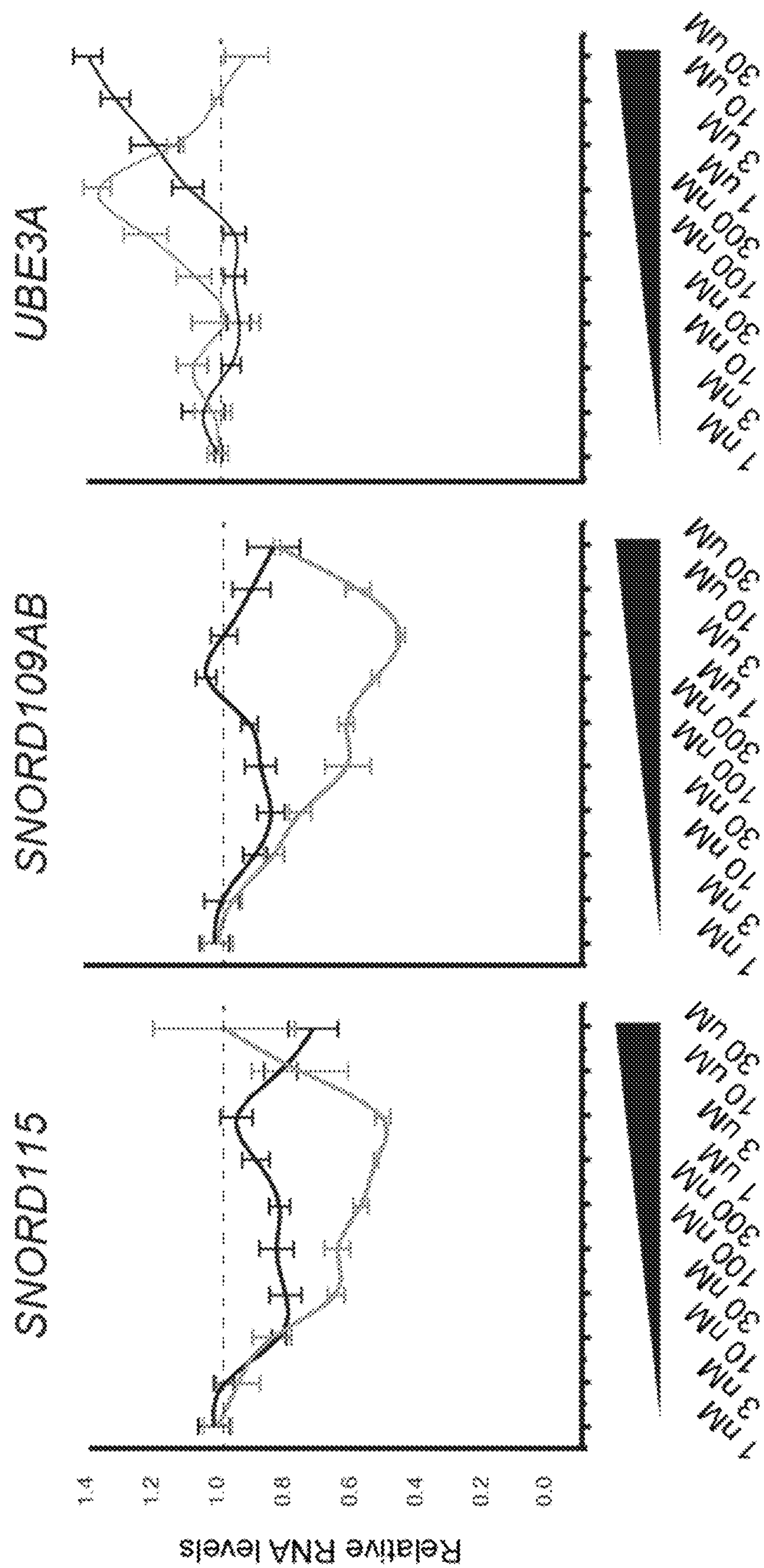

The effects of ASO-4 and Topotecan were then examined on the SNORD116, IPW, SNORD115, and SNORD109A RNAs, which are located upstream of the ASO-4 target region (see FIG. 1A). With the exception of SNORD116, ASO-4 had a significant effect on the RNA levels of IPW, SNORD115, and SNORD109A/B but not in a dose dependent manner. In contrast, Topotecan had a significant effect on SNORD116, IPW, SNORD115, and SNORD109A/B RNA levels that was dose dependent (Table 10 and FIGS. 4B-4E). Both ASO-4 and Topotecan increased total UBE3A RNA levels in a dose-dependent manner, except for Topotecan at higher concentrations (3 μM, 10 μM, and 30 μM; FIG. 4F).

Figure 4I:
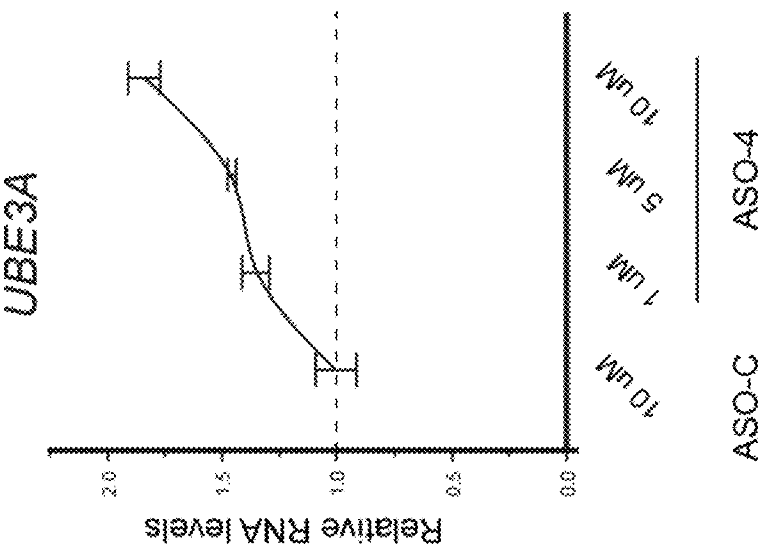
Figure 4H:
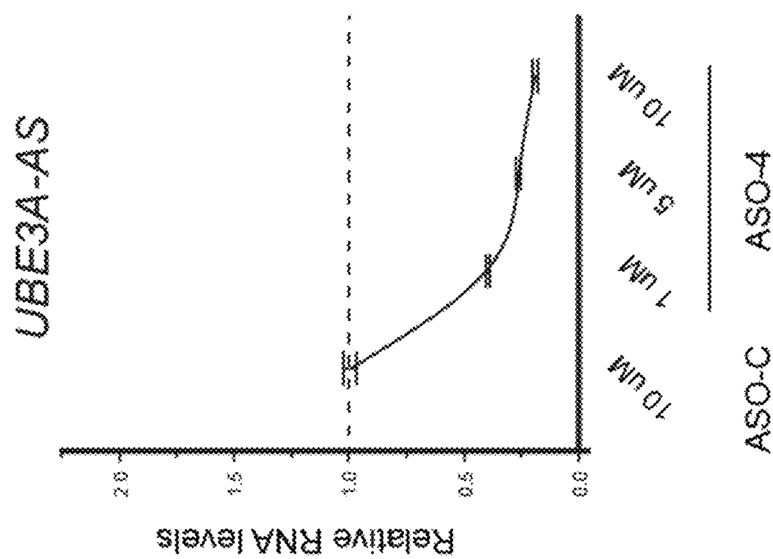
Figure 4G:
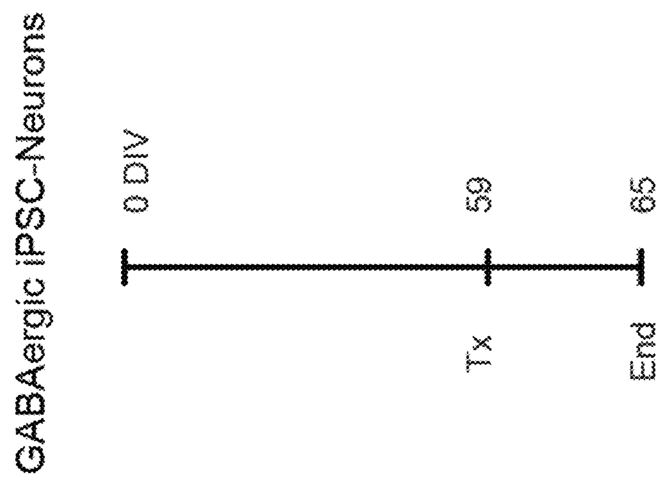

The potency of ASO-4 was further examined in iPSC-derived neurons at a later time point in differentiation. GABAergic iPSC-derived neurons were treated at 59 DIV with a control ASO [ASO-C, 10 μM (n=3)] and ASO-4 [1 uM, 5 μM, and 10 μM (n=3)], and the steady state RNA levels of UBE3A-AS and UBE3A were measured as described above (FIG. 4G). Unlike neurons treated with ASO-4 at an earlier time point, the RNA levels of UBE3A and UBE3A-AS were highly inversely correlated (FIGS. 4H and 4I). For example, the effect of ASO-4 (10 μM) on UBE3A-AS RNA levels was similar between neurons treated at 14 and 59 DIV [20 DIV: UBE3A-AS: ↓87% (95% confidence intervals (CI): 80 to 95%); 65 DIV: ↓81% (95% CI: 74 to 88%)], whereas the effect of ASO-4 on UBE3A RNA levels was substantially larger in neurons treated at 59 DIV [20 DIV: ↑1'30% (95% CI: 16 to 44%); 65 DIV: ↑1'86% (95% CI: 59% to 113%)].

Figure 5A:
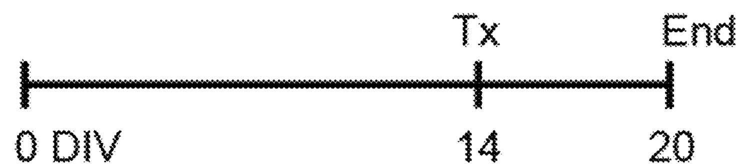
FIGS. 5A to 5F shows analysis of optimized ASOs in human GABAergic and glutamatergic iPSC-derived neurons.
Figure 5B:
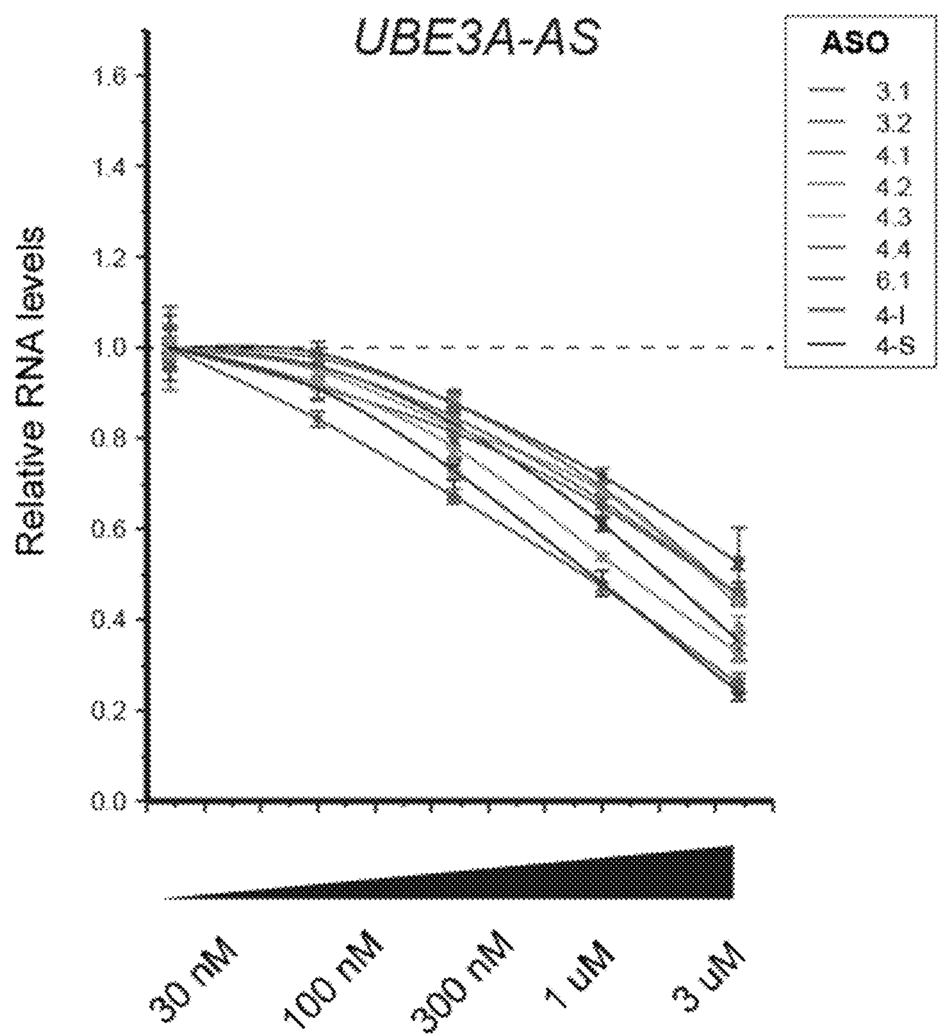

Additional ASOs targeting the 5'-end of UBE3A-AS were then designed to optimize the target sequences of ASO-4 (ASO-4.1, ASO-4.2, ASO-4.3, and ASO-4.4) as well as two other target regions, ASO-3 (ASO-3.1 and ASO-3.2) and ASO-6 (ASO-6.1) (Table 11). Additionally, ASO-4 was manufactured at two different vendors for comparative purposes (ASO-4.S, Sigma; ASO-4.1, Integrated DNA Technologies). Human iPSC-derived neurons (GABAergic) were treated at 14 DIV with a 5-point ½ log dose curve of ASO-3.1, ASO-3.2, ASO-4.S, ASO-4.1, ASO-4.1, ASO-4.2, ASO-4.3, ASO-4.4, and ASO-6.1 [30 nM, 100 nM, 300 nM, 1 μM (n=6)]. At 20 DIV, the $IC_{50}$ and $E_{max}$ of each ASO was estimated as described above (FIGS. 5A-B and Table 12). The dose response curves were similar among ASOs (Parallelism test: $F_{(16,513)}=1.6$, p=0.06), with ASO-4 and ASO-6.1 having the highest relative potency (Table 13). No significant difference was observed between ASO-4.S and ASO-4.1.

Figures 5C, 5D:
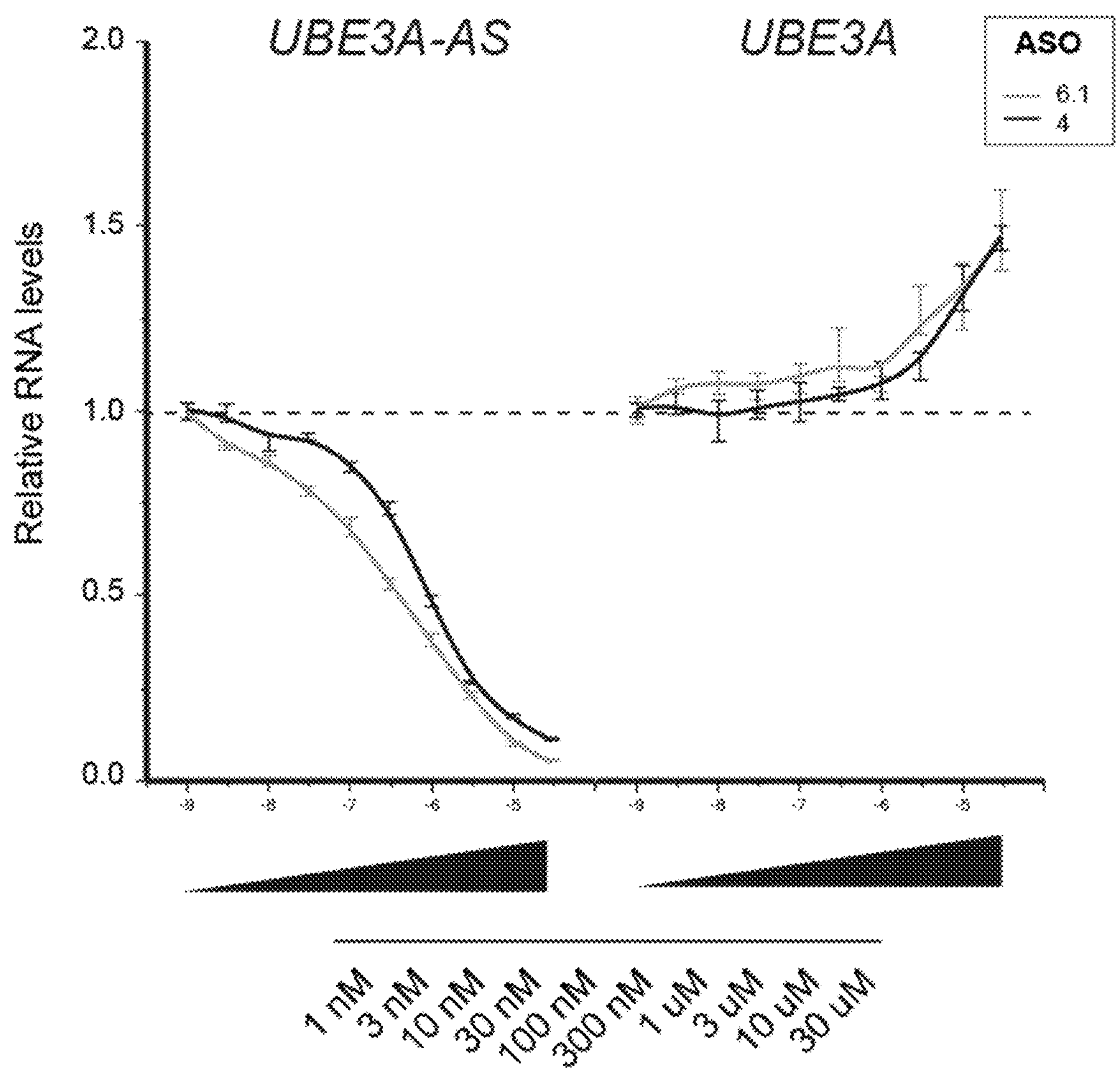

The potency of ASO-4 and ASO-6.1 was further examined in iPSC-derived neurons at a later time point in differentiation. GABAergic iPSC-derived neurons were treated at 29 DIV with a 10-point ½ log dose response curve of ASO-4 and ASO-6.1 [1 nM, 3 nM, 10 nM, 30 nM, 100 nM, 300 nM, 1 μM, 3 μM, 10 μM, and 30 μM (n=3)]. At 35 DIV, the $IC_{50}$ and $E_{max}$ of each ASO was estimated as described above (FIGS. 5C-D and Table 14). The dose response curves of ASO-4 and ASO-6.1 were not similar (Parallelism test: $F_{(3,172)}=22.7$, p<0.0001). An equivalence test indicated that ASO-4 and ASO-6.1 had equivalent potencies but different $E_{max}$ values [ASO-6.1/ASO-4 ratio: $IC_{50}=1.03$ (Lower confidence limit=1.0; Upper confidence limit=1.1); $E_{max}=-1.3$ (Lower confidence limit=−2.6; Upper confidence limit=—0.08)], with ASO-6.1 having the largest inhibition of UBE3A-AS levels. The effect of ASO-4 and ASO-6.1 on UBE3A RNA levels was similar, with each treatment increasing RNA levels in dose dependent manner (FIG. 5D).

Figures 5E, 5F:
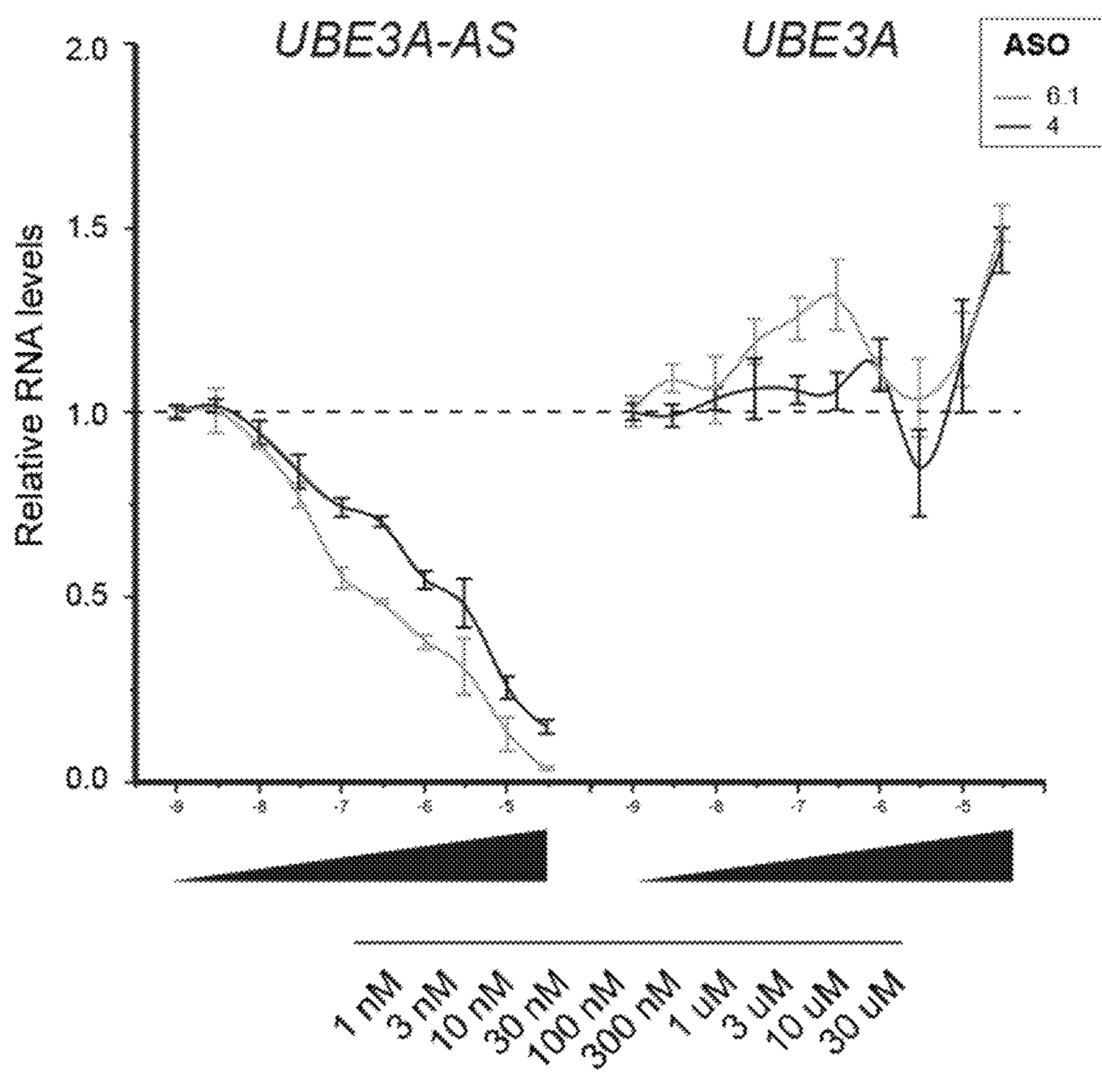
Figure 6A:
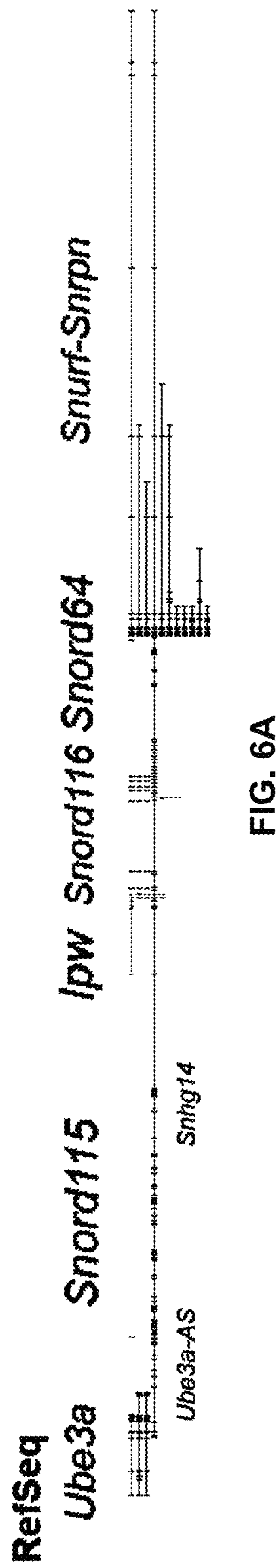
FIG. 6A to 6D show identification of ASO target region in mouse PWS/AS imprinted region.
Figures 6B, 6C:
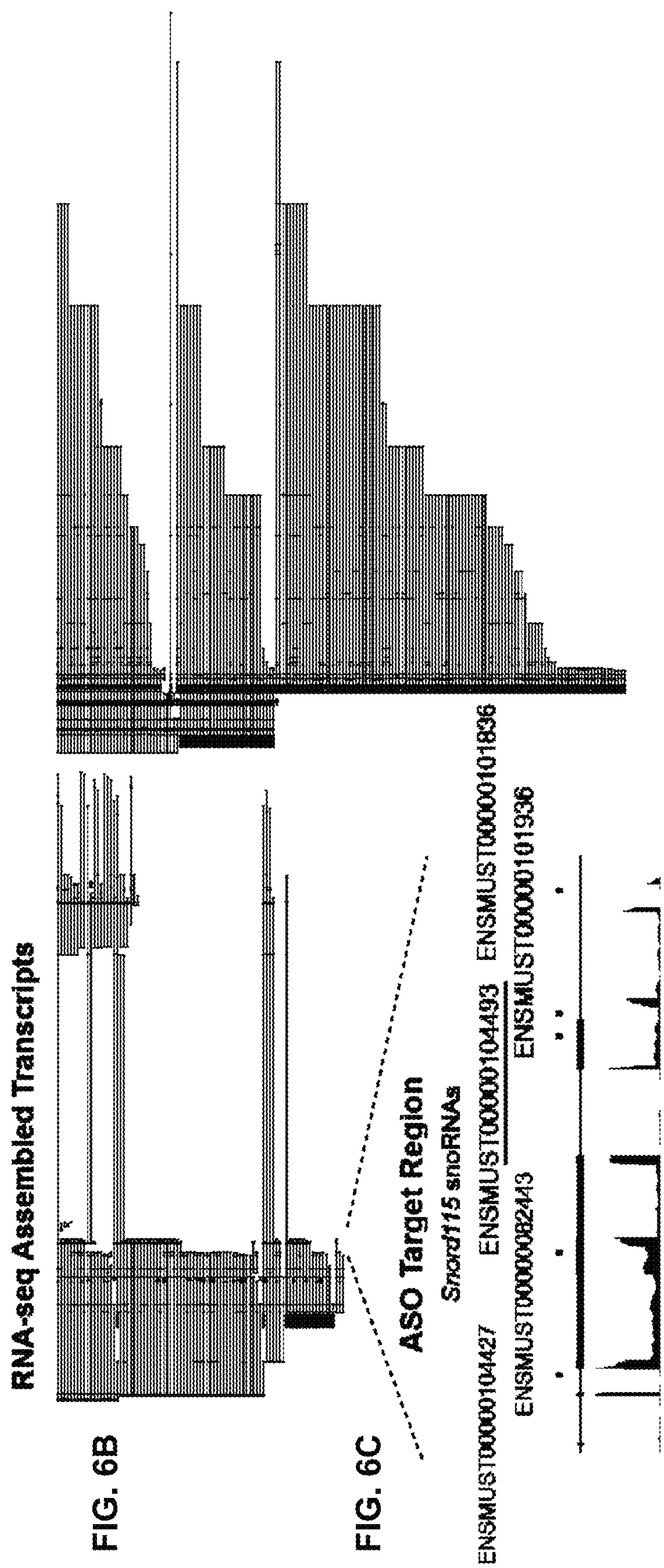
Figure 6D:
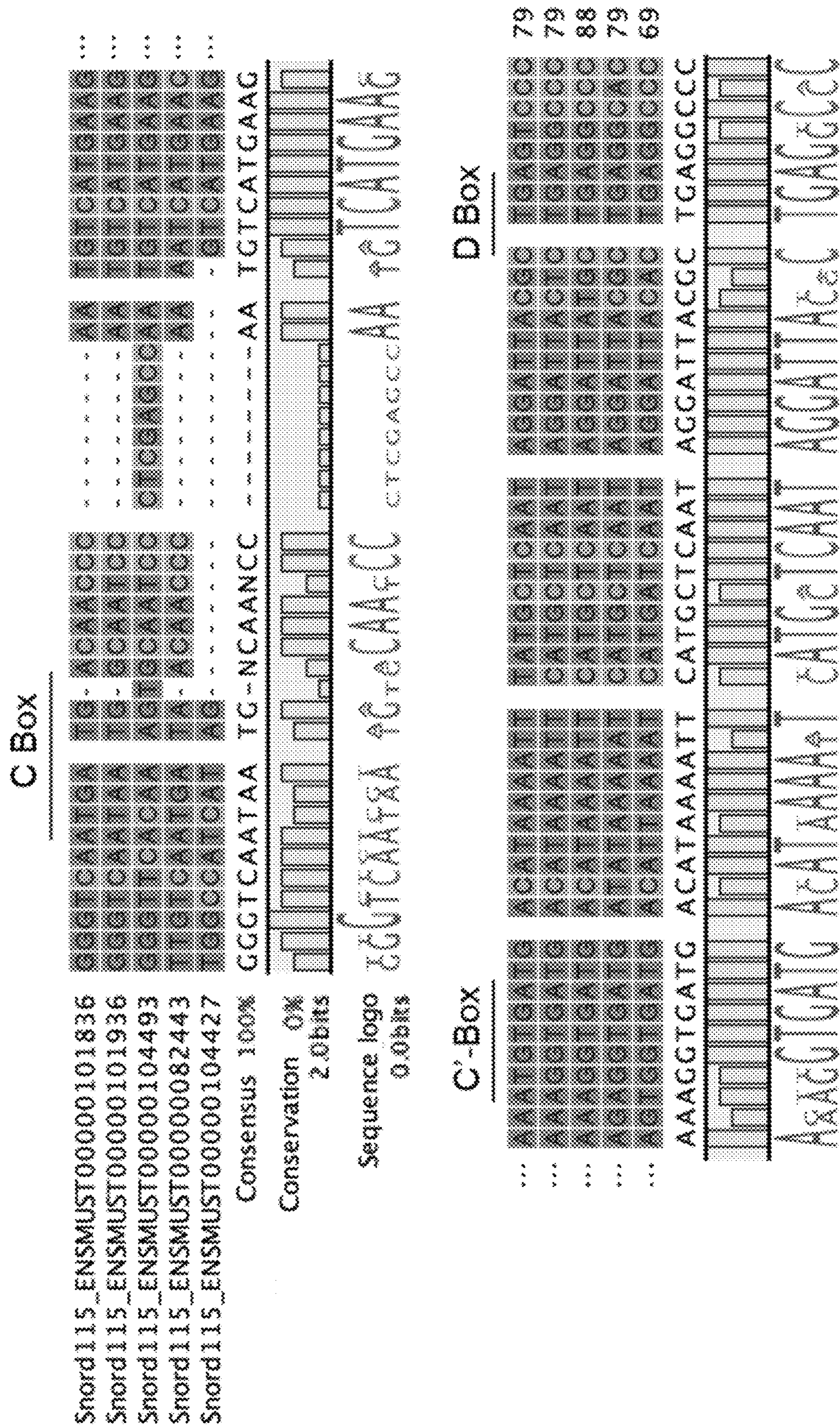
Figure 7A:
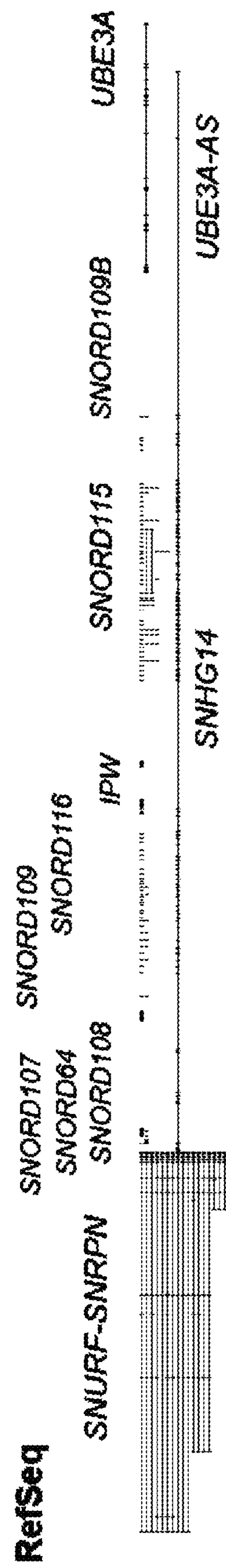
Figure 7B:
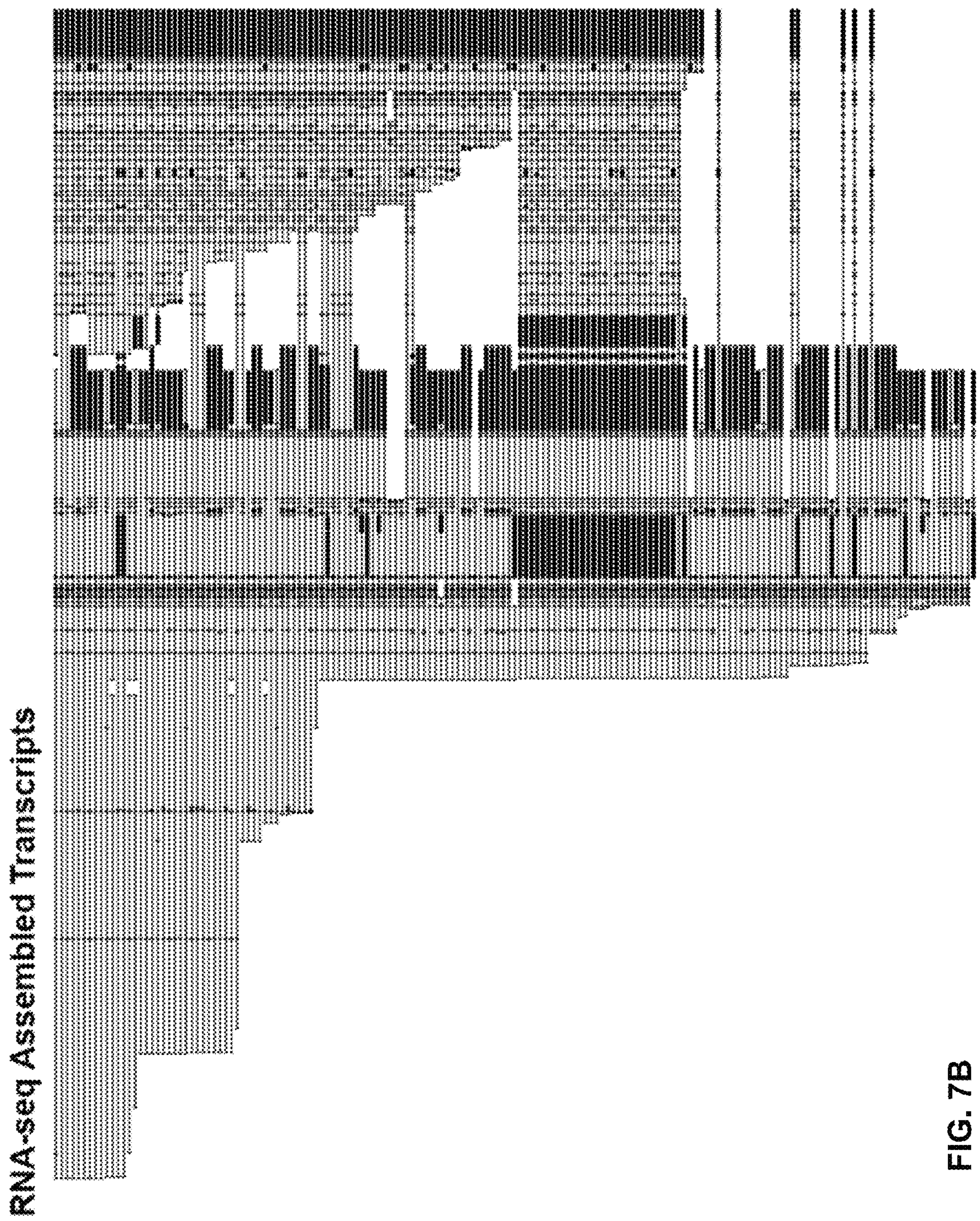
Figure 7C:
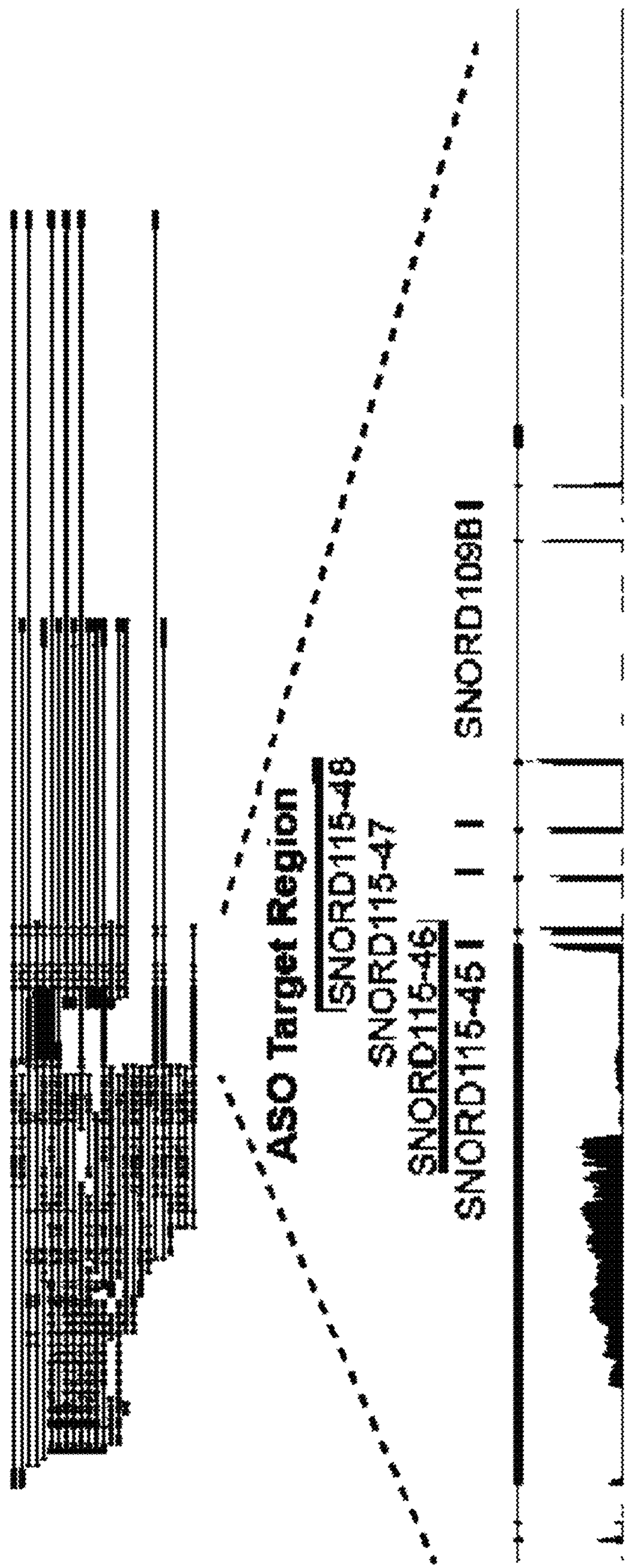
Figure 7G:
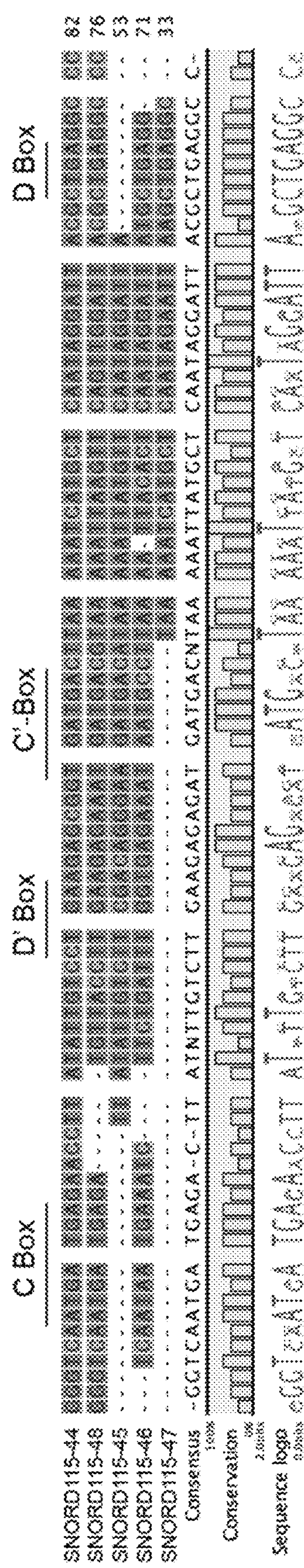

ASO-4 and ASO-6.1 were also examined in glutamatergic iPSC-derived neurons. Glutamatergic iPSC-derived neurons were treated at 14 DIV with a 10-point ½ log dose response curve of ASO-4 and ASO-6.1 [1 nM, 3 nM, 10 nM, 30 nM, 100 nM, 300 nM, 1 μM, 3 μM, 10 μM, and 30 μM (n=3)]. At 20 DIV, the $IC_{50}$ and $E_{max}$ of each ASO was estimated as described above (FIGS. 5E-F and Table 15). The dose response curves of ASO-4 and ASO-6.1 were similar and not significantly different (Parallelism test: $F_{(3,165)}=1.9$, p=0.1), with ASO-6.1 having the highest relative potency (Table 16). As expected, ASO-4 and ASO-6.1 increased UBE3A RNA levels in a dose dependent manner (FIG. 5F); however, there was a high degree of variation for each concentration that was not attributable to treatment (R2=0.17).

Conclusions

Towards developing a therapy for AS, experiments were conducted to determine whether ASOs targeting a specific region inhibit Ube3a-AS/UBE3A-AS and reactivate expression of the paternal Ube3a/UBE3A allele in mouse and human neurons. Altogether, findings show that ASOs targeting this region in mouse and human neurons have potent antisense activity and reverse imprinting of Ube3a/UBE3A.

Two of the three ASOs (ASO-1.1 and ASO-3.1) targeting Ube3a-AS reactivated expression of the paternal Ube3a allele in mouse neurons to a level similar to that achieved by the optimal concentration of Topotecan (300 nM).

Likewise, each of the human-specific ASOs significantly reduced the steady state RNA levels of UBE3A-AS in human iPSC-derived neurons, with higher concentrations of ASO-4 and ASO-6.1 almost completely abolishing expression of UBE3A-AS. Given that ASO-4 and ASO-6.1 target regions that are 100% conserved between human and macaque, the efficacy of these ASOs can be examined in vivo in either Cynomolgus or Rhesus macaque. Unlike Topotecan, ASO-4 has a small, if any, effect on the upstream SNORD116, IPW, SNORD115, or SNORD109A/B RNAs, consistent with the notion that the ASO terminates transcription at or downstream of the target region.

Low concentrations (3 nM) of ASO-4 and ASO-6.1 significantly reduced UBE3A-AS RNA levels; however, higher concentrations (≥100 nM) of ASO were necessary to increase UBE3A RNA levels. This may reflect a certain threshold required for UBE3A-AS to inhibit transcription of UBE3A, or a lag between the time that inactivation of UBE3A-AS leads to reactivation of paternal UBE3A, or the sensitivity of the assay used to quantify UBE3A RNA levels.

Collectively, findings suggest that ASOs targeting a candidate region in UBE3A-AS almost completely abolishes imprinting of UBE3A in neurons and reveals at least two ASOs for future clinical development.

Derivatives of ASO-4 and ASO-6.1 that are comprised of different RNA modifications [2"-hydroxymethyl (2"-OMe), 2"-methoxy-ethyl 2"-MOE, and locked nucleic acid (LNA)] and backbones [phosphorothioate (PS) and phosphodiester (PO)] have also been designed (Table 17).

TABLE 6

Mouse Ube3a-AS Oligonucleotides

| ASO | RNA Modification | RNA Backbone | DNA Backbone | Design (5'-3') | Sequence | SEQ ID |
|---|---|---|---|---|---|---|
| ASO-B | 2'-OMe | PS | PS | 5-10-5 | $C^{O}*C^{O}*A^{O}*G^{O}*C^{O}*c*t*t*g*t*t*g*g*a*t*A^{O}*U^{O}*C^{O}*A^{O}*U^{O}$ | SEQ ID NO: 358 |

TABLE 6-continued

| Mouse Ube3a-AS Oligonucleotides | | | | | | |
|---|---|---|---|---|---|---|
| ASO | RNA Modifi-cation | RNA Back-bone | DNA Back-bone | Design (5'-3') | Sequence | SEQ ID |
| ASO-1.1 | 2'-OMe | PS | PS | 5-10-5 | $C^O*C^O*A^O*C^O*A^O*t*t*t*c*c*t*c*t*c*a*U^O*G^O*G^O*A^O*A^O$ | SEQ ID NO: 359 |
| ASO-1.2 | 2'-OMe | PS | PS | 5-10-5 | $G^O*A^O*G^O*U^O*G^O*t*t*t*g*c*a*a*a*c*c*A^O*A^O*U^O*G^O*U^O$ | SEQ ID NO: 360 |
| ASO-3.1 | 2'-OMe | PS | PS | 5-10-5 | $U^O*G^O*U^O*U^O*U^O*c*t*t*t*g*g*t*g*a*t*U^O*C^O*U^O*G^O*C^O$ | SEQ ID NO: 361 |

Capital letter, RNA;
lower-case letter, DNA;
O, 2'-OMe;
PS & *, phosphorothioate

TABLE 7

| Human UBE3A-AS Oligonucleotides | | | | | | |
|---|---|---|---|---|---|---|
| ASO | RNA Modifi-cation | RNA Back-bone | DNA Back-bone | Design (5'-3') | Sequence | SEQ ID |
| ASO-1 | 2'-OMe | PS | PS | 5-10-5 | $U^O*A^O*G^O*A^O*G^O*g*t*g*a*a*g*g*c*c*a*G^O*G^O*C^O*A^O*C^O$ | SEQ ID NO: 362 |
| ASO-2 | 2'-OMe | PS | PS | 5-10-5 | $G^O*U^O*A^O*C^O*U^O*c*t*t*c*c*t*c*a*g*t*C^O*A^O*U^O*C^O*C^O$ | SEQ ID NO: 363 |
| ASO-3$^C$ | 2'-OMe | PS | PS | 5-10-5 | $U^O*G^O*U^O*C^O*A^O*g*t*t*t*c*t*c*c*c*t*G^O*A^O*A^O*C^O*A^O$ | SEQ ID NO: 364 |
| ASO-4$^C$ | 2'-OMe | PS | PS | 5-10-5 | $U^O*A^O*G^O*A^O*A^O*t*g*g*c*a*c*a*t*c*t*C^O*U^O*U^O*G^O*G^O$ | SEQ ID NO: 365 |
| ASO-5$^C$ | 2'-OMe | PS | PS | 5-10-5 | $G^O*U^O*U^O*U^O*U^O*c*t*t*c*c*t*c*c*a*c*A^O*G^O*U^O*C^O*U^O$ | SEQ ID NO: 366 |
| ASO-6$^C$ | 2'-OMe | PS | PS | 5-10-5 | $C^O*U^O*G^O*G^O*U^O*g*t*c*a*a*c*a*a*g*c*C^O*A^O*A^O*A^O*G^O$ | SEQ ID NO: 367 |

Abbreviations:
$^C$, conserved with macaque & non-polymorphic;
capital letter, RNA nucleotide;
lower-case letter, DNAnucleotide;
$^O$, 2'-OMe;
PS & *, phosphorothioate

TABLE 8

| Analysis of Human ASOs on UBE3A-AS and UBE3A RNA levels | | | | | |
|---|---|---|---|---|---|
| ASO 1 | ASO 2 | Difference | Lower CI | Upper CI | Adj. P |
| UBE3A-AS | | | | | |
| ASO-C | ASO-2 | 0.89 | 0.82 | 0.97 | <.0001 |
| ASO-R | ASO-2 | 0.87 | 0.80 | 0.95 | <.0001 |
| ASO-C | ASO-4 | 0.87 | 0.80 | 0.95 | <.0001 |
| ASO-R | ASO-4 | 0.85 | 0.78 | 0.93 | <.0001 |
| ASO-C | ASO-6 | 0.83 | 0.75 | 0.90 | <.0001 |
| ASO-R | ASO-6 | 0.81 | 0.74 | 0.89 | <.0001 |
| ASO-C | ASO-3 | 0.79 | 0.71 | 0.86 | <.0001 |
| ASO-R | ASO-3 | 0.77 | 0.70 | 0.85 | <.0001 |
| ASO-C | ASO-5 | 0.71 | 0.63 | 0.78 | <.0001 |
| ASO-R | ASO-5 | 0.69 | 0.62 | 0.77 | <.0001 |
| ASO-C | Topo | 0.66 | 0.59 | 0.73 | <.0001 |
| ASO-R | Topo | 0.64 | 0.57 | 0.72 | <.0001 |
| ASO-C | ASO-1 | 0.51 | 0.43 | 0.58 | <.0001 |
| ASO-R | ASO-1 | 0.49 | 0.41 | 0.56 | <.0001 |

TABLE 8-continued

| Analysis of Human ASOs on UBE3A-AS and UBE3A RNA levels | | | | | |
|---|---|---|---|---|---|
| ASO 1 | ASO 2 | Difference | Lower CI | Upper CI | Adj. P |
| ASO-1 | ASO-2 | 0.38 | 0.31 | 0.46 | <.0001 |
| ASO-1 | ASO-4 | 0.36 | 0.29 | 0.44 | <.0001 |
| ASO-1 | ASO-6 | 0.32 | 0.25 | 0.40 | <.0001 |
| ASO-1 | ASO-3 | 0.28 | 0.21 | 0.36 | <.0001 |
| Topo | ASO-2 | 0.23 | 0.16 | 0.31 | <.0001 |
| Topo | ASO-4 | 0.21 | 0.14 | 0.29 | <.0001 |
| ASO-1 | ASO-5 | 0.20 | 0.13 | 0.28 | <.0001 |
| ASO-5 | ASO-2 | 0.18 | 0.11 | 0.26 | <.0001 |
| Topo | ASO-6 | 0.17 | 0.10 | 0.24 | 0.0002 |
| ASO-5 | ASO-4 | 0.16 | 0.09 | 0.24 | 0.0003 |
| ASO-1 | Topo | 0.15 | 0.08 | 0.23 | 0.0004 |
| Topo | ASO-3 | 0.13 | 0.06 | 0.20 | 0.0018 |
| ASO-5 | ASO-6 | 0.12 | 0.04 | 0.20 | 0.0035 |
| ASO-3 | ASO-2 | 0.10 | 0.03 | 0.18 | 0.0111 |
| ASO-3 | ASO-4 | 0.08 | 0.01 | 0.16 | 0.0360 |
| ASO-5 | ASO-3 | 0.08 | 0.00 | 0.15 | 0.0381 |

TABLE 8-continued

| Analysis of Human ASOs on UBE3A-AS and UBE3A RNA levels | | | | | |
|---|---|---|---|---|---|
| ASO 1 | ASO 2 | Difference | Lower CI | Upper CI | Adj. P |
| ASO-6 | ASO-2 | 0.06 | −0.01 | 0.14 | 0.11 |
| Topo | ASO-5 | 0.05 | −0.02 | 0.13 | 0.18 |
| ASO-6 | ASO-4 | 0.04 | −0.03 | 0.12 | 0.27 |
| ASO-3 | ASO-6 | 0.04 | −0.03 | 0.12 | 0.28 |
| ASO-4 | ASO-2 | 0.02 | −0.06 | 0.09 | 0.58 |
| ASO-C | ASO-R | 0.02 | −0.06 | 0.09 | 0.64 |
| UBE3A | | | | | |
| ASO-4 | ASO-C | 0.30 | 0.16 | 0.44 | 0.0004 |
| ASO-4 | ASO-R | 0.29 | 0.14 | 0.45 | 0.001 |
| ASO-2 | ASO-C | 0.21 | 0.09 | 0.34 | 0.002 |
| ASO-2 | ASO-R | 0.21 | 0.07 | 0.35 | 0.006 |
| ASO-1 | ASO-C | 0.18 | 0.06 | 0.31 | 0.007 |
| Topo | ASO-C | 0.18 | 0.04 | 0.32 | 0.01 |
| ASO-1 | ASO-R | 0.18 | 0.04 | 0.32 | 0.02 |
| Topo | ASO-R | 0.18 | 0.03 | 0.33 | 0.02 |
| ASO-4 | ASO-3 | 0.17 | 0.03 | 0.31 | 0.02 |
| ASO-5 | ASO-C | 0.16 | 0.04 | 0.29 | 0.01 |
| ASO-6 | ASO-C | 0.16 | 0.04 | 0.29 | 0.01 |
| ASO-5 | ASO-R | 0.16 | 0.02 | 0.30 | 0.03 |
| ASO-6 | ASO-R | 0.16 | 0.02 | 0.30 | 0.03 |
| ASO-4 | ASO-6 | 0.13 | −0.007 | 0.27 | 0.06 |
| ASO-4 | ASO-5 | 0.13 | −0.007 | 0.27 | 0.06 |
| ASO-3 | ASO-C | 0.13 | 0.00 | 0.26 | 0.04 |
| ASO-3 | ASO-R | 0.13 | −0.015 | 0.27 | 0.08 |

TABLE 8-continued

| Analysis of Human ASOs on UBE3A-AS and UBE3A RNA levels | | | | | |
|---|---|---|---|---|---|
| ASO 1 | ASO 2 | Difference | Lower CI | Upper CI | Adj. P |
| ASO-4 | Topo | 0.11 | −0.04 | 0.27 | 0.1 |
| ASO-4 | ASO-1 | 0.11 | −0.03 | 0.25 | 0.1 |
| ASO-2 | ASO-3 | 0.08 | −0.04 | 0.21 | 0.2 |
| ASO-4 | ASO-2 | 0.08 | −0.06 | 0.22 | 0.2 |
| ASO-1 | ASO-3 | 0.05 | −0.07 | 0.18 | 0.4 |
| Topo | ASO-3 | 0.05 | −0.09 | 0.19 | 0.4 |
| ASO-2 | ASO-6 | 0.05 | −0.08 | 0.18 | 0.4 |
| ASO-2 | ASO-5 | 0.05 | −0.08 | 0.17 | 0.4 |
| ASO-5 | ASO-3 | 0.03 | −0.09 | 0.16 | 0.6 |
| ASO-6 | ASO-3 | 0.03 | −0.09 | 0.16 | 0.6 |
| ASO-2 | Topo | 0.03 | −0.1 | 0.17 | 0.7 |
| ASO-2 | ASO-1 | 0.03 | −0.01 | 0.16 | 0.6 |
| ASO-1 | ASO-6 | 0.02 | −0.1 | 0.15 | 0.7 |
| Topo | ASO-6 | 0.02 | −0.1 | 0.16 | 0.8 |
| ASO-1 | ASO-5 | 0.02 | −0.1 | 0.15 | 0.7 |
| Topo | ASO-5 | 0.02 | −0.1 | 0.16 | 0.8 |
| ASO-R | ASO-C | 0.00 | −0.1 | 0.14 | 0.9 |
| ASO-5 | ASO-6 | 0.00 | −0.1 | 0.13 | 0.9 |
| ASO-1 | Topo | 0.00 | −0.1 | 0.14 | 1.00 |

Abbreviations:
ASO-C, ASO-control;
Topo, Topotecan;
Adj., Adjusted;
CI, 95% confidence interval

TABLE 9

| $IC_{50}$ and $E_{max}$ of ASO-4 and Topotecan | | | | | | | |
|---|---|---|---|---|---|---|---|
| Treatment | $IC_{50}$ Estimate (M) | $IC_{50}$ 95% CI (M) | | $E_{max}$ Estimate | $E_{max}$ 95% CI | | 30 μM (Mean) |
| ASO-4 | 6.13E−07 | 3.47E−07 | 1.08E−06 | −0.06 | −0.23 | 0.10 | 0.09 |
| Topo | 3.37E−08 | 1.85E−08 | 6.14E−08 | 0.26 | 0.20 | 0.32 | 0.21 |

Full model parameter estimates from 4-parameter logistic regression model (Hill). $IC_{50}$ and confidence intervals represent molar concentration. $E_{max}$ and 30 uM values represent normalized UBE3A-AS RNA levels relative to vehicle.

TABLE 10

| Analysis of ASO-4 and Topotecan on UBE3A, SNORD116, SNORD115, SNORD109A/B, and IPW RNA Levels | | | | | |
|---|---|---|---|---|---|
| Treatment | RNA | DF | DFDen | F Ratio | FDR |
| ASO-4 | UBE3A | 9 | 108 | 16.5 | <0.0001 |
| | SNORD109A/B | 9 | 104.9 | 2.6 | 0.01 |
| | SNORD115 | 9 | 108 | 4.0 | 0.0002 |
| | SNORD116 | 9 | 108 | 1.74 | 0.09 |
| | IPW | 9 | 108 | 4.1 | 0.0002 |
| Topotecan | UBE3A | 9 | 29 | 5.6 | 0.0002 |
| | SNORD109A/B | 9 | 29 | 28.2 | <0.0001 |
| | SNORD115 | 9 | 29 | 4.60 | 0.001 |
| | SNORD116 | 9 | 29 | 7.12 | <0.0001 |
| | IPW | 9 | 29 | 49.8 | <0.0001 |

Least squares linear regression.
Abbreviations:
DF, degrees of freedom;
DFDen, degrees of freedom density

TABLE 11

| Optimized Human UBE3A-AS Antisense Oligonucleotides | | | | | | |
|---|---|---|---|---|---|---|
| ASO | RNA Modification | RNA Backbone | DNA Backbone | Design (5'-3') | Sequence | SEQ ID |
| ASO-3.1$^{C}$ | 2'-OMe | PS | PS | 4-10-5 | $G^{O}$*$U^{O}$*$U^{O}$*$G^{O}$*a*g*t*g*g*t*g*t*c*a*$G^{O}$*$U^{O}$*$U^{O}$*$U^{O}$*$C^{O}$ | SEQ ID NO: 368 |
| ASO-3.2$^{C}$ | 2'-OMe | PS | PS | 4-10-4 | $U^{O}$*$U^{O}$*$G^{O}$*$A^{O}$*g*t*g*g*t*g*t*c*a*g*$U^{O}$*$U^{O}$*$U^{O}$*$C^{O}$ | SEQ ID NO: 369 |

TABLE 11-continued

| Optimized Human UBE3A-AS Antisense Oligonucleotides | | | | | | |
|---|---|---|---|---|---|---|
| ASO | RNA Modification | RNA Backbone | DNA Backbone | Design (5'-3') | Sequence | SEQ ID |
| ASO-6.1[C] | 2'-OMe | PS | PS | 4-10-4 | $C^O$*$U^O$*$G^O$*$G^O$*t*g*t*c*a*a*c*a*a*g*$C^O$*$C^O$*$A^O$*$A^O$ | SEQ ID NO: 370 |
| ASO-4.1[C] | 2'-OMe | PS | PS | 5-10-5 | $A^O$*$U^O$*$A^O$*$G^O$*$A^O$*a*t*g*g*c*a*c*a*t*c*$U^O$*$C^O$*$U^O$*$U^O$*$G^O$ | SEQ ID NO: 371 |
| ASO-4.2[C] | 2'-OMe | PS | PS | 4-10-5 | $A^O$*$G^O$*$A^O$*$A^O$*t*g*g*c*a*c*a*t*c*t*$C^O$*$U^O$*$U^O$*$G^O$*$G^O$ | SEQ ID NO: 372 |
| ASO-4.3[C] | 2'-OMe | PS | PS | 4-10-5 | $U^O$*$A^O$*$G^O$*$A^O$*a*t*g*g*c*a*c*a*t*c*$U^O$*$C^O$*$U^O$*$U^O$*$G^O$ | SEQ ID NO: 373 |
| ASO-4.4[C] | 2'-OMe | PS | PS | 4-10-4 | $A^O$*$G^O$*$A^O$*$A^O$*t*g*g*c*a*c*a*t*c*t*$C^O$*$U^O$*$U^O$*$G^O$ | SEQ ID NO: 374 |

[C], conserved with macaque & non-polymorphic;
capital letter, RNA nucleotide;
lower-case letter, DNA nucleotide;
O, 2'-OMe;
PS & *, phosphorothioate

TABLE 12

| IC$_{50}$ and E$_{max}$ of Optimized ASO Target Sequences | | | | |
|---|---|---|---|---|
| Group | IC$_{50}$ Estimate | IC$_{50}$ 95% CI (M) | | 3 μM (Mean) |
| 6.1 | 5.20E−07 | 3.33E−07 | 8.11E−07 | 0.23 |
| 4.0 | 1.06E−06 | 9.31E−07 | 1.21E−06 | 0.29 |
| 4.2 | 1.08E−06 | 8.62E−07 | 1.35E−06 | 0.31 |
| 3.2 | 1.88E−06 | 1.39E−06 | 2.56E−06 | 0.44 |
| 4.3 | 2.03E−06 | 1.67E−06 | 2.47E−06 | 0.40 |
| 4.4 | 2.11E−06 | 1.73E−06 | 2.59E−06 | 0.44 |
| 4.1 | 2.27E−06 | 1.92E−06 | 2.68E−06 | 0.42 |
| 3.1 | 2.98E−06 | 2.45E−06 | 3.62E−06 | 0.51 |

Full model parameter estimates from 3-parameter logistic regression model. IC$_{50}$ and confidence intervals represent molar concentration. E$_{max}$ (3 uM) values represent normalized UBE3A-AS RNA levels relative to vehicle.

TABLE 13

| Relative Potency of Optimized ASOs | | | |
|---|---|---|---|
| ASO | IC$_{50}$ (M) | Relative Potency | Std. Error |
| ASO 3.1 | 2.81E−06 | 0.53 | 0.059 |
| ASO 3.2 | 1.85E−06 | 0.81 | 0.086 |
| ASO 4.1 | 2.25E−06 | 0.66 | 0.072 |
| ASO 4.2 | 1.24E−06 | 1.21 | 0.13 |
| ASO 4.3 | 1.96E−06 | 0.76 | 0.081 |
| ASO 4.4 | 2.04E−06 | 0.73 | 0.079 |
| ASO 6.1 | 7.20E−07 | 2.07 | 0.21 |
| ASO 4.1 | 8.28E−07 | 1.80 | 0.19 |
| ASO 4.S | 1.49E−06 | 1 | 0 |

Parallel model parameter estimates from 3-parameter logistic regression model. Potency represents molar concentration.
Abbreviations: M, molar; Std. Error, standard error of mean.

TABLE 14

| IC$_{50}$ and E$_{max}$ of ASO-4 and ASO-6.1 in GABAergic iPSC Neurons | | | | | | | |
|---|---|---|---|---|---|---|---|
| ASO | IC$_{50}$ Estimate | IC$_{50}$ 95% CI (M) | | E$_{max}$ Estimate | E$_{max}$ 95% CI | | 30 μM (Mean) |
| ASO-4 | 7.77E−07 | 6.86E−07 | 8.79E−07 | 0.08 | 0.05 | 0.11 | 0.11 |
| ASO-6.1 | 5.17E−07 | 3.41E−07 | 7.82E−07 | −0.11 | −0.22 | 0.01 | 0.06 |

Full model parameter estimates from 4-parameter logistic regression model (Hill). IC$_{50}$ and confidence intervals represent molar concentration. E$_{max}$ and 30 uM values represent normalized UBE3A-AS RNA levels relative to vehicle.

TABLE 15

| IC$_{50}$ and E$_{max}$ of ASO-4 and ASO-6.1 in Glutamatergic iPSC Neurons | | | | | | | |
|---|---|---|---|---|---|---|---|
| ASO | IC$_{50}$ Estimate | IC$_{50}$ 95% CI (M) | | E$_{max}$ Estimate | E$_{max}$ 95% CI | | 30 μM (Mean) |
| ASO-4 | 1.21E−04 | 1.12E−13 | 1.32E+05 | −1.45 | −9.01 | 6.12 | 0.17 |
| ASO-6.1 | 2.44E−07 | 2.39E−08 | 2.50E−06 | −0.27 | −1.24 | 0.70 | 0.04 |

Full model parameter estimates from 4-parameter logistic regression model (Hill). IC$_{50}$ and confidence intervals represent molar concentration. E$_{max}$ and 30 uM values represent normalized UBE3A-AS RNA levels relative to vehicle.

TABLE 16

Relative Potency of ASO-4 and ASO-6.1 in Glutamatergic Neurons

| ASO | $IC_{50}$ (M) | Relative Potency | Std. Error |
|---|---|---|---|
| ASO-4 | 3.06E−06 | 1 | 0 |
| ASO-6.1 | 7.8E−07 | 3.89 | 0.72 |

Parallel model parameter estimates from 4 Parameter logistic regression model. Abbreviations: M, molar

TABLE 17

| Derivatives of ASO-4 and ASO-6.1 | | | | | | |
|---|---|---|---|---|---|---|
| ASO | RNA Mod. | Backbone | PO linkages | Design (5'-3') | Sequence (5'-3') | SEQ ID |
| ASO-4.0.PS.O | OMe | PS | 0 | 5-10-5 | $U^{O}$*$A^{O}$*$G^{O}$*$A^{O}$*$A^{O}$*t*g*g*c*a*c*a*t*c*t*$C^{O}$*$U^{O}$*$U^{O}$*$G^{O}$*$G^{O}$ | SEQ ID NO: 375 |
| ASO-4.0.PO-1.O | OMe | PS/PO | 2 | 5-10-5 | $U^{O}$*$A^{O}$*$G^{O}$*$A^{O}$*$A^{O}$-t*g*g*c*a*c*a*t*c*t-$C^{O}$*$U^{O}$*$U^{O}$*$G^{O}$*$G^{O}$ | SEQ ID NO: 376 |
| ASO-4.0.PO-2.O | OMe | PS/PO | 0 | 5-10-5 | $U^{O}$*$A^{O}$-$G^{O}$*$A^{O}$-$A^{O}$*t-g*g-c*a-c*a-t*c-t*$C^{O}$-$U^{O}$*$U^{O}$-$G^{O}$*$G^{O}$ | SEQ ID NO: 377 |
| ASO-4.0.PS.M | MOE | PS | 0 | 5-10-5 | $T^{M}$*$A^{M}$*$G^{M}$*$A^{M}$*$A^{M}$*t*g*g*c*a*c*a*t*c*t*5m$C^{M}$*$T^{M}$*$T^{M}$*$G^{M}$*$G^{M}$ | SEQ ID NO: 378 |
| ASO-4.0.PO-1.M | MOE | PS/PO | 2 | 5-10-5 | $T^{M}$*$A^{M}$*$G^{M}$*$A^{M}$*$A^{M}$-t*g*g*c*a*c*a*t*c*t-5m$C^{M}$*$T^{M}$*$T^{M}$*$G^{M}$*$G^{M}$ | SEQ ID NO: 379 |
| ASO-4.0.PO-2.M | MOE | PS/PO | 9 | 5-10-5 | $T^{M}$*$A^{M}$-$G^{M}$*$A^{M}$-$A^{M}$*t-g*g-c*a-c*a-t*c-t*5m$C^{M}$-$T^{M}$*$T^{M}$-$G^{M}$*$G^{M}$ | SEQ ID NO: 380 |
| ASO-4.4.PS.L | LNA | PS | 0 | 3-11-4 | $A^{L}$*$G^{L}$*$A^{L}$*a*t*g*g*c*a*c*a*t*c*t*5m$C^{L}$-*$T^{L}$-*$T^{L}$*$G^{L}$ | SEQ ID NO: 381 |
| ASO-4.4.PO-1.L | LNA | PS/PO | 2 | 3-11-4 | $A^{L}$*$G^{L}$*$A^{L}$a*t*g*g*c*a*c*a*t*c*t-5m$C^{L}$-*$T^{L}$-*$T^{L}$$G^{L}$ | SEQ ID NO: 382 |
| ASO-4.4.PO-2.L | LNA | PS/PO | 8 | 3-11-4 | $A^{L}$*$G^{L}$-$A^{L}$*a-t*g-g*c-a*c-a*t-c*t-5m$C^{L}$*$T^{L}$-$T^{L}$*$G^{L}$ | SEQ ID NO: 383 |
| ASO-6.1.PS.O | OMe | PS | 0 | 4-10-4 | $C^{O}$*$U^{O}$*$G^{O}$*$G^{O}$*t*g*t*c*a*a*c*a*a*g*$C^{O}$*$C^{O}$*$A^{O}$*$A^{O}$ | SEQ ID NO: 384 |
| ASO-6.1.PO-1.O | OMe | PS/PO | 2 | 4-10-4 | $C^{O}$*$U^{O}$*$G^{O}$*$G^{O}$-t*g*t*c*a*a*c*a*a*g-$C^{O}$*$C^{O}$*$A^{O}$*$A^{O}$ | SEQ ID NO: 385 |
| ASO-6.1.PO-2.O | OMe | PS/PO | 8 | 4-10-4 | $C^{O}$*$U^{O}$-$G^{O}$*$G^{O}$t*g-t*c-a*a-c*a-a*g-$C^{O}$*$C^{O}$$A^{O}$*$A^{O}$ | SEQ ID NO: 386 |
| ASO-6.1.PS.M | MOE | PS | 0 | 4-10-4 | 5m$C^{M}$*$T^{M}$*$G^{M}$*$G^{M}$*t*g*t*c*a*a*c*a*a*g*5m$C^{M}$*5m$C^{M}$*$A^{M}$*$A^{M}$ | SEQ ID NO: 387 |
| ASO-6.1.PO-1.M | MOE | PS/PO | 2 | 4-10-4 | 5m$C^{M}$*$T^{M}$*$G^{M}$*$G^{M}$-t*g*t*c*a*a*c*a*a*g-5m$C^{M}$*5m$C^{M}$*$A^{M}$*$A^{M}$ | SEQ ID NO: 388 |
| ASO-6.1.PO-2.M | MOE | PS/PO | 8 | 4-10-4 | 5m$C^{M}$*$T^{M}$-$G^{M}$*$G^{M}$-t*g-t*c-a*a-c*a-a*g-5m$C^{M}$*5m$C^{M}$-$A^{M}$*$A^{M}$ | SEQ ID NO: 389 |
| ASO-6.1.PS.L | LNA | PS | 0 | 3-10-4 | $T^{L}$*$G^{L}$*$G^{L}$*t*g*t*c*a*a*c*a*a*g*5m$C^{L}$*5m$C^{L}$*$A^{L}$*$A^{L}$ | SEQ ID NO: 390 |
| ASO-6.1.PO-1.L | LNA | PS/PO | 2 | 3-10-4 | $T^{L}$*$G^{L}$*$G^{L}$-t*g*t*c*a*a*c*a*a*g-5m$C^{L}$*5m$C^{L}$*$A^{L}$*$A^{L}$ | SEQ ID NO: 391 |
| ASO-6.1.PO-2.L | LNA | PS/PO | 8 | 3-10-4 | $T^{L}$*$G^{L}$-$G^{L}$*t-g*t-c*a-a*c-a*a-g*5m$C^{L}$-5m$C^{L}$-$A^{L}$*$A^{L}$ | SEQ ID NO: 392 |

Capital letter, RNA;
lower-case letter, DNA.
5mC, 5-methylcytosine.
Superscript:
O, 2'-OMe;
M, 2'-MOE;
L, LNA.
PS & *, phosphorothioate;
PO & -, phosphodiester Materials and Methods Antisense Oligonucleotide Design Antisense oligonucleotides (ASOs) were designed using Soligo (Software for Statistical Folding of Nucleic Acids and Studies of Regulatory RNAs). Briefly, candidate ASOs (20-18mer) with the lowest binding site disruption energy and free binding energy were identified for each target sequence and then inspected for motifs with increased effectiveness. ASOs were further filtered based on accessibility within predicted lowest free energy centroid secondary structure of target sequence generated by Soligo. In some instances, secondary structure models were compared using lowest free energy structures generated by RNAfold and Mfold.

Human ASOs were filtered using the following criteria: 1) target sequence was polymorphic [dbSNP138, dbSNP150, and 1000 Genomes Phase 3 Integrated Variant Calls (SNV, INDEL, and SV)]; 2) target sequence was not 100% conserved with Rhesus and Cynomolgus macaque; 3) target sequence was located upstream of retained Snord115/SNORD115 snoRNA (per exon). Remaining ASOs were then ranked by free energy (<=−8 kcal/mol), average unpaired probability for target site nucleotides, binding site disruption energy (low>high), location within secondary structure (Ensembl Centroid), and presence/absence of sequence motifs associated with high/low effectiveness.

Mouse Primary Hippocampal Neurons

Primary cultures of hippocampal neurons were generated from PO-P1 pups (Ube3a$^{m+/P+}$ and Ube3a$^{m+/pYFP}$) by crossing Ube3a$^{m+/pYFP}$ males with wild-type C57BL/6J females. Genotypes were determined using methods described previously. Briefly, hippocampal neurons were cultured in Neurobasal A medium (Invitrogen, San Diego, CA) supplemented with B27 (Invitrogen) and penicillin/streptomycin (Invitrogen) on 96-well optical bottom plates coated with poly-D-Lysine (152028, Thermo Fisher Scientific) and laminin (23017-01, Thermo Fisher Scientific). Cultures were maintained at 37° C. in 5% $CO_2$ until use.

Mouse Neuron Imaging

Mouse primary hippocampal neurons were fixed at 10 DIV (3 days post treatment) with 4% paraformaldehyde. The cultures were then washed twice with 1×PBS, fixed in 4% paraformaldehyde in PBS for 15 min, and then washed three times in 1×PBS. The cells were blocked in 0.3% Triton-X100 in PBS (T-PBS) plus 5% goat or donkey serum for 1-2 hr at room temperature with gentle agitation. Cells were incubated with anti-GFP [Novus Biologicals, NB 600-308 (rabbit)] and anti-NeuN (Millipore, 05-557 (mouse)] antibodies for 24 hr at 4° C. with gentle agitation. Cells were washed 3 times in 0.1% Tween 20 1×PBS for 15 min each and then incubated with anti-rabbit 488 (Jackson ImmunoResearch, 111-545-144) and anti-mouse Cy3 (Jackson ImmunoResearch, 115-165-166) secondary antibodies for 24 hr at 4° C. in the dark. Cells were then washed 4 times in 0.1% Tween 20 1×PBS for 15 min each. Nuclei were labeled using Hoechst stain (Thermo Fisher Scientific) at a dilution of 1:1000 in the third wash.

Plates were imaged using the Cytation 5 and Gen5 Image+software (BioTek, Winooski, VT). Briefly, a 4×inverted objective was used to generate montage images of each well by acquiring 5×4 autofocused images with overlapping tiles for automatic image stitching. The filters used were DAPI (377,477), GFP (469, 525), and RFP (531, 593). Exposure time and gain were adjusted for each plate using the negative and positive controls. Auto-focus was performed on nuclei (Hoechst stain, DAPI) for each well, with the same focal height used for the GFP and RFP filters. Images were stitched together by Gen5 Image+software.

Single cell image analysis was performed using IN Cell Developer 6.0 (GE Healthcare Life Sciences, Pittsburgh, PA). Briefly, individual track masks were generated for either nuclei (Hoechst stain, DAPI) or mature neurons (NeuN, RFP) by optimizing inclusion and exclusion parameters based on size and intensity of randomly selected cells in the acquired images. The mean and median intensity values of GFP were then acquired within the boundaries of the selected mask, generating intensity values for Ube3aYFP within each cell.

Human Induced Pluripotent Stem Cell Derived Neurons

GABAergic and glutamatergic induced pluripotent stem cell (iPSC) derived neural precursor cells (NRC-100-010-001 and GNC-301-030-001, Cellular Dynamics International, Madison WI) were differentiated into neurons according to the manufactures protocol. Briefly, neural precursor cells were thawed and resuspended in chemically defined medium and added to sterile-culture plates coated with poly-D-lysine and laminin. The medium was replaced 24 hr after plating and then one-half of the medium was replaced every 3-5 days afterwards.

RNA Isolation

For cultured iPSC-derived neurons, RNA isolation and cDNA synthesis were performed using the Cell-to-CT kit (Thermo Fisher Scientific) in a lysate volume of 55 μl.

Analysis of RNA levels

The steady state RNA levels of target transcripts were measured using TaqMan quantitative reverse-transcription PCR (qRT-PCR) assays. Total reaction volume was 10 uL, including 2 μl of cDNA, 1× Gene Expression Master mix (4369016, Thermo Fisher Scientific, Waltham, MA), and 1× TaqMan primer assay (Thermo Fisher Scientific). Cycling conditions were 2 minutes at 50° C., 10 minutes at 95° C., and 40 cycles of 15 seconds at 95° C. and 1 minute at 60° C., with readings taken at the 60° C. step of every cycle. Reactions were run on a BIO-RAD T1000 CFX96 thermocycler (Bio-Rad Laboratories, Hercules CA), with internal control (PPIA, Hs99999904_m1, Thermo Fisher Scientific) and target [UBE3A-AS, Hs01372957_m1; SNORD116-11, Hs04275268_gH; SNORD115, Hs04275288_gH; IPW, Hs03455409_s1; SNORD109A/B, AP47WVR (Thermo Fisher Scientific); UBE3A: forward ATATGTGGAAGCCGGAATCT (SEQ ID NO:500); reverse: CCCAGAACTCCCTAATCAGAA (SEQ ID NO:501); and, probe: ATGACGGTGGCTATACCAGG (SEQ ID NO:502)] reactions performed together. Data was retrieved and analyzed with the BIORAD CFX Maestro software (Bio-Rad Laboratories). Samples with internal control Cq values ≥30 were filtered. Quality of data was visually inspected to identify discrepancies between technical and/or plate replicates. Measurements for inferential statistics and descriptive statistics consist of ΔΔCq values ($2^{-\Delta\Delta Cq}= 2^{-(Cq[target]-Cq[internal\ control])-(Cq[target]-Cq[internal\ control])}$).

Example 2: Identification of ASO Target Region

Analysis of RNA-sequencing data generated from mouse tissues and cells revealed a region located between the 3'-end of the Snord115 cluster and 5'-end of the Ube3a antisense (Ube3a-AS) transcript containing genetic elements believed to be important for processing of the Snord115 host-gene transcript and transcription of Ube3a-AS (FIGS. 6A-6D). Analysis of RNA-sequencing data generated from human tissues revealed a region located between the 3'-end of the SNORD115 cluster and SNORD109B (FIGS. 7A-7G)

that contained elements similar to those observed in mouse; however, comparative analysis of this region indicated that there was little to no sequence conservation between human and rodents.

Materials and Methods

RNA-Sequencing

Figure 8A:
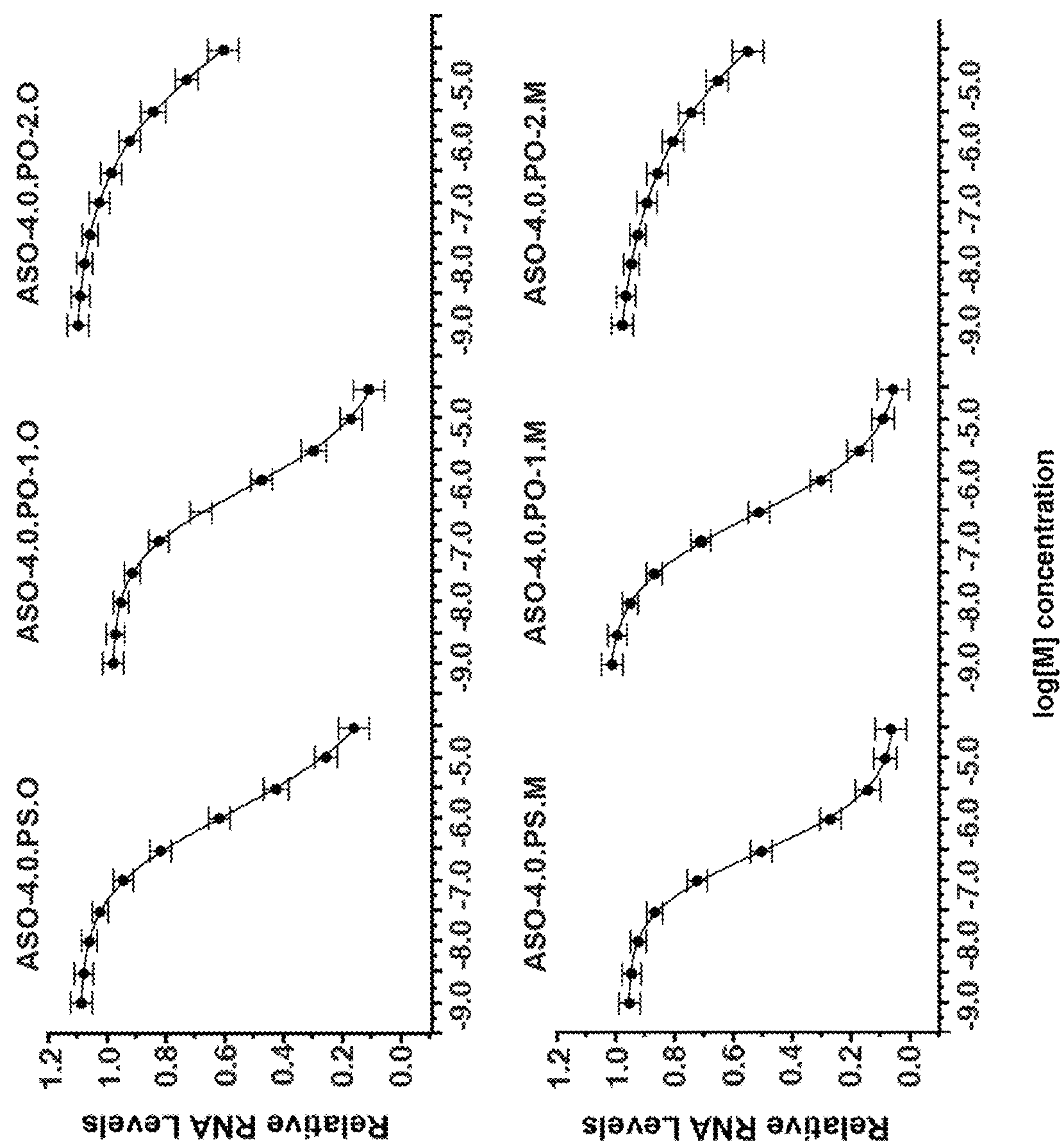
FIGS. 8A to 8C show pharmacodynamic analysis of candidate ASOs.
Figure 8B:
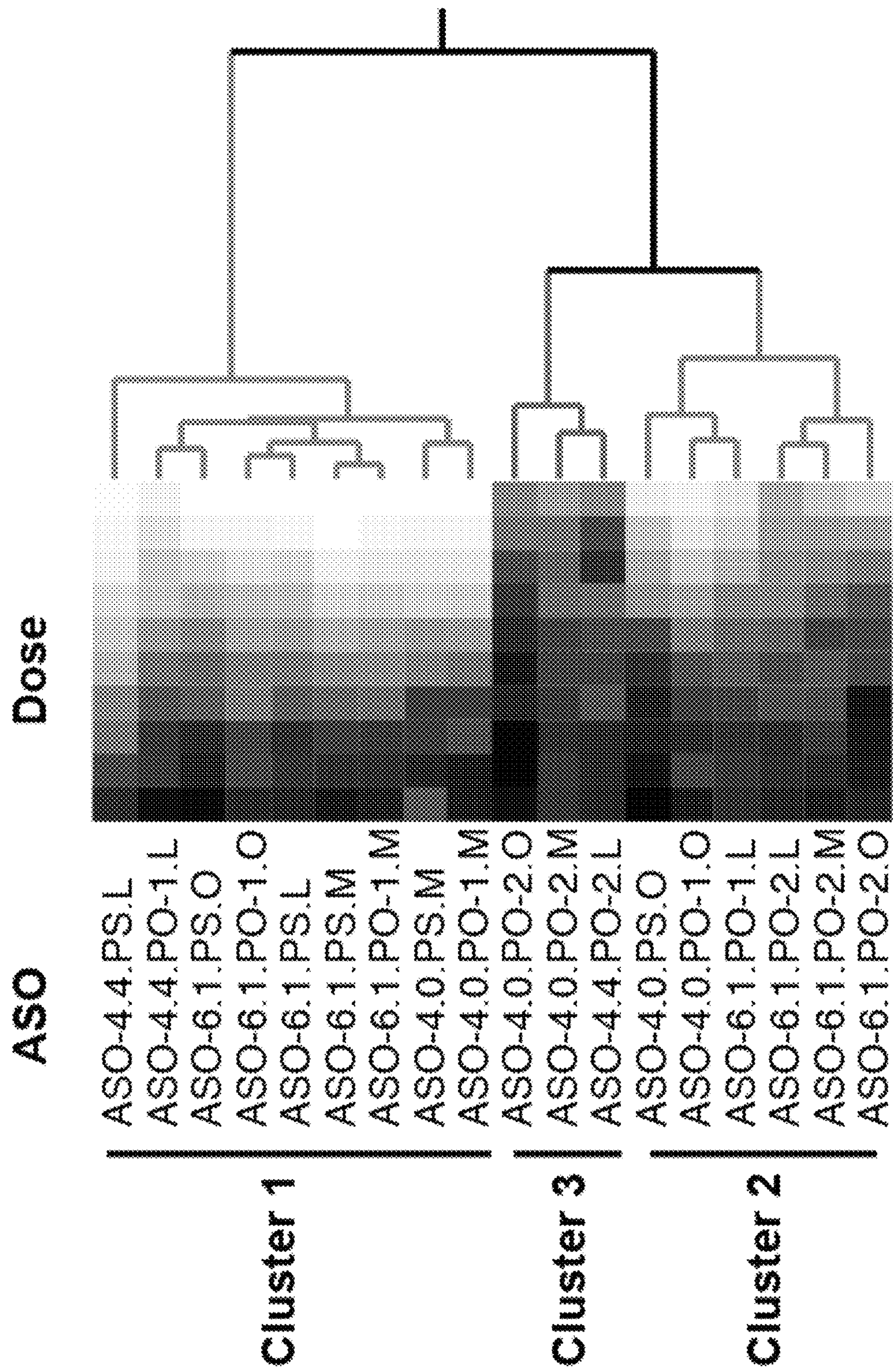
Figure 8C:
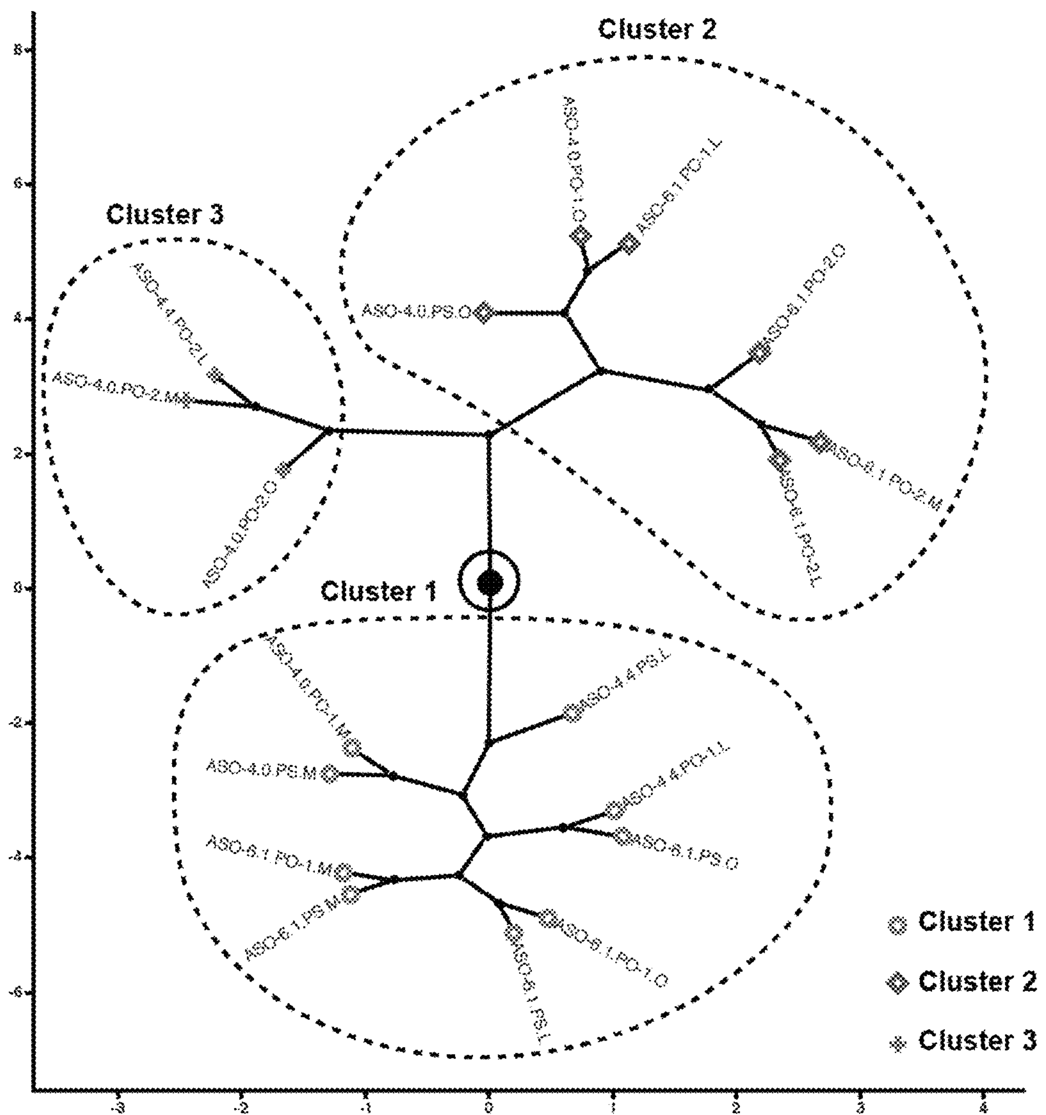

RNA was isolated using Qiagen RNAeasy Plus (74136, Qiagen, Hilden, Germany). RNA concentration was determined using Qubit Fluorometric Quantitation (Thermo Fisher Scientific) and RNA quality was assessed using a 4200 Agilent TapeStation (Agilent, Santa Clara, CA). RNA-sequencing libraries were generated using the Illumina TruSeq Stranded Total RNA kit (20020597, Illumina, Inc., San Diego, CA) according to the manufacturer's protocol. 75 base-pair paired-end sequencing was performed using a NextSeq 500 (Illumina, San Diego, CA) at the Texas A&M Institute for Genome Sciences and Society Genomics core. Raw sequencing reads were processed using CASAVA. The resulting FASTQ sequences were examined using FASTQC.

gic) were treated with a 10-point ½ log dose response curve of each ASO to compare the $IC_{50}$ and $E_{max}$ values. Neural precursor cells were differentiated into neurons for at 18 DIV and then treated with a 10-point ½ log dose response ASOs [1 nM, 3 nM, 10 nM, 30 nM, 100 nM, 300 nM, 1 μM, 3 μM, 10 μM, and 30 μM (n=2)]. At 24 DIV, the steady state RNA levels of UBE3A-AS were measured and dose response curves fitted as described above (FIG. 8A and Table 18). The dose response curves were significantly different (Parallelism test: $F_{(51,606)}=7.86$; $p<0.0001$; R2=0.90), thus relative potencies were not estimated. Hierarchical clustering of the fitted curves revealed 3 Clusters of ASOs, with Cluster 1 representing the 9 most potent ASOs (FIGS. 8B and 8C). Analysis of Cluster 1 indicated that the ASOs had similar curves (Parallelism test: $F_{(24,299)}=1.01$; p=0.5; R2=0.93), and that ASO-4.4.PS.L was at least 3-times as potent as the other ASOs (Table 19). Further analysis, however, indicated that ASO-4.4.PS.L, ASO-6.1.PS.M, and ASO-6.1.PO-1.M had equivalent $IC_{50}$ values, whereas the other ASOs were slightly less potent (Table 20). Based on the relative potencies and internal selection criteria, ASO-4.4.PS.L and ASO-6.1.PO-1.0 were investigated further.

TABLE 18

$IC_{50}$ and $E_{max}$ of Candidate ASOs

| ASO | $IC_{50}$ (M) | $IC_{50}$ 95% CI (M) | | $E_{max}$ | $E_{max}$ 95% CI | | 30 μM (Mean) | Cluster |
|---|---|---|---|---|---|---|---|---|
| ASO-4.4.PS.L | 2.66E−08 | 3.66E−09 | 1.93E−07 | 0.0 | −0.23 | 0.23 | 0.05 | 1 |
| ASO-6.1.PS.M | 1.47E−07 | 6.80E−08 | 3.19E−07 | −0.05 | −0.21 | 0.12 | 0.02 | 1 |
| ASO-6.1.PO-1.M | 1.66E−07 | 7.15E−08 | 3.84E−07 | −0.02 | −0.20 | 0.16 | 0.04 | 1 |
| ASO-4.4.PO-1.L | 2.26E−07 | 8.95E−08 | 5.71E−07 | 0.04 | −0.17 | 0.25 | 0.1 | 1 |
| ASO-4.0.PO-1.M | 2.78E−07 | 1.52E−07 | 5.08E−07 | 0.02 | −0.11 | 0.15 | 0.05 | 1 |
| ASO-4.0.PS.M | 3.00E−07 | 1.80E−07 | 5.00E−07 | 0.05 | −0.06 | 0.15 | 0.05 | 1 |
| ASO-6.1. PO-1.O | 3.15E−07 | 7.98E−08 | 1.24E−06 | −0.1 | −0.50 | 0.26 | 0.04 | 1 |
| ASO-6.1.PS.L | 3.62E−07 | 1.37E−07 | 9.57E−07 | −0.07 | −0.32 | 0.18 | 0.04 | 1 |
| ASO-6.1.PS.O | 5.32E−07 | 1.20E−07 | 2.36E−06 | −0.2 | −0.67 | 0.29 | 0.05 | 1 |
| ASO-6.1.PO-2.L | 7.34E−07 | 5.35E−08 | 1.01E−05 | 0.3 | −0.11 | 0.76 | 0.4 | 2 |
| ASO-4.0.PO-1.O | 7.66E−07 | 3.70E−07 | 1.59E−06 | 0.05 | −0.12 | 0.23 | 0.1 | 2 |
| ASO-4.0.PS.O | 1.27E−06 | 5.13E−07 | 3.13E−06 | 0.06 | −0.20 | 0.31 | 0.1 | 2 |
| ASO-6.1.PO-1.L | 1.89E−06 | 4.42E−07 | 8.06E−06 | 0.03 | −0.34 | 0.39 | 0.2 | 2 |
| ASO-4.0.PO-2.O | 1.30E−04 | 1.65E−17 | 1.03E+09 | −0.3 | −9.51 | 8.94 | 0.6 | 2 |
| ASO-6.1.PO-2.M | 2.69E−04 | 9.85E−16 | 7.37E+07 | −1.2 | −13.16 | 10.77 | 0.3 | 2 |
| ASO-4.4.PO-2.L | 3.27E+01 | 0 | Inf | −2.7 | −577 | 571 | 0.6 | 3 |
| ASO-4.0.PO-2.M | 1.14E+05 | 0 | Inf | −76 | −74,958. | 74,805 | 0.5 | 3 |
| ASO-6.1.PO-2.O | 1.93E+10 | 0 | Inf | −5569 | −85,963,650 | 85,952,510 | 0.3 | 3 |

Full model parameter estimates from 4-parameter logistic regression model (Hill). IC50 and confidence intervals represent molar concentration. Emax and 30 uM values represent normalized UBE3A-AS RNA levels relative to vehicle.
Abbreviations:
Inf, infinity;
95% CI, 95% confidence intervals FASTQ sequences were aligned to the human reference assembly (hg19) using Hisat2 (version 2.1.0), with the following settings: --fr. Aligned SAM sequences were then converted to binary BAM sequences, indexed, and sorted using Samtools. BAM files from individual samples were merged and indexed using Samtools. Aligned sequences were filtered using the view command in Samtools to remove non-uniquely aligned reads (quality >1).

A transcript assembly was generated for merged samples using Stringtie (version 1.3.4.d), with the following options: (stranded) --rf -f 0-j 2. Single exon transcripts were excluded from the assembled transcripts using gffread (GFF utilities, Johns Hopkins University, Center for Computational Biology).

Example 3: Identification of Lead ASOs

Eighteen ASOs targeting the ASO-4 and ASO-6.1 target sequences and consisting of different backbone designs and RNA modifications were designed to identify potential lead ASOs (Table 17). Normal iPSC derived-neurons (GABAer-

TABLE 19

Relative potency of ASOs in Cluster 1

| ASO | $IC_{50}$ (M) | Relative Potency | Std Error |
|---|---|---|---|
| ASO-4.4.PS.L | 5.03E−08 | 1 | 0 |
| ASO-6.1.PS.M | 1.53E−07 | 0.3 | 0.08 |
| ASO-6.1.PO-1.M | 1.77E−07 | 0.3 | 0.07 |
| ASO-6.1.PO-1.O | 1.99E−07 | 0.3 | 0.06 |
| ASO-4.0.PS.M | 2.62E−07 | 0.2 | 0.05 |
| ASO-4.0.PO-1.M | 2.78E−07 | 0.2 | 0.04 |
| ASO-6.1.PS.L | 2.81E−07 | 0.2 | 0.04 |
| ASO-4.4.PO-1.L | 3.22E−07 | 0.2 | 0.04 |
| ASO-6.1.PS.O | 4.32E−07 | 0.1 | 0.03 |

Parallel model parameter estimates from 4 Parameter logistic regression model (Hill).
Abbreviations:
M, molar;
Std, standard

TABLE 20

| Equivalence of ASOs in Cluster 1 Relative to ASO-4.4.PS.L | | | | | |
|---|---|---|---|---|---|
| ASO | ASO | $IC_{50}$ Ratio | Lower and Upper Confidence Limits | | Limit Exceeded |
| ASO-4.4.PS.L | ASO-6.1.PO-1.M | 0.90 | 0.81 | 0.98 | Equivalent |
| | ASO-6.1.PS.M | 0.90 | 0.82 | 0.98 | Equivalent |
| | ASO-4.0.PO-1.M | 0.87 | 0.79 | 0.94 | Lower |
| | ASO-4.0.PS.M | 0.86 | 0.79 | 0.94 | Lower |
| | ASO-4.4.PO-1.L | 0.88 | 0.79 | 0.96 | Lower |
| | ASO-6.1.PO-1.O | 0.86 | 0.77 | 0.95 | Lower |
| | ASO-6.1.PS.L | 0.85 | 0.77 | 0.93 | Lower |
| | ASO-6.1.PS.O | 0.83 | 0.73 | 0.92 | Lower |

Two one-sided Tests

Materials and Methods

Methods were similar to those described in Example 2 unless noted otherwise.

Figure 9:
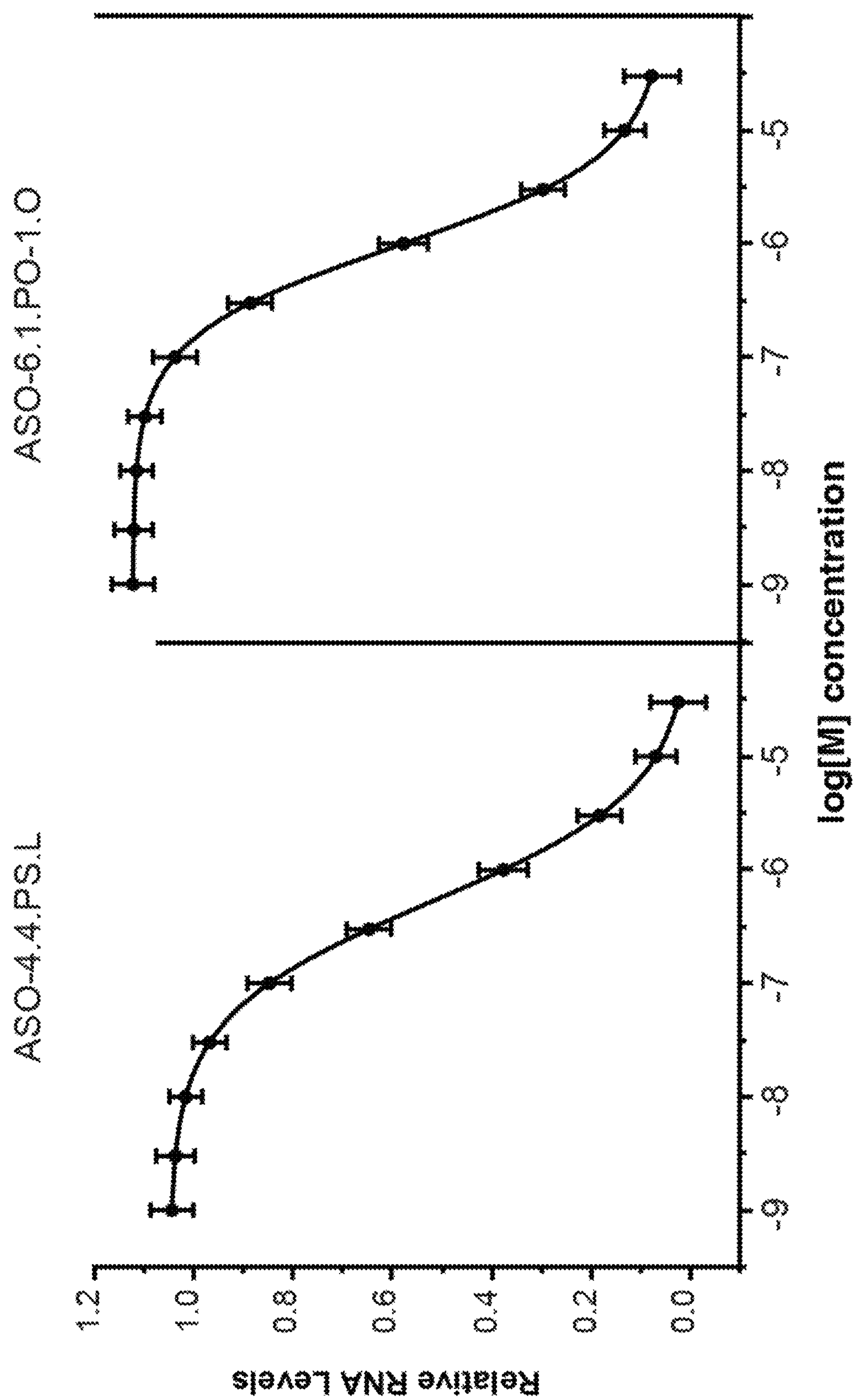
FIG. 9 shows pharmacodynamic analysis of ASO-6.1.PO-1.0 and ASO-4.4.PS.L in Angelman syndrome iPSC-derived neurons. 4-Parameter logistic regression model (Hill) of normalized UBE3A-AS steady state RNA levels in Angelman syndrome iPSC-derived neurons treated with a 10-point ½ log dose curve (1 nM, 3 nM, 10 nM, 30 nM, 100 nM, 300 nM, 1 μM, 3 μM, 10 μM, and 30 μM; n=3) of ASO-6.1.PO-1.0 and ASO-4.4.PS.L.

Example 4: Pharmacodynamic Analysis of ASO-6.1-PO-1.0 and ASO-4.4.PS.L in Angelman Syndrome iPSC Neurons The potencies of ASO-6.1.PS.O and ASO-4.4.PS.L were then examined in iPSC derived-neurons from an Angelman syndrome patient with a maternal derived deletion of the 15q11-q13 region. Induced pluripotent stem cells were differentiated into neurons and then treated with a 10-point ½ log dose response curve of ASO-6.1.PO-1.0 and ASO-4.4.PS.L [1 nM, 3 nM, 10 nM, 30 nM, 100 nM, 300 nM, 1 μM, 3 μM, 10 μM, and 30 μM (n=3)]. Six days following treatment, the steady state RNA levels of UBE3A-AS were measured and dose response curves were fitted as described above (FIG. 9A). The dose response curves were similar between ASOs (Parallelism test: $F_{(3,132)}$=1.07, p=0.4, R2=0.82), with ASO-4.4.PS.L (437 nM) being approximately 2.7-fold more potent than ASO-6.1.PO-1.0 (1.22 uM). The $IC_{50}$ values were equivalent [ASO-6.1.PO-1.0/ASO-4.4.PS.L $IC_{50}$ ratio: =0.96 (Lower confidence limit=0.9; Upper confidence limit=1.0)]. The $E_{max}$ values were similar (30 μM: ASO-4.4.PS.L=0.01±0.0007; ASO-6.1.PO-1.0=0.05±0.004) but not considered equivalent due to the confidence intervals [ASO-6.1.PO-1.0/ASO-4.4.PS.L $E_{max}$ ratio: =−9.1 (Lower confidence limit=−224; Upper confidence limit=205)].

Materials and Methods

Methods were similar to those described in Example 2 unless noted otherwise.

Angelman syndrome induced pluripotent stem cells derived neurons Angelman syndrome iPS cells (AG1-0 iPSCs) (ECN001, Kerafast, Boston, MA) were co-cultured on irradiated murine embryonic fibroblasts in human embryonic stem cell medium [DMEM/F12 (11330-057, Gibco Biosciences, Dublin, Ireland), 20% Knockout Serum Replacement (10828-028, Thermo Fisher Scientific), 1× Non-essential amino acids, 2 mM L-glutamine, 7 μl/mL 2-Mercaptoethanol, and 4 μg/mL basic Fibroblast Growth Factor]. For the first passage, AG1-0 cells were passaged according to the product manual for PluriSTEM Human ES/iPS Medium (SCM130, Millipore Sigma, Burlington, MA), which is feeder-free and utilizes Dispase II (SCM133, Millipore Sigma) to dissociate cells. Matrigel™ hESC-qualified Matrix (354277, Corning BD Biosciences, Corning, NY) was used as an extracellular matrix. At the second passage, the matrix was switched to vitronectin (CC130, Millipore Sigma). During subsequent passages, areas of differentiation were manually removed until differentiated cells represented approximately <5% of the colonies. After four subsequent passages, AG1-0 cells were differentiated using the Millipore ES/iPS Neurogenesis Kit (SCR603, SCM110, and SCM111) but lacking vitronectin as an extracellular matrix. The initial passage was performed with EZ-LiFT (SCM139, Millipore Sigma) to obtain high quality iPS cells. Neural progenitor cells were frozen at stage zero (Po) and subsequently thawed for differentiation. Differentiation was performed on sterile culture plates coated with poly-D-lysine (10 μg/mL) and laminin [10 μg/mL (23017-015, Gibco) in differentiation medium (SCM111) for 10 days of differentiation. In some instances, cells were differentiated in Cellular Dynamics Maintenance Medium (NRM-100-121-001, Cellular Dynamics International, Madison, WI).

Figure 10:
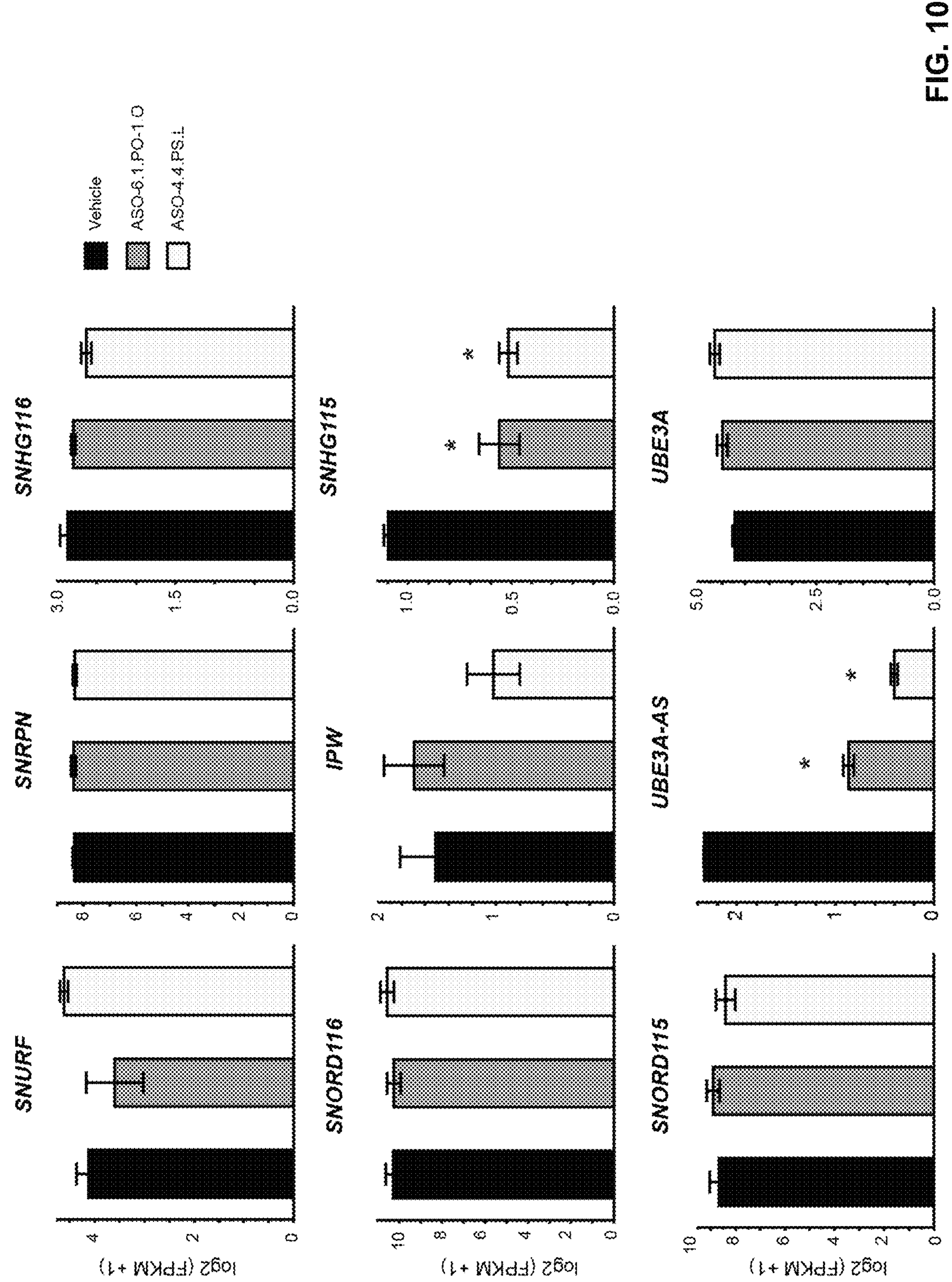
FIG. 10 shows expression analysis of RNAs encoded by the PWS polycistronic transcript in Angelman syndrome iPSC neurons treated with ASO-6.1-PO-1.0 and ASO-4.4.PS.L. Shown are normalized steady state RNA levels of SNURF, SNRPN, SNHG116, SNORD116 snoRNAs, IPW, SNHG115, SNORD115 snoRNAs, UBE3A-AS, and UBE3A in AS iPSC-derived neurons treated with vehicle (1% $H_2O$; n=3), ASO-6.1.PO-1.0 (30 μM; n=3), and ASO-4.4.PS.L (30 μM; n=3). Data represents mean percentage of RNA relative to vehicle. Error bars represent standard error of mean. Asterisk (*) denotes statistically significant differences ($p<0.05$) using one-way ANOVA with Dunnett's multiple comparison test relative to vehicle.

Example 5: Expression Analysis of the PWS Polycistronic Transcript in Angelman Syndrome iPSC Neurons Treated with ASO-6.1-PO-1.0 and ASO-4.4.PS.L To determine whether ASO-4.4.PS.L and ASO-6.1.PO-1.0 affect the levels of RNA transcripts encoded by the PWS polycistronic transcript, RNA-sequencing was performed on AS iPS cells treated with each ASO and the steady state RNA levels of SNURF, SNRPN, the SNORD116 host-gene transcript (SNHG116), the SNORD116 snoRNAs, IPW, the SNORD115 host-gene transcript (SNHG115), the SNORD115 snoRNAs, and UBE3A-AS were quantified. UBE3A steady state RNA levels were also measured. Angelman syndrome iPS cells were differentiated into neurons as described above and then treated with vehicle (1% H2O, n=3), ASO-4.4.PS.L (30 u μM, n=3) and ASO-6.1.PO-1.0 (30 μM, n=3). Six days post-treatment, RNA RNA-sequencing was performed on total RNA (rRNA depleted) isolated from the cultures. To generate annotations of the SNHG116, SNHG115, and UBE3A-AS transcripts, a transcriptome was assembled from the vehicle RNA-seq data and then incorporated into the reference gene annotation. Relative to vehicle, the steady state RNA levels of SNURF, SNRPN, SNHG116, the SNORD116 snoRNAs, and the SNORD115 snoRNAs were similar and not significantly different. ASO-4.4.PS.L, but not ASO-6.1.PO-1.0, reduced IPW levels (1.5-fold), but the effect was not significant. ASO-6.1.PO-1.0 and ASO-4.4.PS.L significantly reduced SNHG115 and UBE3A-AS RNA levels. ASO-6.1.PO-1.0 and ASO-4.4.PS.L had a similar effect on SNHG115 levels; however, ASO-4.4.PS.L had a much larger effect on UBE3A-AS RNA levels than ASO-6.1. PO-1.0 (ASO-4.4.PS.L: −6.1-fold change; ASO-6.1. PO-1.0: −2.8-fold change). ASO treatment increased UBE3A RNA levels by approximately 1.2-fold, but the effect was not significant (FIG. 10 and Table 21).

TABLE 21

Effect of ASO Treatment on RNA Levels of PWS Polycistronic Transcripts and UBE3A

| Gene | Treatment | Difference | Std Error | t Ratio | Adjusted P |
|---|---|---|---|---|---|
| SNURF | ASO-6.1.PO-1.O | −0.53 | 0.51 | −1.02 | 0.5 |
| | ASO-4.4.PS.L | 0.49 | 0.51 | 0.96 | 0.6 |
| SNRPN | ASO-6.1.PO-1.O | 0.03 | 0.11 | 0.30 | 0.9 |
| | ASO-4.4.PS.L | −0.02 | 0.11 | −0.16 | 1.0 |
| SNHG116 | ASO-6.1.PO-1.O | −0.07 | 0.10 | −0.75 | 0.7 |
| | ASO-4.4.PS.L | −0.24 | 0.10 | −2.49 | 0.08 |
| SNORD116 | ASO-6.1.PO-1.O | −0.04 | 0.46 | −0.08 | 1.0 |
| | ASO-4.4.PS.L | 0.27 | 0.45 | 0.60 | 0.8 |
| IPW | ASO-6.1.PO-1.O | 0.18 | 0.37 | 0.49 | 0.8 |
| | ASO-4.4.PS.L | −0.49 | 0.37 | −1.33 | 0.4 |
| SNH115G | ASO-6.1.PO-1.O | −0.55 | 0.09 | −5.92 | 0.002 |
| | ASO-4.4.PS.L | −0.58 | 0.09 | −6.33 | 0.001 |
| SNORD115 | ASO-6.1.PO-1.O | 0.24 | 0.52 | 0.45 | 0.8 |
| | ASO-4.4.PS.L | −0.26 | 0.49 | −0.54 | 0.8 |
| UBE3A-AS | ASO-6.1.PO-1.O | −1.48 | 0.06 | −24.17 | <0.0001 |
| | ASO-4.4.PS.L | −1.94 | 0.06 | −31.56 | <0.0001 |
| UBE3A | ASO-6.1.PO-1.O | 0.74 | 0.48 | 1.53 | 0.3 |
| | ASO-4.4.PS.L | 0.90 | 0.48 | 1.88 | 0.2 |

One way ANOVA with Dunnett's multiple comparison test relative to vehicle.

Materials and Methods

Methods were similar to those described in Example 4 unless noted otherwise.

Differential Expression Analysis of PWS RNAs

Normalized FPKM (fragments per thousand per million) values of the RefSeq gene annotation will be estimated using Cuffnorm with the default settings and the following option: -u. The FPKM values of each gene annotation was determined for each sample from the output file and used for descriptive and inferential statistics.

Figure 11:
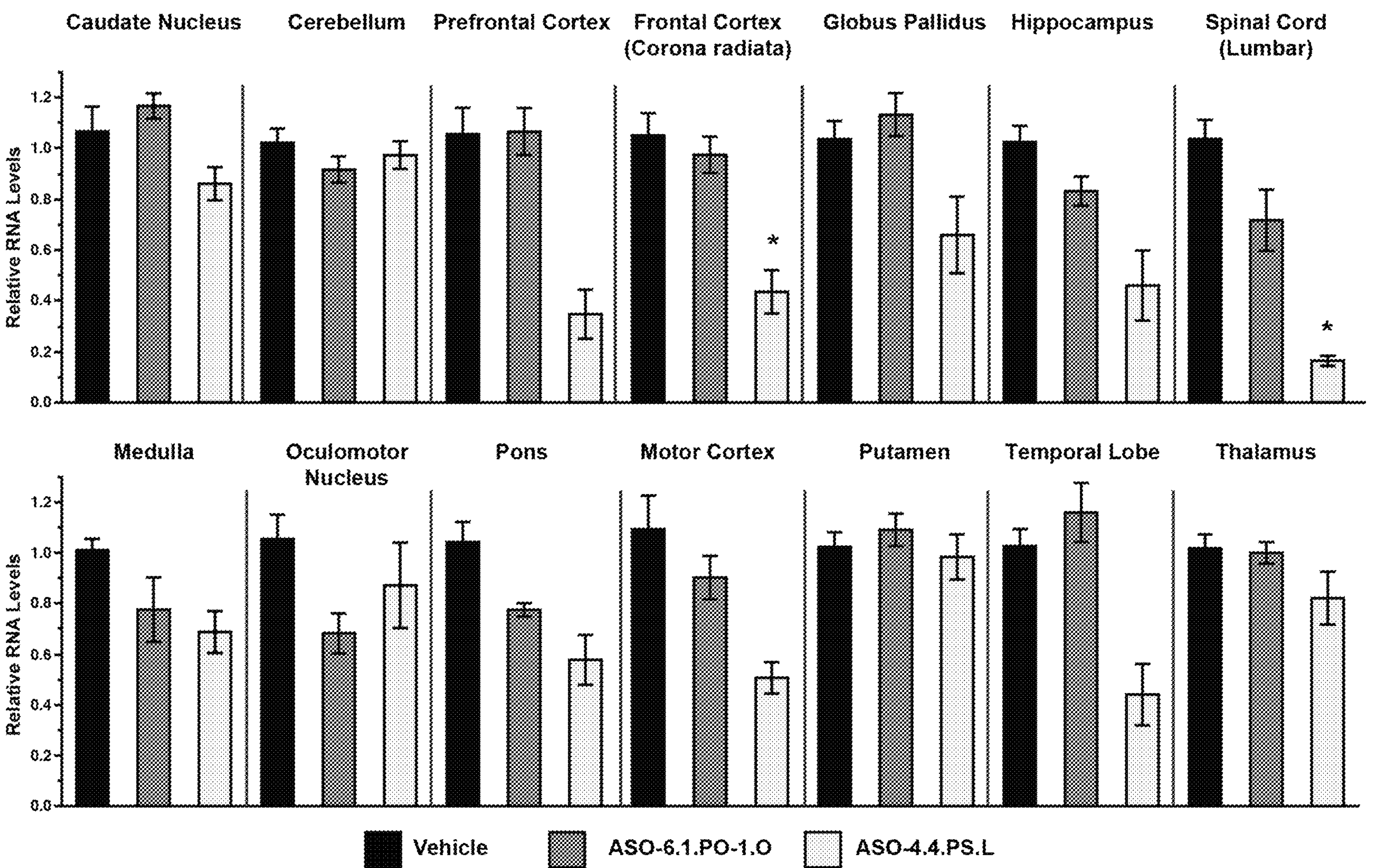
FIG. 11 shows pharmacodynamic analysis of ASO-6.1.PO-1.0 and ASO-4.4.PS.L in Cynomolgus macaque. Shown are steady state RNA levels of UBE3A-AS in macaque CNS regions treated with vehicle (0.9% saline; n=5), ASO-6.1.PO-1.0 (10 mg; n=3), and ASO-4.4.PS.L (10 mg; n=3). Data represents means percentage of UBE3A-AS RNA relative to vehicle. Error bars represent standard error of mean. Asterisk (*) denotes statistically significant differences ($p<0.05$) using one-way ANOVA with Dunnett's multiple comparison test relative to vehicle.

Example 6: Pharmacodynamic Analysis of ASO-6.1-PO-1.0 and ASO-4.4.PS.L in Cynomolgus Macaque The ASO-4 and ASO-6 target regions are conserved across several non-human primate (NHP) species, thus enabling both safety and efficacy studies in a large animal model. To examine the efficacy of ASO-4.4.PS.L and ASO-6.1.PO-1.0 in the central nervous system (CNS), ASOs were delivered to Cynomolgus macaques by intrathecal lumbar puncture. Animals were administered a single bolus injection of vehicle (0.9% saline, n=5), ASO-6.1.PO-1.0 (10 mg, n=3), and ASO.4.4.PS.L (10 mg, n=3). Twenty-eight days following treatment, central nervous (CNS) tissues were collected and the steady state RNA levels of UBE3A-AS were measured. Overall, ASO-4.4.PS.L had a larger effect on UBE3A-AS RNA levels than ASO-6.1.PO-1.0 (Table 22). ASO-4.4.PS.L reduced UBE3A-AS RNA in most CNS regions, with large effects in temporal lobe, primary motor cortex, pons, medulla, hippocampus, globus pallidus, frontal cortex (corona *radiata*), prefrontal cortex, and lumbar spinal cord. Similarly, ASO-6.1.PO-1.0 reduced UBE3A-AS RNA levels in most CNS regions, with large effects observed in pons, oculomotor nucleus, and lumbar spinal cord (FIG. 11 and Table 23).

TABLE 22

Effect Size of ASO Treatment on UBE3A-AS RNA Levels in CNS

| Treatment | Treatment* | Cohen's d | 95% Confidence Intervals | | FDR |
|---|---|---|---|---|---|
| Vehicle | ASO-4.4.PS.L | 1.4 | 1.0 | 1.8 | 2.3E−10 |
| ASO-6.1.PO-1.O | ASO-4.4.PS.L | 1.0 | 0.6 | 1.5 | 6.4E−06 |
| Vehicle | ASO-6.1.PO-1.O | 0.3 | −0.06 | 0.7 | 0.09 |

Students t-test with FDR adjusted P values
Cohen's d effect sizes: 0.2, small; 0.5, medium; 0.8, large; 1.2, very large
Abbreviations:
FDR, false discovery rate

TABLE 23

Effect of ASO Treatment on UBE3A-AS RNA Levels in CNS Regions

| CNS Region | ASO | Difference | Std Error | t Ratio | Adjusted P |
|---|---|---|---|---|---|
| Caudate Nucleus | ASO-6.1.PO-1.O | 0.10 | 0.22 | 0.46 | 0.9 |
| | ASO-4.4.PS.L | −0.21 | 0.22 | −0.94 | 0.6 |
| Cerebellum | ASO-6.1.PO-1.O | −0.11 | 0.09 | −1.15 | 0.5 |
| | ASO-4.4.PS.L | −0.05 | 0.09 | −0.53 | 0.8 |
| Frontal cortex | ASO-6.1.PO-1.O | 0.01 | 0.27 | 0.04 | 0.9 |
| | ASO-4.4.PS.L | −0.71 | 0.27 | −2.66 | 0.05 |
| Frontal Cortex | ASO-6.1.PO-1.O | −0.08 | 0.22 | −0.34 | 0.9 |
| (Corona radiata) | ASO-4.4.PS.L | −0.62 | 0.22 | −2.79 | 0.04 |
| Globus Pallidus | ASO-6.1.PO-1.O | 0.10 | 0.24 | 0.40 | 0.9 |
| | ASO-4.4.PS.L | −0.38 | 0.24 | −1.54 | 0.3 |
| Hippocampus | ASO-6.1.PO-1.O | −0.19 | 0.21 | −0.91 | 0.6 |
| | ASO-4.4.PS.L | −0.57 | 0.21 | −2.66 | 0.05 |
| Spinal Cord | ASO-6.1.PO-1.O | −0.32 | 0.20 | −1.63 | 0.2 |
| (Lumbar) | ASO-4.4.PS.L | −0.87 | 0.20 | −4.46 | 0.004 |
| Medulla | ASO-6.1.PO-1.O | −0.24 | 0.20 | −1.16 | 0.45 |
| | ASO-4.4.PS.L | −0.32 | 0.20 | −1.59 | 0.3 |
| Oculomotor | ASO-6.1.PO-1.O | −0.37 | 0.29 | −1.27 | 0.4 |
| Nucleus | ASO-4.4.PS.L | −0.18 | 0.29 | −0.62 | 0.8 |
| Pons | ASO-6.1.PO-1.O | −0.27 | 0.21 | −1.30 | 0.4 |
| | ASO-4.4.PS.L | −0.47 | 0.21 | −2.25 | 0.1 |
| Motor Cortex | ASO-6.1.PO-1.O | −0.19 | 0.30 | −0.65 | 0.8 |
| | ASO-4.4.PS.L | −0.59 | 0.30 | −1.99 | 0.1 |
| Putamen | ASO-6.1.PO-1.O | 0.07 | 0.15 | 0.44 | 0.9 |
| | ASO-4.4.PS.L | −0.04 | 0.15 | −0.25 | 0.9 |
| Temporal Lobe | ASO-6.1.PO-1.O | 0.13 | 0.25 | 0.54 | 0.8 |
| | ASO-4.4.PS.L | −0.59 | 0.25 | −2.39 | 0.08 |
| Thalamus | ASO-6.1.PO-1.O | −0.02 | 0.14 | −0.14 | 0.9 |
| | ASO-4.4.PS.L | −0.20 | 0.14 | −1.46 | 0.3 |

One way ANOVA with Dunnett's multiple comparison test relative to vehicle.

Materials and Methods

Administration of A SOs

NHP studies were performed at Northern Biomedical Research and Charles River Laboratories using protocols approved by the institutions respective Institutional Animal Care and Use Committees. Male and female Cynomolgus macaques (*Macaca fascicularis*) weighing 2-4 kg were anesthetized and single 1 mL dose of ASO or vehicle was administered via intrathecal lumbar puncture. The dosing solution was prepared by dissolution of lyophilized ASO in the vehicle control article (0.9% sodium chloride) and was filtered through a 0.2-μm filter. CNS and spinal cord samples were harvested, and the CNS was sectioned into 4-mm coronal slices. Tissue samples were flash frozen and stored at −80° C. until RNA isolation.

RNA Isolation

A 4 mm tissue punch was taken from each region of interest of which approximately half was used for RNA isolation. RNA isolation was performed using the Qiagen RNeasy Plus Mini kit (74136, Qiagen) with tissue disruption and lysis performed with 5 mm stainless steel beads in a TissueLyser II. The RNA was eluted in two volumes of 30 μl water, for a total elution volume of 60 μl. RNA was quantified using the Qubit with the RNA XR assay (Q33224, Thermo Fisher Scientific). cDNA was synthesized from 2 μg of input RNA using the High Capacity RNA-to-cDNA kit (4387406, Thermo Fisher Scientific) in a total reaction volume of 50 μl.

Analysis of UBE3A-AS RNA levels in tissues

Cynomolgus macaque UBE3A-AS RNA levels were estimated using SYBR Green quantitative reverse-transcription PCR (qRT-PCR). Total reaction volume was 10 μl, including 2 μl of cDNA, 1× PowerUp SYBR Green Master mix (A25741, Thermo Fisher Scientific), and 500 nM of each primer (forward and reverse). Cycling conditions were 2 minutes at 50° C., 2 minutes at 95° C., and 40 cycles of 15 seconds at 95° C. and 1 minute at 60° C., with readings taken at the 60° C. step of every cycle. Reactions were run on a BIO-RAD T1000 CFX96 thermocycler, with internal control (PPIA, forward: GTCTCCTTCGAGCTGTTTGC (SEQ ID NO:503); reverse: CCTTTCTCTCCAGTGCTCAGA (SEQ ID NO:504)) and target (UBE3A-AS, forward: CCTGTGAACTTTCAACCAGGA (SEQ ID NO:505); reverse: GGATCAGACTCCAGGCCTTC (SEQ ID NO:506)) reactions performed separately. Data was retrieved and initial analysis was done with the BIORAD CFX Maestro software, with in depth statistical analyses performed with Excel and JMP.

Example 7: ASOs Targeting Exonic Boundaries of Spliced UBE3A-AS Transcripts

In some embodiments, the target sequence is an exonic boundary involving UBE3A-AS exons 1-5 and SNORD109B exons 1-2. Target sequences consist of 38 nucleotides (19 nucleotides of each exon) centered on the exonic boundary of each exon (19 nucleotides representing the 5' and 3'-ends of adjacent exons). There were 12 segments of sequences, with exonic boundaries involving segments 1-2, 2-3, 3-4, 5-6, 7-8, 9-10, and 11-12. The chromosomal coordinates are provided in Table 24. A single merged junction sequence was created that shows the spliced exons (I, exonic junction) and intervening exonic sequences ([ ]). ASOs (20-, 19, and 18-mer) targeting the exonic junctions are provided in Table 25.

```
(SEQ ID NO: 489)
AATGAAATCTTCTGATTTG|TAAGACATGCTGCCAAGAG[]ATTAGTTT

TACACCTTCAG|GATAAAGACTGCTGAGAAG[]GTTTAAGGATGCTATT

CTG|AAAAGACTGTGGAGGAAGA[]TTAAGGAAACCATCTCTGG|GATA

AGGATGACTGAGGAA[]ATTTAAGGATGCCACTCTG|GTTAAAAGCTGA

AACAACT[]GAAACTTCAGGGAAAAGAG|AAGGCCTGGAATCTGATCC.
| = 3'-5' exonic junction
[] = intervening exonic sequence
```

TABLE 24

Chromosome 15 coordinates of targeted exonic junctions

| Segment | Start | End | Exonic Region |
|---|---|---|---|
| 1 | 25,511,743 | 25,511,761 | 3' |
| 2 | 25,512,059 | 25,512,079 | 5' |
| 3 | 25,512,175 | 25,512,191 | 3' |
| 4 | 25,513,475 | 25,513,493 | 5' |
| 5 | 25,513,582 | 25,513,600 | 3' |
| 6 | 25,514,752 | 25,514,770 | 5' |
| 7 | 25,514,863 | 25,514,881 | 3' |
| 8 | 25,516,564 | 25,516,582 | 5' |
| 9 | 25,516,663 | 25,516,681 | 3' |
| 10 | 25,522,514 | 25,522,532 | 5' |
| 11 | 25,522,537 | 25,522,556 | 3' |
| 12 | 25,523,994 | 25,524,012 | 5' |

Human chromosome 15 coordinates (hg19 reference assembly)

TABLE 25

List of Junction ASOs and corresponding target regions

| ASO size | Target Sequence (5'-3') | | ASO sequence (5'-3') | |
|---|---|---|---|---|
| 20-mer | GAAACCAUCUCUGGGAUAAG | SEQ ID NO: 393 | CTTATCCCAGAGATGGTTTC | SEQ ID NO: 441 |
| | AAACCAUCUCUGGGAUAAGG | SEQ ID NO: 394 | CCTTATCCCAGAGATGGTTT | SEQ ID NO: 442 |
| | AACCAUCUCUGGGAUAAGGA | SEQ ID NO: 395 | TCCTTATCCCAGAGATGGTT | SEQ ID NO: 443 |
| | ACCAUCUCUGGGAUAAGGAU | SEQ ID NO: 396 | ATCCTTATCCCAGAGATGGT | SEQ ID NO: 444 |
| | CCAUCUCUGGGAUAAGGAUG | SEQ ID NO: 397 | CATCCTTATCCCAGAGATGG | SEQ ID NO: 445 |
| | CAUCUCUGGGAUAAGGAUGA | SEQ ID NO: 398 | TCATCCTTATCCCAGAGATG | SEQ ID NO: 446 |
| | AUCUCUGGGAUAAGGAUGAC | SEQ ID NO: 399 | GTCATCCTTATCCCAGAGAT | SEQ ID NO: 447 |
| | UCUCUGGGAUAAGGAUGACU | SEQ ID NO: 400 | AGTCATCCTTATCCCAGAGA | SEQ ID NO: 448 |
| | CUCUGGGAUAAGGAUGACUG | SEQ ID NO: 401 | CAGTCATCCTTATCCCAGAG | SEQ ID NO: 449 |
| | UCUGGGAUAAGGAUGACUGA | SEQ ID NO: 402 | TCAGTCATCCTTATCCCAGA | SEQ ID NO: 450 |
| | CUGGGAUAAGGAUGACUGAG | SEQ ID NO: 403 | CTCAGTCATCCTTATCCCAG | SEQ ID NO: 451 |
| | UGGGAUAAGGAUGACUGAGG | SEQ ID NO: 404 | CCTCAGTCATCCTTATCCCA | SEQ ID NO: 452 |
| | GGGAUAAGGAUGACUGAGGA | SEQ ID NO: 405 | TCCTCAGTCATCCTTATCCC | SEQ ID NO: 453 |
| | GGAUAAGGAUGACUGAGGAA | SEQ ID NO: 406 | TTCCTCAGTCATCCTTATCC | SEQ ID NO: 454 |
| | GCUGAAACAACUGAAACUUC | SEQ ID NO: 407 | GAAGTTTCAGTTGTTTCAGC | SEQ ID NO: 455 |
| | GAAACAACUGAAACUUCAGG | SEQ ID NO: 408 | CCTGAAGTTTCAGTTGTTTC | SEQ ID NO: 456 |
| | AAACAACUGAAACUUCAGGG | SEQ ID NO: 409 | CCCTGAAGTTTCAGTTGTTT | SEQ ID NO: 457 |
| | AACAACUGAAACUUCAGGGA | SEQ ID NO: 410 | TCCCTGAAGTTTCAGTTGTT | SEQ ID NO: 458 |
| | ACAACUGAAACUUCAGGGAA | SEQ ID NO: 411 | TTCCCTGAAGTTTCAGTTGT | SEQ ID NO: 459 |
| | CAACUGAAACUUCAGGGAAA | SEQ ID NO: 412 | TTTCCCTGAAGTTTCAGTTG | SEQ ID NO: 460 |
| | ACUGAAACUUCAGGGAAAAG | SEQ ID NO: 413 | CTTTTCCCTGAAGTTTCAGT | SEQ ID NO: 461 |

TABLE 25-continued

List of Junction ASOs and corresponding target regions

| ASO size | Target Sequence (5'-3') | | ASO sequence (5'-3') | |
|---|---|---|---|---|
| 19-mer | AACCAUCUCUGGGAUAAGG | SEQ ID NO: 414 | CCTTATCCCAGAGATGGTT | SEQ ID NO: 462 |
| | ACCAUCUCUGGGAUAAGGA | SEQ ID NO: 415 | TCCTTATCCCAGAGATGGT | SEQ ID NO: 463 |
| | CCAUCUCUGGGAUAAGGAU | SEQ ID NO: 416 | ATCCTTATCCCAGAGATGG | SEQ ID NO: 464 |
| | CAUCUCUGGGAUAAGGAUG | SEQ ID NO: 417 | CATCCTTATCCCAGAGATG | SEQ ID NO: 465 |
| | AUCUCUGGGAUAAGGAUGA | SEQ ID NO: 418 | TCATCCTTATCCCAGAGAT | SEQ ID NO: 466 |
| | UCUCUGGGAUAAGGAUGAC | SEQ ID NO: 419 | GTCATCCTTATCCCAGAGA | SEQ ID NO: 467 |
| | CUCUGGGAUAAGGAUGACU | SEQ ID NO: 420 | AGTCATCCTTATCCCAGAG | SEQ ID NO: 468 |
| | UCUGGGAUAAGGAUGACUG | SEQ ID NO: 421 | CAGTCATCCTTATCCCAGA | SEQ ID NO: 469 |
| | CUGGGAUAAGGAUGACUGA | SEQ ID NO: 422 | TCAGTCATCCTTATCCCAG | SEQ ID NO: 470 |
| | UGGGAUAAGGAUGACUGAG | SEQ ID NO: 423 | CTCAGTCATCCTTATCCCA | SEQ ID NO: 471 |
| | GGGAUAAGGAUGACUGAGG | SEQ ID NO: 424 | CCTCAGTCATCCTTATCCC | SEQ ID NO: 472 |
| | GGAUAAGGAUGACUGAGGA | SEQ ID NO: 425 | TCCTCAGTCATCCTTATCC | SEQ ID NO: 473 |
| | AACAACUGAAACUUCAGGG | SEQ ID NO: 426 | CCCTGAAGTTTCAGTTGTT | SEQ ID NO: 474 |
| | ACAACUGAAACUUCAGGGA | SEQ ID NO: 427 | TCCCTGAAGTTTCAGTTGT | SEQ ID NO: 475 |
| | CAACUGAAACUUCAGGGAA | SEQ ID NO: 428 | TTCCCTGAAGTTTCAGTTG | SEQ ID NO: 476 |
| | CAACUGAAACUUCAGGGAA | SEQ ID NO: 429 | TTCCCTGAAGTTTCAGTTG | SEQ ID NO: 477 |
| 18-mer | CCAUCUCUGGGAUAAGGA | SEQ ID NO: 430 | TCCTTATCCCAGAGATGG | SEQ ID NO: 478 |
| | CAUCUCUGGGAUAAGGAU | SEQ ID NO: 431 | ATCCTTATCCCAGAGATG | SEQ ID NO: 479 |
| | AUCUCUGGGAUAAGGAUG | SEQ ID NO: 432 | CATCCTTATCCCAGAGAT | SEQ ID NO: 480 |
| | UCUCUGGGAUAAGGAUGA | SEQ ID NO: 433 | TCATCCTTATCCCAGAGA | SEQ ID NO: 481 |
| | CUCUGGGAUAAGGAUGAC | SEQ ID NO: 434 | GTCATCCTTATCCCAGAG | SEQ ID NO: 482 |
| | UCUGGGAUAAGGAUGACU | SEQ ID NO: 435 | AGTCATCCTTATCCCAGA | SEQ ID NO: 483 |
| | CUGGGAUAAGGAUGACUG | SEQ ID NO: 436 | CAGTCATCCTTATCCCAG | SEQ ID NO: 484 |
| | UGGGAUAAGGAUGACUGA | SEQ ID NO: 437 | TCAGTCATCCTTATCCCA | SEQ ID NO: 485 |
| | GGGAUAAGGAUGACUGAG | SEQ ID NO: 438 | CTCAGTCATCCTTATCCC | SEQ ID NO: 486 |
| | GGAUAAGGAUGACUGAGG | SEQ ID NO: 439 | CCTCAGTCATCCTTATCC | SEQ ID NO: 487 |
| | ACAACUGAAACUUCAGGG | SEQ ID NO: 440 | CCCTGAAGTTTCAGTTGT | SEQ ID NO: 488 |

Example 8: siRNA, shRNA, and CRISPR Guide RNAs Targeting UBE3a-AS Exons 1-5

As noted above, in some embodiments, the disclosed oligonucleotide is a functional nucleic acid, such as a siRNA, shRNA, or nuclease gRNA, that inhibits, mutates, or deletes the target nucleic acid sequence.

Examples of siRNA targeting UBE3a-AS exons 1-5 are provided in Table 26. Examples of shRNA targeting UBE3a-AS exons 1-5 are provided in Table 27. Examples of gRNA targeting UBE3a-AS exons 1-5 are provided in Table 28.

TABLE 26 siRNA targeting UBE3a-AS exons 1-5

| Target sequence | | siRNA | |
|---|---|---|---|
| CCCAGGUGUCCUUUAAUGAA | SEQ ID NO: 507 | TTCATTAAAGGACACCTGGG | SEQ ID NO: 538 |
| CCAGGUGUCCUUUAAUGAAA | SEQ ID NO: 508 | TTTCATTAAAGGACACCTGG | SEQ ID NO: 539 |
| UGAAAAUGCUCUUGACACCA | SEQ ID NO: 509 | TGGTGTCAAGAGCATTTTCA | SEQ ID NO: 540 |
| GAAAAUGCUCUUGACACCAA | SEQ ID NO: 510 | TTGGTGTCAAGAGCATTTTC | SEQ ID NO: 541 |
| AAAUGCUCUUGACACCAAUG | SEQ ID NO: 511 | CATTGGTGTCAAGAGCATTT | SEQ ID NO: 542 |
| AGAUCAGUAGCUUCCUUUAC | SEQ ID NO: 512 | GTAAAGGAAGCTACTGATCT | SEQ ID NO: 543 |
| UCAGUAGCUUCCUUUACCGA | SEQ ID NO: 513 | TCGGTAAAGGAAGCTACTGA | SEQ ID NO: 544 |
| UCUAGAACAUUGAGCUAUGG | SEQ ID NO: 514 | CCATAGCTCAATGTTCTAGA | SEQ ID NO: 545 |
| CUAGAACAUUGAGCUAUGGA | SEQ ID NO: 515 | TCCATAGCTCAATGTTCTAG | SEQ ID NO: 546 |
| AACAUUGAGCUAUGGAAGAC | SEQ ID NO: 516 | GTCTTCCATAGCTCAATGTT | SEQ ID NO: 547 |
| ACAUUGAGCUAUGGAAGACU | SEQ ID NO: 517 | AGTCTTCCATAGCTCAATGT | SEQ ID NO: 548 |
| CUAUGGAAGACUCCCACCUA | SEQ ID NO: 518 | TAGGTGGGAGTCTTCCATAG | SEQ ID NO: 549 |
| UAUGGAAGACUCCCACCUAA | SEQ ID NO: 519 | TTAGGTGGGAGTCTTCCATA | SEQ ID NO: 550 |

TABLE 26-continued

| siRNA targeting UBE3a-AS exons 1-5 | | | |
|---|---|---|---|
| Target sequence | | siRNA | |
| CAAGUGCUACCGCACAGGCA | SEQ ID NO: 520 | TGCCTGTGCGGTAGCACTTG | SEQ ID NO: 551 |
| AAGUGCUACCGCACAGGCAU | SEQ ID NO: 521 | ATGCCTGTGCGGTAGCACTT | SEQ ID NO: 552 |
| UACCGCACAGGCAUGCUGCA | SEQ ID NO: 522 | TGCAGCATGCCTGTGCGGTA | SEQ ID NO: 553 |
| CAGGCAUGCUGCAGUGAAUU | SEQ ID NO: 523 | AATTCACTGCAGCATGCCTG | SEQ ID NO: 554 |
| AGGCAUGCUGCAGUGAAUUU | SEQ ID NO: 524 | AAATTCACTGCAGCATGCCT | SEQ ID NO: 555 |
| ACCGUUGUUUAAGGAUGCUA | SEQ ID NO: 525 | TAGCATCCTTAAACAACGGT | SEQ ID NO: 556 |
| CCGUUGUUUAAGGAUGCUAU | SEQ ID NO: 526 | ATAGCATCCTTAAACAACGG | SEQ ID NO: 557 |
| CUGUGGAGGAAGAAAACCCU | SEQ ID NO: 527 | AGGGTTTTCTTCCTCCACAG | SEQ ID NO: 558 |
| AAGAAAACCCUUUACCCUGU | SEQ ID NO: 528 | ACAGGGTAAAGGGTTTTCTT | SEQ ID NO: 559 |
| AGAAAACCCUUUACCCUGUU | SEQ ID NO: 529 | AACAGGGTAAAGGGTTTTCT | SEQ ID NO: 560 |
| CUCAACUGCCUGGCACUGAA | SEQ ID NO: 530 | TTCAGTGCCAGGCAGTTGAG | SEQ ID NO: 561 |
| AACUGCCUGGCACUGAAAAU | SEQ ID NO: 531 | ATTTTCAGTGCCAGGCAGTT | SEQ ID NO: 562 |
| ACUGCCUGGCACUGAAAAUG | SEQ ID NO: 532 | CATTTTCAGTGCCAGGCAGT | SEQ ID NO: 563 |
| GUGUUUAAGGAAACCAUCUC | SEQ ID NO: 533 | GAGATGGTTTCCTTAAACAC | SEQ ID NO: 564 |
| GUUUAAGGAAACCAUCUCUG | SEQ ID NO: 534 | CAGAGATGGTTTCCTTAAAC | SEQ ID NO: 565 |
| AGGAAACCAUCUCUGAUAAG | SEQ ID NO: 535 | CTTATCAGAGATGGTTTCCT | SEQ ID NO: 566 |
| UCUUUGGCUUGUUGACACCA | SEQ ID NO: 536 | TGGTGTCAACAAGCCAAAGA | SEQ ID NO: 567 |
| CUUUGGCUUGUUGACACCAG | SEQ ID NO: 537 | CTGGTGTCAACAAGCCAAAG | SEQ ID NO: 568 |

TABLE 27

| shRNA targeting UBE3a-AS exons 1-5 | |
|---|---|
| GGTGCCATTCTATTATAAAtaacctgacccattaTTTATAATAGAATGGCACCTTTTT | SEQ ID NO: 569 |
| GCTTTCATCAATAATGAAAtaacctgacccattaTTTCATTATTGATGAAAGCTTTTT | SEQ ID NO: 570 |
| GGTCTTTCATCAATAATGAtaacctgacccattaTCATTATTGATGAAAGACCTTTTT | SEQ ID NO: 571 |
| GAAATCTTCTGATTTGTAAtaacctgacccattaTTACAAATCAGAAGATTTCTTTTT | SEQ ID NO: 572 |
| GCACCTAAGGGAATTAGTAtaacctgacccattaTACTAATTCCCTTAGGTGCTTTTT | SEQ ID NO: 573 |
| GTTTCAACCAGGATTTAAAtaacctgacccattaTTTAAATCCTGGTTGAAACTTTTT | SEQ ID NO: 574 |
| GCTTTCAACCAGGATTTAAtaacctgacccattaTTAAATCCTGGTTGAAAGCTTTTT | SEQ ID NO: 575 |
| GGAGATGTGCCATTCTATAtaacctgacccattaTATAGAATGGCACATCTCCTTTTT | SEQ ID NO: 576 |
| GTCTTTCATCAATAATGAAtaacctgacccattaTTCATTATTGATGAAAGACTTTTT | SEQ ID NO: 577 |
| GATCAATAATGAAATCTTAtaacctgacccattaTAAGATTTCATTATTGATCTTTTT | SEQ ID NO: 578 |
| GTGTCTTTCATCAATAATAtaacctgacccattaTATTATTGATGAAAGACACTTTTT | SEQ ID NO: 579 |
| GCAATAATGAAATCTTCTAtaacctgacccattaTAGAAGATTTCATTATTGCTTTTT | SEQ ID NO: 580 |
| GCATGCTGCAGTGAATTTAtaacctgacccattaTAAATTCACTGCAGCATGCTTTTT | SEQ ID NO: 581 |
| GGAAATCTTCTGATTTGTAtaacctgacccattaTACAAATCAGAAGATTTCCTTTTT | SEQ ID NO: 582 |
| GGTATATTCTATCTAGAAAtaacctgacccattaTTTCTAGATAGAATATACCTTTTT | SEQ ID NO: 583 |
| GTGCTGCAGTGAATTTAAAtaacctgacccattaTTTAAATTCACTGCAGCACTTTTT | SEQ ID NO: 584 |

TABLE 27-continued

| shRNA targeting UBE3a-AS exons 1-5 | |
|---|---|
| GTGTGCCATTCTATTATAAtaacctgacccattaTTATAATAGAATGGCACACTTTTT | SEQ ID NO: 585 |
| GTTACCATCAGTGTTTAAAtaacctgacccattaTTTAAACACTGATGGTAACTTTTT | SEQ ID NO: 586 |
| GCCTGCAACCGTTGTTTAAtaacctgacccattaTTAAACAACGGTTGCAGGCTTTTT | SEQ ID NO: 587 |
| GTATGTCTTTCATCAATAAtaacctgacccattaTTATTGATGAAAGACATACTTTTT | SEQ ID NO: 588 |

TABLE 28

| CRISPR Guide RNAs targeting UBE3a-AS exons 1-5 | | | |
|---|---|---|---|
| Strand | Sequence | SEQ ID | PAM |
| - | ACACTGATGGTAAAGTGGAC | SEQ ID NO: 589 | TGG |
| - | TAGAATATACACGTCGGTAA | SEQ ID NO: 590 | AGG |
| - | TCAACTGTCCCAGTCACAAC | SEQ ID NO: 591 | AGG |
| - | TCTAGATAGAATATACACGT | SEQ ID NO: 592 | CGG |
| - | TCTAGATAGAATATACACGT | SEQ ID NO: 593 | CGG |
| - | CTCCCCATGCACACTTGAGA | SEQ ID NO: 594 | AGG |
| - | CATCCTTAAACAACGGTTGC | SEQ ID NO: 595 | AGG |
| - | GGTGTAAAACTAATTCCCTT | SEQ ID NO: 596 | AGG |
| - | AACAACGGTTGCAGGGACAG | SEQ ID NO: 597 | AGG |
| + | TATGGAAGACTCCCACCTAA | SEQ ID NO: 598 | GGG |
| + | CTATGGAAGACTCCCACCTA | SEQ ID NO: 599 | AGG |

TABLE 28-continued

| CRISPR Guide RNAs targeting UBE3a-AS exons 1-5 | | | |
|---|---|---|---|
| Strand | Sequence | SEQ ID | PAM |
| + | AAGCCTTCTCAAGTGTGCAT | SEQ ID NO: 600 | GGG |
| + | CTATCTAGAACATTGAGCTA | SEQ ID NO: 601 | TGG |
| + | ACCCTCTGGTGTTGTCACAG | SEQ ID NO: 602 | AGG |
| + | AACCCTTTACCCTGTTGTTC | SEQ ID NO: 603 | AGG |

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A modified oligonucleotide comprising a contiguous nucleotide sequence of 13 to 30 nucleotides in length with nucleic acid complementarity to a contiguous portion of the nucleotide sequence set forth in SEQ ID NO: 2, wherein the modified oligonucleotide comprises from 5' to 3' (a) a first segment comprising 3-5 modified ribonucleotides, (b) a second segment comprising at least 7 deoxyribonucleotides, and (c) a third segment comprising 3-5 modified ribonucleotides.

2. The modified oligonucleotide of claim 1, comprising a sequence having nucleic acid sequence complementarity to a nucleotide sequence selected from the group consisting of SEQ ID NOs: 18 to 66.

3. The modified oligonucleotide of claim 1, comprising a sequence selected from the group consisting of SEQ ID NO: 67 to 115.

4. The modified oligonucleotide of claim 1, wherein the modified ribonucleotides of the first segment or the third segment are independently selected from the group consisting of 2-O-alkyl-RNA, 2'-O-methyl-RNA, 2'-alkoxy-RNA, 2-O-methoxyethyl-RNA, 2'-amino-DNA, 2'fluoro-DNA, arabino nucleic acid (ANA), 2-fluoro-ANA, and locked nucleic acid (LNA) nucleoside.

5. The modified oligonucleotide of claim 1, comprising at least one modified internucleoside linkage.

6. The modified oligonucleotide of claim 5, wherein the at least one modified internucleoside linkage comprises a phosphorothioate internucleoside linkage.

7. The modified oligonucleotide of claim 6, wherein the modified oligonucleotide is fully phosphorothioate-modified.

8. The modified oligonucleotide of claim 1, wherein the modified oligonucleotide targets the 5' end of UBE3A-AS transcript and increases UBE3A expression in a target cell.

9. The modified oligonucleotide of claim 1, wherein the modified oligonucleotide is conjugated to one or more non-nucleotide moiety.

10. The modified oligonucleotide of claim 9, wherein the one or more non-nucleotide moiety is selected from the group consisting of carbohydrates, cell surface receptor ligands, drug substances, hormones, lipophilic substances, polymers, proteins, peptides, toxins, vitamins, and viral proteins.

11. The modified oligonucleotide of claim 10, wherein the non-nucleotide moiety is an antibody or antibody fragment.

12. The modified oligonucleotide of claim 11, wherein the antibody or antibody fragment facilitates delivery across the blood-brain-barrier.

13. The modified oligonucleotide of claim 12, wherein the antibody of or antibody fragment targets the transferrin receptor.

* * * * *

SEQUENCE LISTING

```
Sequence total quantity: 605
SEQ ID NO: 1            moltype = DNA  length = 184
FEATURE                 Location/Qualifiers
misc_feature            1..184
                        note = Synthetic Construct
source                  1..184
                        mol_type = other DNA
                        organism = synthetic construct
SEQUENCE: 1
atgatgatat ggaagaaaag cactctttgg cctgttgtga ctgggacagt tgacagcacc  60
caggtgtcct ttaatgaaaa tgctcttgac accaatgcat cctagcatca cagcttcagg  120
aagccttctc aagtgtgcat ggggagtact atgtctttca tcaataatga aatcttctga  180
tttg                                                               184

SEQ ID NO: 2            moltype = DNA  length = 133
FEATURE                 Location/Qualifiers
misc_feature            1..133
                        note = Synthetic Construct
source                  1..133
                        mol_type = other DNA
                        organism = synthetic construct
SEQUENCE: 2
taagacatgc tgccaagaga tgtgccattc tattataaaa gatcagtagc ttcctttacc  60
gacgtgtata ttctatctag aacattgagc tatggaagac tcccacctaa gggaattagt  120
tttacacctt cag                                                     133

SEQ ID NO: 3            moltype = DNA  length = 125
FEATURE                 Location/Qualifiers
misc_feature            1..125
                        note = Synthetic Construct
source                  1..125
                        mol_type = other DNA
```

```
                        organism = synthetic construct
SEQUENCE: 3
ataaagactg ctgagaagag caccctctgg tgttgtcaca gaggcaagtg ctaccgcaca  60
ggcatgctgc agtgaattta actgatcctc tgtccctgca accgttgttt aaggatgcta  120
ttctg                                                              125

SEQ ID NO: 4            moltype = DNA  length = 129
FEATURE                 Location/Qualifiers
misc_feature            1..129
                        note = Synthetic Construct
source                  1..129
                        mol_type = other DNA
                        organism = synthetic construct
SEQUENCE: 4
aaaagactgt ggaggaagaa aaccctttac cctgttgttc agggagaaac tgacaccact  60
caactgcctg gcactgaaaa tgtggcatcc agtccacttt accatcagtg tttaaggaaa  120
ccatctctg                                                          129

SEQ ID NO: 5            moltype = DNA  length = 117
FEATURE                 Location/Qualifiers
misc_feature            1..117
                        note = Synthetic Construct
source                  1..117
                        mol_type = other DNA
                        organism = synthetic construct
SEQUENCE: 5
ataaggatga ctgaggaaga gtactctttg gcttgttgac accagcacag ctgacacacc  60
cagatatctg tttggtctcc tgtgaacttt caaccaggat ttaaggatgc cactctg     117

SEQ ID NO: 6            moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 6
tagaggtgaa ggccaggcac                                              20

SEQ ID NO: 7            moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 7
gtactcttcc tcagtcatcc                                              20

SEQ ID NO: 8            moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 8
tgtcagtttc tccctgaaca                                              20

SEQ ID NO: 9            moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 9
tagaatggca catctcttgg                                              20

SEQ ID NO: 10           moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 10
gttttcttcc tccacagtct                                              20
```

```
SEQ ID NO: 11           moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 11
ctggtgtcaa caagccaaag                                               20

SEQ ID NO: 12           moltype = RNA  length = 18
FEATURE                 Location/Qualifiers
misc_feature            1..18
                        note = Synthetic Construct
source                  1..18
                        mol_type = other RNA
                        organism = synthetic construct
SEQUENCE: 12
gaaaatgctc ttgacacc                                                 18

SEQ ID NO: 13           moltype = RNA  length = 19
FEATURE                 Location/Qualifiers
misc_feature            1..19
                        note = Synthetic Construct
source                  1..19
                        mol_type = other RNA
                        organism = synthetic construct
SEQUENCE: 13
gaaaatgctc ttgacacca                                                19

SEQ ID NO: 14           moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 14
gaaaatgctc ttgacaccaa                                               20

SEQ ID NO: 15           moltype = DNA  length = 18
FEATURE                 Location/Qualifiers
misc_feature            1..18
                        note = Synthetic Construct
source                  1..18
                        mol_type = other DNA
                        organism = synthetic construct
SEQUENCE: 15
ggtgtcaaga gcattttc                                                 18

SEQ ID NO: 16           moltype = DNA  length = 19
FEATURE                 Location/Qualifiers
misc_feature            1..19
                        note = Synthetic Construct
source                  1..19
                        mol_type = other DNA
                        organism = synthetic construct
SEQUENCE: 16
tggtgtcaag agcattttc                                                19

SEQ ID NO: 17           moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 17
ttggtgtcaa gagcattttc                                               20

SEQ ID NO: 18           moltype = RNA  length = 18
FEATURE                 Location/Qualifiers
misc_feature            1..18
                        note = Synthetic Construct
source                  1..18
                        mol_type = other RNA
                        organism = synthetic construct
SEQUENCE: 18
catgctgcca agagatgt                                                 18
```

```
SEQ ID NO: 19           moltype = RNA  length = 19
FEATURE                 Location/Qualifiers
misc_feature            1..19
                        note = Synthetic Construct
source                  1..19
                        mol_type = other RNA
                        organism = synthetic construct
SEQUENCE: 19
catgctgcca agagatgtg                                              19

SEQ ID NO: 20           moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 20
catgctgcca agagatgtgc                                             20

SEQ ID NO: 21           moltype = RNA  length = 18
FEATURE                 Location/Qualifiers
misc_feature            1..18
                        note = Synthetic Construct
source                  1..18
                        mol_type = other RNA
                        organism = synthetic construct
SEQUENCE: 21
atgctgccaa gagatgtg                                               18

SEQ ID NO: 22           moltype = RNA  length = 19
FEATURE                 Location/Qualifiers
misc_feature            1..19
                        note = Synthetic Construct
source                  1..19
                        mol_type = other RNA
                        organism = synthetic construct
SEQUENCE: 22
atgctgccaa gagatgtgc                                              19

SEQ ID NO: 23           moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 23
atgctgccaa gagatgtgcc                                             20

SEQ ID NO: 24           moltype = RNA  length = 19
FEATURE                 Location/Qualifiers
misc_feature            1..19
                        note = Synthetic Construct
source                  1..19
                        mol_type = other RNA
                        organism = synthetic construct
SEQUENCE: 24
tgctgccaag agatgtgcc                                              19

SEQ ID NO: 25           moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 25
tgctgccaag agatgtgcca                                             20

SEQ ID NO: 26           moltype = RNA  length = 19
FEATURE                 Location/Qualifiers
misc_feature            1..19
                        note = Synthetic Construct
source                  1..19
                        mol_type = other RNA
                        organism = synthetic construct
SEQUENCE: 26
```

```
gctgccaaga gatgtgcca                                               19

SEQ ID NO: 27          moltype = RNA  length = 20
FEATURE                Location/Qualifiers
misc_feature           1..20
                       note = Synthetic Construct
source                 1..20
                       mol_type = other RNA
                       organism = synthetic construct
SEQUENCE: 27
gctgccaaga gatgtgccat                                              20

SEQ ID NO: 28          moltype = RNA  length = 18
FEATURE                Location/Qualifiers
misc_feature           1..18
                       note = Synthetic Construct
source                 1..18
                       mol_type = other RNA
                       organism = synthetic construct
SEQUENCE: 28
ctgccaagag atgtgcca                                                18

SEQ ID NO: 29          moltype = RNA  length = 19
FEATURE                Location/Qualifiers
misc_feature           1..19
                       note = Synthetic Construct
source                 1..19
                       mol_type = other RNA
                       organism = synthetic construct
SEQUENCE: 29
ctgccaagag atgtgccat                                               19

SEQ ID NO: 30          moltype = RNA  length = 20
FEATURE                Location/Qualifiers
misc_feature           1..20
                       note = Synthetic Construct
source                 1..20
                       mol_type = other RNA
                       organism = synthetic construct
SEQUENCE: 30
ctgccaagag atgtgccatt                                              20

SEQ ID NO: 31          moltype = RNA  length = 18
FEATURE                Location/Qualifiers
misc_feature           1..18
                       note = Synthetic Construct
source                 1..18
                       mol_type = other RNA
                       organism = synthetic construct
SEQUENCE: 31
tgccaagaga tgtgccat                                                18

SEQ ID NO: 32          moltype = RNA  length = 19
FEATURE                Location/Qualifiers
misc_feature           1..19
                       note = Synthetic Construct
source                 1..19
                       mol_type = other RNA
                       organism = synthetic construct
SEQUENCE: 32
tgccaagaga tgtgccatt                                               19

SEQ ID NO: 33          moltype = RNA  length = 20
FEATURE                Location/Qualifiers
misc_feature           1..20
                       note = Synthetic Construct
source                 1..20
                       mol_type = other RNA
                       organism = synthetic construct
SEQUENCE: 33
tgccaagaga tgtgccattc                                              20

SEQ ID NO: 34          moltype = RNA  length = 18
FEATURE                Location/Qualifiers
misc_feature           1..18
                       note = Synthetic Construct
source                 1..18
                       mol_type = other RNA
                       organism = synthetic construct
```

```
SEQUENCE: 34
gccaagagat gtgccatt                                                    18

SEQ ID NO: 35           moltype = RNA  length = 19
FEATURE                 Location/Qualifiers
misc_feature            1..19
                        note = Synthetic Construct
source                  1..19
                        mol_type = other RNA
                        organism = synthetic construct
SEQUENCE: 35
gccaagagat gtgccattc                                                   19

SEQ ID NO: 36           moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 36
gccaagagat gtgccattct                                                  20

SEQ ID NO: 37           moltype = RNA  length = 18
FEATURE                 Location/Qualifiers
misc_feature            1..18
                        note = Synthetic Construct
source                  1..18
                        mol_type = other RNA
                        organism = synthetic construct
SEQUENCE: 37
ccaagagatg tgccattc                                                    18

SEQ ID NO: 38           moltype = RNA  length = 19
FEATURE                 Location/Qualifiers
misc_feature            1..19
                        note = Synthetic Construct
source                  1..19
                        mol_type = other RNA
                        organism = synthetic construct
SEQUENCE: 38
ccaagagatg tgccattct                                                   19

SEQ ID NO: 39           moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 39
ccaagagatg tgccattcta                                                  20

SEQ ID NO: 40           moltype = RNA  length = 18
FEATURE                 Location/Qualifiers
misc_feature            1..18
                        note = Synthetic Construct
source                  1..18
                        mol_type = other RNA
                        organism = synthetic construct
SEQUENCE: 40
caagagatgt gccattct                                                    18

SEQ ID NO: 41           moltype = RNA  length = 19
FEATURE                 Location/Qualifiers
misc_feature            1..19
                        note = Synthetic Construct
source                  1..19
                        mol_type = other RNA
                        organism = synthetic construct
SEQUENCE: 41
caagagatgt gccattcta                                                   19

SEQ ID NO: 42           moltype = RNA  length = 20
FEATURE                 Location/Qualifiers
misc_feature            1..20
                        note = Synthetic Construct
source                  1..20
                        mol_type = other RNA
```

```
                          organism = synthetic construct
SEQUENCE: 42
caagagatgt gccattctat                                                20

SEQ ID NO: 43             moltype = RNA  length = 18
FEATURE                   Location/Qualifiers
misc_feature              1..18
                          note = Synthetic Construct
source                    1..18
                          mol_type = other RNA
                          organism = synthetic construct
SEQUENCE: 43
tcctttaccg acgtgtat                                                  18

SEQ ID NO: 44             moltype = RNA  length = 19
FEATURE                   Location/Qualifiers
misc_feature              1..19
                          note = Synthetic Construct
source                    1..19
                          mol_type = other RNA
                          organism = synthetic construct
SEQUENCE: 44
tcctttaccg acgtgtata                                                 19

SEQ ID NO: 45             moltype = RNA  length = 20
FEATURE                   Location/Qualifiers
misc_feature              1..20
                          note = Synthetic Construct
source                    1..20
                          mol_type = other RNA
                          organism = synthetic construct
SEQUENCE: 45
tcctttaccg acgtgtatat                                                20

SEQ ID NO: 46             moltype = RNA  length = 18
FEATURE                   Location/Qualifiers
misc_feature              1..18
                          note = Synthetic Construct
source                    1..18
                          mol_type = other RNA
                          organism = synthetic construct
SEQUENCE: 46
cctttaccga cgtgtata                                                  18

SEQ ID NO: 47             moltype = RNA  length = 19
FEATURE                   Location/Qualifiers
misc_feature              1..19
                          note = Synthetic Construct
source                    1..19
                          mol_type = other RNA
                          organism = synthetic construct
SEQUENCE: 47
cctttaccga cgtgtatat                                                 19

SEQ ID NO: 48             moltype = RNA  length = 20
FEATURE                   Location/Qualifiers
misc_feature              1..20
                          note = Synthetic Construct
source                    1..20
                          mol_type = other RNA
                          organism = synthetic construct
SEQUENCE: 48
cctttaccga cgtgtatatt                                                20

SEQ ID NO: 49             moltype = RNA  length = 20
FEATURE                   Location/Qualifiers
misc_feature              1..20
                          note = Synthetic Construct
source                    1..20
                          mol_type = other RNA
                          organism = synthetic construct
SEQUENCE: 49
accgacgtgt atattctatc                                                20

SEQ ID NO: 50             moltype = RNA  length = 19
FEATURE                   Location/Qualifiers
misc_feature              1..19
                          note = Synthetic Construct
source                    1..19
```

```
                        mol_type = other RNA
                        organism = synthetic construct
SEQUENCE: 50
ccgacgtgta tattctatc                                                19

SEQ ID NO: 51           moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 51
ccgacgtgta tattctatct                                               20

SEQ ID NO: 52           moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 52
tctagaacat tgagctatgg                                               20

SEQ ID NO: 53           moltype = RNA  length = 18
FEATURE                 Location/Qualifiers
misc_feature            1..18
                        note = Synthetic Construct
source                  1..18
                        mol_type = other RNA
                        organism = synthetic construct
SEQUENCE: 53
cattgagcta tggaagac                                                 18

SEQ ID NO: 54           moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 54
ctatggaaga ctcccaccta                                               20

SEQ ID NO: 55           moltype = RNA  length = 19
FEATURE                 Location/Qualifiers
misc_feature            1..19
                        note = Synthetic Construct
source                  1..19
                        mol_type = other RNA
                        organism = synthetic construct
SEQUENCE: 55
tatggaagac tcccaccta                                                19

SEQ ID NO: 56           moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 56
tatggaagac tcccacctaa                                               20

SEQ ID NO: 57           moltype = RNA  length = 18
FEATURE                 Location/Qualifiers
misc_feature            1..18
                        note = Synthetic Construct
source                  1..18
                        mol_type = other RNA
                        organism = synthetic construct
SEQUENCE: 57
atggaagact cccaccta                                                 18

SEQ ID NO: 58           moltype = RNA  length = 19
FEATURE                 Location/Qualifiers
misc_feature            1..19
                        note = Synthetic Construct
```

```
source                  1..19
                        mol_type = other RNA
                        organism = synthetic construct
SEQUENCE: 58
atggaagact cccacctaa                                                19

SEQ ID NO: 59           moltype = RNA  length = 18
FEATURE                 Location/Qualifiers
misc_feature            1..18
                        note = Synthetic Construct
source                  1..18
                        mol_type = other RNA
                        organism = synthetic construct
SEQUENCE: 59
tggaagactc ccacctaa                                                 18

SEQ ID NO: 60           moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 60
gactcccacc taagggaatt                                               20

SEQ ID NO: 61           moltype = RNA  length = 18
FEATURE                 Location/Qualifiers
misc_feature            1..18
                        note = Synthetic Construct
source                  1..18
                        mol_type = other RNA
                        organism = synthetic construct
SEQUENCE: 61
actcccacct aagggaat                                                 18

SEQ ID NO: 62           moltype = RNA  length = 19
FEATURE                 Location/Qualifiers
misc_feature            1..19
                        note = Synthetic Construct
source                  1..19
                        mol_type = other RNA
                        organism = synthetic construct
SEQUENCE: 62
actcccacct aagggaatt                                                19

SEQ ID NO: 63           moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 63
actcccacct aagggaatta                                               20

SEQ ID NO: 64           moltype = RNA  length = 18
FEATURE                 Location/Qualifiers
misc_feature            1..18
                        note = Synthetic Construct
source                  1..18
                        mol_type = other RNA
                        organism = synthetic construct
SEQUENCE: 64
ctcccaccta agggaatt                                                 18

SEQ ID NO: 65           moltype = RNA  length = 19
FEATURE                 Location/Qualifiers
misc_feature            1..19
                        note = Synthetic Construct
source                  1..19
                        mol_type = other RNA
                        organism = synthetic construct
SEQUENCE: 65
ctcccaccta agggaatta                                                19

SEQ ID NO: 66           moltype = RNA  length = 18
FEATURE                 Location/Qualifiers
misc_feature            1..18
```

```
                        note = Synthetic Construct
source                  1..18
                        mol_type = other RNA
                        organism = synthetic construct
SEQUENCE: 66
tcccacctaa gggaatta                                             18

SEQ ID NO: 67           moltype = DNA  length = 18
FEATURE                 Location/Qualifiers
misc_feature            1..18
                        note = Synthetic Construct
source                  1..18
                        mol_type = other DNA
                        organism = synthetic construct
SEQUENCE: 67
acatctcttg gcagcatg                                             18

SEQ ID NO: 68           moltype = DNA  length = 19
FEATURE                 Location/Qualifiers
misc_feature            1..19
                        note = Synthetic Construct
source                  1..19
                        mol_type = other DNA
                        organism = synthetic construct
SEQUENCE: 68
cacatctctt ggcagcatg                                            19

SEQ ID NO: 69           moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 69
gcacatctct tggcagcatg                                           20

SEQ ID NO: 70           moltype = DNA  length = 18
FEATURE                 Location/Qualifiers
misc_feature            1..18
                        note = Synthetic Construct
source                  1..18
                        mol_type = other DNA
                        organism = synthetic construct
SEQUENCE: 70
cacatctctt ggcagcat                                             18

SEQ ID NO: 71           moltype = DNA  length = 19
FEATURE                 Location/Qualifiers
misc_feature            1..19
                        note = Synthetic Construct
source                  1..19
                        mol_type = other DNA
                        organism = synthetic construct
SEQUENCE: 71
gcacatctct tggcagcat                                            19

SEQ ID NO: 72           moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 72
ggcacatctc ttggcagcat                                           20

SEQ ID NO: 73           moltype = DNA  length = 19
FEATURE                 Location/Qualifiers
misc_feature            1..19
                        note = Synthetic Construct
source                  1..19
                        mol_type = other DNA
                        organism = synthetic construct
SEQUENCE: 73
ggcacatctc ttggcagca                                            19

SEQ ID NO: 74           moltype = DNA  length = 20
FEATURE                 Location/Qualifiers
```

```
misc_feature            1..20
                        note = Synthetic Construct
source                  1..20
                        mol_type = other DNA
                        organism = synthetic construct
SEQUENCE: 74
tggcacatct cttggcagca                                                20

SEQ ID NO: 75           moltype = DNA  length = 19
FEATURE                 Location/Qualifiers
misc_feature            1..19
                        note = Synthetic Construct
source                  1..19
                        mol_type = other DNA
                        organism = synthetic construct
SEQUENCE: 75
tggcacatct cttggcagc                                                 19

SEQ ID NO: 76           moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 76
atggcacatc tcttggcagc                                                20

SEQ ID NO: 77           moltype = DNA  length = 18
FEATURE                 Location/Qualifiers
misc_feature            1..18
                        note = Synthetic Construct
source                  1..18
                        mol_type = other DNA
                        organism = synthetic construct
SEQUENCE: 77
tggcacatct cttggcag                                                  18

SEQ ID NO: 78           moltype = DNA  length = 19
FEATURE                 Location/Qualifiers
misc_feature            1..19
                        note = Synthetic Construct
source                  1..19
                        mol_type = other DNA
                        organism = synthetic construct
SEQUENCE: 78
atggcacatc tcttggcag                                                 19

SEQ ID NO: 79           moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 79
aatggcacat ctcttggcag                                                20

SEQ ID NO: 80           moltype = DNA  length = 18
FEATURE                 Location/Qualifiers
misc_feature            1..18
                        note = Synthetic Construct
source                  1..18
                        mol_type = other DNA
                        organism = synthetic construct
SEQUENCE: 80
atggcacatc tcttggca                                                  18

SEQ ID NO: 81           moltype = DNA  length = 19
FEATURE                 Location/Qualifiers
misc_feature            1..19
                        note = Synthetic Construct
source                  1..19
                        mol_type = other DNA
                        organism = synthetic construct
SEQUENCE: 81
aatggcacat ctcttggca                                                 19

SEQ ID NO: 82           moltype = DNA  length = 20
```

```
FEATURE                Location/Qualifiers
misc_feature           1..20
                       note = Synthetic Construct
source                 1..20
                       mol_type = other DNA
                       organism = synthetic construct
SEQUENCE: 82
gaatggcaca tctcttggca                                              20

SEQ ID NO: 83          moltype = DNA  length = 18
FEATURE                Location/Qualifiers
misc_feature           1..18
                       note = Synthetic Construct
source                 1..18
                       mol_type = other DNA
                       organism = synthetic construct
SEQUENCE: 83
aatggcacat ctcttggc                                                18

SEQ ID NO: 84          moltype = DNA  length = 19
FEATURE                Location/Qualifiers
misc_feature           1..19
                       note = Synthetic Construct
source                 1..19
                       mol_type = other DNA
                       organism = synthetic construct
SEQUENCE: 84
gaatggcaca tctcttggc                                               19

SEQ ID NO: 85          moltype = DNA  length = 20
FEATURE                Location/Qualifiers
misc_feature           1..20
                       note = Synthetic Construct
source                 1..20
                       mol_type = other DNA
                       organism = synthetic construct
SEQUENCE: 85
agaatggcac atctcttggc                                              20

SEQ ID NO: 86          moltype = DNA  length = 18
FEATURE                Location/Qualifiers
misc_feature           1..18
                       note = Synthetic Construct
source                 1..18
                       mol_type = other DNA
                       organism = synthetic construct
SEQUENCE: 86
gaatggcaca tctcttgg                                                18

SEQ ID NO: 87          moltype = DNA  length = 19
FEATURE                Location/Qualifiers
misc_feature           1..19
                       note = Synthetic Construct
source                 1..19
                       mol_type = other DNA
                       organism = synthetic construct
SEQUENCE: 87
agaatggcac atctcttgg                                               19

SEQ ID NO: 88          moltype = DNA  length = 20
FEATURE                Location/Qualifiers
misc_feature           1..20
                       note = Synthetic Construct
source                 1..20
                       mol_type = other DNA
                       organism = synthetic construct
SEQUENCE: 88
tagaatggca catctcttgg                                              20

SEQ ID NO: 89          moltype = DNA  length = 18
FEATURE                Location/Qualifiers
misc_feature           1..18
                       note = Synthetic Construct
source                 1..18
                       mol_type = other DNA
                       organism = synthetic construct
SEQUENCE: 89
agaatggcac atctcttg                                                18
```

```
SEQ ID NO: 90           moltype = DNA  length = 19
FEATURE                 Location/Qualifiers
misc_feature            1..19
                        note = Synthetic Construct
source                  1..19
                        mol_type = other DNA
                        organism = synthetic construct
SEQUENCE: 90
tagaatggca catctcttg                                            19

SEQ ID NO: 91           moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 91
atagaatggc acatctcttg                                           20

SEQ ID NO: 92           moltype = DNA  length = 18
FEATURE                 Location/Qualifiers
misc_feature            1..18
                        note = Synthetic Construct
source                  1..18
                        mol_type = other DNA
                        organism = synthetic construct
SEQUENCE: 92
atacacgtcg gtaaagga                                             18

SEQ ID NO: 93           moltype = DNA  length = 19
FEATURE                 Location/Qualifiers
misc_feature            1..19
                        note = Synthetic Construct
source                  1..19
                        mol_type = other DNA
                        organism = synthetic construct
SEQUENCE: 93
tatacacgtc ggtaaagga                                            19

SEQ ID NO: 94           moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 94
atatacacgt cggtaaagga                                           20

SEQ ID NO: 95           moltype = DNA  length = 18
FEATURE                 Location/Qualifiers
misc_feature            1..18
                        note = Synthetic Construct
source                  1..18
                        mol_type = other DNA
                        organism = synthetic construct
SEQUENCE: 95
tatacacgtc ggtaaagg                                             18

SEQ ID NO: 96           moltype = DNA  length = 19
FEATURE                 Location/Qualifiers
misc_feature            1..19
                        note = Synthetic Construct
source                  1..19
                        mol_type = other DNA
                        organism = synthetic construct
SEQUENCE: 96
atatacacgt cggtaaagg                                            19

SEQ ID NO: 97           moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 97
aatatacacg tcggtaaagg                                           20
```

```
SEQ ID NO: 98           moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 98
gatagaatat acacgtcggt                                              20

SEQ ID NO: 99           moltype = DNA  length = 19
FEATURE                 Location/Qualifiers
misc_feature            1..19
                        note = Synthetic Construct
source                  1..19
                        mol_type = other DNA
                        organism = synthetic construct
SEQUENCE: 99
gatagaatat acacgtcgg                                               19

SEQ ID NO: 100          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 100
agatagaata tacacgtcgg                                              20

SEQ ID NO: 101          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 101
ccatagctca atgttctaga                                              20

SEQ ID NO: 102          moltype = DNA  length = 18
FEATURE                 Location/Qualifiers
misc_feature            1..18
                        note = Synthetic Construct
source                  1..18
                        mol_type = other DNA
                        organism = synthetic construct
SEQUENCE: 102
gtcttccata gctcaatg                                                18

SEQ ID NO: 103          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 103
taggtgggag tcttccatag                                              20

SEQ ID NO: 104          moltype = DNA  length = 19
FEATURE                 Location/Qualifiers
misc_feature            1..19
                        note = Synthetic Construct
source                  1..19
                        mol_type = other DNA
                        organism = synthetic construct
SEQUENCE: 104
taggtgggag tcttccata                                               19

SEQ ID NO: 105          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 105
```

```
ttaggtggga gtcttccata                                                20

SEQ ID NO: 106          moltype = DNA  length = 18
FEATURE                 Location/Qualifiers
misc_feature            1..18
                        note = Synthetic Construct
source                  1..18
                        mol_type = other DNA
                        organism = synthetic construct
SEQUENCE: 106
taggtgggag tcttccat                                                  18

SEQ ID NO: 107          moltype = DNA  length = 19
FEATURE                 Location/Qualifiers
misc_feature            1..19
                        note = Synthetic Construct
source                  1..19
                        mol_type = other DNA
                        organism = synthetic construct
SEQUENCE: 107
ttaggtggga gtcttccat                                                 19

SEQ ID NO: 108          moltype = DNA  length = 18
FEATURE                 Location/Qualifiers
misc_feature            1..18
                        note = Synthetic Construct
source                  1..18
                        mol_type = other DNA
                        organism = synthetic construct
SEQUENCE: 108
ttaggtggga gtcttcca                                                  18

SEQ ID NO: 109          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 109
aattccctta ggtgggagtc                                                20

SEQ ID NO: 110          moltype = DNA  length = 18
FEATURE                 Location/Qualifiers
misc_feature            1..18
                        note = Synthetic Construct
source                  1..18
                        mol_type = other DNA
                        organism = synthetic construct
SEQUENCE: 110
attcccttag gtgggagt                                                  18

SEQ ID NO: 111          moltype = DNA  length = 19
FEATURE                 Location/Qualifiers
misc_feature            1..19
                        note = Synthetic Construct
source                  1..19
                        mol_type = other DNA
                        organism = synthetic construct
SEQUENCE: 111
aattccctta ggtgggagt                                                 19

SEQ ID NO: 112          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 112
taattccctt aggtgggagt                                                20

SEQ ID NO: 113          moltype = DNA  length = 18
FEATURE                 Location/Qualifiers
misc_feature            1..18
                        note = Synthetic Construct
source                  1..18
                        mol_type = other DNA
                        organism = synthetic construct
```

```
SEQUENCE: 113
aattccctta ggtgggag                                              18

SEQ ID NO: 114          moltype = DNA  length = 19
FEATURE                 Location/Qualifiers
misc_feature            1..19
                        note = Synthetic Construct
source                  1..19
                        mol_type = other DNA
                        organism = synthetic construct
SEQUENCE: 114
taattccctt aggtgggag                                             19

SEQ ID NO: 115          moltype = DNA  length = 18
FEATURE                 Location/Qualifiers
misc_feature            1..18
                        note = Synthetic Construct
source                  1..18
                        mol_type = other DNA
                        organism = synthetic construct
SEQUENCE: 115
taattccctt aggtggga                                              18

SEQ ID NO: 116          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 116
gataaagact gctgagaaga                                            20

SEQ ID NO: 117          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 117
ataaagactg ctgagaagag                                            20

SEQ ID NO: 118          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 118
taaagactgc tgagaagagc                                            20

SEQ ID NO: 119          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 119
aaagactgct gagaagagca                                            20

SEQ ID NO: 120          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 120
aagactgctg agaagagcac                                            20

SEQ ID NO: 121          moltype = RNA  length = 20
FEATURE                 Location/Qualifiers
misc_feature            1..20
                        note = Synthetic Construct
source                  1..20
                        mol_type = other RNA
```

```
                        organism = synthetic construct
SEQUENCE: 121
agactgctga gaagagcacc                                              20

SEQ ID NO: 122          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 122
gactgctgag aagagcaccc                                              20

SEQ ID NO: 123          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 123
caagtgctac cgcacaggca                                              20

SEQ ID NO: 124          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 124
aagtgctacc gcacaggcat                                              20

SEQ ID NO: 125          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 125
agtgctaccg cacaggcatg                                              20

SEQ ID NO: 126          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 126
tgctaccgca caggcatgct                                              20

SEQ ID NO: 127          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 127
taccgcacag gcatgctgca                                              20

SEQ ID NO: 128          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 128
gcacaggcat gctgcagtga                                              20

SEQ ID NO: 129          moltype = RNA  length = 20
FEATURE                 Location/Qualifiers
misc_feature            1..20
                        note = Synthetic Construct
source                  1..20
```

```
                        mol_type = other RNA
                        organism = synthetic construct
SEQUENCE: 129
cacaggcatg ctgcagtgaa                                              20

SEQ ID NO: 130          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 130
acaggcatgc tgcagtgaat                                              20

SEQ ID NO: 131          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 131
caggcatgct gcagtgaatt                                              20

SEQ ID NO: 132          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 132
aggcatgctg cagtgaattt                                              20

SEQ ID NO: 133          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 133
ggcatgctgc agtgaattta                                              20

SEQ ID NO: 134          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 134
gcatgctgca gtgaatttaa                                              20

SEQ ID NO: 135          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 135
catgctgcag tgaatttaac                                              20

SEQ ID NO: 136          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 136
gcagtgaatt taactgatcc                                              20

SEQ ID NO: 137          moltype = RNA  length = 20
FEATURE                 Location/Qualifiers
misc_feature            1..20
                        note = Synthetic Construct
```

```
source                  1..20
                        mol_type = other RNA
                        organism = synthetic construct
SEQUENCE: 137
tccctgcaac cgttgtttaa                                              20

SEQ ID NO: 138          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 138
ccctgcaacc gttgtttaag                                              20

SEQ ID NO: 139          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 139
tcttctcagc agtctttatc                                              20

SEQ ID NO: 140          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 140
ctcttctcag cagtctttat                                              20

SEQ ID NO: 141          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 141
gctcttctca gcagtcttta                                              20

SEQ ID NO: 142          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 142
tgctcttctc agcagtcttt                                              20

SEQ ID NO: 143          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 143
gtgctcttct cagcagtctt                                              20

SEQ ID NO: 144          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 144
ggtgctcttc tcagcagtct                                              20

SEQ ID NO: 145          moltype = DNA  length = 20
FEATURE                 Location/Qualifiers
misc_feature            1..20
```

```
                         note = Synthetic Construct
source                   1..20
                         mol_type = other DNA
                         organism = synthetic construct
SEQUENCE: 145
gggtgctctt ctcagcagtc                                              20

SEQ ID NO: 146           moltype = DNA  length = 20
FEATURE                  Location/Qualifiers
misc_feature             1..20
                         note = Synthetic Construct
source                   1..20
                         mol_type = other DNA
                         organism = synthetic construct
SEQUENCE: 146
tgcctgtgcg gtagcacttg                                              20

SEQ ID NO: 147           moltype = DNA  length = 20
FEATURE                  Location/Qualifiers
misc_feature             1..20
                         note = Synthetic Construct
source                   1..20
                         mol_type = other DNA
                         organism = synthetic construct
SEQUENCE: 147
atgcctgtgc ggtagcactt                                              20

SEQ ID NO: 148           moltype = DNA  length = 20
FEATURE                  Location/Qualifiers
misc_feature             1..20
                         note = Synthetic Construct
source                   1..20
                         mol_type = other DNA
                         organism = synthetic construct
SEQUENCE: 148
catgcctgtg cggtagcact                                              20

SEQ ID NO: 149           moltype = DNA  length = 20
FEATURE                  Location/Qualifiers
misc_feature             1..20
                         note = Synthetic Construct
source                   1..20
                         mol_type = other DNA
                         organism = synthetic construct
SEQUENCE: 149
agcatgcctg tgcggtagca                                              20

SEQ ID NO: 150           moltype = DNA  length = 20
FEATURE                  Location/Qualifiers
misc_feature             1..20
                         note = Synthetic Construct
source                   1..20
                         mol_type = other DNA
                         organism = synthetic construct
SEQUENCE: 150
tgcagcatgc ctgtgcggta                                              20

SEQ ID NO: 151           moltype = DNA  length = 20
FEATURE                  Location/Qualifiers
misc_feature             1..20
                         note = Synthetic Construct
source                   1..20
                         mol_type = other DNA
                         organism = synthetic construct
SEQUENCE: 151
tcactgcagc atgcctgtgc                                              20

SEQ ID NO: 152           moltype = DNA  length = 20
FEATURE                  Location/Qualifiers
misc_feature             1..20
                         note = Synthetic Construct
source                   1..20
                         mol_type = other DNA
                         organism = synthetic construct
SEQUENCE: 152
ttcactgcag catgcctgtg                                              20

SEQ ID NO: 153           moltype = DNA  length = 20
FEATURE                  Location/Qualifiers
```

```
misc_feature           1..20
                       note = Synthetic Construct
source                 1..20
                       mol_type = other DNA
                       organism = synthetic construct
SEQUENCE: 153
attcactgca gcatgcctgt                                              20

SEQ ID NO: 154         moltype = DNA  length = 20
FEATURE                Location/Qualifiers
misc_feature           1..20
                       note = Synthetic Construct
source                 1..20
                       mol_type = other DNA
                       organism = synthetic construct
SEQUENCE: 154
aattcactgc agcatgcctg                                              20

SEQ ID NO: 155         moltype = DNA  length = 20
FEATURE                Location/Qualifiers
misc_feature           1..20
                       note = Synthetic Construct
source                 1..20
                       mol_type = other DNA
                       organism = synthetic construct
SEQUENCE: 155
aaattcactg cagcatgcct                                              20

SEQ ID NO: 156         moltype = DNA  length = 20
FEATURE                Location/Qualifiers
misc_feature           1..20
                       note = Synthetic Construct
source                 1..20
                       mol_type = other DNA
                       organism = synthetic construct
SEQUENCE: 156
taaattcact gcagcatgcc                                              20

SEQ ID NO: 157         moltype = DNA  length = 20
FEATURE                Location/Qualifiers
misc_feature           1..20
                       note = Synthetic Construct
source                 1..20
                       mol_type = other DNA
                       organism = synthetic construct
SEQUENCE: 157
ttaaattcac tgcagcatgc                                              20

SEQ ID NO: 158         moltype = DNA  length = 20
FEATURE                Location/Qualifiers
misc_feature           1..20
                       note = Synthetic Construct
source                 1..20
                       mol_type = other DNA
                       organism = synthetic construct
SEQUENCE: 158
gttaaattca ctgcagcatg                                              20

SEQ ID NO: 159         moltype = DNA  length = 20
FEATURE                Location/Qualifiers
misc_feature           1..20
                       note = Synthetic Construct
source                 1..20
                       mol_type = other DNA
                       organism = synthetic construct
SEQUENCE: 159
ggatcagtta aattcactgc                                              20

SEQ ID NO: 160         moltype = DNA  length = 20
FEATURE                Location/Qualifiers
misc_feature           1..20
                       note = Synthetic Construct
source                 1..20
                       mol_type = other DNA
                       organism = synthetic construct
SEQUENCE: 160
ttaaacaacg gttgcaggga                                              20

SEQ ID NO: 161         moltype = DNA  length = 20
```

-continued

```
FEATURE                 Location/Qualifiers
misc_feature            1..20
                        note = Synthetic Construct
source                  1..20
                        mol_type = other DNA
                        organism = synthetic construct
SEQUENCE: 161
cttaaacaac ggttgcaggg                                              20

SEQ ID NO: 162          moltype = RNA  length = 19
FEATURE                 Location/Qualifiers
misc_feature            1..19
                        note = Synthetic Construct
source                  1..19
                        mol_type = other RNA
                        organism = synthetic construct
SEQUENCE: 162
aaaagactgt ggaggaaga                                               19

SEQ ID NO: 163          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 163
aaaagactgt ggaggaagaa                                              20

SEQ ID NO: 164          moltype = RNA  length = 19
FEATURE                 Location/Qualifiers
misc_feature            1..19
                        note = Synthetic Construct
source                  1..19
                        mol_type = other RNA
                        organism = synthetic construct
SEQUENCE: 164
aaagactgtg gaggaagaa                                               19

SEQ ID NO: 165          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 165
aaagactgtg gaggaagaaa                                              20

SEQ ID NO: 166          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 166
aagactgtgg aggaagaaaa                                              20

SEQ ID NO: 167          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 167
agactgtgga ggaagaaaac                                              20

SEQ ID NO: 168          moltype = RNA  length = 18
FEATURE                 Location/Qualifiers
misc_feature            1..18
                        note = Synthetic Construct
source                  1..18
                        mol_type = other RNA
                        organism = synthetic construct
SEQUENCE: 168
actgtggagg aagaaaac                                                18
```

```
SEQ ID NO: 169          moltype = RNA  length = 19
FEATURE                 Location/Qualifiers
misc_feature            1..19
                        note = Synthetic Construct
source                  1..19
                        mol_type = other RNA
                        organism = synthetic construct
SEQUENCE: 169
actgtggagg aagaaaacc                                                19

SEQ ID NO: 170          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 170
actgtggagg aagaaaaccc                                               20

SEQ ID NO: 171          moltype = RNA  length = 18
FEATURE                 Location/Qualifiers
misc_feature            1..18
                        note = Synthetic Construct
source                  1..18
                        mol_type = other RNA
                        organism = synthetic construct
SEQUENCE: 171
ctgtggagga agaaaacc                                                 18

SEQ ID NO: 172          moltype = RNA  length = 19
FEATURE                 Location/Qualifiers
misc_feature            1..19
                        note = Synthetic Construct
source                  1..19
                        mol_type = other RNA
                        organism = synthetic construct
SEQUENCE: 172
ctgtggagga agaaaaccc                                                19

SEQ ID NO: 173          moltype = RNA  length = 19
FEATURE                 Location/Qualifiers
misc_feature            1..19
                        note = Synthetic Construct
source                  1..19
                        mol_type = other RNA
                        organism = synthetic construct
SEQUENCE: 173
aaaacccttt accctgttg                                                19

SEQ ID NO: 174          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 174
aaaacccttt accctgttgt                                               20

SEQ ID NO: 175          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 175
aaacccttta ccctgttgtt                                               20

SEQ ID NO: 176          moltype = RNA  length = 18
FEATURE                 Location/Qualifiers
misc_feature            1..18
                        note = Synthetic Construct
source                  1..18
                        mol_type = other RNA
                        organism = synthetic construct
SEQUENCE: 176
ttgttcaggg agaaactg                                                 18
```

```
SEQ ID NO: 177          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 177
ttgttcaggg agaaactgac                                              20

SEQ ID NO: 178          moltype = RNA  length = 18
FEATURE                 Location/Qualifiers
misc_feature            1..18
                        note = Synthetic Construct
source                  1..18
                        mol_type = other RNA
                        organism = synthetic construct
SEQUENCE: 178
tgttcaggga gaaactga                                                18

SEQ ID NO: 179          moltype = RNA  length = 19
FEATURE                 Location/Qualifiers
misc_feature            1..19
                        note = Synthetic Construct
source                  1..19
                        mol_type = other RNA
                        organism = synthetic construct
SEQUENCE: 179
tgttcaggga gaaactgac                                               19

SEQ ID NO: 180          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 180
tgttcaggga gaaactgaca                                              20

SEQ ID NO: 181          moltype = RNA  length = 19
FEATURE                 Location/Qualifiers
misc_feature            1..19
                        note = Synthetic Construct
source                  1..19
                        mol_type = other RNA
                        organism = synthetic construct
SEQUENCE: 181
gttcagggag aaactgaca                                               19

SEQ ID NO: 182          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 182
tcagggagaa actgacacca                                              20

SEQ ID NO: 183          moltype = RNA  length = 19
FEATURE                 Location/Qualifiers
misc_feature            1..19
                        note = Synthetic Construct
source                  1..19
                        mol_type = other RNA
                        organism = synthetic construct
SEQUENCE: 183
cagggagaaa ctgacacca                                               19

SEQ ID NO: 184          moltype = RNA  length = 18
FEATURE                 Location/Qualifiers
misc_feature            1..18
                        note = Synthetic Construct
source                  1..18
                        mol_type = other RNA
                        organism = synthetic construct
SEQUENCE: 184
```

```
agggagaaac tgacacca                                                18

SEQ ID NO: 185          moltype = RNA  length = 19
FEATURE                 Location/Qualifiers
misc_feature            1..19
                        note = Synthetic Construct
source                  1..19
                        mol_type = other RNA
                        organism = synthetic construct
SEQUENCE: 185
agggagaaac tgacaccac                                               19

SEQ ID NO: 186          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 186
agggagaaac tgacaccact                                              20

SEQ ID NO: 187          moltype = RNA  length = 18
FEATURE                 Location/Qualifiers
misc_feature            1..18
                        note = Synthetic Construct
source                  1..18
                        mol_type = other RNA
                        organism = synthetic construct
SEQUENCE: 187
gggagaaact gacaccac                                                18

SEQ ID NO: 188          moltype = RNA  length = 19
FEATURE                 Location/Qualifiers
misc_feature            1..19
                        note = Synthetic Construct
source                  1..19
                        mol_type = other RNA
                        organism = synthetic construct
SEQUENCE: 188
gggagaaact gacaccact                                               19

SEQ ID NO: 189          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 189
gggagaaact gacaccactc                                              20

SEQ ID NO: 190          moltype = RNA  length = 18
FEATURE                 Location/Qualifiers
misc_feature            1..18
                        note = Synthetic Construct
source                  1..18
                        mol_type = other RNA
                        organism = synthetic construct
SEQUENCE: 190
ggagaaactg acaccact                                                18

SEQ ID NO: 191          moltype = RNA  length = 19
FEATURE                 Location/Qualifiers
misc_feature            1..19
                        note = Synthetic Construct
source                  1..19
                        mol_type = other RNA
                        organism = synthetic construct
SEQUENCE: 191
ggagaaactg acaccactc                                               19

SEQ ID NO: 192          moltype = RNA  length = 20
FEATURE                 Location/Qualifiers
misc_feature            1..20
                        note = Synthetic Construct
source                  1..20
                        mol_type = other RNA
                        organism = synthetic construct
```

```
SEQUENCE: 192
ggagaaactg acaccactca                                                20

SEQ ID NO: 193          moltype = RNA  length = 18
FEATURE                 Location/Qualifiers
misc_feature            1..18
                        note = Synthetic Construct
source                  1..18
                        mol_type = other RNA
                        organism = synthetic construct
SEQUENCE: 193
gagaaactga caccactc                                                  18

SEQ ID NO: 194          moltype = RNA  length = 19
FEATURE                 Location/Qualifiers
misc_feature            1..19
                        note = Synthetic Construct
source                  1..19
                        mol_type = other RNA
                        organism = synthetic construct
SEQUENCE: 194
gagaaactga caccactca                                                 19

SEQ ID NO: 195          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 195
gagaaactga caccactcaa                                                20

SEQ ID NO: 196          moltype = RNA  length = 18
FEATURE                 Location/Qualifiers
misc_feature            1..18
                        note = Synthetic Construct
source                  1..18
                        mol_type = other RNA
                        organism = synthetic construct
SEQUENCE: 196
agaaactgac accactca                                                  18

SEQ ID NO: 197          moltype = RNA  length = 19
FEATURE                 Location/Qualifiers
misc_feature            1..19
                        note = Synthetic Construct
source                  1..19
                        mol_type = other RNA
                        organism = synthetic construct
SEQUENCE: 197
agaaactgac accactcaa                                                 19

SEQ ID NO: 198          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 198
agaaactgac accactcaac                                                20

SEQ ID NO: 199          moltype = RNA  length = 18
FEATURE                 Location/Qualifiers
misc_feature            1..18
                        note = Synthetic Construct
source                  1..18
                        mol_type = other RNA
                        organism = synthetic construct
SEQUENCE: 199
gaaactgaca ccactcaa                                                  18

SEQ ID NO: 200          moltype = RNA  length = 19
FEATURE                 Location/Qualifiers
misc_feature            1..19
                        note = Synthetic Construct
source                  1..19
                        mol_type = other RNA
```

```
                         organism = synthetic construct
SEQUENCE: 200
gaaactgaca ccactcaac                                                 19

SEQ ID NO: 201           moltype = RNA  length = 20
FEATURE                  Location/Qualifiers
misc_feature             1..20
                         note = Synthetic Construct
source                   1..20
                         mol_type = other RNA
                         organism = synthetic construct
SEQUENCE: 201
gaaactgaca ccactcaact                                                20

SEQ ID NO: 202           moltype = RNA  length = 18
FEATURE                  Location/Qualifiers
misc_feature             1..18
                         note = Synthetic Construct
source                   1..18
                         mol_type = other RNA
                         organism = synthetic construct
SEQUENCE: 202
aaactgacac cactcaac                                                  18

SEQ ID NO: 203           moltype = RNA  length = 19
FEATURE                  Location/Qualifiers
misc_feature             1..19
                         note = Synthetic Construct
source                   1..19
                         mol_type = other RNA
                         organism = synthetic construct
SEQUENCE: 203
aaactgacac cactcaact                                                 19

SEQ ID NO: 204           moltype = RNA  length = 20
FEATURE                  Location/Qualifiers
misc_feature             1..20
                         note = Synthetic Construct
source                   1..20
                         mol_type = other RNA
                         organism = synthetic construct
SEQUENCE: 204
aaactgacac cactcaactg                                                20

SEQ ID NO: 205           moltype = RNA  length = 18
FEATURE                  Location/Qualifiers
misc_feature             1..18
                         note = Synthetic Construct
source                   1..18
                         mol_type = other RNA
                         organism = synthetic construct
SEQUENCE: 205
aactgacacc actcaact                                                  18

SEQ ID NO: 206           moltype = RNA  length = 19
FEATURE                  Location/Qualifiers
misc_feature             1..19
                         note = Synthetic Construct
source                   1..19
                         mol_type = other RNA
                         organism = synthetic construct
SEQUENCE: 206
aactgacacc actcaactg                                                 19

SEQ ID NO: 207           moltype = RNA  length = 20
FEATURE                  Location/Qualifiers
misc_feature             1..20
                         note = Synthetic Construct
source                   1..20
                         mol_type = other RNA
                         organism = synthetic construct
SEQUENCE: 207
aactgacacc actcaactgc                                                20

SEQ ID NO: 208           moltype = RNA  length = 18
FEATURE                  Location/Qualifiers
misc_feature             1..18
                         note = Synthetic Construct
source                   1..18
```

```
                        mol_type = other RNA
                        organism = synthetic construct
SEQUENCE: 208
actgacacca ctcaactg                                                18

SEQ ID NO: 209          moltype = RNA  length = 19
FEATURE                 Location/Qualifiers
misc_feature            1..19
                        note = Synthetic Construct
source                  1..19
                        mol_type = other RNA
                        organism = synthetic construct
SEQUENCE: 209
actgacacca ctcaactgc                                               19

SEQ ID NO: 210          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 210
actgacacca ctcaactgcc                                              20

SEQ ID NO: 211          moltype = RNA  length = 18
FEATURE                 Location/Qualifiers
misc_feature            1..18
                        note = Synthetic Construct
source                  1..18
                        mol_type = other RNA
                        organism = synthetic construct
SEQUENCE: 211
ctgacaccac tcaactgc                                                18

SEQ ID NO: 212          moltype = RNA  length = 19
FEATURE                 Location/Qualifiers
misc_feature            1..19
                        note = Synthetic Construct
source                  1..19
                        mol_type = other RNA
                        organism = synthetic construct
SEQUENCE: 212
ctgacaccac tcaactgcc                                               19

SEQ ID NO: 213          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 213
ctgacaccac tcaactgcct                                              20

SEQ ID NO: 214          moltype = RNA  length = 18
FEATURE                 Location/Qualifiers
misc_feature            1..18
                        note = Synthetic Construct
source                  1..18
                        mol_type = other RNA
                        organism = synthetic construct
SEQUENCE: 214
tgacaccact caactgcc                                                18

SEQ ID NO: 215          moltype = RNA  length = 19
FEATURE                 Location/Qualifiers
misc_feature            1..19
                        note = Synthetic Construct
source                  1..19
                        mol_type = other RNA
                        organism = synthetic construct
SEQUENCE: 215
tgacaccact caactgcct                                               19

SEQ ID NO: 216          moltype = RNA  length = 20
FEATURE                 Location/Qualifiers
misc_feature            1..20
                        note = Synthetic Construct
```

```
source                  1..20
                        mol_type = other RNA
                        organism = synthetic construct
SEQUENCE: 216
tgacaccact caactgcctg                                                      20

SEQ ID NO: 217          moltype = RNA  length = 18
FEATURE                 Location/Qualifiers
misc_feature            1..18
                        note = Synthetic Construct
source                  1..18
                        mol_type = other RNA
                        organism = synthetic construct
SEQUENCE: 217
gacaccactc aactgcct                                                        18

SEQ ID NO: 218          moltype = RNA  length = 19
FEATURE                 Location/Qualifiers
misc_feature            1..19
                        note = Synthetic Construct
source                  1..19
                        mol_type = other RNA
                        organism = synthetic construct
SEQUENCE: 218
gacaccactc aactgcctg                                                       19

SEQ ID NO: 219          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 219
gacaccactc aactgcctgg                                                      20

SEQ ID NO: 220          moltype = RNA  length = 18
FEATURE                 Location/Qualifiers
misc_feature            1..18
                        note = Synthetic Construct
source                  1..18
                        mol_type = other RNA
                        organism = synthetic construct
SEQUENCE: 220
acaccactca actgcctg                                                        18

SEQ ID NO: 221          moltype = RNA  length = 19
FEATURE                 Location/Qualifiers
misc_feature            1..19
                        note = Synthetic Construct
source                  1..19
                        mol_type = other RNA
                        organism = synthetic construct
SEQUENCE: 221
acaccactca actgcctgg                                                       19

SEQ ID NO: 222          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 222
acaccactca actgcctggc                                                      20

SEQ ID NO: 223          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 223
caccactcaa ctgcctggca                                                      20

SEQ ID NO: 224          moltype = RNA  length = 18
FEATURE                 Location/Qualifiers
misc_feature            1..18
```

```
                        note = Synthetic Construct
source                  1..18
                        mol_type = other RNA
                        organism = synthetic construct
SEQUENCE: 224
gaaaatgtgg catccagt                                             18

SEQ ID NO: 225          moltype = RNA  length = 18
FEATURE                 Location/Qualifiers
misc_feature            1..18
                        note = Synthetic Construct
source                  1..18
                        mol_type = other RNA
                        organism = synthetic construct
SEQUENCE: 225
aaaatgtggc atccagtc                                             18

SEQ ID NO: 226          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 226
gcatccagtc cactttacca                                           20

SEQ ID NO: 227          moltype = RNA  length = 18
FEATURE                 Location/Qualifiers
misc_feature            1..18
                        note = Synthetic Construct
source                  1..18
                        mol_type = other RNA
                        organism = synthetic construct
SEQUENCE: 227
catccagtcc actttacc                                             18

SEQ ID NO: 228          moltype = RNA  length = 19
FEATURE                 Location/Qualifiers
misc_feature            1..19
                        note = Synthetic Construct
source                  1..19
                        mol_type = other RNA
                        organism = synthetic construct
SEQUENCE: 228
catccagtcc actttacca                                            19

SEQ ID NO: 229          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 229
catccagtcc actttaccat                                           20

SEQ ID NO: 230          moltype = RNA  length = 18
FEATURE                 Location/Qualifiers
misc_feature            1..18
                        note = Synthetic Construct
source                  1..18
                        mol_type = other RNA
                        organism = synthetic construct
SEQUENCE: 230
atccagtcca ctttacca                                             18

SEQ ID NO: 231          moltype = RNA  length = 19
FEATURE                 Location/Qualifiers
misc_feature            1..19
                        note = Synthetic Construct
source                  1..19
                        mol_type = other RNA
                        organism = synthetic construct
SEQUENCE: 231
atccagtcca ctttaccat                                            19

SEQ ID NO: 232          moltype = RNA  length = 20
FEATURE                 Location/Qualifiers
```

```
misc_feature           1..20
                       note = Synthetic Construct
source                 1..20
                       mol_type = other RNA
                       organism = synthetic construct
SEQUENCE: 232
atccagtcca ctttaccatc                                              20

SEQ ID NO: 233         moltype = RNA  length = 20
FEATURE                Location/Qualifiers
misc_feature           1..20
                       note = Synthetic Construct
source                 1..20
                       mol_type = other RNA
                       organism = synthetic construct
SEQUENCE: 233
gtttaaggaa accatctctg                                              20

SEQ ID NO: 234         moltype = RNA  length = 20
FEATURE                Location/Qualifiers
misc_feature           1..20
                       note = Synthetic Construct
source                 1..20
                       mol_type = other RNA
                       organism = synthetic construct
SEQUENCE: 234
tttaaggaaa ccatctctgg                                              20

SEQ ID NO: 235         moltype = RNA  length = 19
FEATURE                Location/Qualifiers
misc_feature           1..19
                       note = Synthetic Construct
source                 1..19
                       mol_type = other RNA
                       organism = synthetic construct
SEQUENCE: 235
ttaaggaaac catctctgg                                               19

SEQ ID NO: 236         moltype = RNA  length = 18
FEATURE                Location/Qualifiers
misc_feature           1..18
                       note = Synthetic Construct
source                 1..18
                       mol_type = other RNA
                       organism = synthetic construct
SEQUENCE: 236
taaggaaacc atctctgg                                                18

SEQ ID NO: 237         moltype = DNA  length = 19
FEATURE                Location/Qualifiers
misc_feature           1..19
                       note = Synthetic Construct
source                 1..19
                       mol_type = other DNA
                       organism = synthetic construct
SEQUENCE: 237
tcttcctcca cagtctttt                                               19

SEQ ID NO: 238         moltype = DNA  length = 20
FEATURE                Location/Qualifiers
misc_feature           1..20
                       note = Synthetic Construct
source                 1..20
                       mol_type = other DNA
                       organism = synthetic construct
SEQUENCE: 238
ttcttcctcc acagtctttt                                              20

SEQ ID NO: 239         moltype = DNA  length = 19
FEATURE                Location/Qualifiers
misc_feature           1..19
                       note = Synthetic Construct
source                 1..19
                       mol_type = other DNA
                       organism = synthetic construct
SEQUENCE: 239
ttcttcctcc acagtcttt                                               19

SEQ ID NO: 240         moltype = DNA  length = 20
```

```
FEATURE                Location/Qualifiers
misc_feature           1..20
                       note = Synthetic Construct
source                 1..20
                       mol_type = other DNA
                       organism = synthetic construct
SEQUENCE: 240
tttcttcctc cacagtcttt                                              20

SEQ ID NO: 241         moltype = DNA  length = 20
FEATURE                Location/Qualifiers
misc_feature           1..20
                       note = Synthetic Construct
source                 1..20
                       mol_type = other DNA
                       organism = synthetic construct
SEQUENCE: 241
ttttcttcct ccacagtctt                                              20

SEQ ID NO: 242         moltype = DNA  length = 20
FEATURE                Location/Qualifiers
misc_feature           1..20
                       note = Synthetic Construct
source                 1..20
                       mol_type = other DNA
                       organism = synthetic construct
SEQUENCE: 242
gttttcttcc tccacagtct                                              20

SEQ ID NO: 243         moltype = DNA  length = 18
FEATURE                Location/Qualifiers
misc_feature           1..18
                       note = Synthetic Construct
source                 1..18
                       mol_type = other DNA
                       organism = synthetic construct
SEQUENCE: 243
gttttcttcc tccacagt                                                18

SEQ ID NO: 244         moltype = DNA  length = 19
FEATURE                Location/Qualifiers
misc_feature           1..19
                       note = Synthetic Construct
source                 1..19
                       mol_type = other DNA
                       organism = synthetic construct
SEQUENCE: 244
ggttttcttc ctccacagt                                               19

SEQ ID NO: 245         moltype = DNA  length = 20
FEATURE                Location/Qualifiers
misc_feature           1..20
                       note = Synthetic Construct
source                 1..20
                       mol_type = other DNA
                       organism = synthetic construct
SEQUENCE: 245
gggttttctt cctccacagt                                              20

SEQ ID NO: 246         moltype = DNA  length = 18
FEATURE                Location/Qualifiers
misc_feature           1..18
                       note = Synthetic Construct
source                 1..18
                       mol_type = other DNA
                       organism = synthetic construct
SEQUENCE: 246
ggttttcttc ctccacag                                                18

SEQ ID NO: 247         moltype = DNA  length = 19
FEATURE                Location/Qualifiers
misc_feature           1..19
                       note = Synthetic Construct
source                 1..19
                       mol_type = other DNA
                       organism = synthetic construct
SEQUENCE: 247
gggttttctt cctccacag                                               19
```

```
SEQ ID NO: 248          moltype = DNA  length = 19
FEATURE                 Location/Qualifiers
misc_feature            1..19
                        note = Synthetic Construct
source                  1..19
                        mol_type = other DNA
                        organism = synthetic construct
SEQUENCE: 248
caacagggta aagggtttt                                                 19

SEQ ID NO: 249          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 249
acaacagggt aaagggtttt                                                20

SEQ ID NO: 250          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 250
aacaacaggg taaagggttt                                                20

SEQ ID NO: 251          moltype = DNA  length = 18
FEATURE                 Location/Qualifiers
misc_feature            1..18
                        note = Synthetic Construct
source                  1..18
                        mol_type = other DNA
                        organism = synthetic construct
SEQUENCE: 251
cagtttctcc ctgaacaa                                                  18

SEQ ID NO: 252          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 252
gtcagtttct ccctgaacaa                                                20

SEQ ID NO: 253          moltype = DNA  length = 18
FEATURE                 Location/Qualifiers
misc_feature            1..18
                        note = Synthetic Construct
source                  1..18
                        mol_type = other DNA
                        organism = synthetic construct
SEQUENCE: 253
tcagtttctc cctgaaca                                                  18

SEQ ID NO: 254          moltype = DNA  length = 19
FEATURE                 Location/Qualifiers
misc_feature            1..19
                        note = Synthetic Construct
source                  1..19
                        mol_type = other DNA
                        organism = synthetic construct
SEQUENCE: 254
gtcagtttct ccctgaaca                                                 19

SEQ ID NO: 255          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 255
tgtcagtttc tccctgaaca                                                20
```

```
SEQ ID NO: 256          moltype = DNA  length = 19
FEATURE                 Location/Qualifiers
misc_feature            1..19
                        note = Synthetic Construct
source                  1..19
                        mol_type = other DNA
                        organism = synthetic construct
SEQUENCE: 256
tgtcagtttc tccctgaac                                              19

SEQ ID NO: 257          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 257
tggtgtcagt ttctccctga                                             20

SEQ ID NO: 258          moltype = DNA  length = 19
FEATURE                 Location/Qualifiers
misc_feature            1..19
                        note = Synthetic Construct
source                  1..19
                        mol_type = other DNA
                        organism = synthetic construct
SEQUENCE: 258
tggtgtcagt ttctccctg                                              19

SEQ ID NO: 259          moltype = DNA  length = 18
FEATURE                 Location/Qualifiers
misc_feature            1..18
                        note = Synthetic Construct
source                  1..18
                        mol_type = other DNA
                        organism = synthetic construct
SEQUENCE: 259
tggtgtcagt ttctccct                                               18

SEQ ID NO: 260          moltype = DNA  length = 19
FEATURE                 Location/Qualifiers
misc_feature            1..19
                        note = Synthetic Construct
source                  1..19
                        mol_type = other DNA
                        organism = synthetic construct
SEQUENCE: 260
gtggtgtcag tttctccct                                              19

SEQ ID NO: 261          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 261
agtggtgtca gtttctccct                                             20

SEQ ID NO: 262          moltype = DNA  length = 18
FEATURE                 Location/Qualifiers
misc_feature            1..18
                        note = Synthetic Construct
source                  1..18
                        mol_type = other DNA
                        organism = synthetic construct
SEQUENCE: 262
gtggtgtcag tttctccc                                               18

SEQ ID NO: 263          moltype = DNA  length = 19
FEATURE                 Location/Qualifiers
misc_feature            1..19
                        note = Synthetic Construct
source                  1..19
                        mol_type = other DNA
                        organism = synthetic construct
SEQUENCE: 263
```

```
agtggtgtca gtttctccc                                                19

SEQ ID NO: 264          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 264
gagtggtgtc agtttctccc                                               20

SEQ ID NO: 265          moltype = DNA  length = 18
FEATURE                 Location/Qualifiers
misc_feature            1..18
                        note = Synthetic Construct
source                  1..18
                        mol_type = other DNA
                        organism = synthetic construct
SEQUENCE: 265
agtggtgtca gtttctcc                                                 18

SEQ ID NO: 266          moltype = DNA  length = 19
FEATURE                 Location/Qualifiers
misc_feature            1..19
                        note = Synthetic Construct
source                  1..19
                        mol_type = other DNA
                        organism = synthetic construct
SEQUENCE: 266
gagtggtgtc agtttctcc                                                19

SEQ ID NO: 267          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 267
tgagtggtgt cagtttctcc                                               20

SEQ ID NO: 268          moltype = DNA  length = 18
FEATURE                 Location/Qualifiers
misc_feature            1..18
                        note = Synthetic Construct
source                  1..18
                        mol_type = other DNA
                        organism = synthetic construct
SEQUENCE: 268
gagtggtgtc agtttctc                                                 18

SEQ ID NO: 269          moltype = DNA  length = 19
FEATURE                 Location/Qualifiers
misc_feature            1..19
                        note = Synthetic Construct
source                  1..19
                        mol_type = other DNA
                        organism = synthetic construct
SEQUENCE: 269
tgagtggtgt cagtttctc                                                19

SEQ ID NO: 270          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 270
ttgagtggtg tcagtttctc                                               20

SEQ ID NO: 271          moltype = DNA  length = 18
FEATURE                 Location/Qualifiers
misc_feature            1..18
                        note = Synthetic Construct
source                  1..18
                        mol_type = other DNA
                        organism = synthetic construct
```

```
SEQUENCE: 271
tgagtggtgt cagtttct                                                18

SEQ ID NO: 272          moltype = DNA  length = 19
FEATURE                 Location/Qualifiers
misc_feature            1..19
                        note = Synthetic Construct
source                  1..19
                        mol_type = other DNA
                        organism = synthetic construct
SEQUENCE: 272
ttgagtggtg tcagtttct                                               19

SEQ ID NO: 273          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 273
gttgagtggt gtcagtttct                                              20

SEQ ID NO: 274          moltype = DNA  length = 18
FEATURE                 Location/Qualifiers
misc_feature            1..18
                        note = Synthetic Construct
source                  1..18
                        mol_type = other DNA
                        organism = synthetic construct
SEQUENCE: 274
ttgagtggtg tcagtttc                                                18

SEQ ID NO: 275          moltype = DNA  length = 19
FEATURE                 Location/Qualifiers
misc_feature            1..19
                        note = Synthetic Construct
source                  1..19
                        mol_type = other DNA
                        organism = synthetic construct
SEQUENCE: 275
gttgagtggt gtcagtttc                                               19

SEQ ID NO: 276          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 276
agttgagtgg tgtcagtttc                                              20

SEQ ID NO: 277          moltype = DNA  length = 18
FEATURE                 Location/Qualifiers
misc_feature            1..18
                        note = Synthetic Construct
source                  1..18
                        mol_type = other DNA
                        organism = synthetic construct
SEQUENCE: 277
gttgagtggt gtcagttt                                                18

SEQ ID NO: 278          moltype = DNA  length = 19
FEATURE                 Location/Qualifiers
misc_feature            1..19
                        note = Synthetic Construct
source                  1..19
                        mol_type = other DNA
                        organism = synthetic construct
SEQUENCE: 278
agttgagtgg tgtcagttt                                               19

SEQ ID NO: 279          moltype = DNA  length = 20
FEATURE                 Location/Qualifiers
misc_feature            1..20
                        note = Synthetic Construct
source                  1..20
                        mol_type = other DNA
```

```
                        organism = synthetic construct
SEQUENCE: 279
cagttgagtg gtgtcagttt                                              20

SEQ ID NO: 280          moltype = DNA  length = 18
FEATURE                 Location/Qualifiers
misc_feature            1..18
                        note = Synthetic Construct
source                  1..18
                        mol_type = other DNA
                        organism = synthetic construct
SEQUENCE: 280
agttgagtgg tgtcagtt                                                18

SEQ ID NO: 281          moltype = DNA  length = 19
FEATURE                 Location/Qualifiers
misc_feature            1..19
                        note = Synthetic Construct
source                  1..19
                        mol_type = other DNA
                        organism = synthetic construct
SEQUENCE: 281
cagttgagtg gtgtcagtt                                               19

SEQ ID NO: 282          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 282
gcagttgagt ggtgtcagtt                                              20

SEQ ID NO: 283          moltype = DNA  length = 18
FEATURE                 Location/Qualifiers
misc_feature            1..18
                        note = Synthetic Construct
source                  1..18
                        mol_type = other DNA
                        organism = synthetic construct
SEQUENCE: 283
cagttgagtg gtgtcagt                                                18

SEQ ID NO: 284          moltype = DNA  length = 19
FEATURE                 Location/Qualifiers
misc_feature            1..19
                        note = Synthetic Construct
source                  1..19
                        mol_type = other DNA
                        organism = synthetic construct
SEQUENCE: 284
gcagttgagt ggtgtcagt                                               19

SEQ ID NO: 285          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 285
ggcagttgag tggtgtcagt                                              20

SEQ ID NO: 286          moltype = DNA  length = 18
FEATURE                 Location/Qualifiers
misc_feature            1..18
                        note = Synthetic Construct
source                  1..18
                        mol_type = other DNA
                        organism = synthetic construct
SEQUENCE: 286
gcagttgagt ggtgtcag                                                18

SEQ ID NO: 287          moltype = DNA  length = 19
FEATURE                 Location/Qualifiers
misc_feature            1..19
                        note = Synthetic Construct
source                  1..19
```

```
                        mol_type = other DNA
                        organism = synthetic construct
SEQUENCE: 287
ggcagttgag tggtgtcag                                                19

SEQ ID NO: 288          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 288
aggcagttga gtggtgtcag                                               20

SEQ ID NO: 289          moltype = DNA  length = 18
FEATURE                 Location/Qualifiers
misc_feature            1..18
                        note = Synthetic Construct
source                  1..18
                        mol_type = other DNA
                        organism = synthetic construct
SEQUENCE: 289
ggcagttgag tggtgtca                                                 18

SEQ ID NO: 290          moltype = DNA  length = 19
FEATURE                 Location/Qualifiers
misc_feature            1..19
                        note = Synthetic Construct
source                  1..19
                        mol_type = other DNA
                        organism = synthetic construct
SEQUENCE: 290
aggcagttga gtggtgtca                                                19

SEQ ID NO: 291          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 291
caggcagttg agtggtgtca                                               20

SEQ ID NO: 292          moltype = DNA  length = 18
FEATURE                 Location/Qualifiers
misc_feature            1..18
                        note = Synthetic Construct
source                  1..18
                        mol_type = other DNA
                        organism = synthetic construct
SEQUENCE: 292
aggcagttga gtggtgtc                                                 18

SEQ ID NO: 293          moltype = DNA  length = 19
FEATURE                 Location/Qualifiers
misc_feature            1..19
                        note = Synthetic Construct
source                  1..19
                        mol_type = other DNA
                        organism = synthetic construct
SEQUENCE: 293
caggcagttg agtggtgtc                                                19

SEQ ID NO: 294          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 294
ccaggcagtt gagtggtgtc                                               20

SEQ ID NO: 295          moltype = DNA  length = 18
FEATURE                 Location/Qualifiers
misc_feature            1..18
                        note = Synthetic Construct
```

```
source                  1..18
                        mol_type = other DNA
                        organism = synthetic construct
SEQUENCE: 295
caggcagttg agtggtgt                                                18

SEQ ID NO: 296          moltype = DNA  length = 19
FEATURE                 Location/Qualifiers
misc_feature            1..19
                        note = Synthetic Construct
source                  1..19
                        mol_type = other DNA
                        organism = synthetic construct
SEQUENCE: 296
ccaggcagtt gagtggtgt                                               19

SEQ ID NO: 297          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 297
gccaggcagt tgagtggtgt                                              20

SEQ ID NO: 298          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 298
tgccaggcag ttgagtggtg                                              20

SEQ ID NO: 299          moltype = DNA  length = 18
FEATURE                 Location/Qualifiers
misc_feature            1..18
                        note = Synthetic Construct
source                  1..18
                        mol_type = other DNA
                        organism = synthetic construct
SEQUENCE: 299
actggatgcc acattttc                                                18

SEQ ID NO: 300          moltype = DNA  length = 18
FEATURE                 Location/Qualifiers
misc_feature            1..18
                        note = Synthetic Construct
source                  1..18
                        mol_type = other DNA
                        organism = synthetic construct
SEQUENCE: 300
gactggatgc cacatttt                                                18

SEQ ID NO: 301          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 301
tggtaaagtg gactggatgc                                              20

SEQ ID NO: 302          moltype = DNA  length = 18
FEATURE                 Location/Qualifiers
misc_feature            1..18
                        note = Synthetic Construct
source                  1..18
                        mol_type = other DNA
                        organism = synthetic construct
SEQUENCE: 302
ggtaaagtgg actggatg                                                18

SEQ ID NO: 303          moltype = DNA  length = 19
FEATURE                 Location/Qualifiers
misc_feature            1..19
```

```
                        note = Synthetic Construct
source                  1..19
                        mol_type = other DNA
                        organism = synthetic construct
SEQUENCE: 303
tggtaaagtg gactggatg                                               19

SEQ ID NO: 304          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 304
atggtaaagt ggactggatg                                              20

SEQ ID NO: 305          moltype = DNA  length = 18
FEATURE                 Location/Qualifiers
misc_feature            1..18
                        note = Synthetic Construct
source                  1..18
                        mol_type = other DNA
                        organism = synthetic construct
SEQUENCE: 305
tggtaaagtg gactggat                                                18

SEQ ID NO: 306          moltype = DNA  length = 19
FEATURE                 Location/Qualifiers
misc_feature            1..19
                        note = Synthetic Construct
source                  1..19
                        mol_type = other DNA
                        organism = synthetic construct
SEQUENCE: 306
atggtaaagt ggactggat                                               19

SEQ ID NO: 307          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 307
gatggtaaag tggactggat                                              20

SEQ ID NO: 308          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 308
cagagatggt ttccttaaac                                              20

SEQ ID NO: 309          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 309
ccagagatgg tttccttaaa                                              20

SEQ ID NO: 310          moltype = DNA  length = 19
FEATURE                 Location/Qualifiers
misc_feature            1..19
                        note = Synthetic Construct
source                  1..19
                        mol_type = other DNA
                        organism = synthetic construct
SEQUENCE: 310
ccagagatgg tttccttaa                                               19

SEQ ID NO: 311          moltype = DNA  length = 18
FEATURE                 Location/Qualifiers
```

```
misc_feature         1..18
                     note = Synthetic Construct
source               1..18
                     mol_type = other DNA
                     organism = synthetic construct
SEQUENCE: 311
ccagagatgg tttcctta                                              18

SEQ ID NO: 312       moltype = RNA  length = 19
FEATURE              Location/Qualifiers
misc_feature         1..19
                     note = Synthetic Construct
source               1..19
                     mol_type = other RNA
                     organism = synthetic construct
SEQUENCE: 312
ataaggatga ctgaggaag                                             19

SEQ ID NO: 313       moltype = RNA  length = 20
FEATURE              Location/Qualifiers
misc_feature         1..20
                     note = Synthetic Construct
source               1..20
                     mol_type = other RNA
                     organism = synthetic construct
SEQUENCE: 313
ataaggatga ctgaggaaga                                            20

SEQ ID NO: 314       moltype = RNA  length = 18
FEATURE              Location/Qualifiers
misc_feature         1..18
                     note = Synthetic Construct
source               1..18
                     mol_type = other RNA
                     organism = synthetic construct
SEQUENCE: 314
taaggatgac tgaggaag                                              18

SEQ ID NO: 315       moltype = RNA  length = 19
FEATURE              Location/Qualifiers
misc_feature         1..19
                     note = Synthetic Construct
source               1..19
                     mol_type = other RNA
                     organism = synthetic construct
SEQUENCE: 315
taaggatgac tgaggaaga                                             19

SEQ ID NO: 316       moltype = RNA  length = 20
FEATURE              Location/Qualifiers
misc_feature         1..20
                     note = Synthetic Construct
source               1..20
                     mol_type = other RNA
                     organism = synthetic construct
SEQUENCE: 316
taaggatgac tgaggaagag                                            20

SEQ ID NO: 317       moltype = RNA  length = 18
FEATURE              Location/Qualifiers
misc_feature         1..18
                     note = Synthetic Construct
source               1..18
                     mol_type = other RNA
                     organism = synthetic construct
SEQUENCE: 317
aaggatgact gaggaaga                                              18

SEQ ID NO: 318       moltype = RNA  length = 19
FEATURE              Location/Qualifiers
misc_feature         1..19
                     note = Synthetic Construct
source               1..19
                     mol_type = other RNA
                     organism = synthetic construct
SEQUENCE: 318
aaggatgact gaggaagag                                             19

SEQ ID NO: 319       moltype = RNA  length = 20
```

```
FEATURE                Location/Qualifiers
misc_feature           1..20
                       note = Synthetic Construct
source                 1..20
                       mol_type = other RNA
                       organism = synthetic construct
SEQUENCE: 319
aaggatgact gaggaagagt                                              20

SEQ ID NO: 320         moltype = RNA  length = 18
FEATURE                Location/Qualifiers
misc_feature           1..18
                       note = Synthetic Construct
source                 1..18
                       mol_type = other RNA
                       organism = synthetic construct
SEQUENCE: 320
aggatgactg aggaagag                                                18

SEQ ID NO: 321         moltype = RNA  length = 19
FEATURE                Location/Qualifiers
misc_feature           1..19
                       note = Synthetic Construct
source                 1..19
                       mol_type = other RNA
                       organism = synthetic construct
SEQUENCE: 321
aggatgactg aggaagagt                                               19

SEQ ID NO: 322         moltype = RNA  length = 20
FEATURE                Location/Qualifiers
misc_feature           1..20
                       note = Synthetic Construct
source                 1..20
                       mol_type = other RNA
                       organism = synthetic construct
SEQUENCE: 322
aggatgactg aggaagagta                                              20

SEQ ID NO: 323         moltype = RNA  length = 18
FEATURE                Location/Qualifiers
misc_feature           1..18
                       note = Synthetic Construct
source                 1..18
                       mol_type = other RNA
                       organism = synthetic construct
SEQUENCE: 323
ggatgactga ggaagagt                                                18

SEQ ID NO: 324         moltype = RNA  length = 19
FEATURE                Location/Qualifiers
misc_feature           1..19
                       note = Synthetic Construct
source                 1..19
                       mol_type = other RNA
                       organism = synthetic construct
SEQUENCE: 324
ggatgactga ggaagagta                                               19

SEQ ID NO: 325         moltype = RNA  length = 20
FEATURE                Location/Qualifiers
misc_feature           1..20
                       note = Synthetic Construct
source                 1..20
                       mol_type = other RNA
                       organism = synthetic construct
SEQUENCE: 325
ggatgactga ggaagagtac                                              20

SEQ ID NO: 326         moltype = RNA  length = 18
FEATURE                Location/Qualifiers
misc_feature           1..18
                       note = Synthetic Construct
source                 1..18
                       mol_type = other RNA
                       organism = synthetic construct
SEQUENCE: 326
gatgactgag gaagagta                                                18
```

```
SEQ ID NO: 327          moltype = RNA  length = 19
FEATURE                 Location/Qualifiers
misc_feature            1..19
                        note = Synthetic Construct
source                  1..19
                        mol_type = other RNA
                        organism = synthetic construct
SEQUENCE: 327
gatgactgag gaagagtac                                                   19

SEQ ID NO: 328          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 328
gatgactgag gaagagtact                                                  20

SEQ ID NO: 329          moltype = RNA  length = 18
FEATURE                 Location/Qualifiers
misc_feature            1..18
                        note = Synthetic Construct
source                  1..18
                        mol_type = other RNA
                        organism = synthetic construct
SEQUENCE: 329
atgactgagg aagagtac                                                    18

SEQ ID NO: 330          moltype = RNA  length = 19
FEATURE                 Location/Qualifiers
misc_feature            1..19
                        note = Synthetic Construct
source                  1..19
                        mol_type = other RNA
                        organism = synthetic construct
SEQUENCE: 330
atgactgagg aagagtact                                                   19

SEQ ID NO: 331          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 331
atgactgagg aagagtactc                                                  20

SEQ ID NO: 332          moltype = RNA  length = 18
FEATURE                 Location/Qualifiers
misc_feature            1..18
                        note = Synthetic Construct
source                  1..18
                        mol_type = other RNA
                        organism = synthetic construct
SEQUENCE: 332
tgactgagga agagtact                                                    18

SEQ ID NO: 333          moltype = RNA  length = 19
FEATURE                 Location/Qualifiers
misc_feature            1..19
                        note = Synthetic Construct
source                  1..19
                        mol_type = other RNA
                        organism = synthetic construct
SEQUENCE: 333
tgactgagga agagtactc                                                   19

SEQ ID NO: 334          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 334
tgactgagga agagtactct                                                  20
```

```
SEQ ID NO: 335          moltype = DNA  length = 19
FEATURE                 Location/Qualifiers
misc_feature            1..19
                        note = Synthetic Construct
source                  1..19
                        mol_type = other DNA
                        organism = synthetic construct
SEQUENCE: 335
cttcctcagt catccttat                                                19

SEQ ID NO: 336          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 336
tcttcctcag tcatccttat                                               20

SEQ ID NO: 337          moltype = DNA  length = 18
FEATURE                 Location/Qualifiers
misc_feature            1..18
                        note = Synthetic Construct
source                  1..18
                        mol_type = other DNA
                        organism = synthetic construct
SEQUENCE: 337
cttcctcagt catcctta                                                 18

SEQ ID NO: 338          moltype = DNA  length = 19
FEATURE                 Location/Qualifiers
misc_feature            1..19
                        note = Synthetic Construct
source                  1..19
                        mol_type = other DNA
                        organism = synthetic construct
SEQUENCE: 338
tcttcctcag tcatcctta                                                19

SEQ ID NO: 339          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 339
ctcttcctca gtcatcctta                                               20

SEQ ID NO: 340          moltype = DNA  length = 18
FEATURE                 Location/Qualifiers
misc_feature            1..18
                        note = Synthetic Construct
source                  1..18
                        mol_type = other DNA
                        organism = synthetic construct
SEQUENCE: 340
tcttcctcag tcatcctt                                                 18

SEQ ID NO: 341          moltype = DNA  length = 19
FEATURE                 Location/Qualifiers
misc_feature            1..19
                        note = Synthetic Construct
source                  1..19
                        mol_type = other DNA
                        organism = synthetic construct
SEQUENCE: 341
ctcttcctca gtcatcctt                                                19

SEQ ID NO: 342          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 342
```

```
actcttcctc agtcatcctt                                              20

SEQ ID NO: 343          moltype = DNA  length = 18
FEATURE                 Location/Qualifiers
misc_feature            1..18
                        note = Synthetic Construct
source                  1..18
                        mol_type = other DNA
                        organism = synthetic construct
SEQUENCE: 343
ctcttcctca gtcatcct                                                18

SEQ ID NO: 344          moltype = DNA  length = 19
FEATURE                 Location/Qualifiers
misc_feature            1..19
                        note = Synthetic Construct
source                  1..19
                        mol_type = other DNA
                        organism = synthetic construct
SEQUENCE: 344
actcttcctc agtcatcct                                               19

SEQ ID NO: 345          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 345
tactcttcct cagtcatcct                                              20

SEQ ID NO: 346          moltype = DNA  length = 18
FEATURE                 Location/Qualifiers
misc_feature            1..18
                        note = Synthetic Construct
source                  1..18
                        mol_type = other DNA
                        organism = synthetic construct
SEQUENCE: 346
actcttcctc agtcatcc                                                18

SEQ ID NO: 347          moltype = DNA  length = 19
FEATURE                 Location/Qualifiers
misc_feature            1..19
                        note = Synthetic Construct
source                  1..19
                        mol_type = other DNA
                        organism = synthetic construct
SEQUENCE: 347
tactcttcct cagtcatcc                                               19

SEQ ID NO: 348          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 348
gtactcttcc tcagtcatcc                                              20

SEQ ID NO: 349          moltype = DNA  length = 18
FEATURE                 Location/Qualifiers
misc_feature            1..18
                        note = Synthetic Construct
source                  1..18
                        mol_type = other DNA
                        organism = synthetic construct
SEQUENCE: 349
tactcttcct cagtcatc                                                18

SEQ ID NO: 350          moltype = DNA  length = 19
FEATURE                 Location/Qualifiers
misc_feature            1..19
                        note = Synthetic Construct
source                  1..19
                        mol_type = other DNA
                        organism = synthetic construct
```

```
SEQUENCE: 350
gtactcttcc tcagtcatc                                                19

SEQ ID NO: 351          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 351
agtactcttc ctcagtcatc                                               20

SEQ ID NO: 352          moltype = DNA  length = 18
FEATURE                 Location/Qualifiers
misc_feature            1..18
                        note = Synthetic Construct
source                  1..18
                        mol_type = other DNA
                        organism = synthetic construct
SEQUENCE: 352
gtactcttcc tcagtcat                                                 18

SEQ ID NO: 353          moltype = DNA  length = 19
FEATURE                 Location/Qualifiers
misc_feature            1..19
                        note = Synthetic Construct
source                  1..19
                        mol_type = other DNA
                        organism = synthetic construct
SEQUENCE: 353
agtactcttc ctcagtcat                                                19

SEQ ID NO: 354          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 354
gagtactctt cctcagtcat                                               20

SEQ ID NO: 355          moltype = DNA  length = 18
FEATURE                 Location/Qualifiers
misc_feature            1..18
                        note = Synthetic Construct
source                  1..18
                        mol_type = other DNA
                        organism = synthetic construct
SEQUENCE: 355
agtactcttc ctcagtca                                                 18

SEQ ID NO: 356          moltype = DNA  length = 19
FEATURE                 Location/Qualifiers
misc_feature            1..19
                        note = Synthetic Construct
source                  1..19
                        mol_type = other DNA
                        organism = synthetic construct
SEQUENCE: 356
gagtactctt cctcagtca                                                19

SEQ ID NO: 357          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 357
agagtactct tcctcagtca                                               20

SEQ ID NO: 358          moltype = DNA  length = 20
FEATURE                 Location/Qualifiers
misc_feature            1..20
                        note = Synthetic Construct
modified_base           1..2
                        mod_base = cm
```

```
                        note = 2'-O-methylcytidine
misc_feature            1..20
                        note = phosphorothioate backbone
modified_base           3
                        mod_base = OTHER
                        note = 2'-O-methyladenosine
modified_base           4
                        mod_base = gm
                        note = 2'-O-methylguanosine
modified_base           5
                        mod_base = cm
                        note = 2'-O-methylcytidine
modified_base           16
                        mod_base = OTHER
                        note = 2'-O-methyladenosine
modified_base           17
                        mod_base = um
                        note = 2'-O-methyluridine
modified_base           18
                        mod_base = cm
                        note = 2'-O-methylcytidine
modified_base           19
                        mod_base = OTHER
                        note = 2'-O-methyladenosine
modified_base           20
                        mod_base = um
                        note = 2'-O-methyluridine
source                  1..20
                        mol_type = other DNA
                        organism = synthetic construct
SEQUENCE: 358
nnnnncttgt tggatnnnnn                                                  20

SEQ ID NO: 359          moltype = DNA  length = 20
FEATURE                 Location/Qualifiers
misc_feature            1..20
                        note = Synthetic Construct
modified_base           1..2
                        mod_base = cm
                        note = 2'-O-methylcytidine
misc_feature            1..20
                        note = phosphorothioate backbone
modified_base           3
                        mod_base = OTHER
                        note = 2'-O-methyladenosine
modified_base           4
                        mod_base = cm
                        note = 2'-O-methylcytidine
modified_base           5
                        mod_base = OTHER
                        note = 2'-O-methyladenosine
modified_base           16
                        mod_base = um
                        note = 2'-O-methyluridine
modified_base           17..18
                        mod_base = gm
                        note = 2'-O-methylguanosine
modified_base           19..20
                        mod_base = OTHER
                        note = 2'-O-methyladenosine
source                  1..20
                        mol_type = other DNA
                        organism = synthetic construct
SEQUENCE: 359
nnnnntttcc tctcannnnn                                                  20

SEQ ID NO: 360          moltype = DNA  length = 20
FEATURE                 Location/Qualifiers
misc_feature            1..20
                        note = Synthetic Construct
misc_feature            1..20
                        note = phosphorothioate backbone
modified_base           1
                        mod_base = gm
                        note = 2'-O-methylguanosine
modified_base           2
                        mod_base = OTHER
                        note = 2'-O-methyladenosine
modified_base           3
```

```
                        mod_base = gm
                        note = 2'-O-methylguanosine
modified_base           4
                        mod_base = um
                        note = 2'-O-methyluridine
modified_base           5
                        mod_base = gm
                        note = 2'-O-methylguanosine
modified_base           16..17
                        mod_base = OTHER
                        note = 2'-O-methyladenosine
modified_base           18
                        mod_base = um
                        note = 2'-O-methyluridine
modified_base           19
                        mod_base = gm
                        note = 2'-O-methylguanosine
modified_base           20
                        mod_base = um
                        note = 2'-O-methyluridine
source                  1..20
                        mol_type = other DNA
                        organism = synthetic construct
SEQUENCE: 360
nnnnntttgc aaaccnnnnn                                                20

SEQ ID NO: 361          moltype = DNA  length = 20
FEATURE                 Location/Qualifiers
misc_feature            1..20
                        note = Synthetic Construct
modified_base           1
                        mod_base = OTHER
                        note = 2'-O-methyluridine
misc_feature            1..20
                        note = phosphorothioate backbone
modified_base           2
                        mod_base = OTHER
                        note = 2'-O-methylguanosine
modified_base           3..5
                        mod_base = OTHER
                        note = 2'-O-methyluridine
modified_base           16
                        mod_base = um
                        note = 2'-O-methyluridine
modified_base           17
                        mod_base = OTHER
                        note = 2'-O-methylcytidine
modified_base           18
                        mod_base = OTHER
                        note = 2'-O-methyluridine
modified_base           19
                        mod_base = OTHER
                        note = 2'-O-methylguanosine
modified_base           20
                        mod_base = OTHER
                        note = 2'-O-methylcytidine
source                  1..20
                        mol_type = other DNA
                        organism = synthetic construct
SEQUENCE: 361
nnnnnctttg gtgatnnnnn                                                20

SEQ ID NO: 362          moltype = DNA  length = 20
FEATURE                 Location/Qualifiers
misc_feature            1..20
                        note = Synthetic Construct
modified_base           1
                        mod_base = OTHER
                        note = 2'-O-methyluridine
misc_feature            1..20
                        note = phosphorothioate backbone
modified_base           2
                        mod_base = OTHER
                        note = 2'-O-methyladenosine
modified_base           3
                        mod_base = OTHER
                        note = 2'-O-methylguanosine
modified_base           4
                        mod_base = OTHER
```

```
                        note = 2'-O-methyladenosine
modified_base           5
                        mod_base = OTHER
                        note = 2'-O-methylguanosine
modified_base           16..17
                        mod_base = OTHER
                        note = 2'-O-methylguanosine
modified_base           18
                        mod_base = OTHER
                        note = 2'-O-methylcytidine
modified_base           19
                        mod_base = OTHER
                        note = 2'-O-methyladenosine
modified_base           20
                        mod_base = OTHER
                        note = 2'-O-methylcytidine
source                  1..20
                        mol_type = other DNA
                        organism = synthetic construct
SEQUENCE: 362
nnnnngtgaa ggccannnnn                                              20

SEQ ID NO: 363          moltype = DNA  length = 20
FEATURE                 Location/Qualifiers
misc_feature            1..20
                        note = Synthetic Construct
modified_base           1
                        mod_base = OTHER
                        note = 2'-O-methylguanosine
misc_feature            1..20
                        note = phosphorothioate backbone
modified_base           2
                        mod_base = OTHER
                        note = 2'-O-methyluridine
modified_base           3
                        mod_base = OTHER
                        note = 2'-O-methyladenosine
modified_base           4
                        mod_base = OTHER
                        note = 2'-O-methylcytidine
modified_base           5
                        mod_base = OTHER
                        note = 2'-O-methyluridine
modified_base           16
                        mod_base = OTHER
                        note = 2'-O-methylcytidine
modified_base           17
                        mod_base = OTHER
                        note = 2'-O-methyladenosine
modified_base           18
                        mod_base = OTHER
                        note = 2'-O-methyluridine
modified_base           19..20
                        mod_base = OTHER
                        note = 2'-O-methylcytidine
source                  1..20
                        mol_type = other DNA
                        organism = synthetic construct
SEQUENCE: 363
nnnnncttcc tcagtnnnnn                                              20

SEQ ID NO: 364          moltype = DNA  length = 20
FEATURE                 Location/Qualifiers
misc_feature            1..20
                        note = Synthetic Construct
modified_base           1
                        mod_base = OTHER
                        note = 2'-O-methyluridine
misc_feature            1..20
                        note = phosphorothioate backbone
modified_base           2
                        mod_base = OTHER
                        note = 2'-O-methylguanosine
modified_base           3
                        mod_base = OTHER
                        note = 2'-O-methyluridine
modified_base           4
                        mod_base = OTHER
                        note = 2'-O-methylcytidine
```

```
modified_base          5
                       mod_base = OTHER
                       note = 2'-O-methyladenosine
modified_base          16
                       mod_base = OTHER
                       note = 2'-O-methylguanosine
modified_base          17..18
                       mod_base = OTHER
                       note = 2'-O-methyladenosine
modified_base          19
                       mod_base = OTHER
                       note = 2'-O-methylcytidine
modified_base          20
                       mod_base = OTHER
                       note = 2'-O-methyladenosine
source                 1..20
                       mol_type = other DNA
                       organism = synthetic construct
SEQUENCE: 364
nnnnngtttc tccctnnnnn                                                   20

SEQ ID NO: 365         moltype = DNA  length = 20
FEATURE                Location/Qualifiers
misc_feature           1..20
                       note = Synthetic Construct
modified_base          1
                       mod_base = OTHER
                       note = 2'-O-methyluridine
misc_feature           1..20
                       note = phosphorothioate backbone
modified_base          2
                       mod_base = OTHER
                       note = 2'-O-methyladenosine
modified_base          3
                       mod_base = OTHER
                       note = 2'-O-methylguanosine
modified_base          4..5
                       mod_base = OTHER
                       note = 2'-O-methyladenosine
modified_base          16
                       mod_base = OTHER
                       note = 2'-O-methylcytidine
modified_base          17..18
                       mod_base = OTHER
                       note = 2'-O-methyluridine
modified_base          19..20
                       mod_base = OTHER
                       note = 2'-O-methylguanosine
source                 1..20
                       mol_type = other DNA
                       organism = synthetic construct
SEQUENCE: 365
nnnnntggca catctnnnnn                                                   20

SEQ ID NO: 366         moltype = DNA  length = 20
FEATURE                Location/Qualifiers
misc_feature           1..20
                       note = Synthetic Construct
modified_base          1
                       mod_base = OTHER
                       note = 2'-O-methylguanosine
misc_feature           1..20
                       note = phosphorothioate backbone
modified_base          2..5
                       mod_base = OTHER
                       note = 2'-O-methyluridine
modified_base          16
                       mod_base = OTHER
                       note = 2'-O-methyladenosine
modified_base          17
                       mod_base = OTHER
                       note = 2'-O-methylguanosine
modified_base          18
                       mod_base = OTHER
                       note = 2'-O-methyluridine
modified_base          19
                       mod_base = OTHER
                       note = 2'-O-methylcytidine
modified_base          20
```

```
                         mod_base = OTHER
                         note = 2'-O-methyluridine
source                   1..20
                         mol_type = other DNA
                         organism = synthetic construct
SEQUENCE: 366
nnnnncttcc tccacnnnnn                                              20

SEQ ID NO: 367           moltype = DNA  length = 20
FEATURE                  Location/Qualifiers
misc_feature             1..20
                         note = Synthetic Construct
modified_base            1
                         mod_base = OTHER
                         note = 2'-O-methylcytidine
misc_feature             1..20
                         note = phosphorothioate backbone
modified_base            2
                         mod_base = OTHER
                         note = 2'-O-methyluridine
modified_base            3..4
                         mod_base = OTHER
                         note = 2'-O-methylguanosine
modified_base            5
                         mod_base = OTHER
                         note = 2'-O-methyluridine
modified_base            16
                         mod_base = OTHER
                         note = 2'-O-methylcytidine
modified_base            17..19
                         mod_base = OTHER
                         note = 2'-O-methyladenosine
modified_base            20
                         mod_base = OTHER
                         note = 2'-O-methylguanosine
source                   1..20
                         mol_type = other DNA
                         organism = synthetic construct
SEQUENCE: 367
nnnnngtcaa caagcnnnnn                                              20

SEQ ID NO: 368           moltype = DNA  length = 19
FEATURE                  Location/Qualifiers
misc_feature             1..19
                         note = Synthetic Construct
modified_base            1
                         mod_base = OTHER
                         note = 2'-O-methylguanosine
misc_feature             1..19
                         note = phosphorothioate backbone
modified_base            2..3
                         mod_base = OTHER
                         note = 2'-O-methyluridine
modified_base            4
                         mod_base = OTHER
                         note = 2'-O-methylguanosine
modified_base            15
                         mod_base = OTHER
                         note = 2'-O-methylguanosine
modified_base            16..18
                         mod_base = OTHER
                         note = 2'-O-methyluridine
modified_base            19
                         mod_base = OTHER
                         note = 2'-O-methylcytidine
source                   1..19
                         mol_type = other DNA
                         organism = synthetic construct
SEQUENCE: 368
nnnnagtggt gtcannnnn                                               19

SEQ ID NO: 369           moltype = DNA  length = 18
FEATURE                  Location/Qualifiers
misc_feature             1..18
                         note = Synthetic Construct
modified_base            1..2
                         mod_base = OTHER
                         note = 2'-O-methyluridine
misc_feature             1..18
```

```
                        note = phosphorothioate backbone
modified_base           3
                        mod_base = OTHER
                        note = 2'-O-methylguanosine
modified_base           4
                        mod_base = OTHER
                        note = 2'-O-methyladenosine
modified_base           15..17
                        mod_base = OTHER
                        note = 2'-O-methyluridine
modified_base           18
                        mod_base = OTHER
                        note = 2'-O-methylcytidine
source                  1..18
                        mol_type = other DNA
                        organism = synthetic construct
SEQUENCE: 369
nnnngtggtg tcagnnnn                                                18

SEQ ID NO: 370          moltype = DNA  length = 18
FEATURE                 Location/Qualifiers
misc_feature            1..18
                        note = Synthetic Construct
modified_base           1
                        mod_base = OTHER
                        note = 2'-O-methylcytidine
modified_base           1..18
                        mod_base = OTHER
                        note = phosphorothioate backbone
modified_base           2
                        mod_base = OTHER
                        note = 2'-O-methyluridine
modified_base           3..4
                        mod_base = OTHER
                        note = 2'-O-methylguanosine
modified_base           15..16
                        mod_base = OTHER
                        note = 2'-O-methylcytidine
modified_base           17..18
                        mod_base = OTHER
                        note = 2'-O-methyladenosine
source                  1..18
                        mol_type = other DNA
                        organism = synthetic construct
SEQUENCE: 370
nnnntgtcaa caagnnnn                                                18

SEQ ID NO: 371          moltype = DNA  length = 20
FEATURE                 Location/Qualifiers
misc_feature            1..20
                        note = Synthetic Construct
modified_base           1
                        mod_base = OTHER
                        note = 2'-O-methyladenosine
misc_feature            1..20
                        note = phosphorothioate backbone
modified_base           2
                        mod_base = OTHER
                        note = 2'-O-methyluridine
modified_base           3
                        mod_base = OTHER
                        note = 2'-O-methyladenosine
modified_base           4
                        mod_base = OTHER
                        note = 2'-O-methylguanosine
modified_base           5
                        mod_base = OTHER
                        note = 2'-O-methyladenosine
modified_base           16
                        mod_base = OTHER
                        note = 2'-O-methyluridine
modified_base           17
                        mod_base = OTHER
                        note = 2'-O-methylcytidine
modified_base           18..19
                        mod_base = OTHER
                        note = 2'-O-methyluridine
modified_base           20
                        mod_base = OTHER
```

```
                        note = 2'-O-methylguanosine
source                  1..20
                        mol_type = other DNA
                        organism = synthetic construct
SEQUENCE: 371
nnnnnatggc acatcnnnnn                                               20

SEQ ID NO: 372          moltype = DNA  length = 19
FEATURE                 Location/Qualifiers
misc_feature            1..19
                        note = Synthetic Construct
modified_base           1
                        mod_base = OTHER
                        note = 2'-O-methyladenosine
misc_feature            1..19
                        note = phosphorothioate backbone
modified_base           2
                        mod_base = OTHER
                        note = 2'-O-methylguanosine
modified_base           3..4
                        mod_base = OTHER
                        note = 2'-O-methyladenosine
modified_base           15
                        mod_base = OTHER
                        note = 2'-O-methylcytidine
modified_base           16..17
                        mod_base = OTHER
                        note = 2'-O-methyluridine
modified_base           18..19
                        mod_base = OTHER
                        note = 2'-O-methylguanosine
source                  1..19
                        mol_type = other DNA
                        organism = synthetic construct
SEQUENCE: 372
nnnntggcac atctnnnnn                                                19

SEQ ID NO: 373          moltype = DNA  length = 19
FEATURE                 Location/Qualifiers
misc_feature            1..19
                        note = Synthetic Construct
modified_base           1
                        mod_base = OTHER
                        note = 2'-O-methyluridine
misc_feature            1..19
                        note = phosphorothioate backbone
modified_base           2
                        mod_base = OTHER
                        note = 2'-O-methyladenosine
modified_base           3
                        mod_base = OTHER
                        note = 2'-O-methylguanosine
modified_base           4
                        mod_base = OTHER
                        note = 2'-O-methyladenosine
modified_base           15
                        mod_base = OTHER
                        note = 2'-O-methyluridine
modified_base           16
                        mod_base = OTHER
                        note = 2'-O-methylcytidine
modified_base           17..18
                        mod_base = OTHER
                        note = 2'-O-methyluridine
modified_base           19
                        mod_base = OTHER
                        note = 2'-O-methylguanosine
source                  1..19
                        mol_type = other DNA
                        organism = synthetic construct
SEQUENCE: 373
nnnnatggca catcnnnnn                                                19

SEQ ID NO: 374          moltype = DNA  length = 18
FEATURE                 Location/Qualifiers
misc_feature            1..18
                        note = Synthetic Construct
modified_base           1
                        mod_base = OTHER
```

```
                        note = 2'-O-methyladenosine
misc_feature            1..18
                        note = phosphorothioate backbone
modified_base           2
                        mod_base = OTHER
                        note = 2'-O-methylguanosine
modified_base           3..4
                        mod_base = OTHER
                        note = 2'-O-methyladenosine
modified_base           15
                        mod_base = OTHER
                        note = 2'-O-methylcytidine
modified_base           16..17
                        mod_base = OTHER
                        note = 2'-O-methyluridine
modified_base           18
                        mod_base = OTHER
                        note = 2'-O-methylguanosine
source                  1..18
                        mol_type = other DNA
                        organism = synthetic construct
SEQUENCE: 374
nnnntggcac atctnnnn                                              18

SEQ ID NO: 375          moltype = DNA  length = 20
FEATURE                 Location/Qualifiers
misc_feature            1..20
                        note = Synthetic Construct
modified_base           1
                        mod_base = OTHER
                        note = 2'-O-methyluridine
misc_feature            1..20
                        note = phosphorothioate backbone
modified_base           2
                        mod_base = OTHER
                        note = 2'-O-methyladenosine
modified_base           3
                        mod_base = OTHER
                        note = 2'-O-methylguanosine
modified_base           4..5
                        mod_base = OTHER
                        note = 2'-O-methyladenosine
modified_base           16
                        mod_base = OTHER
                        note = 2'-O-methylcytidine
modified_base           17..18
                        mod_base = OTHER
                        note = 2'-O-methyluridine
modified_base           19..20
                        mod_base = OTHER
                        note = 2'-O-methylguanosine
source                  1..20
                        mol_type = other DNA
                        organism = synthetic construct
SEQUENCE: 375
nnnnntggca catctnnnnn                                            20

SEQ ID NO: 376          moltype = DNA  length = 20
FEATURE                 Location/Qualifiers
misc_feature            1..20
                        note = Synthetic Construct
modified_base           1
                        mod_base = OTHER
                        note = 2'-O-methyluridine
misc_feature            1..5
                        note = phosphorothioate backbone
modified_base           2
                        mod_base = OTHER
                        note = 2'-O-methyladenosine
modified_base           3
                        mod_base = OTHER
                        note = 2'-O-methylguanosine
modified_base           4..5
                        mod_base = OTHER
                        note = 2'-O-methyladenosine
misc_feature            5..6
                        note = phosphodiester backbone
misc_feature            6..15
                        note = phosphorothioate backbone
```

```
misc_feature            15..16
                        note = phosphodiester backbone
misc_feature            16..20
                        note = phosphorothioate backbone
modified_base           16
                        mod_base = OTHER
                        note = 2'-O-methylcytidine
modified_base           17..18
                        mod_base = OTHER
                        note = 2'-O-methyluridine
modified_base           19..20
                        mod_base = OTHER
                        note = 2'-O-methylguanosine
source                  1..20
                        mol_type = other DNA
                        organism = synthetic construct
SEQUENCE: 376
nnnnntggca catctnnnnn                                                20

SEQ ID NO: 377          moltype = DNA  length = 20
FEATURE                 Location/Qualifiers
misc_feature            1..20
                        note = Synthetic Construct
modified_base           1
                        mod_base = OTHER
                        note = 2'-O-methyluridine
misc_feature            1..2
                        note = phosphorothioate backbone
misc_feature            2..3
                        note = phosphodiester backbone
modified_base           2
                        mod_base = OTHER
                        note = 2'-O-methyladenosine
modified_base           3
                        mod_base = OTHER
                        note = 2'-O-methylguanosine
misc_feature            4..5
                        note = phosphodiester backbone
modified_base           4..5
                        mod_base = OTHER
                        note = 2'-O-methyladenosine
misc_feature            6..7
                        note = phosphodiester backbone
misc_feature            8..9
                        note = phosphodiester backbone
misc_feature            10..11
                        note = phosphodiester backbone
misc_feature            12..13
                        note = phosphodiester backbone
misc_feature            14..15
                        note = phosphodiester backbone
misc_feature            16..17
                        note = phosphodiester backbone
modified_base           16
                        mod_base = OTHER
                        note = 2'-O-methylcytidine
modified_base           17..18
                        mod_base = OTHER
                        note = 2'-O-methyluridine
misc_feature            18..19
                        note = phosphodiester backbone
modified_base           19..20
                        mod_base = OTHER
                        note = 2'-O-methylguanosine
source                  1..20
                        mol_type = other DNA
                        organism = synthetic construct
misc_feature            3..4
                        note = phosphorothioate backbone
misc_feature            5..6
                        note = phosphorothioate backbone
misc_feature            7..8
                        note = phosphorothioate backbone
misc_feature            9..10
                        note = phosphorothioate backbone
misc_feature            11..12
                        note = phosphorothioate backbone
misc_feature            13..14
                        note = phosphorothioate backbone
```

```
misc_feature            15..16
                        note = phosphorothioate backbone
misc_feature            17..18
                        note = phosphorothioate backbone
misc_feature            19..20
                        note = phosphorothioate backbone
SEQUENCE: 377
nnnnntggca catctnnnnn                                          20

SEQ ID NO: 378          moltype = DNA  length = 20
FEATURE                 Location/Qualifiers
misc_feature            1..20
                        note = Synthetic Construct
modified_base           1
                        mod_base = OTHER
                        note = 2'-O-(2-methoxyethyl)-modified thymidine
misc_feature            1..20
                        note = phosphorothioate backbone
modified_base           2
                        mod_base = OTHER
                        note = 2'-O-(2-methoxyethyl)-modified adenosine
modified_base           3
                        mod_base = OTHER
                        note = 2'-O-(2-methoxyethyl)-modified guanosine
modified_base           4..5
                        mod_base = OTHER
                        note = 2'-O-(2-methoxyethyl)-modified adenosine
modified_base           16
                        mod_base = OTHER
                        note = 2'-O-(2-methoxyethyl)-modified 5-methylcytidine
modified_base           17..18
                        mod_base = OTHER
                        note = 2'-O-(2-methoxyethyl)-modified thymidine
modified_base           19..20
                        mod_base = OTHER
                        note = 2'-O-(2-methoxyethyl)-modified guanosine
source                  1..20
                        mol_type = other DNA
                        organism = synthetic construct
SEQUENCE: 378
nnnnntggca catctnnnnn                                          20

SEQ ID NO: 379          moltype = DNA  length = 20
FEATURE                 Location/Qualifiers
misc_feature            1..20
                        note = Synthetic Construct
misc_feature            1..5
                        note = phosphorothioate backbone
modified_base           1
                        mod_base = OTHER
                        note = 2'-O-(2-methoxyethyl)-modified thymidine
modified_base           2
                        mod_base = OTHER
                        note = 2'-O-(2-methoxyethyl)-modified adenosine
modified_base           3
                        mod_base = OTHER
                        note = 2'-O-(2-methoxyethyl)-modified guanosine
modified_base           4..5
                        mod_base = OTHER
                        note = 2'-O-(2-methoxyethyl)-modified adenosine
misc_feature            5..6
                        note = phosphodiester backbone
misc_feature            6..15
                        note = phosphorothioate backbone
misc_feature            15..16
                        note = phosphodiester backbone
modified_base           16
                        mod_base = OTHER
                        note = 2'-O-(2-methoxyethyl)-modified 5-methylcytidine
misc_feature            16..20
                        note = phosphorothioate backbone
modified_base           17..18
                        mod_base = OTHER
                        note = 2'-O-(2-methoxyethyl)-modified thymidine
modified_base           19..20
                        mod_base = OTHER
                        note = 2'-O-(2-methoxyethyl)-modified guanosine
source                  1..20
                        mol_type = other DNA
```

```
                         organism = synthetic construct
SEQUENCE: 379
nnnnntggca catctnnnnn                                            20

SEQ ID NO: 380           moltype = DNA  length = 20
FEATURE                  Location/Qualifiers
misc_feature             1..20
                         note = Synthetic Construct
modified_base            1
                         mod_base = OTHER
                         note = 2'-O-(2-methoxyethyl)-modified thymidine
misc_feature             1..2
                         note = phosphorothioate backbone
misc_feature             2..3
                         note = phosphodiester backbone
modified_base            2
                         mod_base = OTHER
                         note = 2'-O-(2-methoxyethyl)-modified adenosine
misc_feature             3..4
                         note = phosphorothioate backbone
modified_base            3
                         mod_base = OTHER
                         note = 2'-O-(2-methoxyethyl)-modified guanosine
misc_feature             4..5
                         note = phosphodiester backbone
modified_base            4..5
                         mod_base = OTHER
                         note = 2'-O-(2-methoxyethyl)-modified adenosine
misc_feature             5..6
                         note = phosphorothioate backbone
misc_feature             6..7
                         note = phosphodiester backbone
misc_feature             7..8
                         note = phosphorothioate backbone
misc_feature             8..9
                         note = phosphodiester backbone
misc_feature             9..10
                         note = phosphorothioate backbone
misc_feature             10..11
                         note = phosphodiester backbone
misc_feature             11..12
                         note = phosphorothioate backbone
misc_feature             12..13
                         note = phosphodiester backbone
misc_feature             13..14
                         note = phosphorothioate backbone
misc_feature             14..15
                         note = phosphodiester backbone
misc_feature             15..16
                         note = phosphorothioate backbone
misc_feature             16..17
                         note = phosphodiester backbone
modified_base            16
                         mod_base = OTHER
                         note = 2'-O-(2-methoxyethyl)-modified 5-methylcytidine
misc_feature             17..18
                         note = phosphorothioate backbone
modified_base            17..18
                         mod_base = OTHER
                         note = 2'-O-(2-methoxyethyl)-modified thymidine
misc_feature             18..19
                         note = phosphodiester backbone
misc_feature             19..20
                         note = phosphorothioate backbone
modified_base            19..20
                         mod_base = OTHER
                         note = 2'-O-(2-methoxyethyl)-modified guanosine
source                   1..20
                         mol_type = other DNA
                         organism = synthetic construct
SEQUENCE: 380
nnnnntggca catctnnnnn                                            20

SEQ ID NO: 381           moltype = DNA  length = 18
FEATURE                  Location/Qualifiers
misc_feature             1..18
                         note = Synthetic Construct
modified_base            1
                         mod_base = OTHER
```

```
                        note = locked nucleic acid adenosine
misc_feature            1..18
                        note = phosphorothioate backbone
modified_base           2
                        mod_base = OTHER
                        note = locked nucleic acid guanosine
modified_base           3
                        mod_base = OTHER
                        note = locked nucleic acid adenosine
modified_base           15
                        mod_base = OTHER
                        note = locked nucleic acid 5-methylcytidine
modified_base           16..17
                        mod_base = OTHER
                        note = locked nucleic acid thymidine
modified_base           18
                        mod_base = OTHER
                        note = locked nucleic acid guanosine
source                  1..18
                        mol_type = other DNA
                        organism = synthetic construct
SEQUENCE: 381
nnnatggcac atctnnnn                                                  18

SEQ ID NO: 382          moltype = DNA  length = 18
FEATURE                 Location/Qualifiers
misc_feature            1..18
                        note = Synthetic Construct
modified_base           1
                        mod_base = OTHER
                        note = locked nucleic acid adenosine
misc_feature            1..3
                        note = phosphorothioate backbone
modified_base           2
                        mod_base = OTHER
                        note = locked nucleic acid guanosine
misc_feature            3..4
                        note = phosphodiester backbone
modified_base           3
                        mod_base = OTHER
                        note = locked nucleic acid adenosine
misc_feature            4..14
                        note = phosphorothioate backbone
misc_feature            14..15
                        note = phosphodiester backbone
misc_feature            15..18
                        note = phosphorothioate backbone
modified_base           15
                        mod_base = OTHER
                        note = locked nucleic acid 5-methylcytidine
modified_base           16..17
                        mod_base = OTHER
                        note = locked nucleic acid thymidine
modified_base           18
                        mod_base = OTHER
                        note = locked nucleic acid guanosine
source                  1..18
                        mol_type = other DNA
                        organism = synthetic construct
SEQUENCE: 382
nnnatggcac atctnnnn                                                  18

SEQ ID NO: 383          moltype = DNA  length = 18
FEATURE                 Location/Qualifiers
misc_feature            1..18
                        note = Synthetic Construct
modified_base           1
                        mod_base = OTHER
                        note = locked nucleic acid adenosine
misc_feature            1..2
                        note = phosphorothioate backbone
misc_feature            2..3
                        note = phosphodiester backbone
modified_base           2
                        mod_base = OTHER
                        note = locked nucleic acid guanosine
misc_feature            3..4
                        note = phosphorothioate backbone
modified_base           3
```

```
                        mod_base = OTHER
                        note = locked nucleic acid adenosine
misc_feature            4..5
                        note = phosphodiester backbone
misc_feature            5..6
                        note = phosphorothioate backbone
misc_feature            6..7
                        note = phosphodiester backbone
misc_feature            7..8
                        note = phosphorothioate backbone
misc_feature            8..9
                        note = phosphodiester backbone
misc_feature            9..10
                        note = phosphorothioate backbone
misc_feature            10..11
                        note = phosphodiester backbone
misc_feature            11..12
                        note = phosphorothioate backbone
misc_feature            12..13
                        note = phosphodiester backbone
misc_feature            13..14
                        note = phosphorothioate backbone
misc_feature            14..15
                        note = phosphodiester backbone
misc_feature            15..16
                        note = phosphorothioate backbone
modified_base           15
                        mod_base = OTHER
                        note = locked nucleic acid 5-methylcytidine
misc_feature            16..17
                        note = phosphodiester backbone
modified_base           16..17
                        mod_base = OTHER
                        note = locked nucleic acid thymidine
misc_feature            17..18
                        note = phosphorothioate backbone
modified_base           18
                        mod_base = OTHER
                        note = locked nucleic acid guanosine
source                  1..18
                        mol_type = other DNA
                        organism = synthetic construct
SEQUENCE: 383
nnnatggcac atctnnnn                                              18

SEQ ID NO: 384          moltype = DNA  length = 18
FEATURE                 Location/Qualifiers
misc_feature            1..18
                        note = Synthetic Construct
modified_base           1
                        mod_base = OTHER
                        note = 2'-O-methylcytidine
misc_feature            1..18
                        note = phosphorothioate backbone
modified_base           2
                        mod_base = OTHER
                        note = 2'-O-methyluridine
modified_base           3..4
                        mod_base = OTHER
                        note = 2'-O-methylguanosine
modified_base           15..16
                        mod_base = OTHER
                        note = 2'-O-methylcytidine
modified_base           17..18
                        mod_base = OTHER
                        note = 2'-O-methyladenosine
source                  1..18
                        mol_type = other DNA
                        organism = synthetic construct
SEQUENCE: 384
nnnntgtcaa caagnnnn                                              18

SEQ ID NO: 385          moltype = DNA  length = 18
FEATURE                 Location/Qualifiers
misc_feature            1..18
                        note = Synthetic Construct
modified_base           1
                        mod_base = OTHER
                        note = 2'-O-methylcytidine
```

```
misc_feature            1..4
                        note = phosphorothioate backbone
modified_base           2
                        mod_base = OTHER
                        note = 2'-O-methyluridine
modified_base           3..4
                        mod_base = OTHER
                        note = 2'-O-methylguanosine
misc_feature            4..5
                        note = phosphodiester backbone
misc_feature            5..14
                        note = phosphorothioate backbone
misc_feature            14..15
                        note = phosphodiester backbone
misc_feature            15..18
                        note = phosphorothioate backbone
modified_base           15..16
                        mod_base = OTHER
                        note = 2'-O-methylcytidine
modified_base           17..18
                        mod_base = OTHER
                        note = 2'-O-methyladenosine
source                  1..18
                        mol_type = other DNA
                        organism = synthetic construct
SEQUENCE: 385
nnnntgtcaa caagnnnn                                                  18

SEQ ID NO: 386          moltype = DNA  length = 18
FEATURE                 Location/Qualifiers
misc_feature            1..18
                        note = Synthetic Construct
modified_base           1
                        mod_base = OTHER
                        note = 2'-O-methylcytidine
misc_feature            1..2
                        note = phosphorothioate backbone
misc_feature            2..3
                        note = phosphodiester backbone
modified_base           2
                        mod_base = OTHER
                        note = 2'-O-methyluridine
misc_feature            3..4
                        note = phosphorothioate backbone
modified_base           3..4
                        mod_base = OTHER
                        note = 2'-O-methylguanosine
misc_feature            4..5
                        note = phosphodiester backbone
misc_feature            5..6
                        note = phosphorothioate backbone
misc_feature            6..7
                        note = phosphodiester backbone
misc_feature            7..8
                        note = phosphorothioate backbone
misc_feature            8..9
                        note = phosphodiester backbone
misc_feature            9..10
                        note = phosphorothioate backbone
misc_feature            10..11
                        note = phosphodiester backbone
misc_feature            11..12
                        note = phosphorothioate backbone
misc_feature            12..13
                        note = phosphodiester backbone
misc_feature            13..14
                        note = phosphorothioate backbone
misc_feature            14..15
                        note = phosphodiester backbone
misc_feature            15..16
                        note = phosphorothioate backbone
modified_base           15..16
                        mod_base = OTHER
                        note = 2'-O-methylcytidine
misc_feature            16..17
                        note = phosphodiester backbone
misc_feature            17..18
                        note = phosphorothioate backbone
modified_base           17..18
```

```
                         mod_base = OTHER
                         note = 2'-O-methyladenosine
source                   1..18
                         mol_type = other DNA
                         organism = synthetic construct
SEQUENCE: 386
nnnntgtcaa caagnnnn                                                18

SEQ ID NO: 387           moltype = DNA  length = 18
FEATURE                  Location/Qualifiers
misc_feature             1..18
                         note = Synthetic Construct
modified_base            1
                         mod_base = OTHER
                         note = 2'-O-(2-methoxyethyl)-modified 5-methylcytidine
misc_feature             1..18
                         note = phosphorothioate backbone
modified_base            2
                         mod_base = OTHER
                         note = 2'-O-(2-methoxyethyl)-modified thymidine
modified_base            3..4
                         mod_base = OTHER
                         note = 2'-O-(2-methoxyethyl)-modified guanosine
modified_base            15..16
                         mod_base = OTHER
                         note = 2'-O-(2-methoxyethyl)-modified 5-methylcytidine
modified_base            17..18
                         mod_base = OTHER
                         note = 2'-O-(2-methoxyethyl)-modified adenosine
source                   1..18
                         mol_type = other DNA
                         organism = synthetic construct
SEQUENCE: 387
nnnntgtcaa caagnnnn                                                18

SEQ ID NO: 388           moltype = DNA  length = 18
FEATURE                  Location/Qualifiers
misc_feature             1..18
                         note = Synthetic Construct
modified_base            1
                         mod_base = OTHER
                         note = 2'-O-(2-methoxyethyl)-modified 5-methylcytidine
misc_feature             1..4
                         note = phosphorothioate backbone
modified_base            2
                         mod_base = OTHER
                         note = 2'-O-(2-methoxyethyl)-modified thymidine
modified_base            3..4
                         mod_base = OTHER
                         note = 2'-O-(2-methoxyethyl)-modified guanosine
misc_feature             4..5
                         note = phosphodiester backbone
misc_feature             5..14
                         note = phosphorothioate backbone
misc_feature             14..15
                         note = phosphodiester backbone
misc_feature             15..18
                         note = phosphorothioate backbone
modified_base            15..16
                         mod_base = OTHER
                         note = 2'-O-(2-methoxyethyl)-modified 5-methylcytidine
modified_base            17..18
                         mod_base = OTHER
                         note = 2'-O-(2-methoxyethyl)-modified adenosine
source                   1..18
                         mol_type = other DNA
                         organism = synthetic construct
SEQUENCE: 388
nnnntgtcaa caagnnnn                                                18

SEQ ID NO: 389           moltype = DNA  length = 18
FEATURE                  Location/Qualifiers
misc_feature             1..18
                         note = Synthetic Construct
modified_base            1
                         mod_base = OTHER
                         note = 2'-O-(2-methoxyethyl)-modified 5-methylcytidine
misc_feature             1..2
                         note = phosphorothioate backbone
```

```
misc_feature            2..3
                        note = phosphodiester backbone
modified_base           2
                        mod_base = OTHER
                        note = 2'-O-(2-methoxyethyl)-modified thymidine
misc_feature            3..4
                        note = phosphorothioate backbone
modified_base           3..4
                        mod_base = OTHER
                        note = 2'-O-(2-methoxyethyl)-modified guanosine
misc_feature            4..5
                        note = phosphodiester backbone
misc_feature            5..6
                        note = phosphorothioate backbone
misc_feature            6..7
                        note = phosphodiester backbone
misc_feature            7..8
                        note = phosphorothioate backbone
misc_feature            8..9
                        note = phosphodiester backbone
misc_feature            9..10
                        note = phosphorothioate backbone
misc_feature            10..11
                        note = phosphodiester backbone
misc_feature            11..12
                        note = phosphorothioate backbone
misc_feature            12..13
                        note = phosphodiester backbone
misc_feature            13..14
                        note = phosphorothioate backbone
misc_feature            14..15
                        note = phosphodiester backbone
misc_feature            15..16
                        note = phosphorothioate backbone
modified_base           15..16
                        mod_base = OTHER
                        note = 2'-O-(2-methoxyethyl)-modified 5-methylcytidine
misc_feature            16..17
                        note = phosphodiester backbone
misc_feature            17..18
                        note = phosphorothioate backbone
modified_base           17..18
                        mod_base = OTHER
                        note = 2'-O-(2-methoxyethyl)-modified adenosine
source                  1..18
                        mol_type = other DNA
                        organism = synthetic construct
SEQUENCE: 389
nnnntgtcaa caagnnnn                                                      18

SEQ ID NO: 390          moltype = DNA  length = 17
FEATURE                 Location/Qualifiers
misc_feature            1..17
                        note = Synthetic Construct
modified_base           1
                        mod_base = OTHER
                        note = locked nucleic acid thymidine
misc_feature            1..17
                        note = phosphorothioate backbone
modified_base           2..3
                        mod_base = OTHER
                        note = locked nucleic acid guanosine
modified_base           14..15
                        mod_base = OTHER
                        note = locked nucleic acid 5-methylcytidine
modified_base           16..17
                        mod_base = OTHER
                        note = locked nucleic acid adenosine
source                  1..17
                        mol_type = other DNA
                        organism = synthetic construct
SEQUENCE: 390
nnntgtcaac aagnnnn                                                       17

SEQ ID NO: 391          moltype = DNA  length = 17
FEATURE                 Location/Qualifiers
misc_feature            1..17
                        note = Synthetic Construct
modified_base           1
```

```
                         mod_base = OTHER
                         note = locked nucleic acid thymidine
misc_feature             1..3
                         note = phosphorothioate backbone
modified_base            2..3
                         mod_base = OTHER
                         note = locked nucleic acid guanosine
misc_feature             3..4
                         note = phosphodiester backbone
misc_feature             4..13
                         note = phosphorothioate backbone
misc_feature             13..14
                         note = phosphodiester backbone
misc_feature             14..17
                         note = phosphorothioate backbone
modified_base            14..15
                         mod_base = OTHER
                         note = locked nucleic acid 5-methylcytidine
modified_base            16..17
                         mod_base = OTHER
                         note = locked nucleic acid adenosine
source                   1..17
                         mol_type = other DNA
                         organism = synthetic construct
SEQUENCE: 391
nnntgtcaac aagnnnn                                                17

SEQ ID NO: 392           moltype = DNA  length = 17
FEATURE                  Location/Qualifiers
misc_feature             1..17
                         note = Synthetic Construct
modified_base            1
                         mod_base = OTHER
                         note = locked nucleic acid thymidine
misc_feature             1..2
                         note = phosphorothioate backbone
misc_feature             2..3
                         note = phosphodiester backbone
modified_base            2..3
                         mod_base = OTHER
                         note = locked nucleic acid guanosine
misc_feature             3..4
                         note = phosphorothioate backbone
misc_feature             4..5
                         note = phosphodiester backbone
misc_feature             5..6
                         note = phosphorothioate backbone
misc_feature             6..7
                         note = phosphodiester backbone
misc_feature             7..8
                         note = phosphorothioate backbone
misc_feature             8..9
                         note = phosphodiester backbone
misc_feature             9..10
                         note = phosphorothioate backbone
misc_feature             10..11
                         note = phosphodiester backbone
misc_feature             11..12
                         note = phosphorothioate backbone
misc_feature             12..13
                         note = phosphodiester backbone
misc_feature             13..14
                         note = phosphorothioate backbone
misc_feature             14..16
                         note = phosphodiester backbone
modified_base            14..15
                         mod_base = OTHER
                         note = locked nucleic acid 5-methylcytidine
misc_feature             16..17
                         note = phosphorothioate backbone
modified_base            16..17
                         mod_base = OTHER
                         note = locked nucleic acid adenosine
source                   1..17
                         mol_type = other DNA
                         organism = synthetic construct
SEQUENCE: 392
nnntgtcaac aagnnnn                                                17
```

```
SEQ ID NO: 393          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 393
gaaaccatct ctgggataag                                              20

SEQ ID NO: 394          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 394
aaaccatctc tgggataagg                                              20

SEQ ID NO: 395          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 395
aaccatctct gggataagga                                              20

SEQ ID NO: 396          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 396
accatctctg ggataaggat                                              20

SEQ ID NO: 397          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 397
ccatctctgg gataaggatg                                              20

SEQ ID NO: 398          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 398
catctctggg ataaggatga                                              20

SEQ ID NO: 399          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 399
atctctggga taaggatgac                                              20

SEQ ID NO: 400          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 400
tctctgggat aaggatgact                                              20
```

```
SEQ ID NO: 401          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 401
ctctgggata aggatgactg                                              20

SEQ ID NO: 402          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 402
tctgggataa ggatgactga                                              20

SEQ ID NO: 403          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 403
ctgggataag gatgactgag                                              20

SEQ ID NO: 404          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 404
tgggataagg atgactgagg                                              20

SEQ ID NO: 405          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 405
gggataagga tgactgagga                                              20

SEQ ID NO: 406          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 406
ggataaggat gactgaggaa                                              20

SEQ ID NO: 407          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 407
gctgaaacaa ctgaaacttc                                              20

SEQ ID NO: 408          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 408
```

```
gaaacaactg aaacttcagg                                                    20

SEQ ID NO: 409          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 409
aaacaactga aacttcaggg                                                    20

SEQ ID NO: 410          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 410
aacaactgaa acttcaggga                                                    20

SEQ ID NO: 411          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 411
acaactgaaa cttcagggaa                                                    20

SEQ ID NO: 412          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 412
caactgaaac ttcagggaaa                                                    20

SEQ ID NO: 413          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 413
actgaaactt cagggaaaag                                                    20

SEQ ID NO: 414          moltype = RNA  length = 19
FEATURE                 Location/Qualifiers
misc_feature            1..19
                        note = Synthetic Construct
source                  1..19
                        mol_type = other RNA
                        organism = synthetic construct
SEQUENCE: 414
aaccatctct gggataagg                                                     19

SEQ ID NO: 415          moltype = RNA  length = 19
FEATURE                 Location/Qualifiers
misc_feature            1..19
                        note = Synthetic Construct
source                  1..19
                        mol_type = other RNA
                        organism = synthetic construct
SEQUENCE: 415
accatctctg ggataagga                                                     19

SEQ ID NO: 416          moltype = RNA  length = 19
FEATURE                 Location/Qualifiers
misc_feature            1..19
                        note = Synthetic Construct
source                  1..19
                        mol_type = other RNA
                        organism = synthetic construct
```

```
SEQUENCE: 416
ccatctctgg gataaggat                                               19

SEQ ID NO: 417          moltype = RNA  length = 19
FEATURE                 Location/Qualifiers
misc_feature            1..19
                        note = Synthetic Construct
source                  1..19
                        mol_type = other RNA
                        organism = synthetic construct
SEQUENCE: 417
catctctggg ataaggatg                                               19

SEQ ID NO: 418          moltype = RNA  length = 19
FEATURE                 Location/Qualifiers
misc_feature            1..19
                        note = Synthetic Construct
source                  1..19
                        mol_type = other RNA
                        organism = synthetic construct
SEQUENCE: 418
atctctggga taaggatga                                               19

SEQ ID NO: 419          moltype = RNA  length = 19
FEATURE                 Location/Qualifiers
misc_feature            1..19
                        note = Synthetic Construct
source                  1..19
                        mol_type = other RNA
                        organism = synthetic construct
SEQUENCE: 419
tctctgggat aaggatgac                                               19

SEQ ID NO: 420          moltype = RNA  length = 19
FEATURE                 Location/Qualifiers
misc_feature            1..19
                        note = Synthetic Construct
source                  1..19
                        mol_type = other RNA
                        organism = synthetic construct
SEQUENCE: 420
ctctgggata aggatgact                                               19

SEQ ID NO: 421          moltype = RNA  length = 19
FEATURE                 Location/Qualifiers
misc_feature            1..19
                        note = Synthetic Construct
source                  1..19
                        mol_type = other RNA
                        organism = synthetic construct
SEQUENCE: 421
tctgggataa ggatgactg                                               19

SEQ ID NO: 422          moltype = RNA  length = 19
FEATURE                 Location/Qualifiers
misc_feature            1..19
                        note = Synthetic Construct
source                  1..19
                        mol_type = other RNA
                        organism = synthetic construct
SEQUENCE: 422
ctgggataag gatgactga                                               19

SEQ ID NO: 423          moltype = RNA  length = 19
FEATURE                 Location/Qualifiers
misc_feature            1..19
                        note = Synthetic Construct
source                  1..19
                        mol_type = other RNA
                        organism = synthetic construct
SEQUENCE: 423
tgggataagg atgactgag                                               19

SEQ ID NO: 424          moltype = RNA  length = 19
FEATURE                 Location/Qualifiers
misc_feature            1..19
                        note = Synthetic Construct
source                  1..19
                        mol_type = other RNA
```

```
                        organism = synthetic construct
SEQUENCE: 424
gggataagga tgactgagg                                                19

SEQ ID NO: 425          moltype = RNA  length = 19
FEATURE                 Location/Qualifiers
misc_feature            1..19
                        note = Synthetic Construct
source                  1..19
                        mol_type = other RNA
                        organism = synthetic construct
SEQUENCE: 425
ggataaggat gactgagga                                                19

SEQ ID NO: 426          moltype = RNA  length = 19
FEATURE                 Location/Qualifiers
misc_feature            1..19
                        note = Synthetic Construct
source                  1..19
                        mol_type = other RNA
                        organism = synthetic construct
SEQUENCE: 426
aacaactgaa acttcaggg                                                19

SEQ ID NO: 427          moltype = RNA  length = 19
FEATURE                 Location/Qualifiers
misc_feature            1..19
                        note = Synthetic Construct
source                  1..19
                        mol_type = other RNA
                        organism = synthetic construct
SEQUENCE: 427
acaactgaaa cttcaggga                                                19

SEQ ID NO: 428          moltype = RNA  length = 19
FEATURE                 Location/Qualifiers
misc_feature            1..19
                        note = Synthetic Construct
source                  1..19
                        mol_type = other RNA
                        organism = synthetic construct
SEQUENCE: 428
caactgaaac ttcagggaa                                                19

SEQ ID NO: 429          moltype = RNA  length = 19
FEATURE                 Location/Qualifiers
misc_feature            1..19
                        note = Synthetic Construct
source                  1..19
                        mol_type = other RNA
                        organism = synthetic construct
SEQUENCE: 429
caactgaaac ttcagggaa                                                19

SEQ ID NO: 430          moltype = RNA  length = 18
FEATURE                 Location/Qualifiers
misc_feature            1..18
                        note = Synthetic Construct
source                  1..18
                        mol_type = other RNA
                        organism = synthetic construct
SEQUENCE: 430
ccatctctgg gataagga                                                 18

SEQ ID NO: 431          moltype = RNA  length = 18
FEATURE                 Location/Qualifiers
misc_feature            1..18
                        note = Synthetic Construct
source                  1..18
                        mol_type = other RNA
                        organism = synthetic construct
SEQUENCE: 431
catctctggg ataaggat                                                 18

SEQ ID NO: 432          moltype = RNA  length = 18
FEATURE                 Location/Qualifiers
misc_feature            1..18
                        note = Synthetic Construct
source                  1..18
```

```
                        mol_type = other RNA
                        organism = synthetic construct
SEQUENCE: 432
atctctggga taaggatg                                                18

SEQ ID NO: 433          moltype = RNA  length = 18
FEATURE                 Location/Qualifiers
misc_feature            1..18
                        note = Synthetic Construct
source                  1..18
                        mol_type = other RNA
                        organism = synthetic construct
SEQUENCE: 433
tctctgggat aaggatga                                                18

SEQ ID NO: 434          moltype = RNA  length = 18
FEATURE                 Location/Qualifiers
misc_feature            1..18
                        note = Synthetic Construct
source                  1..18
                        mol_type = other RNA
                        organism = synthetic construct
SEQUENCE: 434
ctctgggata aggatgac                                                18

SEQ ID NO: 435          moltype = RNA  length = 18
FEATURE                 Location/Qualifiers
misc_feature            1..18
                        note = Synthetic Construct
source                  1..18
                        mol_type = other RNA
                        organism = synthetic construct
SEQUENCE: 435
tctgggataa ggatgact                                                18

SEQ ID NO: 436          moltype = RNA  length = 18
FEATURE                 Location/Qualifiers
misc_feature            1..18
                        note = Synthetic Construct
source                  1..18
                        mol_type = other RNA
                        organism = synthetic construct
SEQUENCE: 436
ctgggataag gatgactg                                                18

SEQ ID NO: 437          moltype = RNA  length = 18
FEATURE                 Location/Qualifiers
misc_feature            1..18
                        note = Synthetic Construct
source                  1..18
                        mol_type = other RNA
                        organism = synthetic construct
SEQUENCE: 437
tgggataagg atgactga                                                18

SEQ ID NO: 438          moltype = RNA  length = 18
FEATURE                 Location/Qualifiers
misc_feature            1..18
                        note = Synthetic Construct
source                  1..18
                        mol_type = other RNA
                        organism = synthetic construct
SEQUENCE: 438
gggataagga tgactgag                                                18

SEQ ID NO: 439          moltype = RNA  length = 18
FEATURE                 Location/Qualifiers
misc_feature            1..18
                        note = Synthetic Construct
source                  1..18
                        mol_type = other RNA
                        organism = synthetic construct
SEQUENCE: 439
ggataaggat gactgagg                                                18

SEQ ID NO: 440          moltype = RNA  length = 18
FEATURE                 Location/Qualifiers
misc_feature            1..18
                        note = Synthetic Construct
```

```
source                  1..18
                        mol_type = other RNA
                        organism = synthetic construct
SEQUENCE: 440
acaactgaaa cttcaggg                                                    18

SEQ ID NO: 441          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 441
cttatcccag agatggtttc                                                  20

SEQ ID NO: 442          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 442
ccttatccca gagatggttt                                                  20

SEQ ID NO: 443          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 443
tccttatccc agagatggtt                                                  20

SEQ ID NO: 444          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 444
atccttatcc cagagatggt                                                  20

SEQ ID NO: 445          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 445
catccttatc ccagagatgg                                                  20

SEQ ID NO: 446          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 446
tcatccttat cccagagatg                                                  20

SEQ ID NO: 447          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 447
gtcatcctta tcccagagat                                                  20

SEQ ID NO: 448          moltype = DNA  length = 20
FEATURE                 Location/Qualifiers
misc_feature            1..20
```

```
                        note = Synthetic Construct
source                  1..20
                        mol_type = other DNA
                        organism = synthetic construct
SEQUENCE: 448
agtcatcctt atcccagaga                                              20

SEQ ID NO: 449          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 449
cagtcatcct tatcccagag                                              20

SEQ ID NO: 450          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 450
tcagtcatcc ttatcccaga                                              20

SEQ ID NO: 451          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 451
ctcagtcatc cttatcccag                                              20

SEQ ID NO: 452          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 452
cctcagtcat ccttatccca                                              20

SEQ ID NO: 453          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 453
tcctcagtca tccttatccc                                              20

SEQ ID NO: 454          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 454
ttcctcagtc atccttatcc                                              20

SEQ ID NO: 455          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 455
gaagtttcag ttgtttcagc                                              20

SEQ ID NO: 456          moltype = DNA  length = 20
FEATURE                 Location/Qualifiers
```

```
misc_feature          1..20
                      note = Synthetic Construct
source                1..20
                      mol_type = other DNA
                      organism = synthetic construct
SEQUENCE: 456
cctgaagttt cagttgtttc                                              20

SEQ ID NO: 457        moltype = DNA  length = 20
FEATURE               Location/Qualifiers
misc_feature          1..20
                      note = Synthetic Construct
source                1..20
                      mol_type = other DNA
                      organism = synthetic construct
SEQUENCE: 457
ccctgaagtt tcagttgttt                                              20

SEQ ID NO: 458        moltype = DNA  length = 20
FEATURE               Location/Qualifiers
misc_feature          1..20
                      note = Synthetic Construct
source                1..20
                      mol_type = other DNA
                      organism = synthetic construct
SEQUENCE: 458
tccctgaagt ttcagttgtt                                              20

SEQ ID NO: 459        moltype = DNA  length = 20
FEATURE               Location/Qualifiers
misc_feature          1..20
                      note = Synthetic Construct
source                1..20
                      mol_type = other DNA
                      organism = synthetic construct
SEQUENCE: 459
ttccctgaag tttcagttgt                                              20

SEQ ID NO: 460        moltype = DNA  length = 20
FEATURE               Location/Qualifiers
misc_feature          1..20
                      note = Synthetic Construct
source                1..20
                      mol_type = other DNA
                      organism = synthetic construct
SEQUENCE: 460
tttccctgaa gtttcagttg                                              20

SEQ ID NO: 461        moltype = DNA  length = 20
FEATURE               Location/Qualifiers
misc_feature          1..20
                      note = Synthetic Construct
source                1..20
                      mol_type = other DNA
                      organism = synthetic construct
SEQUENCE: 461
cttttccctg aagtttcagt                                              20

SEQ ID NO: 462        moltype = DNA  length = 19
FEATURE               Location/Qualifiers
misc_feature          1..19
                      note = Synthetic Construct
source                1..19
                      mol_type = other DNA
                      organism = synthetic construct
SEQUENCE: 462
ccttatccca gagatggtt                                               19

SEQ ID NO: 463        moltype = DNA  length = 19
FEATURE               Location/Qualifiers
misc_feature          1..19
                      note = Synthetic Construct
source                1..19
                      mol_type = other DNA
                      organism = synthetic construct
SEQUENCE: 463
tccttatccc agagatggt                                               19

SEQ ID NO: 464        moltype = DNA  length = 19
```

```
FEATURE                 Location/Qualifiers
misc_feature            1..19
                        note = Synthetic Construct
source                  1..19
                        mol_type = other DNA
                        organism = synthetic construct
SEQUENCE: 464
atccttatcc cagagatgg                                               19

SEQ ID NO: 465          moltype = DNA  length = 19
FEATURE                 Location/Qualifiers
misc_feature            1..19
                        note = Synthetic Construct
source                  1..19
                        mol_type = other DNA
                        organism = synthetic construct
SEQUENCE: 465
catccttatc ccagagatg                                               19

SEQ ID NO: 466          moltype = DNA  length = 19
FEATURE                 Location/Qualifiers
misc_feature            1..19
                        note = Synthetic Construct
source                  1..19
                        mol_type = other DNA
                        organism = synthetic construct
SEQUENCE: 466
tcatccttat cccagagat                                               19

SEQ ID NO: 467          moltype = DNA  length = 19
FEATURE                 Location/Qualifiers
misc_feature            1..19
                        note = Synthetic Construct
source                  1..19
                        mol_type = other DNA
                        organism = synthetic construct
SEQUENCE: 467
gtcatcctta tcccagaga                                               19

SEQ ID NO: 468          moltype = DNA  length = 19
FEATURE                 Location/Qualifiers
misc_feature            1..19
                        note = Synthetic Construct
source                  1..19
                        mol_type = other DNA
                        organism = synthetic construct
SEQUENCE: 468
agtcatcctt atcccagag                                               19

SEQ ID NO: 469          moltype = DNA  length = 19
FEATURE                 Location/Qualifiers
misc_feature            1..19
                        note = Synthetic Construct
source                  1..19
                        mol_type = other DNA
                        organism = synthetic construct
SEQUENCE: 469
cagtcatcct tatcccaga                                               19

SEQ ID NO: 470          moltype = DNA  length = 19
FEATURE                 Location/Qualifiers
misc_feature            1..19
                        note = Synthetic Construct
source                  1..19
                        mol_type = other DNA
                        organism = synthetic construct
SEQUENCE: 470
tcagtcatcc ttatcccag                                               19

SEQ ID NO: 471          moltype = DNA  length = 19
FEATURE                 Location/Qualifiers
misc_feature            1..19
                        note = Synthetic Construct
source                  1..19
                        mol_type = other DNA
                        organism = synthetic construct
SEQUENCE: 471
ctcagtcatc cttatccca                                               19
```

```
SEQ ID NO: 472          moltype = DNA  length = 19
FEATURE                 Location/Qualifiers
misc_feature            1..19
                        note = Synthetic Construct
source                  1..19
                        mol_type = other DNA
                        organism = synthetic construct
SEQUENCE: 472
cctcagtcat ccttatccc                                                   19

SEQ ID NO: 473          moltype = DNA  length = 19
FEATURE                 Location/Qualifiers
misc_feature            1..19
                        note = Synthetic Construct
source                  1..19
                        mol_type = other DNA
                        organism = synthetic construct
SEQUENCE: 473
tcctcagtca tccttatcc                                                   19

SEQ ID NO: 474          moltype = DNA  length = 19
FEATURE                 Location/Qualifiers
misc_feature            1..19
                        note = Synthetic Construct
source                  1..19
                        mol_type = other DNA
                        organism = synthetic construct
SEQUENCE: 474
ccctgaagtt tcagttgtt                                                   19

SEQ ID NO: 475          moltype = DNA  length = 19
FEATURE                 Location/Qualifiers
misc_feature            1..19
                        note = Synthetic Construct
source                  1..19
                        mol_type = other DNA
                        organism = synthetic construct
SEQUENCE: 475
tccctgaagt ttcagttgt                                                   19

SEQ ID NO: 476          moltype = DNA  length = 19
FEATURE                 Location/Qualifiers
misc_feature            1..19
                        note = Synthetic Construct
source                  1..19
                        mol_type = other DNA
                        organism = synthetic construct
SEQUENCE: 476
ttccctgaag tttcagttg                                                   19

SEQ ID NO: 477          moltype = DNA  length = 19
FEATURE                 Location/Qualifiers
misc_feature            1..19
                        note = Synthetic Construct
source                  1..19
                        mol_type = other DNA
                        organism = synthetic construct
SEQUENCE: 477
ttccctgaag tttcagttg                                                   19

SEQ ID NO: 478          moltype = DNA  length = 18
FEATURE                 Location/Qualifiers
misc_feature            1..18
                        note = Synthetic Construct
source                  1..18
                        mol_type = other DNA
                        organism = synthetic construct
SEQUENCE: 478
tccttatccc agagatgg                                                    18

SEQ ID NO: 479          moltype = DNA  length = 18
FEATURE                 Location/Qualifiers
misc_feature            1..18
                        note = Synthetic Construct
source                  1..18
                        mol_type = other DNA
                        organism = synthetic construct
SEQUENCE: 479
atccttatcc cagagatg                                                    18
```

```
SEQ ID NO: 480          moltype = DNA  length = 18
FEATURE                 Location/Qualifiers
misc_feature            1..18
                        note = Synthetic Construct
source                  1..18
                        mol_type = other DNA
                        organism = synthetic construct
SEQUENCE: 480
catccttatc ccagagat                                                   18

SEQ ID NO: 481          moltype = DNA  length = 18
FEATURE                 Location/Qualifiers
misc_feature            1..18
                        note = Synthetic Construct
source                  1..18
                        mol_type = other DNA
                        organism = synthetic construct
SEQUENCE: 481
tcatccttat cccagaga                                                   18

SEQ ID NO: 482          moltype = DNA  length = 18
FEATURE                 Location/Qualifiers
misc_feature            1..18
                        note = Synthetic Construct
source                  1..18
                        mol_type = other DNA
                        organism = synthetic construct
SEQUENCE: 482
gtcatcctta tcccagag                                                   18

SEQ ID NO: 483          moltype = DNA  length = 18
FEATURE                 Location/Qualifiers
misc_feature            1..18
                        note = Synthetic Construct
source                  1..18
                        mol_type = other DNA
                        organism = synthetic construct
SEQUENCE: 483
agtcatcctt atcccaga                                                   18

SEQ ID NO: 484          moltype = DNA  length = 18
FEATURE                 Location/Qualifiers
misc_feature            1..18
                        note = Synthetic Construct
source                  1..18
                        mol_type = other DNA
                        organism = synthetic construct
SEQUENCE: 484
cagtcatcct tatcccag                                                   18

SEQ ID NO: 485          moltype = DNA  length = 18
FEATURE                 Location/Qualifiers
misc_feature            1..18
                        note = Synthetic Construct
source                  1..18
                        mol_type = other DNA
                        organism = synthetic construct
SEQUENCE: 485
tcagtcatcc ttatccca                                                   18

SEQ ID NO: 486          moltype = DNA  length = 18
FEATURE                 Location/Qualifiers
misc_feature            1..18
                        note = Synthetic Construct
source                  1..18
                        mol_type = other DNA
                        organism = synthetic construct
SEQUENCE: 486
ctcagtcatc cttatccc                                                   18

SEQ ID NO: 487          moltype = DNA  length = 18
FEATURE                 Location/Qualifiers
misc_feature            1..18
                        note = Synthetic Construct
source                  1..18
                        mol_type = other DNA
                        organism = synthetic construct
SEQUENCE: 487
```

```
cctcagtcat ccttatcc                                              18

SEQ ID NO: 488         moltype = DNA  length = 18
FEATURE                Location/Qualifiers
misc_feature           1..18
                       note = Synthetic Construct
source                 1..18
                       mol_type = other DNA
                       organism = synthetic construct
SEQUENCE: 488
ccctgaagtt tcagttgt                                              18

SEQ ID NO: 489         moltype = DNA  length = 228
FEATURE                Location/Qualifiers
misc_feature           1..228
                       note = Synthetic Construct
source                 1..228
                       mol_type = other DNA
                       organism = synthetic construct
SEQUENCE: 489
aatgaaatct tctgatttgt aagacatgct gccaagagat tagttttaca ccttcaggat  60
aaagactgct gagaaggttt aaggatgcta ttctgaaaag actgtggagg aagattaagg  120
aaaccatctc tgggataagg atgactgagg aaatttaagg atgccactct ggttaaaagc  180
tgaaacaact gaaacttcag ggaaaagaga aggcctggaa tctgatcc              228

SEQ ID NO: 490         moltype = DNA  length = 79
FEATURE                Location/Qualifiers
misc_feature           1..79
                       note = Synthetic Construct
source                 1..79
                       mol_type = other DNA
                       organism = synthetic construct
SEQUENCE: 490
gggtcaatga tgacaaccca atgtcatgaa gaaatgtgat gacataaaat ttatgctcaa  60
taggattacg ctgagtccc                                             79

SEQ ID NO: 491         moltype = DNA  length = 79
FEATURE                Location/Qualifiers
misc_feature           1..79
                       note = Synthetic Construct
source                 1..79
                       mol_type = other DNA
                       organism = synthetic construct
SEQUENCE: 491
gggtcaataa tggcaatcca atgtcatgaa gaaaggtgat gacataaaat tcatgctcaa  60
taggattact ctgaggccc                                             79

SEQ ID NO: 492         moltype = DNA  length = 88
FEATURE                Location/Qualifiers
misc_feature           1..88
                       note = Synthetic Construct
source                 1..88
                       mol_type = other DNA
                       organism = synthetic construct
SEQUENCE: 492
gggttcacaa agtgcaatcc ctcgagccaa tgtcatgaag aaaggtgatg acataaaatt  60
catgctcaat aggattatgc tgaggccc                                   88

SEQ ID NO: 493         moltype = DNA  length = 79
FEATURE                Location/Qualifiers
misc_feature           1..79
                       note = Synthetic Construct
source                 1..79
                       mol_type = other DNA
                       organism = synthetic construct
SEQUENCE: 493
ttgtcaatga taacaaccca aaatcatgaa cagaggtgat gatataaaaa tcatgctcaa  60
taggattacg ctgaggcac                                             79

SEQ ID NO: 494         moltype = DNA  length = 69
FEATURE                Location/Qualifiers
misc_feature           1..69
                       note = Synthetic Construct
source                 1..69
                       mol_type = other DNA
                       organism = synthetic construct
SEQUENCE: 494
tggccatcat aggtcatgaa gagtggtgat gacattaaaa tcatgatcaa taggattaca  60
ctgaggccc                                                        69
```

```
SEQ ID NO: 495          moltype = DNA  length = 82
FEATURE                 Location/Qualifiers
misc_feature            1..82
                        note = Synthetic Construct
source                  1..82
                        mol_type = other DNA
                        organism = synthetic construct
SEQUENCE: 495
gggtcaatga tgagaacctt atattgtcct gaagagcggt gatgacttaa aaatcatgct  60
caataggatt acgctgaggc cc                                            82

SEQ ID NO: 496          moltype = DNA  length = 76
FEATURE                 Location/Qualifiers
misc_feature            1..76
                        note = Synthetic Construct
source                  1..76
                        mol_type = other DNA
                        organism = synthetic construct
SEQUENCE: 496
gggtcaatga tgagatgtta ccttgaagag aaatgatgac gtaaaaatta agttcagttg  60
gattacgctg aggccc                                                   76

SEQ ID NO: 497          moltype = DNA  length = 53
FEATURE                 Location/Qualifiers
misc_feature            1..53
                        note = Synthetic Construct
source                  1..53
                        mol_type = other DNA
                        organism = synthetic construct
SEQUENCE: 497
ttatattgtc ttcgacaggg aagatgacat aaaaattatg ttcaatagga tta         53

SEQ ID NO: 498          moltype = DNA  length = 71
FEATURE                 Location/Qualifiers
misc_feature            1..71
                        note = Synthetic Construct
source                  1..71
                        mol_type = other DNA
                        organism = synthetic construct
SEQUENCE: 498
tcaataatga aatcttctga tttggtgaga aataatgcct taaaattaca ctcaatagga  60
ttatgctgag g                                                        71

SEQ ID NO: 499          moltype = DNA  length = 33
FEATURE                 Location/Qualifiers
misc_feature            1..33
                        note = Synthetic Construct
source                  1..33
                        mol_type = other DNA
                        organism = synthetic construct
SEQUENCE: 499
taaaaatcat gctcaataga attaagctga ggc                                33

SEQ ID NO: 500          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 500
atatgtggaa gccggaatct                                               20

SEQ ID NO: 501          moltype = DNA  length = 21
FEATURE                 Location/Qualifiers
misc_feature            1..21
                        note = Synthetic Construct
source                  1..21
                        mol_type = other DNA
                        organism = synthetic construct
SEQUENCE: 501
cccagaactc cctaatcaga a                                             21

SEQ ID NO: 502          moltype = DNA  length = 20
FEATURE                 Location/Qualifiers
misc_feature            1..20
                        note = Synthetic Construct
source                  1..20
```

```
                        mol_type = other DNA
                        organism = synthetic construct
SEQUENCE: 502
atgacggtgg ctataccagg                                              20

SEQ ID NO: 503          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 503
gtctccttcg agctgtttgc                                              20

SEQ ID NO: 504          moltype = DNA  length = 21
FEATURE                 Location/Qualifiers
misc_feature            1..21
                        note = Synthetic Construct
source                  1..21
                        mol_type = other DNA
                        organism = synthetic construct
SEQUENCE: 504
cctttctctc cagtgctcag a                                            21

SEQ ID NO: 505          moltype = DNA  length = 21
FEATURE                 Location/Qualifiers
misc_feature            1..21
                        note = Synthetic Construct
source                  1..21
                        mol_type = other DNA
                        organism = synthetic construct
SEQUENCE: 505
cctgtgaact ttcaaccagg a                                            21

SEQ ID NO: 506          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 506
ggatcagact ccaggccttc                                              20

SEQ ID NO: 507          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 507
cccaggtgtc ctttaatgaa                                              20

SEQ ID NO: 508          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 508
ccaggtgtcc tttaatgaaa                                              20

SEQ ID NO: 509          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 509
tgaaaatgct cttgacacca                                              20

SEQ ID NO: 510          moltype = RNA  length = 20
FEATURE                 Location/Qualifiers
misc_feature            1..20
                        note = Synthetic Construct
```

```
source                  1..20
                        mol_type = other RNA
                        organism = synthetic construct
SEQUENCE: 510
gaaaatgctc ttgacaccaa                                             20

SEQ ID NO: 511          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 511
aaatgctctt gacaccaatg                                             20

SEQ ID NO: 512          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 512
agatcagtag cttcctttac                                             20

SEQ ID NO: 513          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 513
tcagtagctt cctttaccga                                             20

SEQ ID NO: 514          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 514
tctagaacat tgagctatgg                                             20

SEQ ID NO: 515          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 515
ctagaacatt gagctatgga                                             20

SEQ ID NO: 516          moltype = RNA  length = 20
FEATURE                 Location/Qualifiers
source                  1..20
                        mol_type = other RNA
                        organism = synthetic construct
SEQUENCE: 516
aacattgagc tatggaagac                                             20

SEQ ID NO: 517          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 517
acattgagct atggaagact                                             20

SEQ ID NO: 518          moltype = RNA  length = 20
FEATURE                 Location/Qualifiers
misc_feature            1..20
                        note = Synthetic Construct
source                  1..20
```

```
                        mol_type = other RNA
                        organism = synthetic construct
SEQUENCE: 518
ctatggaaga ctcccaccta                                                20

SEQ ID NO: 519          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 519
tatggaagac tcccacctaa                                                20

SEQ ID NO: 520          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 520
caagtgctac cgcacaggca                                                20

SEQ ID NO: 521          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 521
aagtgctacc gcacaggcat                                                20

SEQ ID NO: 522          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 522
taccgcacag gcatgctgca                                                20

SEQ ID NO: 523          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 523
caggcatgct gcagtgaatt                                                20

SEQ ID NO: 524          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 524
aggcatgctg cagtgaattt                                                20

SEQ ID NO: 525          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 525
accgttgttt aaggatgcta                                                20

SEQ ID NO: 526          moltype = RNA  length = 20
FEATURE                 Location/Qualifiers
misc_feature            1..20
                        note = Synthetic Construct
```

```
source                  1..20
                        mol_type = other RNA
                        organism = synthetic construct
SEQUENCE: 526
ccgttgttta aggatgctat                                                    20

SEQ ID NO: 527          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 527
ctgtggagga agaaaaccct                                                    20

SEQ ID NO: 528          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 528
aagaaaaccc tttaccctgt                                                    20

SEQ ID NO: 529          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 529
agaaaaccct ttaccctgtt                                                    20

SEQ ID NO: 530          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 530
ctcaactgcc tggcactgaa                                                    20

SEQ ID NO: 531          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 531
aactgcctgg cactgaaaat                                                    20

SEQ ID NO: 532          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 532
actgcctggc actgaaaatg                                                    20

SEQ ID NO: 533          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 533
gtgtttaagg aaaccatctc                                                    20

SEQ ID NO: 534          moltype = RNA  length = 20
FEATURE                 Location/Qualifiers
misc_feature            1..20
```

```
                        note = Synthetic Construct
source                  1..20
                        mol_type = other RNA
                        organism = synthetic construct
SEQUENCE: 534
gtttaaggaa accatctctg                                          20

SEQ ID NO: 535          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 535
aggaaaccat ctctgataag                                          20

SEQ ID NO: 536          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 536
tctttggctt gttgacacca                                          20

SEQ ID NO: 537          moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 537
ctttggcttg ttgacaccag                                          20

SEQ ID NO: 538          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 538
ttcattaaag gacacctggg                                          20

SEQ ID NO: 539          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 539
tttcattaaa ggacacctgg                                          20

SEQ ID NO: 540          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 540
tggtgtcaag agcattttca                                          20

SEQ ID NO: 541          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 541
ttggtgtcaa gagcattttc                                          20

SEQ ID NO: 542          moltype = DNA  length = 20
FEATURE                 Location/Qualifiers
```

```
misc_feature          1..20
                      note = Synthetic Construct
source                1..20
                      mol_type = other DNA
                      organism = synthetic construct
SEQUENCE: 542
cattggtgtc aagagcattt                                              20

SEQ ID NO: 543        moltype = DNA  length = 20
FEATURE               Location/Qualifiers
misc_feature          1..20
                      note = Synthetic Construct
source                1..20
                      mol_type = other DNA
                      organism = synthetic construct
SEQUENCE: 543
gtaaaggaag ctactgatct                                              20

SEQ ID NO: 544        moltype = DNA  length = 20
FEATURE               Location/Qualifiers
misc_feature          1..20
                      note = Synthetic Construct
source                1..20
                      mol_type = other DNA
                      organism = synthetic construct
SEQUENCE: 544
tcggtaaagg aagctactga                                              20

SEQ ID NO: 545        moltype = DNA  length = 20
FEATURE               Location/Qualifiers
misc_feature          1..20
                      note = Synthetic Construct
source                1..20
                      mol_type = other DNA
                      organism = synthetic construct
SEQUENCE: 545
ccatagctca atgttctaga                                              20

SEQ ID NO: 546        moltype = DNA  length = 20
FEATURE               Location/Qualifiers
misc_feature          1..20
                      note = Synthetic Construct
source                1..20
                      mol_type = other DNA
                      organism = synthetic construct
SEQUENCE: 546
tccatagctc aatgttctag                                              20

SEQ ID NO: 547        moltype = DNA  length = 20
FEATURE               Location/Qualifiers
misc_feature          1..20
                      note = Synthetic Construct
source                1..20
                      mol_type = other DNA
                      organism = synthetic construct
SEQUENCE: 547
gtcttccata gctcaatgtt                                              20

SEQ ID NO: 548        moltype = DNA  length = 20
FEATURE               Location/Qualifiers
misc_feature          1..20
                      note = Synthetic Construct
source                1..20
                      mol_type = other DNA
                      organism = synthetic construct
SEQUENCE: 548
agtcttccat agctcaatgt                                              20

SEQ ID NO: 549        moltype = DNA  length = 20
FEATURE               Location/Qualifiers
misc_feature          1..20
                      note = Synthetic Construct
source                1..20
                      mol_type = other DNA
                      organism = synthetic construct
SEQUENCE: 549
taggtgggag tcttccatag                                              20

SEQ ID NO: 550        moltype = DNA  length = 20
```

```
FEATURE                 Location/Qualifiers
misc_feature            1..20
                        note = Synthetic Construct
source                  1..20
                        mol_type = other DNA
                        organism = synthetic construct
SEQUENCE: 550
ttaggtggga gtcttccata                                                20

SEQ ID NO: 551          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 551
tgcctgtgcg gtagcacttg                                                20

SEQ ID NO: 552          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 552
atgcctgtgc ggtagcactt                                                20

SEQ ID NO: 553          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 553
tgcagcatgc ctgtgcggta                                                20

SEQ ID NO: 554          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 554
aattcactgc agcatgcctg                                                20

SEQ ID NO: 555          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 555
aaattcactg cagcatgcct                                                20

SEQ ID NO: 556          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 556
tagcatcctt aaacaacggt                                                20

SEQ ID NO: 557          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 557
atagcatcct taaacaacgg                                                20
```

```
SEQ ID NO: 558          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 558
agggttttct tcctccacag                                              20

SEQ ID NO: 559          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 559
acagggtaaa gggttttctt                                              20

SEQ ID NO: 560          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 560
aacagggtaa agggttttct                                              20

SEQ ID NO: 561          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 561
ttcagtgcca ggcagttgag                                              20

SEQ ID NO: 562          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 562
attttcagtg ccaggcagtt                                              20

SEQ ID NO: 563          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 563
cattttcagt gccaggcagt                                              20

SEQ ID NO: 564          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 564
gagatggttt ccttaaacac                                              20

SEQ ID NO: 565          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 565
cagagatggt ttccttaaac                                              20
```

```
SEQ ID NO: 566          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 566
cttatcagag atggtttcct                                              20

SEQ ID NO: 567          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 567
tggtgtcaac aagccaaaga                                              20

SEQ ID NO: 568          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 568
ctggtgtcaa caagccaaag                                              20

SEQ ID NO: 569          moltype = DNA  length = 58
FEATURE                 Location/Qualifiers
misc_feature            1..58
                        note = Synthetic Construct
source                  1..58
                        mol_type = other DNA
                        organism = synthetic construct
SEQUENCE: 569
ggtgccattc tattataaat aacctgaccc attatttata atagaatggc accttttt    58

SEQ ID NO: 570          moltype = DNA  length = 58
FEATURE                 Location/Qualifiers
misc_feature            1..58
                        note = Synthetic Construct
source                  1..58
                        mol_type = other DNA
                        organism = synthetic construct
SEQUENCE: 570
gctttcatca ataatgaaat aacctgaccc attatttcat tattgatgaa agcttttt    58

SEQ ID NO: 571          moltype = DNA  length = 58
FEATURE                 Location/Qualifiers
misc_feature            1..58
                        note = Synthetic Construct
source                  1..58
                        mol_type = other DNA
                        organism = synthetic construct
SEQUENCE: 571
ggtctttcat caataatgat aacctgaccc attatcatta ttgatgaaag accttttt    58

SEQ ID NO: 572          moltype = DNA  length = 58
FEATURE                 Location/Qualifiers
misc_feature            1..58
                        note = Synthetic Construct
source                  1..58
                        mol_type = other DNA
                        organism = synthetic construct
SEQUENCE: 572
gaaatcttct gatttgtaat aacctgaccc attattacaa atcagaagat ttcttttt    58

SEQ ID NO: 573          moltype = DNA  length = 58
FEATURE                 Location/Qualifiers
misc_feature            1..58
                        note = Synthetic Construct
source                  1..58
                        mol_type = other DNA
                        organism = synthetic construct
SEQUENCE: 573
```

```
gcacctaagg gaattagtat aacctgaccc attatactaa ttcccttagg tgcttttt    58

SEQ ID NO: 574         moltype = DNA  length = 58
FEATURE                Location/Qualifiers
misc_feature           1..58
                       note = Synthetic Construct
source                 1..58
                       mol_type = other DNA
                       organism = synthetic construct
SEQUENCE: 574
gtttcaacca ggatttaaat aacctgaccc attatttaaa tcctggttga aacttttt    58

SEQ ID NO: 575         moltype = DNA  length = 58
FEATURE                Location/Qualifiers
misc_feature           1..58
                       note = Synthetic Construct
source                 1..58
                       mol_type = other DNA
                       organism = synthetic construct
SEQUENCE: 575
gctttcaacc aggatttaat aacctgaccc attattaaat cctggttgaa agcttttt    58

SEQ ID NO: 576         moltype = DNA  length = 58
FEATURE                Location/Qualifiers
misc_feature           1..58
                       note = Synthetic Construct
source                 1..58
                       mol_type = other DNA
                       organism = synthetic construct
SEQUENCE: 576
ggagatgtgc cattctatat aacctgaccc attatataga atggcacatc tccttttt    58

SEQ ID NO: 577         moltype = DNA  length = 58
FEATURE                Location/Qualifiers
misc_feature           1..58
                       note = Synthetic Construct
source                 1..58
                       mol_type = other DNA
                       organism = synthetic construct
SEQUENCE: 577
gtctttcatc aataatgaat aacctgaccc attattcatt attgatgaaa gacttttt    58

SEQ ID NO: 578         moltype = DNA  length = 58
FEATURE                Location/Qualifiers
misc_feature           1..58
                       note = Synthetic Construct
source                 1..58
                       mol_type = other DNA
                       organism = synthetic construct
SEQUENCE: 578
gatcaataat gaaatcttat aacctgaccc attataagat ttcattattg atcttttt    58

SEQ ID NO: 579         moltype = DNA  length = 58
FEATURE                Location/Qualifiers
misc_feature           1..58
                       note = Synthetic Construct
source                 1..58
                       mol_type = other DNA
                       organism = synthetic construct
SEQUENCE: 579
gtgtctttca tcaataatat aacctgaccc attatattat tgatgaaaga cacttttt    58

SEQ ID NO: 580         moltype = DNA  length = 58
FEATURE                Location/Qualifiers
misc_feature           1..58
                       note = Synthetic Construct
source                 1..58
                       mol_type = other DNA
                       organism = synthetic construct
SEQUENCE: 580
gcaataatga aatcttctat aacctgaccc attatagaag atttcattat tgcttttt    58

SEQ ID NO: 581         moltype = DNA  length = 58
FEATURE                Location/Qualifiers
misc_feature           1..58
                       note = Synthetic Construct
source                 1..58
                       mol_type = other DNA
                       organism = synthetic construct
```

```
SEQUENCE: 581
gcatgctgca gtgaatttat aacctgaccc attataaatt cactgcagca tgcttttt    58

SEQ ID NO: 582          moltype = DNA  length = 58
FEATURE                 Location/Qualifiers
misc_feature            1..58
                        note = Synthetic Construct
source                  1..58
                        mol_type = other DNA
                        organism = synthetic construct
SEQUENCE: 582
ggaaatcttc tgatttgtat aacctgaccc attatacaaa tcagaagatt tccttttt    58

SEQ ID NO: 583          moltype = DNA  length = 58
FEATURE                 Location/Qualifiers
misc_feature            1..58
                        note = Synthetic Construct
source                  1..58
                        mol_type = other DNA
                        organism = synthetic construct
SEQUENCE: 583
ggtatattct atctagaaat aacctgaccc attatttcta gatagaatat accttttt    58

SEQ ID NO: 584          moltype = DNA  length = 58
FEATURE                 Location/Qualifiers
misc_feature            1..58
                        note = Synthetic Construct
source                  1..58
                        mol_type = other DNA
                        organism = synthetic construct
SEQUENCE: 584
gtgctgcagt gaatttaaat aacctgaccc attatttaaa ttcactgcag cacttttt    58

SEQ ID NO: 585          moltype = DNA  length = 58
FEATURE                 Location/Qualifiers
misc_feature            1..58
                        note = Synthetic Construct
source                  1..58
                        mol_type = other DNA
                        organism = synthetic construct
SEQUENCE: 585
gtgtgccatt ctattataat aacctgaccc attattataa tagaatggca cacttttt    58

SEQ ID NO: 586          moltype = DNA  length = 58
FEATURE                 Location/Qualifiers
misc_feature            1..58
                        note = Synthetic Construct
source                  1..58
                        mol_type = other DNA
                        organism = synthetic construct
SEQUENCE: 586
gttaccatca gtgtttaaat aacctgaccc attatttaaa cactgatggt aacttttt    58

SEQ ID NO: 587          moltype = DNA  length = 58
FEATURE                 Location/Qualifiers
misc_feature            1..58
                        note = Synthetic Construct
source                  1..58
                        mol_type = other DNA
                        organism = synthetic construct
SEQUENCE: 587
gcctgcaacc gttgtttaat aacctgaccc attattaaac aacggttgca ggcttttt    58

SEQ ID NO: 588          moltype = DNA  length = 58
FEATURE                 Location/Qualifiers
misc_feature            1..58
                        note = Synthetic Construct
source                  1..58
                        mol_type = other DNA
                        organism = synthetic construct
SEQUENCE: 588
gtatgtcttt catcaataat aacctgaccc attattattg atgaaagaca tacttttt    58

SEQ ID NO: 589          moltype = DNA  length = 20
FEATURE                 Location/Qualifiers
misc_feature            1..20
                        note = Synthetic Construct
source                  1..20
                        mol_type = other DNA
```

```
                       organism = synthetic construct
SEQUENCE: 589
acactgatgg taaagtggac                                              20

SEQ ID NO: 590         moltype = DNA  length = 20
FEATURE                Location/Qualifiers
misc_feature           1..20
                       note = Synthetic Construct
source                 1..20
                       mol_type = other DNA
                       organism = synthetic construct
SEQUENCE: 590
tagaatatac acgtcggtaa                                              20

SEQ ID NO: 591         moltype = DNA  length = 20
FEATURE                Location/Qualifiers
misc_feature           1..20
                       note = Synthetic Construct
source                 1..20
                       mol_type = other DNA
                       organism = synthetic construct
SEQUENCE: 591
tcaactgtcc cagtcacaac                                              20

SEQ ID NO: 592         moltype = DNA  length = 20
FEATURE                Location/Qualifiers
misc_feature           1..20
                       note = Synthetic Construct
source                 1..20
                       mol_type = other DNA
                       organism = synthetic construct
SEQUENCE: 592
tctagataga atatacacgt                                              20

SEQ ID NO: 593         moltype = DNA  length = 20
FEATURE                Location/Qualifiers
misc_feature           1..20
                       note = Synthetic Construct
source                 1..20
                       mol_type = other DNA
                       organism = synthetic construct
SEQUENCE: 593
tctagataga atatacacgt                                              20

SEQ ID NO: 594         moltype = DNA  length = 20
FEATURE                Location/Qualifiers
misc_feature           1..20
                       note = Synthetic Construct
source                 1..20
                       mol_type = other DNA
                       organism = synthetic construct
SEQUENCE: 594
ctccccatgc acacttgaga                                              20

SEQ ID NO: 595         moltype = DNA  length = 20
FEATURE                Location/Qualifiers
misc_feature           1..20
                       note = Synthetic Construct
source                 1..20
                       mol_type = other DNA
                       organism = synthetic construct
SEQUENCE: 595
catccttaaa caacggttgc                                              20

SEQ ID NO: 596         moltype = DNA  length = 20
FEATURE                Location/Qualifiers
misc_feature           1..20
                       note = Synthetic Construct
source                 1..20
                       mol_type = other DNA
                       organism = synthetic construct
SEQUENCE: 596
ggtgtaaaac taattccctt                                              20

SEQ ID NO: 597         moltype = DNA  length = 20
FEATURE                Location/Qualifiers
misc_feature           1..20
                       note = Synthetic Construct
source                 1..20
```

```
                        mol_type = other DNA
                        organism = synthetic construct
SEQUENCE: 597
aacaacggtt gcagggacag                                              20

SEQ ID NO: 598          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 598
tatggaagac tcccacctaa                                              20

SEQ ID NO: 599          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 599
ctatggaaga ctcccaccta                                              20

SEQ ID NO: 600          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 600
aagccttctc aagtgtgcat                                              20

SEQ ID NO: 601          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 601
ctatctagaa cattgagcta                                              20

SEQ ID NO: 602          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 602
accctctggt gttgtcacag                                              20

SEQ ID NO: 603          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 603
aaccctttac cctgttgttc                                              20

SEQ ID NO: 604          moltype = DNA  length = 79
FEATURE                 Location/Qualifiers
source                  1..79
                        mol_type = other DNA
                        organism = synthetic construct
SEQUENCE: 604
gggtcaataa tgncaancca atgtcatgaa gaaaggtgat gacataaaat tcatgctcaa  60
taggattacg ctgaggccc                                               79

SEQ ID NO: 605          moltype = DNA  length = 78
FEATURE                 Location/Qualifiers
source                  1..78
                        mol_type = other DNA
                        organism = synthetic construct
```

```
SEQUENCE: 605
ggtcaatgat gagacttatn ttgtcttgaa gagagatgat gacntaaaaa ttatgctcaa  60
taggattacg ctgaggcc                                                78
```